US007790390B2

(12) United States Patent
Vance et al.

(10) Patent No.: US 7,790,390 B2
(45) Date of Patent: Sep. 7, 2010

(54) METHODS FOR IDENTIFYING AN INDIVIDUAL AT INCREASED RISK OF DEVELOPING CORONARY ARTERY DISEASE

(75) Inventors: Jeffery M. Vance, Coral Gables, FL (US); Pascal J. Goldschmidt, Miami, FL (US); Simon G. Gregory, Durham, NC (US); William E. Kraus, Hillsborough, NC (US); Elizabeth R. Hauser, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 12/031,528

(22) Filed: Feb. 14, 2008

(65) Prior Publication Data

US 2009/0087844 A1  Apr. 2, 2009

Related U.S. Application Data

(63) Continuation-in-part of application No. 11/260,842, filed on Oct. 27, 2005.

(60) Provisional application No. 60/622,447, filed on Oct. 27, 2004.

(51) Int. Cl.
C12Q 1/68 (2006.01)
C12P 19/34 (2006.01)
C07H 21/02 (2006.01)
C07H 21/04 (2006.01)

(52) U.S. Cl. .................. 435/6; 435/91.2; 536/23.1; 536/23.5; 536/24.31

(58) Field of Classification Search ........................ None
See application file for complete search history.

(56) References Cited

U.S. PATENT DOCUMENTS

| | | | |
|---|---|---|---|
| 5,449,604 A | 9/1995 | Schellenberg et al. | |
| 5,508,167 A | 4/1996 | Roses et al. | |
| 5,879,884 A | 3/1999 | Peroutka | |
| 5,922,556 A | 7/1999 | Mayeux et al. | |
| 5,958,684 A | 9/1999 | Van Leeuwen et al. | |
| 6,027,896 A | 2/2000 | Roses et al. | |
| 6,108,635 A | 8/2000 | Herren et al. | |
| 6,165,727 A | 12/2000 | Lalouel et al. | |
| 6,194,153 B1 | 2/2001 | St. George-Hyslop et al. | |
| 6,342,350 B1 | 1/2002 | Tanzi et al. | |
| 2002/0037508 A1 | 3/2002 | Cargill et al. | |
| 2004/0014109 A1 | 1/2004 | Pericak-Vance et al. | |
| 2004/0053251 A1 | 3/2004 | Pericak-Vance et al. | |
| 2004/0248092 A1 | 12/2004 | Vance et al. | |
| 2005/0191652 A1 | 9/2005 | Vance et al. | |
| 2006/0068428 A1 | 3/2006 | Vance et al. | |
| 2006/0115845 A1 | 6/2006 | Vance et al. | |
| 2007/0148661 A1 | 6/2007 | Vance et al. | |

2009/0226420 A1  9/2009  Hauser et al.

FOREIGN PATENT DOCUMENTS

| | | |
|---|---|---|
| WO | WO 99/57129 A1 | 11/1999 |
| WO | WO 00/31253 A2 | 6/2000 |
| WO | WO 01/20998 A1 | 3/2001 |
| WO | WO 01/92576 A1 | 12/2001 |
| WO | WO 02/02000 A3 | 1/2002 |
| WO | WO 2004/005534 A3 | 1/2004 |
| WO | WO 2004/007681 A3 | 1/2004 |
| WO | WO 2007/086980 A2 | 8/2007 |

OTHER PUBLICATIONS

NCBI SNP Database, National Center for Biotechnology Information, National Library of Medicine (Bethesda, MD, USA), rs4404477, printed Mar. 24, 2010, available via url: <ncbi.nlm.nih.gov/projects/SNP/snp_ref.cgi?rs=4404477>.*
Abbas et al. "A Wide Variety of Mutations in the *Parkin* Gene are Responsible for Autosomal Recessive Parkinsonism in Europe" *Hum. Mol. Genet.* 8(4):567-574 (1999).
Amos "Robust Variance-Components Approach for Assessing Genetic Linkage in Pedigrees" *Am J Human Genetics* 54:535-543 (1994).
Antonarakis et al. "Recommendations for a Nomenclature System for Human Gene Mutations" *Human Mutation* 11:1-3 (1998).
Baker "Association of an extended haplotype in the *tau* gene with progressive supranuclear palsy" *Hum. Mol. Genet.* 8(4):711-715 (1999).
Bengtsson et al. "Polymorphism in the β1-Adrenergic Receptor Gene and Hypertension" *Circulation* 104:187-190 (2001).
Bertram et al. "No Association between marker D10S1423 and Alzheimer's Disease" *Molecular Psychiatry* 8:571-573 (2003).
Bertram et al. "Evidence for Genetic Linkage of Alzheimer's Disease to Chromosome 10q" *Science* 290:2302-2305 (2000).
Blacker et al. "Results of high-resolution genome screen of 437 Alzheimer's Disease families" *Hum. Mol. Genet.* 12(1):23-32 (2003).
Blangero et al. "Multipoint Oligogenic Linkage Anaylsis of Quantitative Traits" *Genetic Epidemiology* 14:959-964 (1997).

(Continued)

*Primary Examiner*—Carla Myers
(74) *Attorney, Agent, or Firm*—Myers Bigel Sibley & Sajovec, P.A.

(57) ABSTRACT

The present invention provides methods of identifying a subject having an increased or decreased risk of developing cardiovascular disease, comprising:
a) correlating the presence of one or more genetic markers in chromosome 3q13.31 with an increased or decreased risk of developing cardiovascular disease; and
b) detecting the one or more genetic markers of step (a) in the subject, thereby identifying the subject as having an increased or decreased risk of developing cardiovascular disease. Also provided are methods of identifying subjects with cardiovascular disease as having a good or poor prognosis, as well as methods of identifying effective treatment regimens for cardiovascular disease, based on correlation with genetic markers in chromosome 3q13.31.

7 Claims, 9 Drawing Sheets

OTHER PUBLICATIONS

Board et al. "Identification, Characterization, and Crystal Structure of the Omega Class Glutathione Transferases" *Journal of Biological Chemistry* 275(32):24798-24806 (2000).

Bouffard et al. GenBank Accession No. G20124. Sep. 28, 1998.

Boyles et al. "Linkage Disequilibrium Inflates Type 1 Error Rates in Multipoint Linkage Analysis when Parental Genotypes Are Missing" *Hum Hered.* 59(4):220-227 (2005).

Specification for U.S. Appl. No. 10/520,695, filed Jan. 7, 2005.

Specification for U.S. Appl. No. 10/520,779, filed Jan. 7, 2005.

Corder et al. "Gene dose of Apolipoprotein E Type 4 Allele and the Risk of Alzheimer's Disease in Late Onset Families" *Science* 261(5123):921-923 (1993).

Daw et al. "Multipoint Oligogenic Analysis of Age-at-Onset Data with Applications to Alzheimer Disease Pedigrees" *Am J Human Genetics* 64:839-851 (1999).

Daw et al. "The Number of Trait Loci in Late-Onset Alzheimer Disease" *Am J Human Genetics* 66:196-204 (2000).

DeStefano et al. "Genome-Wide Scan for Parkinson's Disease: The GenePD Study" *Neurology* 57:1124-1126 (2001).

Dizier et al. "Genome screen for asthma and related phenotypes in the French EGEA study" *American Journal Respiratory and Critical Care Medicine* 162:1812-1818 (2000).

Duggirala et al. "Linkage of Type 2 Diabetes Mellitus and of Age at Onset to a Genetic Location on Chromosome 10q in Mexican Americans" *Am J Human Genetics* 64:1127-1140 (1999).

Dulhunty et al. "The Glutathione Transferase Structural Family Includes a Nuclear Chloride Channel and a Ryanodine Receptor Calcium Release Channel Modulator" *Journal of Biological Chemistry* 276(5):3319-3323 (2001).

Ertekin-Taner et al. "Linkage of Plasma Aβ42 to a Quantitative Locus on Chromosome 10 in Late-Onset Alzheimer's Disease Pedigrees" *Science* 290:2303-2304 (2000).

GenBank Accession No. rs4925, Reference SNP.

Goate et al. "Segregation of a Missense Mutation in the Amyloid Precursor Protein Gene with Familial Alzheimer's Disease" *Nature* 349:704-706 (1991).

Goldgar "Mulitipoint Analysis of Human Quantitative Genetic Variation" *Am J Human Genetics* 47:957-967 (1990).

Grover et al. "Effects on splicing and protein function of three mutations in codon N296 of *tau* in vitro"*Neuroscience Letters* 323:33-36 (2002).

Hattori et al. "Point Mutations (Thr240Arg and Ala311Stop) in the *Parkin* Gene" *Biochem. Biophys. Res. Commun.* 249:754-758 (1998).

Hiltunen et al. "Linkage disequilibrium in the 13q12 region in Finnish late onset Alzheimer's disease patients" *European Journal of Human Genetics* 7:652-658 (1999).

Hiltunen et al. "Linkage disequilibrium of Late-Onset Alzheimer's Disease at 13q12 Region" *Society for Neuroscience* 24:1218m entry 478.4 (1998).

Hauser et al. "A Genomewide Scan for Early-Onset Coronary Artery Disease in 438 Families: The GENECARD Study" *Am. J. Hum. Genet.* 75:436-447 (2004).

International Search Report corresponding to PCT/US03/22259 dated Mar. 5, 2004.

International Search Report corresponding to PCT/US01/16940 dated Aug. 24, 2001.

International Search Report corresponding to PCT/US03/21963 dated Sep. 9, 2004.

International Search Report corresponding to PCT/US01/41224 dated Jan. 15, 2002.

Ioannidis et al. "Replication validity of genetic association studies" *Nature Genetics* 29:306-309 (2001).

Kehoe et al. "A Full Genome Scan for Late Onset Alzheimer's Disease" *Human Molecular Genetics.* 8(2):237-245 (1999).

Khan et al. "Parkinson's Disease Is Not Associated With the Combined α-Synuclein/Apolipoprotein E Susceptibility Genotype" *Annals of Neurology* 49(5):665-668 (2001).

Kitada et al. "Mutations in the *parkin* gene cause autosomal recessive juvenile parkinsonism" *Nature* 392:605-608 (1998).

Levy-Lahad et al. "Candidate Gene for the Chromosome 1 Familial Alzheimer's Disease Locus" *Science* 269:973-977 (1995).

Li et al. "Modulation of Age at Onset and Risk in Alzheimer Disease" Abstract presented at American Society of Human Genetics Meeting, San Diego, CA Oct. 2001.

Li et al. "Glutathione S-transferase omega-1 modifies age-at-onset of Alzheimer disease and Parkinson disease" *Human Molecular Genetics* 12(24):3259-3267 (2003).

Li et al. "Age at Onset in Two Common Neurodegenerative Diseases Is Genetically Controlled" *Am. J. Hum. Genet.* 70:985-993 (2002).

Li et al. "Revealing the role of glutathione S-transferase omega in age-at-onset of Alzheimer and Parkinson Disease" *Neurobiology of Aging* 27:1087-93 (Epub. Jun. 27, 2005).

Liang et al. "Covariate analysis of late-onset Alzheimer disease refines the chromosome 12 locus" *Molecular Psychiatry* 11:280-285 (2006).

Lippa et al." α-Synuclein in Familial Alzheimer Disease" *Arch Neurol.* 58:1817-1820 (2001).

Lucentini et al. "Gene Association Studies Typically Wrong," *The Scientist* 18(24):20 (2004).

Martin et al. "Association of Single-Nucleotide Polymorphisms of the *Tau* Gene with Late-Onset Parkinson Disease" *JAMA* 286(18):2245-2250 (2001).

Martin et al. "SNPing Away at Complex Diseases: Analysis of Single-Nucleotide Polymorphisms around APOE in Alzheimer Disease" *Am. J. Hum. Genet.* 67:383-394 (2000).

Morris et al. "The *tau* gene A0 polymorphism in progressive supranuclear palsy and related neurodegenerative diseases" *J. Neurol. Neurosurg. Psychiatry* 66:665-667 (1999).

Murray et al. GenBank Accession No. G08525. Feb. 5, 1997.

Murray et al. GenBank Accession No. G08539. Feb. 5, 1997.

Myers et al. "Susceptibility Locus for Alzheimer's Disease on Chromosome 10" *Science* 290:2304-2305 (2000).

Neuman et al. "Linkage Analysis of a Complex Disease: Application to Familial Alzheimer's Disease" *Genetic Epidemiology* 10:419-424 (1993).

Nussbaum et al. "Genetics of Parkinson's Disease" *Human Molecular Genetics* 6(10):1687-1691 (1997).

Oliveira et al. "Association Study of Parkin Gene Polymorphisms With Idiopathic Parkinson Disease" *Arch Neurol.* 60:975-980 (2003).

Oliveira et al. "Identification of Risk and Age-at-Onset Genes on Chromosome 1p in Parkinson Disease" *Am. J. Hum. Genet.* 77:252-264 (2005).

Oliveira et al. "Linkage disequilibrium and haplotype tagging polymorphisms in the *Tau* H1 haplotype" *Neurogenetics* 5:147-155 (2004).

Oliveira et al. "Parkin Mutations and Susceptibility Alleles in Late-Onset Parkinson's Disease" *Ann Neurol* 53:624-629 (2003).

Pastor et al. "Significant Association between the tau Gene A0/A0 Genotype and Parkinson's Disease" *Annals of Neurology* 47(2):242-245 (2000).

Perez et al. "β1-adrenergic receptor polymorphisms confer differential function and predisposition to heart failure" *Nature Medicine* 9(10):1300-1305 (2003).

Pericak-Vance et al. "Complete Genomic Screen in Late-Onset Familial Alzheimer's Disease" *Neurobiology of Aging* 19(1S):S39-S42 (1998).

Pericak-Vance et al. "Modulation of Age at Onset and Risk in Alzheimer Disease" Abstract presented at the National Institute on Aging, Neuroscience Symposium on the Genetics of Alzheimer Disease, Nov. 2001.

Pericak-Vance et al. "Identification of Novel Genes in Late-Onset Alzheimer's Disease " *Exp. Gerontol.* 35:1343-1352 (2000).

Polymeropoulos et al. "Mapping of a Gene for Parkinson's Disease to Chromosome 4q21-q23" *Science* 274(5290):1197-1199 (1996).

Results of Search for "MAPT" in SNP database in GenBank.

Rogaev et al. "Familial Alzheimer's disease in kindreds with missense mutations in a gene on chromosome 1 related to the Alzheimer's disease type 3 gene" *Nature* 376:775-778 (1995).

Scott et al. "Complete Genomic Screen in Parkinson Disease" *JAMA* 286(18):2239-2244 (2001).

Scott et al. "Fine Mapping of the Chromosome 12 Late-Onset Alzheimer Disease Locus: Potential Genetic and Phenotypic Heterogeneity" *Am. J. Hum. Genet*. 66:922-932 (2000).

Scott et al. "Ordered Subsets Linkage Analysis Detects Novel Alzheimer Disease Loci on Chromosomes 2q34 and 15q22" *Am. J. Hum. Genet*. 73:1041-1051 (2003).

Shashidharan et al. "*TorsinA accumulation in Lewy bodies in sporadic Parkinson's disease*" *Brain Research* 877:379-381 (2000).

Sherrington et al. "Cloning of a gene bearing missense mutations in early-onset familial Alzheimer's disease" *Nature* 375:754-760 (1995).

Van der Walt et al. "Genetic polymorphisms of the N-acetyltransferase genes and risk of Parkinson's dieseas e" *Neurology* 60:1189-1191 (2003).

Van der Walt et al. "Mitochondrial Polymorphisms Significantly Reduce the Risk of Parkinson Disease" *Am. J. Hum. Genet*. 72:804-811 (2003).

Van der Walt et al. "Fibroblast Growth Factor 20 Polymorphisms and Haplotypes Strongly Influence Risk of Parkinson Disease" *Am. J. Hum. Genet*. 74:1121-1127 (2004).

Vance et al. "Methods of Genotyping" in *Approaches to Gene Mapping in Complex Human Diseases*, pp. 213-228, Eds. J. Haines and M. Pericak-Vance, John Wiley & Sons, Inc. New York.

Wacholder et al. "Assessing the Probability That a Positive Report is False: An Approach for Molecular Epidemiology Studies" *Journal of the National Cancer Institute* 96(6):434-442 (2004).

Wjst et al. "A Genome-Wide Search for Linkage to Asthma," *Genomics* 58:1-8 (1999).

Xu et al. "Genomewide Screen and Identification of Gene-Gene Interactions for Asthma-Susceptibility in three U.S. Populations: Collaborative Study on Genetics in Asthma" *American Journal of Human Genetics* 68:1437-1446 (2001).

Zakharyan et al. "Human Monomethylarsonic Acid (MMA$^V$) Reductase Is a Member of the Glutathione-S-transferase Superfamily" *Chem. Res. Toxicol*. 14:1051-1057 (2001).

Brasch-Andersen et al. Journal of Medical Genetics. 2006. 43:e10.

Haluska et al. Nature. Jul. 1999. 22:239-247.

Hirschhorn et al. Genetics in Medicine. 2002. 4(2):45-.

NCBI Database, National Center for Biotechnology Information, National Library of Medicine, NIH (Bethesda, MD, USA), rs1875518 (ss2752812) Jan. 2, 2001.

Sanghera et al. Arteriosclerosis. 1997. 17:1067-1073.

Wu et al. Circulation. 2001. 103:1386-1389.

Connelly et al. "*GATA2* is Associated with Familial Early-Onset Coronary Artery Disease" *PLoS Genetics* 2(8):1265-1273 (2006).

Perez et al. "$\beta_1$-adrenergic Receptor Polymorphisms Confer Differential Function and Predisposition to Heart Failure" *Nat Med* 9(10):1300-1305 (2003).

Vance et al. "A 100 kb Region in 3q13.31 is Significantly Associated with Coronary Artery Disease: the Power of Genome-Wide Linkage Combined with Peak-Wide Association Analysis" Abstract/Session Information for Program No. 27, Meeting of the American Society of Human Genetics, Oct. 26-30, 2004. Toronto, Canada (Abstract available online Sep. 2004).

Wang et al. "Peakwide Mapping on Chromosome 3q13 Identifies the Kalirin Gene as a Novel Candidate Gene for Coronary Artery Disease" *Am J Hum Genet* 80:650-663 (2007).

Wang et al. "Polymorphisms of the Tumor Suppressor Gene LSAMP are Associated with Left Main Coronary Artery Disease" *Ann Hum Genet* 72(Pt 4):443-453 (2008).

* cited by examiner

Quantitative trait loci (QTL) map, HDL cholesterol, chromosome 3.

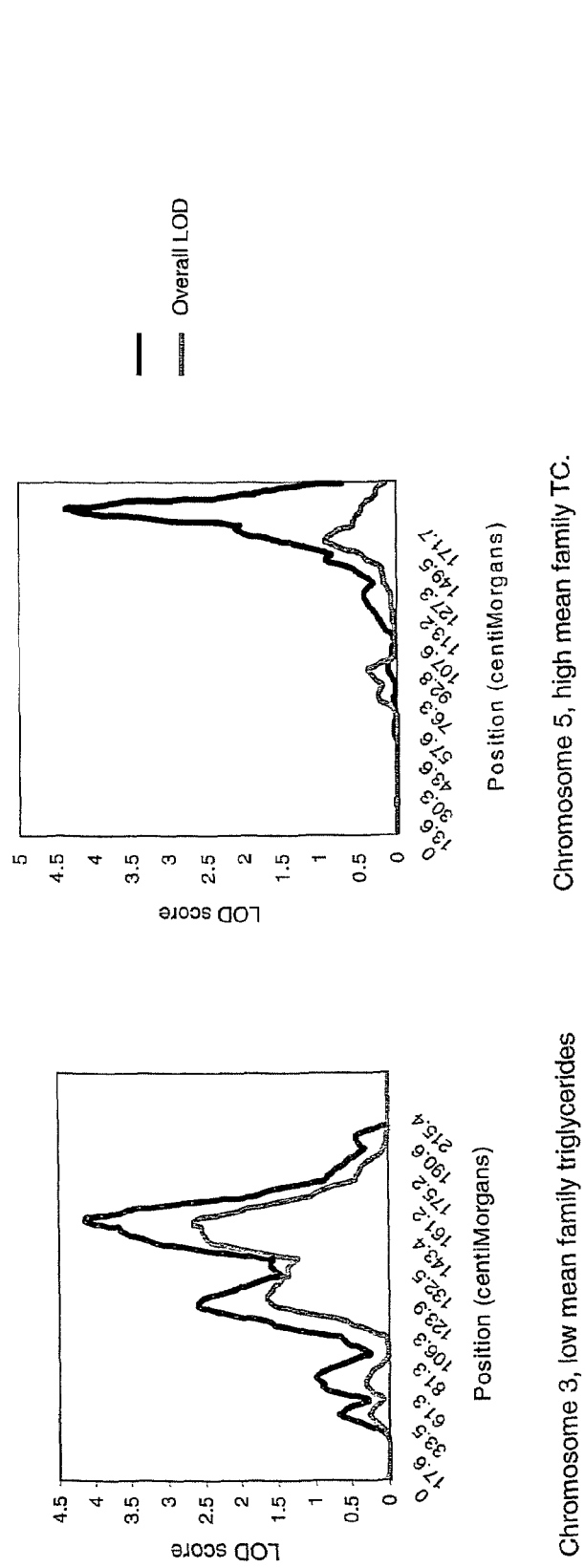
Figure 5. OSA results, chromosomes 3 and 5.
*Max LOD: maximum lod in subset of families with most extreme of covariate means.

Figure 6. Genotypes of affected vs. normal individuals

| Phenotype | OA | OA | OA | OA | OA | OA | OA | OA | OA | ON | ON | ON | ON | ON | ON | YA |
|---|---|---|---|---|---|---|---|---|---|---|---|---|---|---|---|---|
| ID | 1 | 2 | 3 | 4 | 5 | 6 | 7 | 8 | 9 | 10 | 11 | 12 | 13 | 14 | 15 | 16 |
| A Deletion | -/- | -/- | -/- | -/- | -/- | -/- | -/- | -/- | -/- | +/+ | +/+ | +/+ | +/+ | +/+ | +/+ | +/- |
| CAA Insertion | -/- | -/- | -/- | -/- | -/- | -/- | -/- | -/- | -/- | +/+ | -/- | -/- | +/- | +/+ | +/+ | -/- |
| 27 bp Duplication | -/- | -/- | -/+ | -/- | -/- | -/- | n/a | -/- | -/- | +/+ | +/+ | +/+ | +/+ | +/+ | n/a | n/a |

Allele frequency differences between case and control (DNA pooling)

Identification of a significant haplotype

Association analysis of SNPs with CAD

US 7,790,390 B2

METHODS FOR IDENTIFYING AN INDIVIDUAL AT INCREASED RISK OF DEVELOPING CORONARY ARTERY DISEASE

CROSS REFERENCE TO RELATED APPLICATIONS

This application is a continuation-in-part application of, and claims priority to, U.S. application Ser. No. 11/260,842, filed Oct. 27, 2005, which claims the benefit of U.S. Provisional Application Ser. No. 60/622,447, filed Oct. 27, 2004, the contents of each of which are herein incorporated by reference in their entireties.

GOVERNMENT SUPPORT

The present invention was made, in part, with the support of grant numbers HL073389, HL073042, HL73005, AG021547 and AG019757 from the National Institutes of Health/National Heart, Lung and Blood Institute. The United States Government has certain rights to this invention.

FIELD OF THE INVENTION

The present invention provides methods and compositions directed to identification of genetic markers in chromosome 3 and their correlation with cardiovascular disease.

BACKGROUND OF THE INVENTION

It is estimated that more than 13 million Americans are afflicted with clinically significant coronary artery disease (CAD) (American Heart Association 2004) and the care of these patients costs greater than $133 billion annually. Of those afflicted, 10% are less than 54 years old. Although a minority of the patient base, this group provides a valuable source for the investigation of the genetics underlying cardiac disease risk, because family history is known to be a robust predictor of cardiovascular disease, even after adjustment for known risk factors, which may be shared within families (Shea et al. 1984). Furthermore, these diseases inflict a high economic impact on this group of patients with early onset CAD. The identification of novel markers correlated with CAD is important in order to understand the pathophysiological mechanisms of this disease state and develop effective prevention and treatment regimens.

Cardiovascular disease is the leading killer in America today. Over 50 million Americans have heart and cardiovascular related problems. By the time that cardiovascular heart problems are usually detected, the disease is usually quite advanced, having progressed for decades, and often too advanced to allow successful prevention of major permanent disability.

Circulatory disease is caused by the normal flow of blood through the body being restricted or blocked as a result of arterial plaque. This may cause damage to the heart, brain, kidneys or other organs and tissues. Plaque build-up is a slow and progressive progress that is dependent on our environmental and genetic environment.

Cardiovascular disease refers to all disease, which involves the heart and/or blood vessels, arteries, and occasionally veins. These problems are most commonly due to consequences of arterial disease, atherosclerosis, atheroma, but also can be related to infection, valvular and clotting problems.

In humans, $\beta_1$-adrenergic receptors ($\beta_1$-ARs) are polymorphic at amino acid residue 389 (Arg/Gly). Mialet-Perez et al. (2003) Nat Med. 9:1260-1262, catecholamines stimulate cardiac contractility through reported that the human Arg389 variant predisposes to heart failure by instigating hyperactive signaling programs leading to depressed receptor coupling and ventricular dysfunction, and influences the therapeutic response to $\beta$-receptor blockade.

The present invention overcomes previous shortcomings in the art by providing methods and compositions for correlating genetic markers in a subject with various aspects of cardiovascular disease and its treatment.

SUMMARY OF THE INVENTION

The inventors have carried out a genome wide screening in 420 families with early-onset CAD disease (GENECARD study) and found significant linkage evidence (multipoint lod score=3.5) in chromosome 3q13 spanning over 60 mega bases. Systematic association analysis using single nucleotide polymorphism (SNP) was performed in case-control sets from the CATHGEN study. Subjects were selected based on their CAD index ($CAD_i$), a validated angiographical measure of the extent of CAD. CATHGEN included 301 young affected (YA: age $\leq$55, $CAD_i$ >32), 168 older affected (OA: age >55, $CAD_i$ >74), and 204 controls (ON: age >60, $CAD_i$ <23). A two-stage approach was taken: a preliminary screening in pooled DNA followed by individual genotyping around significant markers at higher density to define the boundaries of the linkage disequilibrium (LD) block. Initial screening of 16 SNPs by DNA pooling revealed that the frequency of the G allele of rs1875518 is significantly higher in OA than ON (OA-ON=12.2%, p=0.001), which is confirmed by individual genotyping (OA=57.2%; ON=45.5%). Additional genotyping around rs1875518 defined an LD block extending ~100 kb that is highly associated with OA in Caucasians. Moreover, preliminary evidence supports the association of this block in the GENECARD probands versus Cathgen ON. Finally, a novel microsatellite marker (3M0238) within the block was identified, which breaks the LD and formed a significant risk haplotype (P<0.005) with rs1875518: rs1875518_G-3M0238__253 is twice as prevalent in OA (21.39%) as in ON (11.39%). In sum, the inventors have identified a 100 kb region in 3q13.31 containing genetic susceptibility for CAD. In particular, these data indicate that carriers of rs1875518_G-3M0238__253 are at higher risk of developing CAD.

The present invention provides a method of identifying a subject having an increased or decreased risk of developing cardiovascular disease, comprising detecting in the subject one or more genetic markers in chromosome 3q13.31 correlated with an increased or decreased risk of developing cardiovascular disease.

Further provided is a method of identifying a subject having an increased or decreased risk of developing cardiovascular disease, comprising: a) correlating the presence of one or more genetic markers in chromosome 3q13.31 with an increased or decreased risk of developing cardiovascular disease; and b) detecting the one or more genetic markers of step (a) in the subject, thereby identifying the subject as having an increased or decreased risk of developing cardiovascular disease.

In further embodiments, the present invention provides a method of correlating a genetic marker in chromosome 3q13.31 with an increased risk of developing cardiovascular disease, comprising: a) detecting in a subject with cardiovascular disease the presence of one or more genetic markers in chromosome 3q13.31; and b) correlating the presence of the one or more genetic markers of step (a) with cardiovascular disease in the subject.

Also provided is a method of correlating a genetic marker in chromosome 3q13.31 with a decreased risk of developing cardiovascular disease, comprising: a) detecting in a subject without cardiovascular disease the presence of one or more genetic markers in chromosome 3q13.31; and b) correlating the presence of the one or more genetic markers of step (a) with the absence of cardiovascular disease in the subject.

Additionally provided herein is a method of diagnosing cardiovascular disease in a subject, comprising detecting in the subject one or more genetic markers correlated with a diagnosis of cardiovascular disease, as well as a method of diagnosing cardiovascular disease in a subject, comprising: a) correlating the presence of one or more genetic markers in chromosome 3q13.31 with a diagnosis of cardiovascular disease; and b) detecting the one or more genetic markers of step (a) in the subject, thereby diagnosing cardiovascular disease in the subject.

A method is also provided of correlating a genetic marker in chromosome 3q13.31 with a diagnosis of cardiovascular disease, comprising: a) detecting in a subject diagnosed with cardiovascular disease the presence of one or genetic markers in chromosome 3q13.31; and b) correlating the presence of the one or more genetic markers of step (a) with a diagnosis of cardiovascular disease in a subject.

In yet further embodiments, the present invention provides a method of identifying a subject with cardiovascular disease as having a good or a poor prognosis, comprising detecting in the subject one or more markers genetic markers in chromosome 3q13.31 correlated with a good or a poor prognosis for cardiovascular disease.

Furthermore, the present invention provides a method of identifying a subject with cardiovascular disease as having a good or a poor prognosis, comprising: a) correlating the presence of one or more genetic markers in chromosome 3q13.31 with a good or a poor prognosis for cardiovascular disease; and b) detecting the one or more markers of step (a) in the subject, thereby identifying the subject as having a good or a poor prognosis.

In addition, the present invention provides a method of correlating a genetic marker in chromosome 3q13.31 with a good or a poor prognosis for cardiovascular disease, comprising: a) detecting in a subject with cardiovascular disease and having a good or a poor prognosis, the presence of one or more genetic markers in chromosome 3q13.31; and b) correlating the presence of the one or more genetic markers of step (a) with a good or a poor prognosis for cardiovascular disease.

Additionally provided herein is a method of identifying an effective treatment regimen for a subject with cardiovascular disease, comprising detecting one or more genetic markers in chromosome 3q13.31 in the subject correlated with an effective treatment regimen for cardiovascular disease.

Also provided is a method of identifying an effective treatment regimen for a subject with cardiovascular disease, comprising: a) correlating the presence of one or more genetic markers in chromosome 3q13.31 in a test subject with cardiovascular disease for whom an effective treatment regimen has been identified; and b) detecting the one or more markers of step (a) in the subject, thereby identifying an effective treatment regimen for the subject.

Further provided is a method of correlating a genetic marker of chromosome 3q13.31 with an effective treatment regimen for cardiovascular disease, comprising: a) detecting in a subject with cardiovascular disease and for whom an effective treatment regimen has been identified, the presence of one or more genetic markers in chromosome 3q13.31; and b) correlating the presence of the one or more genetic markers of step (a) with a an effective treatment regimen for cardiovascular disease.

The present invention additionally provides a method of identifying a Caucasian subject having an increased risk of developing coronary artery disease, comprising detecting in a nucleic acid sample of the subject an allele at a single nucleotide polymorphism in the LSAMP gene of the subject, selected from the group consisting of: a) an A allele at single nucleotide polymorphism rs1910040; b) an A allele at single nucleotide polymorphism ss70458782; c) a G allele at single nucleotide polymorphism rs1875518; d) an A allele at single nucleotide polymorphism rs1676232; e) an A allele at single nucleotide polymorphism rs4404477; and f) any combination of (a)-(e) above, wherein the detection of said allele(s) identifies the subject as having an increased risk of developing coronary artery disease.

Also provided herein is a method of identifying a Caucasian subject having an increased risk of developing coronary artery disease, comprising detecting in a nucleic acid sample of the subject a haplotype in the LSAMP gene of the subject comprising, consisting essentially of and/or consisting of an A allele at single nucleotide polymorphism ss70458782 and an A allele at single nucleotide polymorphism rs4404477, wherein the detection of said haplotype identifies the subject as having an increased risk of developing coronary artery disease.

BRIEF DESCRIPTION OF THE DRAWINGS

FIG. 5 depicts chromosome 3 lod score curves using OSA that corroborate, strengthen and narrow the linkage peaks previously observed on chromosome 3q.

FIG. 6 depicts the genotypes of normal versus affected individuals with respect to three polymorphisms.

DETAILED DESCRIPTION OF THE INVENTION

Figure 1:
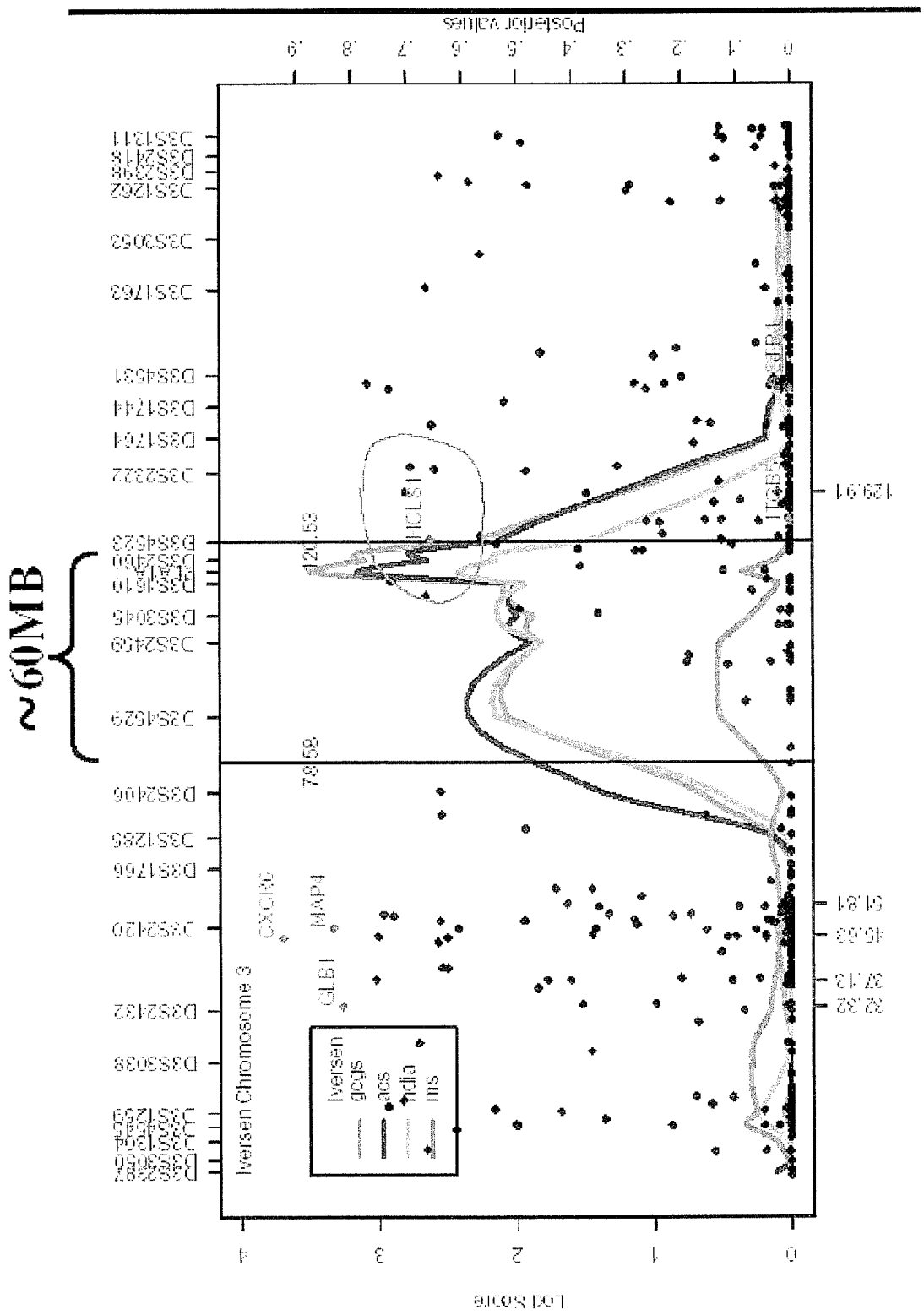
FIG. 1 depicts linkage evidence of the susceptibility for CAD (multipoint lod score=3.5) in chromosome 3q13 spanning over 120 megabases (Mb).

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Definitions

As used herein, the term "cardiovascular disease" includes any disease, disorder or pathological state or condition that involves the heart and/or blood vessels, arteries and veins. Examples of such diseases and disorders include, but are not limited to, arterial disease, atheroma, atherosclerosis, arteriosclerosis, coronary artery disease, arrhythmia, angina pectoris, congestive heart disease, myocardial infarction, stroke, transient ischemic attack (TIA), aortic aneurysm, cardiopericarditis, infection and/or inflammation of these tissues and/or organs, as well as valvular, vascular and clotting problems, insufficiencies and/or disorders, etc.

Also as used herein, "linked" describes a region of a chromosome that is shared more frequently in family members affected by a particular disease or disorder, than would be expected or observed by chance, thereby indicating that the gene or genes or other identified marker(s) within the linked chromosome region contain or are associated with an allele that is correlated with the presence of, or increased or decreased risk of the disease or disorder. Once linkage is established, association studies (linkage disequilibrium) can be used to narrow the region of interest or to identify the marker correlated with the disease or disorder.

The term "genetic marker" as used herein refers to a region of a nucleotide sequence (e.g., in a chromosome) that is subject to variability (i.e., the region can be polymorphic for a variety of alleles). For example, a single nucleotide polymorphism (SNP) in a nucleotide sequence is a genetic marker that is polymorphic for two alleles. Other examples of genetic markers of this invention can include but are not limited to microsatellites, restriction fragment length polymorphisms (RFLPs), repeats (i.e., duplications), insertions, deletions, etc.

A subject of this invention is any animal that is susceptible to cardiovascular disease as defined herein and can include mammals, birds and reptiles. Examples of subjects of this invention can include, but are not limited to, humans, non-human primates, dogs, cats, horses, cows, goats, guinea pigs, mice, rats and rabbits, as well as any other domestic or commercially valuable animal including animal models of cardiovascular disease.

As used herein, "nucleic acids" encompass both RNA and DNA, including cDNA, genomic DNA, mRNA, synthetic (e.g., chemically synthesized) DNA and chimeras of RNA and DNA. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An "isolated nucleic acid" is a DNA or RNA that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence.

The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an "isolated fragment" is a fragment of a nucleic acid or polypeptide that is not naturally occurring as a fragment and would not be found in the natural state.

The term "oligonucleotide" refers to a nucleic acid sequence of at least about six nucleotides to about 100 nucleotides, for example, about 15 to 30 nucleotides, or about 20 to 25 nucleotides, which can be used, for example, as a primer in a PCR amplification or as a probe in a hybridization assay or in a microarray. Oligonucleotides can be natural or synthetic, e.g., DNA, RNA, modified backbones, etc.

The present invention further provides fragments or oligonucleotides of the nucleic acids of this invention, which can be used as primers or probes. Thus, in some embodiments, a fragment or oligonucleotide of this invention is a nucleotide sequence that is at least 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, 750, 800, 850, 900, 1000, 1500, 2000, 2500 or 3000 contiguous nucleotides of the nucleotide sequence set forth in SEQ ID NO:1, or the nucleotide sequence set forth from nucleotides 118500001 to 118761789 of the NCBI Build 35 sequence of human chromosome 3 (SEQ ID NO:1). Such fragments or oligonucleotides can be detectably labeled or modified, for example, to include and/or incorporate a restriction enzyme cleavage site when employed as a primer in an amplification (e.g., PCR) assay.

The present invention is based on the inventors' discovery of a correlation between genetic markers in chromosome 3q13.31 and various aspects of cardiovascular disease. Thus, in one aspect, the present invention provides a method of identifying a subject having either an increased or decreased risk of developing cardiovascular disease, comprising detecting in the subject one or more genetic markers in chromosome 3q13.31 correlated with an increased or decreased risk of developing cardiovascular disease.

Further provided is a method of identifying a subject having either an increased or decreased risk of developing cardiovascular disease, comprising: a) correlating the presence of one or more genetic markers in chromosome 3q13.31 with an increased or decreased risk of developing cardiovascular disease; and b) detecting the one or more genetic markers of step (a) in the subject, thereby identifying the subject as having an increased or decreased risk of developing cardiovascular disease.

In further embodiments, the present invention provides a method of correlating a genetic marker in chromosome 3q13.31 with an increased risk of developing cardiovascular disease, comprising: a) detecting in a subject with cardiovascular disease the presence of one or more genetic markers in chromosome 3q13.31; and b) correlating the presence of the one or more genetic markers of step (a) with cardiovascular disease in the subject.

Also provided is a method of correlating a genetic marker in chromosome 3q13.31 with a decreased risk of developing cardiovascular disease, comprising: a) detecting in a subject without cardiovascular disease the presence of one or more genetic markers in chromosome 3q13.31; and b) correlating the presence of the one or more genetic markers of step (a) with the absence of cardiovascular disease in the subject.

Additionally provided herein is a method of diagnosing cardiovascular disease in a subject, comprising detecting in the subject one or more genetic markers correlated with a diagnosis of cardiovascular disease, as well as a method of diagnosing cardiovascular disease in a subject, comprising: a) correlating the presence of one or more genetic markers in chromosome 3q13.31 with a diagnosis of cardiovascular disease; and b) detecting the one or more genetic markers of step (a) in the subject, thereby diagnosing cardiovascular disease in the subject.

A method is also provided of correlating a genetic marker in chromosome 3q13.31 with a diagnosis of cardiovascular disease, comprising: a) detecting in a subject diagnosed with cardiovascular disease the presence of one or genetic markers in chromosome 3q13.31; and b) correlating the presence of the one or more genetic markers of step (a) with a diagnosis of cardiovascular disease in a subject.

In the methods described herein, the detection of a genetic marker in a subject can be carried out according to methods well known in the art. For example DNA is obtained from any suitable sample from the subject that will contain DNA and the DNA is then prepared and analyzed according to well-established protocols for the presence of genetic markers according to the methods of this invention. In some embodiments, analysis of the DNA can be carried by amplification of the region of interest according to amplification protocols well known in the art (e.g., polymerase chain reaction, ligase chain reaction, strand displacement amplification, transcription-based amplification, self-sustained sequence replication (3SR), Qβ replicase protocols, nucleic acid sequence-based amplification (NASBA), repair chain reaction (RCR) and boomerang DNA amplification (BDA)). The amplification product can then be visualized directly in a gel by staining or the product can be detected by hybridization with a detectable probe. When amplification conditions allow for amplification of all allelic types of a genetic marker, the types can be distinguished by a variety of well-known methods, such as hybridization with an allele-specific probe, secondary amplification with allele-specific primers, by restriction endonuclease digestion, or by electrophoresis. Thus, the present invention further provides oligonucleotides for use as primers and/or probes for detecting and/or identifying genetic markers according to the methods of this invention.

The genetic markers of this invention are correlated with various aspects of cardiovascular disease as described herein according to methods well known in the art and as disclosed in the Examples provided herein for correlating genetic markers with various phenotypic traits, including disease states and pathological conditions and levels of risk associated with developing a disease or pathological condition. In general, identifying such correlation involves conducting analyses that establish a statistically significant association and/or a statistically significant correlation between the presence of a genetic marker or a combination of markers and the phenotypic trait in the subject. An analysis that identifies a statistical association (e.g., a significant association) between the marker or combination of markers and the phenotype establishes a correlation between the presence of the marker or combination of markers in a subject and the particular phenotype being analyzed.

The correlation can involve one or more than one genetic marker of this invention (e.g., two, three, four, five, or more) in any combination. In some embodiments of this invention, the genetic markers are located on chromosome 3 and can be localized to the region 3q13.31. However, in other embodiments, the methods of this invention can include correlations between genetic markers on chromosome 3 (e.g., at 3q13.31) in combination with genetic markers on other chromosomes (e.g., chromosome 1) and various aspects of cardiovascular disease as described herein. For example, the genetic markers of this invention can be combined with genetic markers in the ApoE gene on chromosome 19, genetic markers in the MEF21 gene on chromosome 15, genetic markers in the matrix metalloproteinase 3 gene on chromosome 11 and/or genetic markers in the $\beta_1$-adrenergic receptor gene in chromosome 10 (e.g., the allele producing the Arg389 variant Perez et al., *Nature Medicine* 9:1300-1305 (2003); Bengtsson et al. *Circulation* 104:187-190 (2001)) in the methods of this invention and in establishing correlations between genetic markers and various aspects of cardiovascular disease as described herein.

Non-limiting examples of genetic markers of this invention are set forth in Tables 9, 10 and 11, which are located in the region from nucleotides 118500001 to 118761789 of human chromosome 3, NCBI Build 35 (SEQ ID NO:1).

In some embodiments, the genetic marker is a single nucleotide polymorphism (SNP). Exemplary single nucleotide polymorphisms include but are not limited to T for G, T for A, C for A, C for T, A for G, A for C, A for T, G for A and G for T substitutions. Other examples of genetic markers include insertions, deletions and duplications, including but not limited to an adenine deletion, a CAA insertion, and a 27-base pair duplication on human chromosome 3. Further examples of genetic markers of this invention include but are not limited to microsatellite markers such as 3M0238, which has a variety of alleles, such as alleles 245, 249, 250, 253 and 256, wherein each allele is defined by the length of the PCR product (245, 249, 250, 253 basepairs, etc.) produced using the 3M0238 primers (SEQ ID NOS:34 and 35) shown in Table 4. In a representative embodiment of the invention, the microsatellite marker is a tetranucleotide repeat, optionally, the tetranucleotide repeat sequence is GATA.

In the methods of this invention, particular alleles of the genetic markers are identified as being correlated with various aspects of cardiovascular disease. Thus, for example, an allele correlated with an increased risk of cardiovascular disease in a subject or with a diagnosis of cardiovascular disease in a subject can be a G allele at single nucleotide polymorphism rs1875518 (rs1875518_G), a T allele at single nucleotide polymorphism rs2937666 (rs2937666_T), a 253 allele at microsatellite marker 3M0238 (tetranucleotide GATA repeat, 253 basepair PCR product, 3M0238__253), a C allele at single nucleotide polymorphism hcv1602689 (hcv1602689_C), an A allele at single nucleotide polymorphism rs2272486 (rs2272486_A), an A allele at single nucleotide polymorphism rs1676232 (rs1676232_A), or an A allele at single nucleotide polymorphism rs4404477 (rs4404477_A), as well as any combination thereof. In some embodiments, a combination of genetic markers is provided that defines a haplotype that is correlated with an aspect of cardiovascular disease as described herein. Thus, for example, haplotypes correlated with increased risk of cardiovascular disease or with a diagnosis of cardiovascular disease include: rs1875518_G and G3M0238__253; rs1875518_G with G3M0238__253 and the A allele for rs2937666 (rs2937666_A); and/or the A allele for rs1875518 (rs1875518_A) with a non 253 allele of 3M0238 (3M0238_non253) and rs2937666_T.

Other examples of haplotypes correlated with cardiovascular disease are: the adenine deletion allele of the single nucleotide polymorphism of SEQ ID NO:15; the 27 basepair duplication allele of the polymorphism of SEQ ID NO:28; the CM insertion allele of the polymorphism of SEQ ID NO:29, and any combination thereof (Table 10). Still further examples of haplotypes correlated with cardiovascular disease are the A alleles for single nucleotide polymorphism rs1676232 or rs4404477 (rs1676232_A, rs4404477_A), or a combination thereof. Furthermore, rs4404477 appears to have an interaction with rs1676232 such that when both SNPs are homozygous for the A allele, the risk for CAD is significantly increased over that which is observed for a single SNP that is homozygous for the A allele, each of which is also associated with enhanced risk for CAD.

Additional alleles of this invention include an allele at a single nucleotide polymorphism in the LSAMP gene of the subject, which can be: a) an A allele at single nucleotide polymorphism rs1910040; b) an A allele at single nucleotide polymorphism ss70458782; c) a G allele at single nucleotide polymorphism rs1875518; d) an A allele at single nucleotide polymorphism rs1676232; e) an A allele at single nucleotide polymorphism rs4404477; and f) any combination of (a)-(e) above, wherein the detection of said allele(s) identifies the subject as having an increased risk of developing coronary artery disease.

Also provided herein is a method of identifying a Caucasian subject having an increased risk of developing coronary artery disease, comprising detecting in a nucleic acid sample of the subject a haplotype in the LSAMP gene of the subject comprising, consisting essentially of and/or consisting of an A allele at single nucleotide polymorphism ss70458782 and an A allele at single nucleotide polymorphism rs4404477, wherein the detection of said haplotype identifies the subject as having an increased risk of developing coronary artery disease.

An example of a haplotype correlated with decreased risk of cardiovascular disease is rs1875518_A with G3M0238_non253 and rs2937666_A.

Other genetic markers associated with cardiovascular disease are set forth in Tables 9, 10 and 11 and the Examples. The genetic markers of the invention can be used individually or in any combination.

In yet further embodiments, the present invention provides a method of identifying a subject with cardiovascular disease as having a good or a poor prognosis, comprising detecting in the subject one or more genetic markers in chromosome 3q13.31 correlated with a good or a poor prognosis for cardiovascular disease.

Furthermore, the present invention provides a method of identifying a subject with cardiovascular disease as having a good or a poor prognosis, comprising: a) correlating the presence of one or more genetic markers in chromosome 3q13.31 with a good or a poor prognosis for cardiovascular disease; and b) detecting the one or more markers of step (a) in the subject, thereby identifying the subject as having a good or a poor prognosis.

In addition, the present invention provides a method of correlating a genetic marker in chromosome 3q13.31 with a good or a poor prognosis for cardiovascular disease, comprising: a) detecting in a subject with cardiovascular disease and having a good or a poor prognosis, the presence of one or more genetic markers in chromosome 3q13.31; and b) correlating the present of the one or more genetic markers of step (a) with a good or a poor prognosis for cardiovascular disease.

A subject is identified as having cardiovascular disease according to diagnostic parameters well known in the art and can have a good or poor prognosis according to diagnostic and/or clinical parameters that are also known in the art. A correlation can be made between good and poor prognosis and a subject's genetic markers according to the methods of this invention, which can allow a clinician to determine the most effective treatment regimen for the subject.

The present invention further provides a method of identifying an effective treatment regimen for a subject with cardiovascular disease, comprising detecting one or more genetic markers in chromosome 3q13.31 in the subject correlated with an effective treatment regimen for cardiovascular disease.

Also provided is a method of identifying an effective treatment regimen for a subject with cardiovascular disease, comprising: a) correlating the presence of one or more genetic markers in chromosome 3q13.31 in a test subject with cardiovascular disease for whom an effective treatment regimen has been identified; and b) detecting the one or more markers of step (a) in the subject, thereby identifying an effective treatment regimen for the subject.

Further provided is a method of correlating a genetic marker of chromosome 3q13.31 with an effective treatment regimen for cardiovascular disease, comprising: a) detecting in a subject with cardiovascular disease and for whom an effective treatment regimen has been identified, the presence of one or more genetic markers in chromosome 3q13.31; and b) correlating the presence of the one or more genetic markers of step (a) with an effective treatment regimen for cardiovascular disease. Examples of treatment regimens for cardiovascular disease are well known in the art.

Patients who respond well to particular treatment protocols can be analyzed for specific genetic markers and a correlation can be established according to the methods provided herein. Alternatively, patients who respond poorly to a particular treatment regimen can also be analyzed for particular genetic markers correlated with the poor response. Then, a subject who is a candidate for treatment for cardiovascular disease can be assessed for the presence of the appropriate genetic markers and the most appropriate treatment regimen can be provided.

In some embodiments, the methods of correlating genetic markers with treatment regimens can be carried out using a computer database. Thus the present invention provides a computer-assisted method of identifying a proposed treatment for cardiovascular disease. The method involves the steps of (a) storing a database of biological data for a plurality of patients, the biological data that is being stored including for each of said plurality of patients (i) a treatment type, (ii) at least one genetic marker associated with cardiovascular disease and (iii) at least one disease progression measure for cardiovascular disease from which treatment efficacy can be determined; and then (b) querying the database to determine the dependence on said genetic marker of the effectiveness of a treatment type in treating cardiovascular disease, to thereby identify a proposed treatment as an effective treatment for a subject carrying a genetic marker correlated with cardiovascular disease.

In one embodiment, treatment information for a patient is entered into the database (through any suitable means such as a window or text interface), genetic marker information for that patient is entered into the database, and disease progression information is entered into the database. These steps are then repeated until the desired number of patients has been entered into the database. The database can then queried to determine whether a particular treatment is effective for patients carrying a particular marker, not effective for patients carrying a particular marker, etc. Such querying can be carried out prospectively or retrospectively on the database by any suitable means, but is generally done by statistical analysis in accordance with known techniques, as described herein.

The present invention is more particularly described in the following examples that are intended as illustrative only since numerous modifications and variations therein will be apparent to those skilled in the art.

EXAMPLES

Example 1

Overall summary: Using linkage analysis and association studies in families and isolated patients with cardiovascular disease (CAD), a 400 kb region in 3q13.31 was identified, containing a DNA region that affects susceptibility for CAD. A specific DNA haplotype was identified that is highly associated with CAD (p=0.0001) in Caucasians. This haplotype is defined by three markers: the single nucleotide polymorphism (SNP) marker rs1875518; a previously unidentified tetranucleotide GATA repeat, named 3M0238, and a third SNP, rs2937666. The actual alleles that are associated with susceptibility are shown in Tables 2 and 3. Both young onset and old onset CAD are affected by these haplotypes.

A genome wide screening in 420 families (GENECARD study Table 1) found the most significant linkage evidence (multipoint lod score=3.5) in chromosome 3q13 spanning over 120 megabases (Mb). This is shown in FIG. 1. Within this region is a genetic entity that influences the susceptibility for CAD. The present study was carried out to narrow the critical region and identify genetic variants conferring susceptibility to CAD in 3q13.

METHODS: Systematic association analysis using SNPs was performed in the 60 mB centered around the peak area of FIG. 1. A modified DNA pooling method was used to screen 16 SNPs, 100 kb apart, to look for association with CAD. To do this, another data set was used, different from the GENECARD data set, the CATHGEN samples, from a study of the Duke Catheterization Laboratory Database. Subjects were selected according to their CAD index ($CAD_i$), a validated angiographical measure of the extent of CAD. CATHGEN included 301 young affected (YA: age $\leq$55, $CAD_i$ >32), 168 older affected (OA: age >55, $CAD_i$ >74), and 204 controls (ON: age >60, $CAD_i$ <23). Association analysis was performed separately by ethnicity and adjusting for gender.

Figure 2:
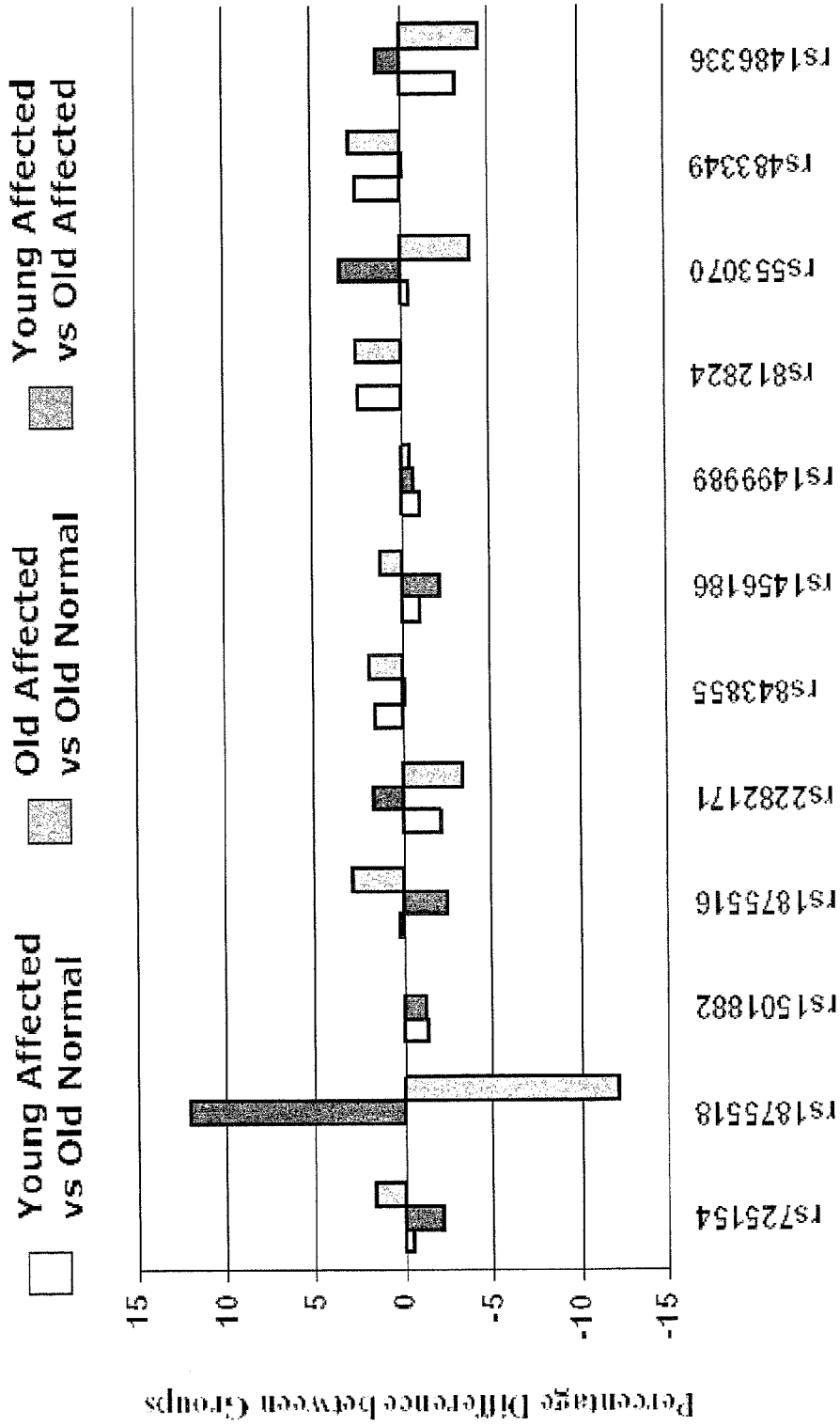
FIG. 2 depicts the screening of 16 SNPs for linkage to the susceptibility for CAD.
Figure 3:
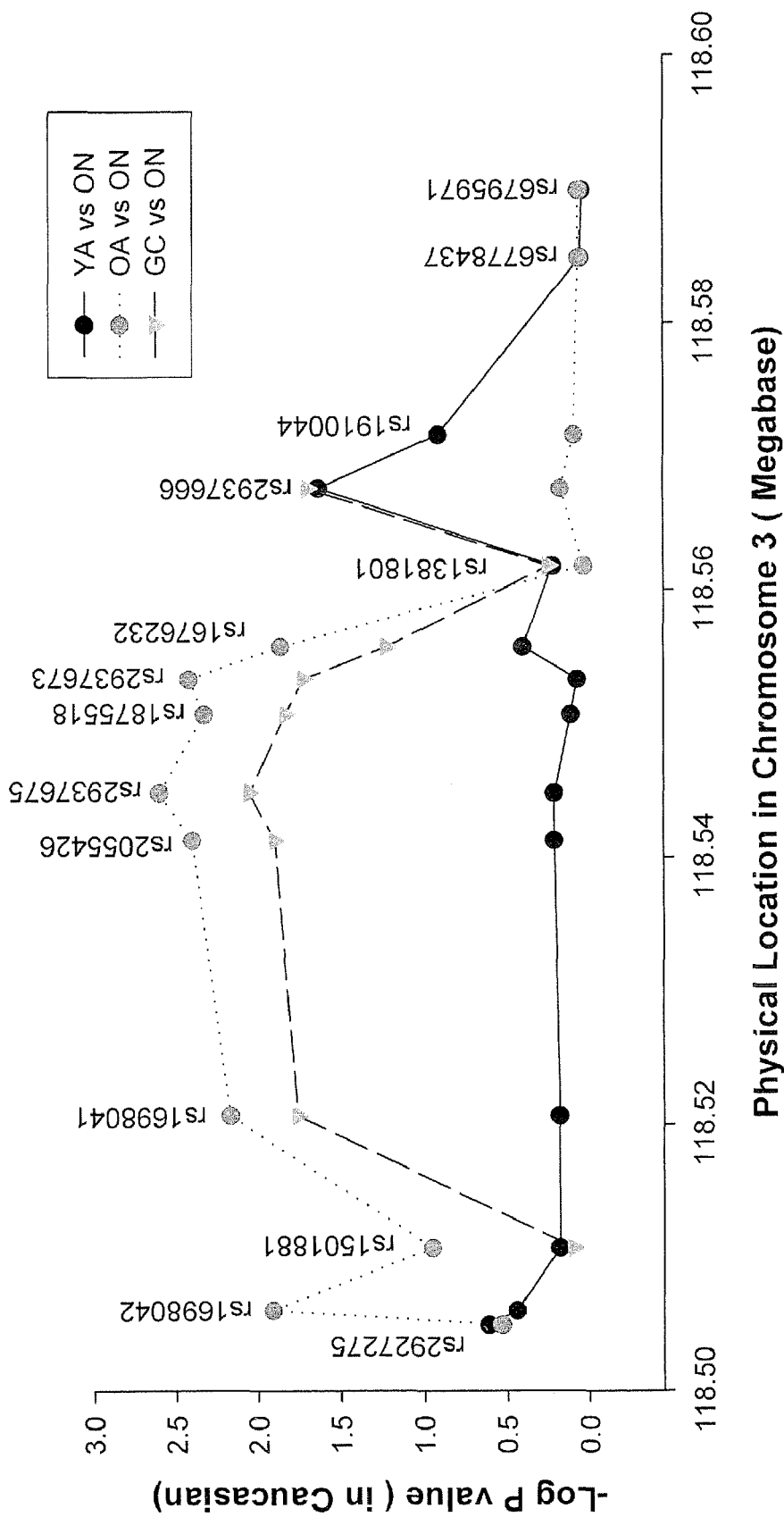
FIG. 3 depicts association analysis of SNPs around rs1875518 with risk for CAD.

Initial screening of 16 SNPs revealed that the frequency of the G allele of rs1875518 (A/G) is significantly higher in OA than ON (OA-ON=12.2%, p=0.001) in Caucasians (FIG. 2), which is confirmed by individual genotyping (OA=57.2%; ON=45.5%). Additional genotyping flanking rs1875518 defined a linkage disequilibrium (LD) block extending ~60 kb that is highly associated with OA in Caucasians. Moreover, evidence supports the association of this block in the GENECARD probands versus Cathgen ON (FIG. 3). Finally, a novel microsatellite marker (3M0238) was identified within the block, which broke the LD and formed a significant risk haplotype (P<0.005) with rs1875518: rs1875518_G-3M0238__253 is twice as prevalent in OA (21.39%) as in ON (11.39%).

Additional markers surrounding this region were genotyped and a further haplotype was obtained that defines the risks and protection, as seen in Tables 2 and 3. Multiple risk haplotypes exist, which could represent different alleles of the actual causal change. Primers and probes used in the analysis are shown in Table 4.

Example 2

Coronary artery disease (CAD) is the leading cause of death in the United States and approximately 8% of CAD occurs in Americans under 50 years of age (AHA website). It is well established that CAD and death from CAD have a hereditary component (Marenberg, Zradkovic). The strong genetic predisposition of CAD may be partially explained by the heritability of disease related intermediate traits such as dyslipidemia. Dyslipidemia is a well-recognized risk factor for CAD, and abnormalities in serum lipids have been shown to have a genetic component (Breslow). Further, there is an increased incidence of familial lipoprotein abnormalities in family members of patients with premature CAD (Genest). Twin and adoption studies suggest that at least 50% of the observed variation in low-density lipoprotein (LDL) cholesterol is genetically determined (Austin, Rice) and segregation analysis has shown evidence for a major gene for high-density lipoprotein (HDL) cholesterol (Mahaney 1995). The Family Heart Study has found evidence for a common major gene accounting for mild elevations of LDL cholesterol (Coon, 1999), although the exact gene has yet to be identified. Familial combined hyperlipidemia (FCH) has been mapped to chromosome 1q (Pajukanta Nat Gen 1998), with subsequent identification of the USF1 gene (Pajukanta 2004). Linkage of HDL cholesterol to chromosomes 5 and 13 has been reported (Peacock 2000), and recently, a pooled analysis of patients with FCH has revealed a susceptibility locus for low HDL on chromosome 16q (Pajukanta 2003).

Many candidate genes have been implicated in the development of coronary heart disease (CHD) and dyslipidemia, but none have been shown to account for even a modest fraction of the burden of CHD in the general population. One reason is that CHD is likely an oligogenic disease with multiple genetic loci conferring susceptibility to the disease, with the phenotype determined by complex gene-gene and gene-environment interactions. One approach to unraveling these complex relationships is to examine intermediate traits. Methods to map genes for complex traits that explicitly take into account the presence of such heterogeneity are likely to have greater power to identify subtle changes. Two such methods for incorporation of covariates into linkage mapping include examination of the extremes of the covariate distribution to find genes that cause gross perturbations (ordered subset analysis (OSA)), or examination of the entire covariate distribution to find genes for trait variability (quantitative trait loci (QTL) analysis).

The Genetics of Early Onset Cardiovascular Disease (GENECARD) linkage study was designed to conduct affected sibling pair (ASP) analysis for the identification of genes contributing to early onset CAD. Linkage studies employ an unbiased, genome-wide approach to identify genetic regions shared in excess between affected relative pairs. This strategy for gene mapping has been widely used and has led to the discovery of many disease susceptibility genes. Strong evidence has been provided for linkage to early onset CAD in GENECARD families to chromosome 3q13 in the overall population (lod 3.50), and in stratified analyses by families presenting with acute coronary syndrome (ACS; lod 3.16) and non-diabetic (NDIA) families (lod 2.42; Hauser 2004). Chromosome 1 q25 was significant in ACS families (lod 2.17); other regions showing evidence for linkage included 5q13, 7p14 and 19p13. Previous studies have also implicated regions on chromosome 3q26-27 in CAD (over 60 cM distal to the peak in the GENECARD analysis) (Francke 2001, Broeckel 2002, Harrap 2002), metabolic syndrome (Kissebah 2000), and type II diabetes mellitus (DM) (Vionett 2000, Mori 2002). There is also evidence of QTL for triglyceride-HDL cholesterol ratio (Shearman 2000), HDL cholesterol (Imperatore 2000, Coon 2001) and fractionated low-density lipoprotein (LDL) particles (Rainwater 1999) in the region of the GENECARD 3q peak. These results suggest potential interactions between CAD genes and intermediate lipid traits.

To incorporate disease-related risk factors, lipid phenotypes in the GENECARD study were examined. Incorporation of lipid phenotypes increases the power to map CAD susceptibility genes; uncovers additional regions of linkage, narrows linkage peaks, and identifies phenotypic subsets for further study. Since it is well known that lipid phenotypes themselves have a high heritability, QTL analysis was performed to identify chromosomal regions linked to variability in lipid values within high-risk CAD families. OSA was also performed using subclassification by lipid phenotypes to reduce etiologic heterogeneity.

Clinical data collection. The GENECARD study enrolled 900 families with early onset CAD to perform an ASP genetic linkage study for identification of genetic variants. The study design has been previously reported. Briefly, families with at least two siblings having early onset CAD were recruited from multiple sites. Individuals were recruited if they met the diagnosis of CAD and if the qualifying event occurred before the age of 51 years for men and 56 years for women. For the diagnosis of CAD, a sentinel event or diagnostic study was required that was verified by primary medical documents. Subjects were required to have myocardial infarction (MI) or unstable angina, significant CAD on coronary angiography, coronary revascularization procedure, or a functional test documenting reversible ischemia with imaging. Medical history was confirmed by inspection of medical records. A system of periodic review was implemented to establish quality control and to ensure consistency among all clinical sites in diagnostic criteria. A genome-wide linkage analysis for early onset CAD was undertaken on the first 420 families enrolled in GENECARD, and these families form the basis for the analyses presented in this study Laboratory methods. Blood samples were obtained by study staff primarily at the medical center or clinic, or by field trip to participants' homes. DNA was extracted using the Puregene system (Gentra Systems, Minneapolis, Minn.). Quality control (QC) samples were incorporated into specified slots in the genotyping lists. Laboratory technicians were blinded to the identity of the QC samples, and to affection status and family composition of all samples. Genotyping was performed using the gel-based FAAST method (Vance and Ben Othmane 1998). Quality control checks were implemented to maximize data quality during genotyping (Hauser 2004). A total of 395 (98.3%) markers out of 402 attempted passed the QC tests and were included in these analyses. The mean genotyping efficiency (proportion of non-zero genotypes) over the 395 markers was 97.6%. Using data from several large studies performed in the Duke Center for Human Genetics, we estimated an error rate in sample processing and allocation in 0.14% and we estimated the genotyping error rate to be approximately 0.8%. Given that GENECARD families were collected from six sites in the US and Europe, it is possible that they represent genetically distinct subpopulations. To test for population substructure Structure (Pritchard 2000) and Arlequin (Arlequin) were employed, using an indicator for each site. There was no evidence from either analysis that the sites could be distinguished on the basis of allele frequencies at the 395 markers in the genome scan. Based on these results, estimated allele frequencies were estimated from the family members in the entire sample (Broman 2001).

Serum lipoprotein measurements were done in the fasting state for 229 of the 420 families (54.5%) using a centralized core laboratory. Levels of plasma total cholesterol (TC) and triglycerides were measured as reported previously (Vega). Briefly, plasma lipids were measured enzymatically using the Boehringer Mannheim cholesterol enzymatic kit (Roche Diagnostics, Indianapolis, Ind.) and the Sigma-Aldrich kit for triglycerides (St. Louis, Mo.). HDL cholesterol was measured after precipitation of non-HDL cholesterol with dextran sulfate (Sigma-Aldrich, St. Louis, Mo.) (Warnick). The coefficients of inter- and intra-assay variation were $\leq 3\%$. The remaining 191 families, consisting mostly of United States participants, had lipoprotein measurements abstracted from the medical records. Adjustment for treatment with medications for dyslipidemia was done when creating the polygenic model used for quantitative trait loci analyses. 27 families were excluded for missing values. Reported results include all 393 families for the lipid parameters of TC, LDL, HDL cholesterol, and HDL/TC ratio, which has been shown to be an independent risk factor for CAD (Jeppesen). Reported results for triglycerides are restricted to the 229 families with measured lipid parameters, since serum triglyceride levels are highly affected by the non-fasting state. There were fewer than 10 families who would potentially meet broad diagnostic criteria for FCH; the family-specific lod scores did not identify specific FCH loci nor did these families appear to contribute an excess amount to the overall CAD genome scan, and therefore these families were included in all further analyses.

Analytic methods. Descriptive analysis for lipid values and for all covariates were performed using SAS software (SAS, Cary N.C.).

Quantitative trait loci (QTL). To identify genetic loci associated with lipid phenotypes, QTL linkage analysis was performed using a genome wide scan of 395 microsatellite markers. All lipoprotein subgroups had an approximately normal distribution, except serum triglycerides, which were log-transformed to approximate a normal distribution. QTL analysis was performed using the variance components approach as implemented in the Sequential Oligogenic Linkage Analysis Routines (SOLAR) software package, which uses maximum likelihood methods to estimate the genetic variance components (Almasy). The SOLAR package utilizes multipoint identical-by-descent (IBD) methods where the proportion of alleles shared IBD at genotyped loci are used to estimate IBD sharing at arbitrary points along a chromosome for each relative pair (Almasy, 1998). IBD and multipoint IBD matrices were constructed using the observed family pedigrees. An initial polygenic model was constructed adjusting for sex, age at exam, and treatment with dyslipidemia medications for each quantitative trait and used as the foundation for two-point and multipoint linkage analyses. Use of dyslipidemia medications was a binary, self-reported variable coded yes/no. A lod adjustment was calculated (lodadj=0.61) and used for analysis of TC because of a high residual kurtosis of 1.6. Although the GENECARD probands were not ascertained on lipid values, the relationship between CAD and lipid values does not reflect normal population values, implying an ascertainment bias. As a result, analyses were done with and without adjustment for proband lipid values and the results did not differ appreciably. Therefore, only results with proband ascertainment are presented. Empirical p-values were calculated using models with 10000 simulations in each of which a fully-informative marker, unlinked to the trait, is simulated and trait linkage is then tested at that marker (SOLAR). QTL mapping results that achieved a multipoint lod score of greater than 1.2 (corresponding to an empirical p-value of 0.007-0.03 depending on the covariate analyzed) were flagged for further study.

Ordered subset analysis (OSA). OSA examines evidence for linkage in a more homogeneous subset of families defined by a trait-related covariate. The average lipid values in the affected individuals from each family were chosen as trait-related covariates. In addition to the family-specific covariate values, a matrix of linkage statistics $Zi(d,\gamma)$ is required as input, where d represents the disease location parameter and $\gamma$ represents the genetic model, and the maximum ordered subset statistic for each family is calculated at a set of values for d and $\gamma$. OSA begins by ordering N number of families by the covariate value xi, both in an ascending and a descending order, where $Z_{(j)}(d,\gamma)$ is the linkage statistic matrix for ordered family j. The maximum lod score is calculated for the $j^{th}$ family, as well as the estimates of $d_{(j)}$ and $\gamma_{(j)}$ at which the maximum occurs. Then, element-wise addition is used to add the matrix for the next ordered family $Z_{(j+1)}(d,\gamma)$ to the matrix for family 1 through j. In summary, the $j^{th}$ partial sum is created by adding each element of the linkage statistic matrix for each family up to and including ordered family j. The maximum subset lod score (the highest lod score using subsets of families with the highest or lowest mean covariate) represents the linkage evidence in a subset of families defined by that covariate. OSA also provides an estimate of the disease location on the specified chromosome. A permutation procedure, randomly ordering families and recalculating the OSA test statistic, provides an empirical p-value to assess the significance of the increase in the maximum lod score using the ordered subset of families compared to the overall lod score using all families. Significance was defined as a p-value <0.05 for an increase in the maximum subset lod when compared to the overall lod score. To further characterize subsets of families with significant results, the family-specific means of each covariate comparing families comprising the maximum subset lod score and the remainder of the GENECARD families. Mean family values for quantitative traits were compared using a univariate t-test (SAS).

Table 5 outlines baseline characteristics in the 420 GENECARD families, overall and by affection status, comprising a total of 1129 individuals, 952 affected with early onset CAD and 177 unaffected family members. Consistent with other studies, there was a high prevalence of cardiovascular risk factors among affected individuals, including hypertension (55.2%), diabetes (21.0%), tobacco use (32.9% currently smoking), dyslipidemia (82.3%) and metabolic syndrome (46.8%). As expected, these risk factors were more prevalent in affected individuals than in unaffected individuals. However, the mean values of total cholesterol, LDL and systolic blood pressure were higher in the unaffected group, consistent with the 14-year increase in the mean age of the unaffected family members and increased use of medications for dyslipidemia in the affected group. Heritability estimates revealed strong heritability of all lipid subgroups (Table 6), consistent with previous reports.

Figure 4:
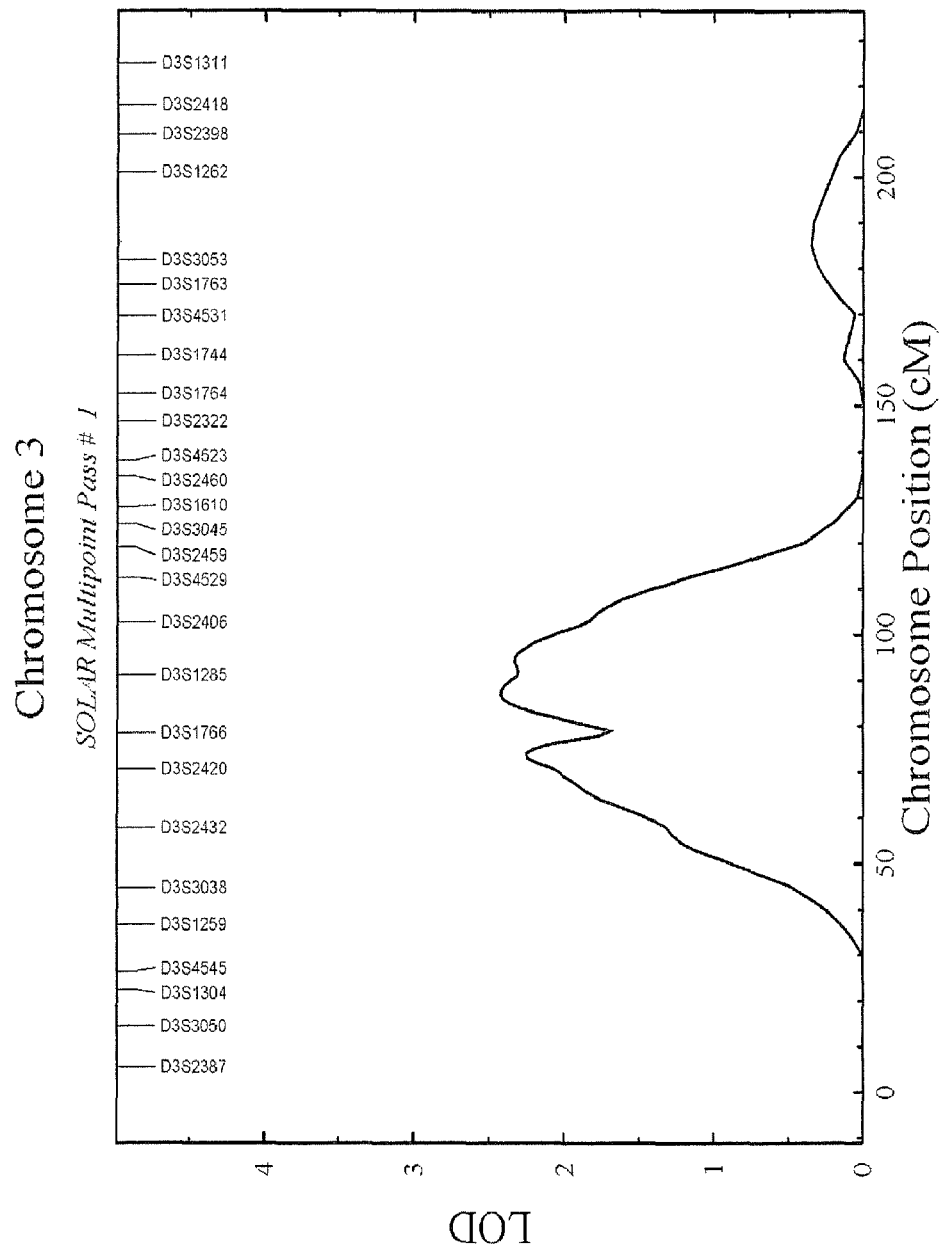
FIG. 4 depicts the quantitative trait loci (QTL) map for HDL cholesterol on chromosome 3.

QTL results. The overall results of the QTL analysis are shown in Table 6. The largest lod score for a QTL was for HDL cholesterol on chromosome 3p (FIG. 4), with weaker evidence on chromosomes 7 and 15. QTLs for TC were found on chromosome 18p and 5p, and for LDL cholesterol on chromosomes 6 and 16. There was evidence for QTL for triglycerides on chromosome 13, 14, and 18, and there was evidence for loci for HDL/TC ratio on chromosome 3q, 7q and 8q. Three regions showing evidence for linkage in the overall genome scan (3q, 7p and 19p) also showed evidence for lipid QTLs (HDL/TC ratio, triglycerides and LDL cholesterol, respectively).

OSA results. Significant OSA results are shown in Table 7. FIG. 5 shows chromosome 3 lod score curves using OSA that corroborate, strengthen and narrow the linkage peaks previously observed on chromosome 3q. The increase in the lod score is intriguing because it occurs on top of already strong linkage evidence in this region. The 167 families in the OSA subset represent 39.7% of the GENECARD families. These families appear to have a different phenotypic profile with significantly fewer CAD risk factors than the remainder of the families (Table 8). FIG. 5 also shows a lod score curve using OSA showing a strong linkage peak on chromosome 5q, but more distal to the linkage peak observed on the overall genome scan. This set of 54 (12.8%) families represents a high-risk lipid phenotype with elevated TC, high LDL and triglycerides and having a significantly lower average age of onset. However, these families cannot be distinguished on the basis of other CAD risk factors such as BMI, gender, or smoking. The chromosome 5 subset of families is a distinct set of CAD families from the chromosome 3 subset, with the two subsets of families representing the two tails of the lipid distributions among these CAD families. OSA also revealed significant LOD scores in subsets of families on chromosomal regions not previously found to be significant in this sample, including peaks on 9p, 10q, 12q, 14p, 17q, and 22p. The subsets identified in these regions are smaller, ranging from 22 to 80 families (5.2% to 19.0%).

These results reveal evidence for several QTL for lipid subgroups in families with early onset CAD. OSA results corroborated and strengthened areas of strong linkage in the overall population on chromosome 3q and 5q, helped narrow the linkage peaks, identified new regions for further analysis, and defined phenotypic subsets comprising the peaks.

Specifically, QTL mapping of lipid phenotypes in the GENECARD population revealed multiple chromosomal areas with significant lod scores for lipid subtypes, with the strongest lod score for HDL cholesterol on chromosome 3p (lod 2.43). Evidence was also found for linkage for HDL cholesterol to chromosome 7q (156 cM), a region also found to link to HDL/TC ratio (143 cM). This area has previously been linked to TG and TG/HDL ratio (Shearman 2000), and is proximal to another reported peak for TG (186 cM) (Duggirala). This locus contains several candidate genes, including ABC28 (ATP-binding cassette subfamily F, member 2, similar to ABC1 which causes Tangier's disease, characterized by HDL deficiency and premature atherosclerosis). A QTL for LDL cholesterol was identified on chromosome 6q, which contains the gene for apolipoprotein (a) (Lp(a)), a well recognized cardiovascular risk factor (Murai), and has previously been linked to small LDL particles in the San Antonio Family Heart Study (Imperatore). There was evidence for linkage to triglycerides on chromosome 18 (near QTL for total cholesterol at 55 cM); though not as strongly linked, this region is interesting because it contains the gene for Niemann-Pick disease type C1 (NPC1), an autosomal recessive lipid storage disorder. These results did not corroborate previous results on chromosomes 4 (TG, LDL) (Arnett 2001), 15 (HDL, TG) (Almasy, Duggirala, Arnett), and 2 (TG HDL) (Pajukanata, Imperatore, Almasy).

To understand the impact of heterogeneity, it is useful to compare these results to the OSA analysis. At least two phenotypically distinct sets of families with early-onset CAD were identified that contributed to linkage evidence. On chromosome 3q, evidence was found for linkage to early onset CAD in families with lower TC and triglycerides, higher HDL cholesterol and overall lesser prevalence of metabolic syndrome, when compared to families not included in the OSA peak. These results were corroborated by the finding of a QTL for HDL/TC ratio in the same region. Therefore, it appears that the previously reported strong linkage peak on chromosome 3q is comprised of families without a preponderance of traditional cardiovascular risk factors. A recent meta-analysis of four genome-wide scans for CAD revealed strongest evidence for linkage on chromosome 3q26-27 (Chiodini), and this region has shown linkage to metabolic syndrome (Kissebah 2000) and type II diabetes mellitus (Vionett 2000, Mori 2002, Hegele 1999). However, in each of these genome scans the evidence for linkage to CAD is over 60 cM distal to the peak in the GENECARD analyses. In QTL analysis of plasma lipids, there is evidence of linkage with triglyceride-high density lipoprotein (HDL) cholesterol ratio in the peak 3q13 region (Shearman et al. 2000). There is also evidence for linkage to HDL cholesterol itself (Imperatore et al. 2000; Coon et al. 2001) and fractionated low-density lipoprotein (LDL) particles (Rainwater et al. 1999) in this region. A genome scan of lipid traits in Pima Indians found a locus on chromosome 3, but more distal to this peak (182 cM) (Imperatore 2000). The 3q26-qter region harbors several candidate genes involved in glucose homeostasis and lipid metabolism. The 3q13 region, however, is an area of relative paucity of genes. This area may harbor a previously undiscovered gene, represent a genetic area exerting a downstream influence, or may be in linkage disequilibrium with more distal candidate genes.

A linkage peak for early onset CAD was again observed on chromosome 5q using OSA, but more distal on the chromosome than seen in the overall genome scan, and is comprised of a subset of families who are younger with higher total cholesterol values. This area contains many genes, including HNRPAB (apolipoprotein B mRNA-editing enzyme) and F12 (factor XII deficiency), though none have been previously implicated in the pathogenesis of dyslipidemia or CAD.

OSA and QTL mapping are alternate methods for incorporating phenotypic data in linkage studies. Overall it was found that OSA and QTL results did not overlap, except on chromosome 3q. This is most likely related to the fact that QTL and OSA analyses model different aspects of lipid phenotypes and address different issues. The lod score for the OSA analysis is still linkage to CAD and the phenotype data are used as a measure of similarity to help identify homogeneous subsets. QTL mapping models the quantitative traits of lipid phenotypes specifically, in attempts to identify chromosomal regions that may harbor genes for normal variation in lipid phenotypes. OSA was used to identify and narrow chromosomal regions harboring candidate genes for the phenotype of early onset CAD, using lipid subtypes to create more etiologic homogeneity and potentially concentrate the genetic effect.

The study population consists of those who remain alive despite early onset CAD, a so-called "survivor effect." Therefore, inferences drawn about genetic effects will be confined to familial early onset CAD, and may not be applicable to premature sudden cardiac death. Because the GENECARD families were ascertained on the basis of early onset CAD, their lipid values may not represent the normal distribution of lipid values. The phenotypic differences in the GENECARD sample compared to samples of unselected families, or families ascertained on the basis of hypertension or metabolic syndrome, may explain why QTL analysis did not identify the regions identified in other studies. Although genome-wide linkage studies may be superior in determining significant genetic loci, affected sibling pair studies only provide a general view of the true gene location. The permutation test employed by OSA analyses controls for the inflation in the false positive rate induced by examining multiple family subsets for a given covariate, and appears to give the proper type I error rate in previously done simulations (Hauser). However, these analyses do not control for OSA over multiple trait-related covariates, but the strong correlation between the lipid parameters makes it difficult to appropriately correct for multiple comparisons.

Regardless, the GENECARD cohort is an ideal population for genetic studies. Setting an age criteria for CAD selects for patients with a strong genetic predisposition and enriches the sample for CAD caused by genetic etiologies. It is also an ideal population for primary prevention, an eventual goal of the utilization of genetics in clinical cardiology. Furthermore, GENECARD represents a model database for evaluation of genotype-phenotype interactions in the pathogenesis of CAD, by virtue of its sibling pair approach; international population allowing for ethnic heterogeneity; relatively large sample size; and genome-wide methodology. The combined approach of using QTL and OSA analysis for incorporation of disease-related lipid phenotypes in a genome scan of CAD is unique. Such modeling of genotype-phenotype interactions in a multi-analytic approach will enhance discovery of genetic loci and aid in the eventual goal in creation of a comprehensive cardiovascular risk assessment model.

These results show strong evidence of linkage to chromosomal region 3q13 in families with early onset CAD but with more favorable lipid profiles, possibly due to a concentrated non-lipid-related genetic effect on CAD, and to chromosome 5q in families with early onset CAD but with higher total and LDL cholesterol values, possibly representing a hereditary lipid phenotype predisposing to early onset CAD. QTL mapping identified multiple loci for lipid phenotypes and overall corroborated results from the initial genome scan. These results suggest presence of etiologic heterogeneity in families with early onset CAD, potentially due to differential lipid phenotypes.

Example 3

Sequences of exemplary polymorphisms within the region of human chromosome 3q13.31 are depicted in Table 10. Of particular note are: the single nucleotide polymorphism as set forth by an adenine deletion in SEQ ID NO:15; the polymorphism as set forth by a 27 basepair duplication in SEQ ID NO:28; and the polymorphism as set forth by a CM insertion in SEQ ID NO:29. FIG. 6 depicts the genotypes of normal versus affected individuals with respect to these three variations.

Figure 7:
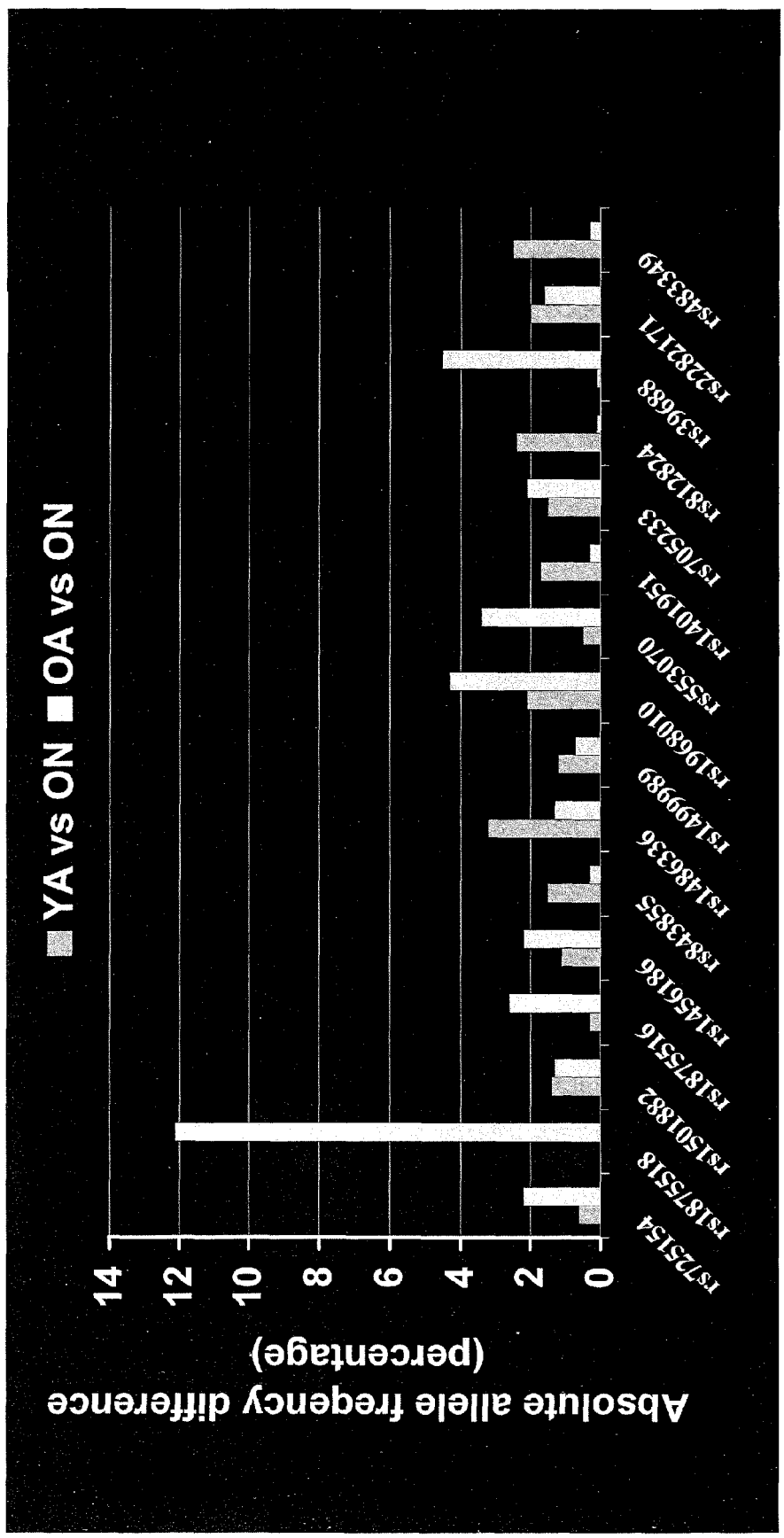
FIG. 7 depicts differences in allele frequency between affected versus control (normal) cases with exemplary SNPs within the region of human chromosome 3q13.31.

FIG. 7 depicts differences in allele frequency between affected versus control (normal) cases with exemplary SNPs within the region of human chromosome 3q13.31.

Figure 8:
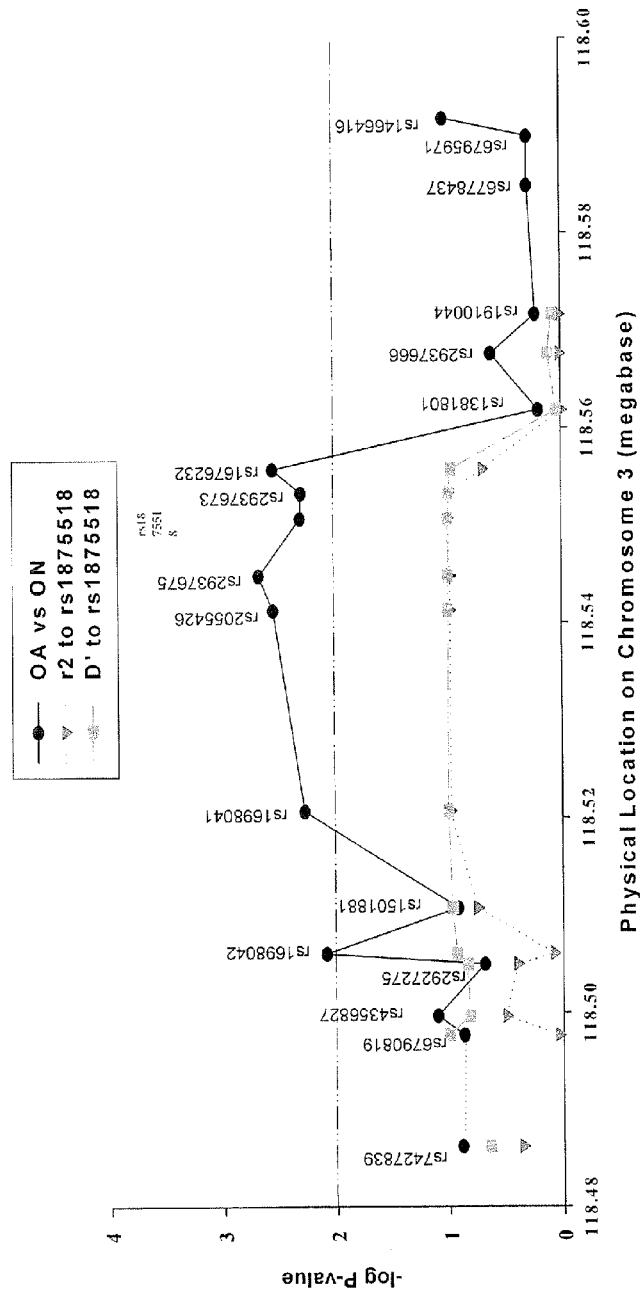
FIG. 8 depicts the frequency of genetic markers within the region of human chromosome 3q13.31 correlated with affected and control (normal cases) and the significance of the correlation of the G allele of rs1875518 and the 253 allele of 3M0238 with CAD.

FIG. 8 depicts the frequency of genetic markers within the region of human chromosome 3q13.31 correlated with affected and control (normal cases) and the significance of the correlation of the G allele of rs1875518 and the 253 allele of 3M0238 with CAD.

Example 4

Figure 9:
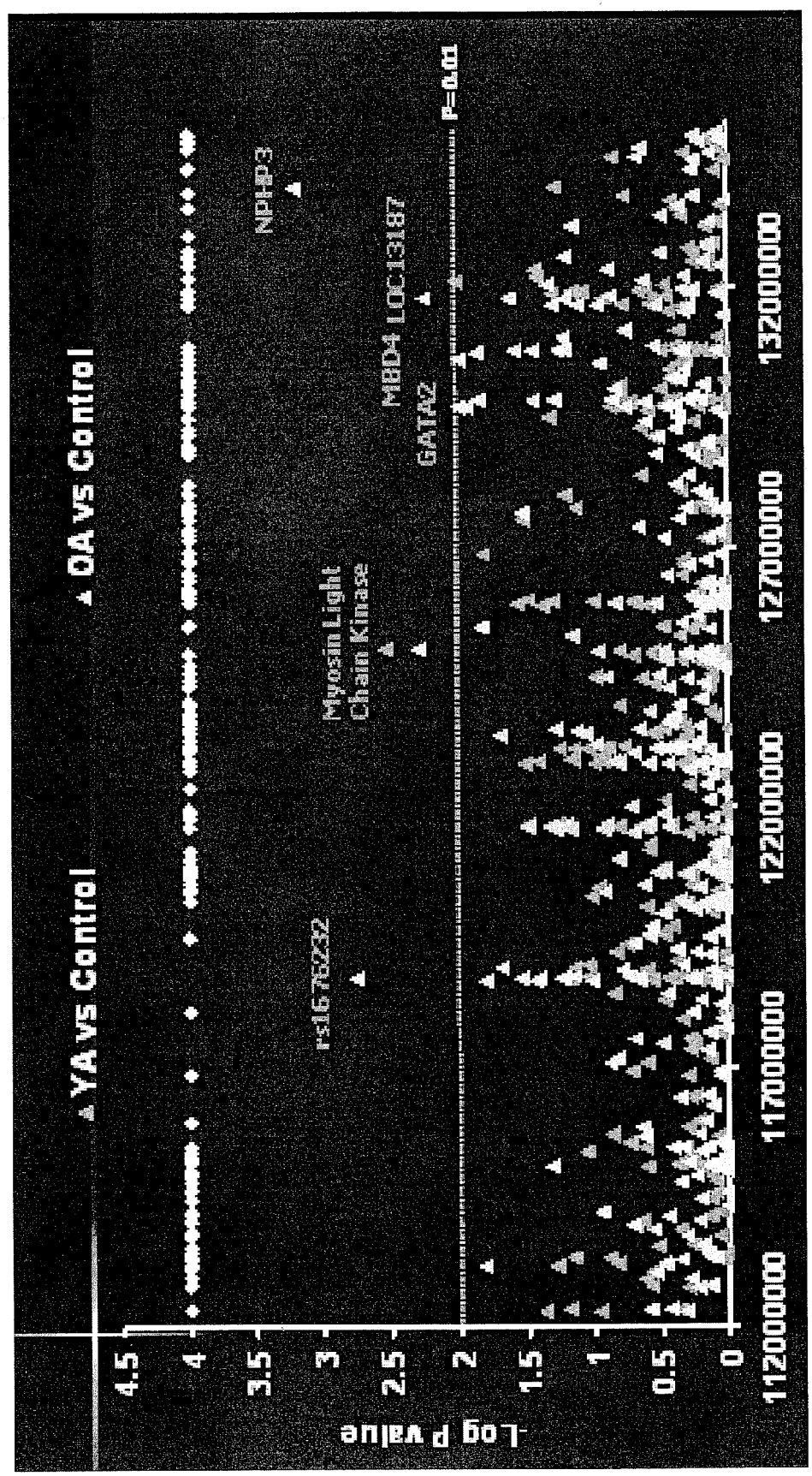
FIG. 9 depicts additional SNPs associated with the risk for CAD on chromosome 3.

Association analysis of additional SNPs with risk for CAD is depicted in FIG. 9. Of particular note are the SNPs rs2272486 and hcv1602689 in Huntington-associated protein-interacting protein (HAPIP) and myosin light chain kinase (MLCK), respectively. The locations of these SNPs on human chromosome 3 are listed in Table 11. Particularly, the C allele for hcv1602689 (SNP is C/G) and/or the A allele for rs2272486 (SNP is A/G) is associated with increased risk for CAD.

Additional SNPs associated with risk for CAD are the A alleles for rs1676232 and rs4404477 found in the gene for the limbic system-associated membrane protein (LSAMP; both SNPs are A/G). Furthermore, rs4404477 appears to have an interaction with rs1676232 so that when both SNPs are homozygous for the A allele, the risk for CAD is significantly increased over that which is observed for a single SNP that is homozygous for the A allele.

Example 5

Initial and Validation Datasets: Subjects in the initial and validation datasets were ascertained through the cardiac catheterization laboratories at Duke University Hospital and have been previously described (CATHGEN) (Wang et al. 2007). All subjects undergoing catheterization were offered participation in the study. To reduce confounding by population substructure, only Caucasians were used for the association analyses. Subjects were chronologically divided into sequential initial and validation datasets. The initial dataset included old affecteds, left main cases, and controls. The validation dataset included left main cases and controls. Briefly, the old affected has age-at-onset $\geq 51$ in male and $\geq 56$ in female and CAD index (Table 16), a numerical summary of angiographic data, greater than 72. Subjects with 75% or greater stenosis in the left main coronary artery were defined as left main cases regardless of age-at-onset. Controls were >60 years old at the time of angiography, and had no diseased vessels, history of myocardial infarction (MI) or interventional cardiac procedures. The major indications for cardiac catheterization for controls were possible ischemic heart disease (66%), valvular heart disease (8%), congenital heart disease (<1%), and "other" (25%, including evaluation for fatigue, pre-operative clearance, and asymptomatic decreased ejection fraction).

Third Control Dataset: Additional control subjects were recruited from community meetings and unrelated family members (e.g., spouses) of Alzheimer patients in an ongoing study of Alzheimer Disease (Margaret A. Pericak-Vance, P. I.). All members were self-reported Caucasians >60 years old, and had no history of MI, diabetes, stroke, or peripheral vascular disease based on a detailed questionnaire for medical history. Their mental status was normal as evaluated by the Modified Mini-Mental Status exam (Teng & Chui 1987). Unlike the CATHGEN controls, no angiographic data were available for a definite phenotypic classification for this dataset. It is possible that some subjects have subclinical undiagnosed CAD. However, this dataset matched the phenotypic definition of controls in most of other genetic epidemiologic studies on CAD and provided an independent set of controls to validate associations in the CATHGEN subjects.

GENECARD Dataset: The sample collection and study design of the GENECARD study have been reported (Hauser et al. 2004). The family-based GENECARD dataset was composed of families with at least two affected siblings who met the criteria for early-onset CAD. The majority (>90%) of the GENECARD subjects were Caucasians. Unlike the CATHGEN samples, angiographic data in GENECARD samples was not available and left main CAD status was not determined.

The Duke Institutional Review Board approved all studies, and all subjects signed informed consent.

SNP Selection, Genotyping, and Sequencing Non-redundant SNPs ($r^2 < 0.7$) were chosen across the LSAMP gene using the software program SNPSelector (Xu et al. 2005). SNPgenotyping and sequencing were performed using reagents and instruments from Applied Biosystems (Foster City, Calif.). SNP genotyping was performed using the TaqMan® Allelic Discrimination assay in 384-well format, and quality control was implemented as described previously (Connelly et al. 2006). Duplicated quality-control samples were placed within and across plates to identify potential sample-plating error and genotype-calling inconsistency. Hardy-Weinberg equilibrium (HWE) testing was performed for all markers. SNPs with mismatches on quality-control samples or failed HWE test (p<0.05) in white controls were reviewed by an independent genotyping supervisor for potential genotyping errors. All examined SNPs had a calling rate >95% in the studied population. On the basis of 26,000 duplicate genotypes, genotyping error-rate estimates for SNPs meeting the quality-control benchmarks were <0.2%. Direct PCR sequencing was performed using the Big Dye 3.1 and ABI 3730 automated sequencer. Sequences derived from nine patients with CAD and seven controls were assembled using Sequencher 4.7 (Gene Codes, Ann Arbor, Mich., United States) to discover novel polymorphisms.

Stepwise Validations To minimize false positive findings attendant to the multiple SNPs tested, we applied stepwise validations in the SNP association study. First, all SNPs were screened in the initial dataset. Then, promising SNPs (p<0.1) were further analyzed in the validation dataset. Joint analysis using the combined initial and validation dataset were performed to maximize the statistical power. Significant SNPs derived from this analysis were further examined in the third control dataset and the family-based GENECARD dataset. Finally, we performed pairwise haplotype analysis in our largest case-control dataset consisting of the initial, validation, and the third control datasets.

Gene Expression Analysis Human aortic endothelial cells and smooth muscle cells (SMCs) were purchased from Cambrex Bio Science, Inc. (Walkersville, Md.), and cultured following the manufacturer's instructions. Human aortas were collected from heart transplant donors and graded for atherosclerosis as previously described (Seo et al. 2004). Total RNAs were extracted from cells or aortas and were used to synthesize first strand cDNA using Advantage™ RT-for-PCR Kit (BD Biosciences, Palo Alto, Calif.). Gene expression was measured by TaqMan® real-time, reverse-transcriptase PCR (RT-PCR) in triplicate and normalized to glyceraldehyde-3-phosphate dehydrogenase (GAPDH) expression.

RNA Interference Small interfering RNA (siRNA) specific for LSAMP and a negative control siRNA targeting no known gene were purchased from Silencers Pre-designed siRNAs (Ambion/Applied Biosystems). SMCs were plated at a density of $1.3 \times 10^4$ cells/cm$^2$ two days before transfection. Cells were then transfected with LSAMP or negative control siRNA (25 nmol/L) using the Lipofectamine™ RNAiMax transfection reagent (Invitrogen), following the manufacturer's instructions. Twenty-four hours after siRNA transfection, SMCs were made quiescent for 72 hours with serum-free SmGM-2 medium, and then subjected to thymidine incorporation, quantitative RT-PCR, or immunoblotting of SMC membrane fractions, as described (Zhang et al. 2007) with anti-LSAMP IgG (the kind gift of Dr. A. F. Pimenta) (Levitt 1984).

Thymidine Incorporation Quiescent SMCs were then challenged with SmGM-2 containing 5% fetal bovine serum for 20 hours before [$^3$H]thymidine was added to the medium (1 μCi/ml). Incorporation of thymidine into SMC DNA was determined as we reported previously (Peppel et al. 2000).

Statistical Analysis The association between CAD and SNPs was examined using multivariable logistic regression analyses that adjusted for (a) gender (the "basic model") or (b) gender, age-at-exam, hypertension, diabetes mellitus, body mass index, dyslipidemia, and smoking history (the "full" model). The genotype case-control statistic provided by SAS 9.0 was used to perform the association analysis, which tests both dominance genotypic effects and additive allelic effects. The Association in the Presence of Linkage (APL) (Martin et al. 2003b) test, Pedigree Disequilibrium Test (PDT) (Martin et al. 2003b) and GenoPDT (Martin et al. 2003a) were used to evaluate family-based association in the GENECARD samples. Each of the three analytic approaches offers distinct merits. The APL test takes into account for linkage and correctly infers missing parental genotypes in regions of linage by estimating identity-by-descent parameters. The PDT allows incorporation of extended pedigrees. Both APL and PDT are allele-based tests while GenoPDT examine the association between genotypes and disease status. The Graphical Overview of Linkage Disequilibrium (GOLD) program was used to assess linkage disequilibrium (LD) between SNPs (Abecasis & Cookson 2000). Haplotype association was performed using HaploStats 1.1.0 (Mayo Clinic, Rochester, Minn.).

To increase statistical power, we analyzed all the available aorta samples for the haplotype-specific gene expression. In some cases, two pieces of sample from the same aorta were assayed for gene expression. Therefore, a random effect was used for each aorta along with fixed effects for atherosclerosis burden and haplotype in a mixed model for the haplotype-specific gene expression analysis. An F-test was used to test for differences in gene expression for the atherosclerosis and haplotype. For the SMC proliferation assay, two-way ANOVA was performed. SAS 9.0 (SAS, Cary, N.C.) was used for statistical analyses.

Datasets for Association Studies The initial dataset included 168 old affecteds, 102 left main cases, and 149 controls. The validation dataset included an additional 141 left main cases and 215 controls. The third control dataset comprised 255 individuals. Baseline clinical characteristics for each dataset are given in Table 12. In general, the case groups had a higher prevalence of clinical CAD risk factors than the controls. The GENECARD samples have been described elsewhere (Hauser et al. 2004; Connelly et al. 2006). In brief, this dataset consisted of 2954 individuals, among which were 966 affected sibling pairs and 825 discordant sibling pairs.

Selected SNPs for Screening LSAMP It was recently reported that the mouse lsamp gene has an alternative first exon 1a located 1.5 megabases from the originally described first exon (now exon 1b) (Pimenta & Levitt 2004). Using RT-PCR, we confirmed the existence of these LSAMP alternative transcripts generated by exon 1a (LSAMP_1a) and exon 1b (LSAMP_1b) in several human tissues, including aorta. Ninety tagSNPs across both LSAMP transcripts were examined in the initial analysis (Table 17).

Association Tests in the Initial Dataset To test our hypothesis that association in LSAMP was driven by severe CAD as represented by left main cases, subset analysis in the old affected and the left main cases was performed in the initial dataset. Despite the smaller sample size of the left main CAD subgroup, this analysis revealed stronger SNP associations in the left main cases than in the old affecteds, supporting our hypothesis that left main CAD was the major phenotype underlying the association at LSAMP.

The strongest association was found at rs1875518 (p=0.008, OR=1.7, Table 17). Additional genotyping surrounding rs1875518 and linkage disequilibrium analysis found that LD surrounding rs1875518 extends over 40 kb, from rs1501885 to rs2937673. Therefore, novel SNPs were sought to partition this LD block by resequencing this 40 kb region. Two novel SNPs (ss70458781 and ss70458782) and one novel 27 bp duplication (ss70458783) were identified through this effort. However, only ss70458782 was not highly correlated with rs1875518 ($r^2$=0.27). As a single marker, ss70458782 was marginally associated with left main CAD (p=0.091) (Table 17).

Validation of the Association in Multiple Additional Datasets To validate the left main CAD-associated LSAMP SNPs identified in the initial analysis, we tested the promising SNPs (p<0.1 in the initial dataset) in an independent validation dataset of left main CAD cases and controls ascertained by the same criteria as the initial dataset. Odds ratio (OR) estimates were compared between the initial and validation datasets to identify consistent trends of association. Since analyzing genetic markers in large datasets may be more effective in identifying true-positive associations for complex traits than replicating analyses in two smaller datasets (Shephard et al. 2005), joint analysis of both the initial and validation datasets was also performed. Among the ten SNPs tested in the validation dataset, five SNPs were designated as "significant SNPs," as they displayed the same risk allele in both the initial and validation datasets and met the significant level of 0.05 in the joint analysis adjusting for gender (p=0.005 to 0.028, Table 13). In the full model analysis, which includes additional CAD risk factors as covariates, three of the five SNPs remained significant (p=0.021 to 0.044, listed in Table 13).

To avoid potential ascertainment bias with control subjects identified through the cardiac catheterization laboratory, and to provide an independent control dataset, we then studied the five significant LSAMP SNPs by analyzing the independent third control dataset along with the combined left main CAD cases from the initial and validation datasets. This analysis demonstrated significant association of rs4404477 with left main CAD (p=0.006) (Table 14). To maximize the statistical power and the precision of OR estimate, we then compared the combined left main CAD cases with all control subjects from the initial, validation, and third control datasets. This analysis found that four LSAMP SNPs were significantly associated with left main CAD, with rs4404477 being the most significant (p=0.003, OR=1.7) (Table 14). Finally, we evaluated association of the five significant SNP in the family-based GENECARD samples. Both SNP rs1676232 (p=0.020, 0.087 and 0.285, evaluated by APL, PDT, and GenoPDT, respectively) and rs4404477 (p=0.091, 0.011 and 0.044, evaluated by APL, PDT, and GenoPDT, respectively) displayed evidence for association in the GENECARD dataset.

The LSAMP Risk Haplotype Associates Strongly with Left Main CAD Haplotype analysis using more than one SNP at a time can greatly increase information generated through each SNP genotype by itself. Hence, we performed pairwise haplotype analyses using the five significant SNPs in our largest case-control dataset (comprising the initial and validation datasets, as well as the third control dataset). This analysis found that the ss70458782A_rs4404477A haplotype (HAP L) was highly significantly associated with left main CAD (p=0.00004, Table 15), and accounted for 35% of the risk for left main CAD, as estimated by the population attributable risk in our largest dataset (95% CI: 13 to 52%). In addition, HAP L demonstrated significant association with left main CAD in all independent subsets that composed the largest datasets (p=0.0001 to 0.021, Table 15).

The Reduced LSAMP Expression in Human Aortas: Association with Increased Atherosclerosis and Dosage of Risk Haplotype Since LSAMP has been shown to function as a tumor suppressor gene (Chen et al. 2003), we reasoned that diminished expression or function of LSAMP could promote atherogenesis by potentiating smooth muscle cells (SMC) and/or macrophage proliferation in atherosclerotic plaques (Hansson 2005). Alternatively, enhanced LSAMP expression or function could diminish endothelial cell proliferation, and thereby promote atherosclerosis (Hansson 2005). To begin testing these possibilities, we first examined LSAMP expression in cultured human aortic endothelial cells and SMCs. We found that neither LSAMP_1a nor LSAMP_1b was expressed in the endothelial cells, while both LSAMP isoforms were expressed in the SMCs. Thus, we inferred that the genetic risk conferred by the LSAMP SNPs was most likely playing out through LSAMP's potentially pro-atherogenic role in SMCs, and not endothelial cells.

Within the aortic SMCs, LSAMP_1a was the more abundant transcript. Interestingly, all the significant SNPs and haplotype also reside in the intron 1 of the LSAMP_1a. To determine whether LSAMP expression in arterial tissue correlates with human atherosclerosis, we measured LSAMP_1a mRNA in 28 human thoracic aortas with varying amounts of atherosclerosis (Seo et al. 2004). Quantitative RT-PCR revealed that aortas with severe atherosclerosis (N=7) contained 2.7-fold less LSAMP_1a transcript than those with mild or no atherosclerosis (N=21) (p=0.0001). As the haplotype HAP L is strongly associated with risk for CAD, we examined whether the decreased expression of LSAMP_1a mRNA was correlated with the presence of this risk haplotype. Indeed, we found that LSAMP_1a mRNA levels correlated inversely not only with the extent of aortic atherosclerosis, but also with the "dosage" of HAP L; i.e., mRNA levels for LSAMP_1a were twice as low in aortas with two copies (N=17) of the risk haplotype HAP L as they were in aortas with zero or one copy (N=11) of HAP L (p=0.0002), thus tying the risk genotype directly with the LSAMP atherosclerotic expression changes.

Down-regulation of LSAMP Promotes SMC Proliferation Data from our human aortas displayed ~2-3-fold LSAMP_1a down-regulation with atherogenesis. To test directly whether LSAMP down-regulation could promote SMC proliferation and thereby conceivably aggravate atherogenesis (Boucher et al. 2003), we used siRNA to achieve a 2-3 fold knockdown of total LSAMP expression in human aortic SMCs. In response to serum, SMCs with reduced LSAMP expression demonstrated a 2-fold increase in cell proliferation as measured by thymidine incorporation. Thus, the magnitude of LSAMP down-regulation observed in aortas from subjects with two copies of LSAMP HAP L might indeed be expected to potentiate atherogenic SMC proliferation.

The foregoing is illustrative of the present invention, and is not to be construed as limiting thereof. The invention is defined by the following claims, with equivalents of the claims to be included therein.

All publications, patent applications, patents, patent publications, sequences identified by Genbank and/or SNP accession numbers, NCBI Build 35 of human chromosome 3 and other references cited herein are incorporated by reference in their entireties for the teachings relevant to the sentence and/or paragraph in which the reference is presented.

REFERENCES

Hauser et al. "A genomewide scan for early-onset coronary artery disease in 438 families: the GENECARD study" Am. J Hum. Genet. 75:436-447 (2004)

Marenberg M, Risch N, Berkman L F, Floderus B, de Faire U. Genetic susceptibility to death from coronary heart disease in a study of twins. New Engl J Med 1994; 330:1041-46.

Zdravkovic S, Wienke A, Pedersen N L, Marenberg M E, Yashin A I, de Faire U. Heritability of death from coronary heart disease: a 36-year follow-up of 20 966 Swedish twins. J Int Med 2002; 252:247-254.

Sorensen T I, Nielsen G G, Anderson P K, Teasdale T W. Genetic and environmental influences on premature death in adult adoptees. New Engl J Med 1988; 318:727-32.

Shearman A M. Ordovas J M. Cupples L A. Schaefer E J. Harmon M D. Shao Y. Keen J D. DeStefano A L. Joost O. Wilson P W. Housman D E. Myers R H. Evidence for a gene influencing the TG/HDL-C ratio on chromosome 7q32.3-qter: a genome-wide scan in the Framingham study. Hum Mol Genet. 9(9):1315-20, 2000 May 22.

Mahaney M C, Blangero J, Rainwater D L, Comuzzie A G, VandeBerg J L, Stern M P, MacCluer J W, Hixson J E. A major locus influencing plasma high-density lipoprotein cholesterol levels in the San Antonio Family Heart Study: segregation and linkage analyses. Arterioscler Thromb Vasc Biol 1995; 15:1730-1739.

Peacock J M, Arnett D K, Atwood L D, Myers R H, Coon H, Rich S S, Province M A, Heiss G. Genome scan for quantitative trait loci linked to high-density lipoprotein cholesterol: the NHLBI Family Heart Study. Arterioscler Thromb Vasc Biol 2001; 21:1823-1828.

Imperatore G, Knowler W C, Pettitt D J, Kobes S, Fuller J H, Bennett P H, Hanson R L. A locus influencing total serum cholesterol on chromosome 19p: results from an autosomal genomic scan of serum lipid concentrations in Pima Indians. Arterioscler Thromb Vasc Biol 2000; 12:2651-2656.

Duggirala R, Blangero J, Almasy L, Dyer T D, Williams K L, Leach R J, O'Connell P, Stern M. A major susceptibility locus influencing plasma triglyceride concentration is located on chromosome 15q in Mexican Americans. Am J Hum Genet 2000; 66:1237-1245.

Almasy L, Hixson J E, Rainwater D L, Cole S, Williams J T, Mahaney M C, VandeBerg J L, Stern M P, MacCluer J W, Blangero J. Human pedigree-based quantitative-trait-locus mapping: localization of two genes influencing HDL-cholesterol metabolism. Am J Hum Genet 1999; 64:1686-1693.

Pajukanata P, Terwilliger D, Perola M, Hiekkalinna T, Nuotio I, Ellonen P, Parkkonen M, Hartiala J, Ylitalo K, Pihlajamaki J, et al. Genomewide scan for familial combined hyperlipidemia genes in Finnish families, suggesting multiple susceptibility loci influencing triglyceride, cholesterol, and apolipoprotein B levels. Am J Hum Genet 1999; 64:1453-1463.

Arnett 2001

J. J. Genest, Jr, S. S. Martin-Munley, J. R. McNamara et al., Familial lipoprotein disorders in patients with premature coronary heart disease. Circulation 85 (1992), pp. 2025-2033.

Pajukanta P. Allayee H. Krass K L. Kuraishy A. Soro A. Lilja H E. Mar R. Taskinen M R. Nuotio I. Laakso M. Rotter J I. de Bruin T W. Cantor R M. Lusis A J. Peltonen L. Combined analysis of genome scans of dutch and finnish families reveals a susceptibility locus for high-density lipoprotein cholesterol on chromosome 16q. [Journal Article] *American Journal of Human Genetics.* 72(4):903-17, 2003 Apr.

Pajukanta P. Nuotio I. Terwilliger J D. Porkka K V. Ylitalo K. Pihlajamaki J. Suomalainen A J. Syvanen A C. Lehtimaki T. Viikari J S. Laakso M. Taskinen M R. Ehnholm C. Peltonen L. Linkage of familial combined hyperlipidaemia to chromosome 1q21-q23. Nat Genet 1998; 18:369-373.

Pritchard J K, Stephens M, Rosenberg N A, et al. Association mapping in structured populations. Am J Hum Genet 2000; 67:170-181.

Ariquin ver. 2.000: a software for population genetics data analysis. Genetics and Biometry Laboratory, University of Geneva, Switzerland: 2000.

Broman K W. Estimation of allele frequencies with data on sibships. Genet Epidemiol. 2001; 20:307-315.

Chiodini B D, Lewis C M. Meta-analysis of 4 coronary heart disease genome-wide linkage studies confirms a susceptibility locus on chromosome 3q. Arterioscler Thromb Vasc Biol. 2003; 23:1863-1868.

Vionnet N, Hani E, Dupont S, Gallina S, Francke S, Dofte S, De Matos F, Durand E, Lepretre F, Lecoeur C, Gallina P, Zekiri L, Dina C, Froguel P. Genome-wide search for type 2 diabetes-susceptibility genes in French whites: evidence for a novel susceptibility locus for early-onset diabetes on chromosome 3q27-qter and independent replication of a type 2-diabetes locus on chromosome 1q21-q24. Am J Hum Genet 2000; 67:1470-1480.

Mori Y, Otabe S, Dina C, Yasuda K, Populaire C, Lecoeur C, Vatin V, Durand E, Hara K, Okada T, To be K, Boutin P, Kadowaki T, Froguel P. Genome-wide search for type 2 diabetes in Japanese affected sib-pairs confirms susceptibility genes on 3q, 15q, and 20q and identifies two new candidate loci on 7p and 11p. Diabetes. 2002; 51:1247-1255.

Hegele R A, Sun F, Harris S B, Anderson C, Hanley A J G, Zinman B. Genome-wide scanning for type 2 diabetes susceptibility in Canadian Oji-Cree, using 190 microsatellite markers. J Hum Genet. 1999; 44:10-14.

Kissebah A H, Sonnenberg G E, Myklebust J, Goldstein M, Broman K, James R G, marks J A, Krakower G R, Jacob H J, Weber A, Martin L, Blangero J, Comuzzie A G. Quantitative trait loci on chromosomes 3 and 17 influence phenotypes of the metabolic syndrome. Proc Natl Acad Sci USA 2000; 97:14478-144783.

Schellenberg G D, Bird T D, Wijsman E M, et al. Genetic linkage evidence for a familial Alzheimer's disease locus on chromosome 14. Science. 1992; 258:668-671.

Horikawa Y. Oda N. Cox N J. Li X. Orho-Melander M. Hara M. Hinokio Y. Lindner T H. Mashima H. Schwarz P E. del Bosque-Plata L. Horikawa Y. Oda Y. Yoshiuchi I. Colilla S. Polonsky K S. Wei S. Concannon P. Iwasaki N. Schulze J. Baier L J. Bogardus C. Groop L. Boerwinkle E. Hanis CL. Bell G I. Genetic variation in the gene encoding calpain-10 is associated with type 2 diabetes mellitus. Nat Genetics. 26(2):163-75, 2000 Oct.

Breslow J L. Genetics of lipoprotein disorders. Circulation. 1993; 87(suppl III):III-16-III-21.

Austin M A. King M C. Bawol R D. Hulley S B. Friedman G D. Risk factors for coronary heart disease in adult female twins. Genetic heritability and shared environmental influences. American Journal of Epidemiology. 125(2):308-18, 1987 Feb.

Rice T. Vogler G P. Perry T S. Laskarzewski P M. Rao D C. Familial aggregation of lipids and lipoproteins in families ascertained through random and nonrandom probands in the Iowa Lipid Research Clinics family study. Human Heredity. 41(2):107-21, 1991.

Murai A, Miyahara T, Fujimoto N, Matsuda M, Kameyama M. Lp(a) lipoprotein as a risk factor for coronary heart disease and cerebral infarction. Atherosclerosis 1986; 59 (2): 199-204.

Jeppesen J. Hein H O. Suadicani P. Gyntelberg F. Relation of high TG-low HDL cholesterol and LDL cholesterol to the incidence of ischemic heart disease. An 8-year follow-up in the Copenhagen Male Study. [Journal Article] Arteriosclerosis, Thrombosis & Vascular Biology. 17(6):1114-20, 1997 Jun. Abecasis G. R. & Cookson W. O. (2000) GOLD—graphical overview of linkage disequilibrium. *BioInformatics* 16, 182-183.

Boucher P., Gotthardt M., Li W. P., Anderson R. G. & Herz J. (2003) LRP: role in vascular wall integrity and protection from atherosclerosis. *Science* 300, 329-332.

Chen J., Lui W. O., Vos M. D., Clark G. J., Takahashi M., Schoumans J., Khoo S. K., Petillo D., Layery T., Sugimura J., Astuti D., Zhang C., Kagawa S., Maher E. R., Larsson C., Alberts A. S., Kanayama H. O. & Teh B. T. (2003) The t(1;3) breakpoint-spanning genes LSAMP and NORE1 are involved in clear cell renal cell carcinomas. *Cancer Cell* 4, 405-413.

Connelly J. J., Wang T., Cox J. E., Haynes C., Wang L., Shah S. H., Crosslin D. R., Hale A. B., Nelson S., Crossman D. C., Granger C. B., Haines J. L., Jones C. J., Vance J. M., Goldschmidt-Clermont P. J., Kraus W. E., Hauser E. R. & Gregory S. G. (2006) GATA2 Is Associated with Familial Early-Onset Coronary Artery Disease. *PLoS Genet* 2.

Hansson G. K. (2005) Inflammation, atherosclerosis, and coronary artery disease. *N Engl J Med* 352, 1685-1695.

Levitt P. (1984) A monoclonal antibody to limbic system neurons. *Science* 223, 299-301.

Martin E. R., Bass M. P., Gilbert J. R., Pericak-Vance M. A. & Hauser E. R. (2003a) Genotype-based association test for general pedigrees: the genotype-PDT. *Genet Epidemiol* 25, 203-213.

Martin E. R., Bass M. P., Hauser E. R. & Kaplan N. L. (2003b) Accounting for linkage in family-based tests of association with missing parental genotypes. *Am J Hum Genet* 73, 1016-1026.

Peppel K., Jacobson A., Huang X., Murray J. P., Oppermann M. & Freedman N. J. (2000) Overexpression of G protein-coupled receptor kinase-2 in smooth muscle cells attenuates mitogenic signaling via G protein-coupled and platelet-derived growth factor receptors. *Circulation* 102, 793-799.

Pimenta A. F. & Levitt P. (2004) Characterization of the genomic structure of the mouse limbic system-associated membrane protein (Lsamp) gene. *Genomics* 83, 790-801.

Seo D., Wang T., Dressman H., Herderick E. E., Iversen E. S., Dong C., Vata K., Milano C. A., Rigat F., Pittman J., Nevins J. R., West M. & Goldschmidt-Clermont P. J. (2004) Gene Expression Phenotypes of Atherosclerosis. *Arterioscler Thromb Vasc Biol* 24, 1922-1927.

Shephard N., John S., Cardon L., McCarthy M. I. & Zeggini E. (2005) Will the real disease gene please stand up? *BMC Genet* 6 Suppl 1, S66.

Teng E. L. & Chui H. C. (1987) The modified Mini-Mental State (3MS) examination. *Journal of Clinical Psychiatry* 48, 314-318.

Wang L., Hauser E. R., Shah S. H., Pericak-Vance M. A., Haynes C., Crosslin D., Harris M., Nelson S., Hale A. B., Granger C. B., Haines J. L., Jones C. J., Crossman D., Seo D., Gregory S. G., Kraus W. E., Goldschmidt-Clermont P. J. & Vance J. M. (2007) Peakwide mapping on chromosome 3q13 identifies the kalirin gene as a novel candidate gene for coronary artery disease. *Am J Hum Genet* 80, 650-663.

Xu H., Gregory S. G., Hauser E. R., Stenger J. E., Pericak-Vance M. A., Vance J. M., Zuchner S. & Hauser M. A. (2005) SNPselector: a web tool for selecting SNPs for genetic association studies. *BioInformatics* 21, 4181-4186.

Zhang L., Peppel K., Sivashanmugam P., Orman E. S., Brian L., Exum S. T. & Freedman N. J. (2007) Expression of tumor necrosis factor receptor-1 in arterial wall cells promotes atherosclerosis. *Arterioscler Thromb Vasc Biol* 27, 1087-1094.

TABLE 1

GENECARD Study

| | |
|---|---|
| Families ascertained | 438 |
| Sampled individuals | 1174 |
| Number of affected individuals | 976 |
| Total affected sib pairs | 491 |
| Number of microsatellite markers | 395 |
| Distance between markers | ~10 cM |

TABLE 2

Haplotypes for maximum hap scores (from Table 3)

| Comparison | Effect | 3M0238 | RS1875518 | RS2937666 |
|---|---|---|---|---|
| YA vs ON | Protective | NON 253 | A | A |
| | RISK | NON 253 | A | T |
| OA vs ON | Protective | NON 253 | A | A |
| | RISK | 253 | G | A |
| All Affected vs Control | Protective | NON 253 | A | A |
| | RISK 1 | NON 253 | A | T |
| | RISK 2 | 253 | G | A |

TABLE 3

Haplotype table showing protective and risk effects for all age groups. Negative hap score is protective, positive hapscore is risk

CAUCASIANS

| hap# | Hap. Score | p.val | sim. p. val | Hap. Freq | CONTROL | CASE | 3M0238 | RS1875518 | RS2937666 |
|---|---|---|---|---|---|---|---|---|---|
| | CATHGEN Young Affecteds vs. CATHGEN Old Normals |

| hap# | Hap. Score | p.val | sim. p. val | Hap. Freq | CONTROL | CASE | 3M0238 | RS1875518 | RS2937666 |
|---|---|---|---|---|---|---|---|---|---|
| Protective | −3.038 | 0.00238 | 0.0022 | 0.2296 | 0.30747 | 0.17375 | NON 253 | A | A |
| 2 | −0.55983 | 0.57559 | 0.5787 | 0.22209 | 0.22007 | 0.22444 | NON 253 | G | A |
| 3 | −0.2186 | 0.82696 | 0.8293 | 0.0595 | 0.05444 | 0.06302 | 253 | G | A |
| 4 | −0.07475 | 0.94042 | 0.9414 | 0.01434 | 0.01889 | 0.01105 | 253 | A | T |
| 5 | 0.46021 | 0.64537 | 0.6533 | 0.02893 | 0.01689 | 0.03616 | 253 | A | A |
| 6 | 0.55006 | 0.58228 | 0.582 | 0.06217 | 0.0628 | 0.06363 | 253 | G | T |
| 7 | 0.7818 | 0.43433 | 0.4331 | 0.16742 | 0.1594 | 0.17108 | 253 | G | T |
| RISK | 2.67549 | 0.00746 | 0.0066 | 0.21595 | 0.16004 | 0.25688 | NON253 | A | T |

*CATHGEN Old Affecteds vs. CATHGEN Old Normals*

| Protective | −3.34905 | 0.00081 | 0.0011 | 0.25059 | 0.30747 | 0.18609 | NON 253 | A | A |
|---|---|---|---|---|---|---|---|---|---|
| 2 | −0.35638 | 0.72155 | 0.733 | 0.01108 | 0.01689 | 0.00742 | 253 | A | A |
| 3 | −0.13402 | 0.89339 | 0.8899 | 0.16355 | 0.16004 | 0.16955 | NON 253 | A | T |
| 4 | 0.2043 | 0.83812 | 0.8432 | 0.01813 | 0.01889 | 0.01702 | 253 | A | T |
| 5 | 0.4506 | 0.65227 | 0.6599 | 0.21883 | 0.22007 | 0.22307 | NON 253 | G | A |
| 6 | 0.48243 | 0.6295 | 0.62 | 0.16897 | 0.1594 | 0.17521 | NON 253 | G | T |
| 7 | 1.59332 | 0.11109 | 0.1092 | 0.06765 | 0.0628 | 0.07454 | 253 | G | T |
| RISK | 2.55689 | 0.01056 | 0.0098 | 0.1012 | 0.05444 | 0.1471 | 253 | G | A |

*CATHGEN Young Affecteds, Old Affecteds and GENECARD-DNC Affected probands vs. CATHGEN Old Normals*

| Protective | −3.87691 | 0.00011 | 0.0003 | 0.2123 | 0.30747 | 0.17659 | NON 253 | A | A |
|---|---|---|---|---|---|---|---|---|---|
| 2 | 0.14011 | 0.88858 | 0.8886 | 0.02028 | 0.01689 | 0.02209 | 253 | A | A |
| 3 | 0.15602 | 0.87602 | 0.8759 | 0.22737 | 0.22007 | 0.232 | NON 253 | G | A |
| 4 | 0.18761 | 0.85118 | 0.8515 | 0.01902 | 0.01889 | 0.01876 | 253 | A | T |
| 5 | 1.0031 | 0.31581 | 0.3225 | 0.06158 | 0.0628 | 0.06134 | 253 | G | T1 |
| 6 | 1.09965 | 0.27149 | 0.2792 | 0.08415 | 0.05444 | 0.09424 | 253 | G | A |
| 7 | 1.27078 | 0.20381 | 0.206 | 0.17844 | 0.1594 | 0.18358 | NON 253 | G | T |
| RISK | 1.29849 | 0.19412 | 0.1927 | 0.19687 | 0.16004 | 0.2114 | NON 253 | A | T |

TABLE 4

Primer and probe information of genetic markers

| Marker | PCR Primers | Probe* |
|---|---|---|
| rs1875518 | Forward: GGGCCTAGTGTGCTAATCTCTT (SEQ ID NO: 30) | A allele = FAM-AGGTATTACTtAATCT AGTTCA-MGB (SEQ ID NO: 36) |
| | Reverse: TTATTTTACACTTAAGGGTGCTCA (SEQ ID NO: 31) | G allele = TET-AGGTATTACTcAATCT AGTTCA-MGB (SEQ ID NO: 37) |
| rs2937666 | Forward: GCAGTTTTTGTAGCTGCTGTTG (SEQ ID NO: 32) | A allele = TET-CCATCAACaATTGCAT C-MGB |

TABLE 4-continued

Primer and probe information of genetic markers

| Marker | PCR Primers | Probe* |
|---|---|---|
| | | (SEQ ID NO: 38) |
| | Reverse:<br>TTTATAGTCCATTTTGGCTTGCTT<br>(SEQ ID NO: 33) | T allele = FAM-<br>TCCATCAACtATTGCA<br>TC-MGB<br>(SEQ ID NO: 39) |
| 3M0238 | Forward:<br>CTTGCACCTGGGAGGTAGAG<br>(SEQ ID NO: 34) | N/A |
| | Reverse:<br>CACAACTGTTGCTTTTCCAT<br>(SEQ ID NO: 35) | N/A |

*The polymorphic site is in lower letter bold case.

TABLE 5

Baseline characteristics of GENECARD individuals (420 families).

| Variable | Affected (N = 952) | Unaffected (N = 177) | All (N = 1129) |
|---|---|---|---|
| Mean age (SD) | 51.4 (7.1) | 65.3 (11.3) | 53.6 (9.4) |
| Mean age of onset (SD) | 43.7 (5.8) | — | — |
| Sex (%) | | | |
| Male | 71.4% | 36.0% | 65.8% |
| Female | 28.6% | 64.0% | 34.2% |
| Dyslipidemia | 82.3% | 57.1% | 78.4% |
| Meds for dyslipidemia | 84.7% | 60.6% | 81.9% |
| Lipids (mean, SD) | | | |
| TC | 205.7 (57.3) | 220.6 (50.3) | 206.9 (56.9) |
| TG | 222.1 (167.1) | 213.8 (142.9) | 221.5 (165.2) |
| HDL | 39.1 (19.0) | 48.1 (34.9) | 39.9 (20.9) |
| LDL | 117.7 (49.5) | 124.7 (40.0) | 118.3 (48.8) |
| Hypertension | 55.2% | 49.1% | 54.2% |
| Blood pressure (mean, SD) | | | |
| Systolic | 141.1 (22.7) | 151.8 (26.3) | 146.1 (24.7) |
| Diastolic | 81.2 (12.2) | 81.4 (9.8) | 81.3 (11.0) |
| Diabetes mellitus (DM) | 21.0% | 15.4% | 20.1% |
| Waist circumference (SD) | 99.0 (14.2) | 96.4 (16.4) | 98.6 (14.6) |
| Obesity | | | |
| BMI < 25 | 19.6% | 35.0% | 22.1% |
| BMI 25-29 | 38.3% | 37.3% | 38.2% |
| BMI ≥ 30 | 42.0% | 27.7% | 39.8% |
| Metabolic syndrome*** | 46.8% | 30.3% | 44.2% |
| Pack-years smoked | 34.8 (23.4) | 42.7 (36.7) | 35.7 (25.3) |
| Currently smoking | 32.9% | 28.3% | 32.4% |
| Post-menopausal | 55.8% | 82.1% | 63.4% |
| History of MI | 62.9% | — | 59.8% |
| Multiple vessel CAD | 66.0% | — | 66.0% |

TC = total cholesterol,
TG = triglycerides,
HDL = high density lipoprotein,
MI = myocardial infarction.
***Presence of 3 out of 5 of the following: history of DM; HTN or BP > 130/85; HDL < 40 in men and <50 in women; waist circumference >88 in women, >102 in men; TG ≥ 150.

TABLE 6

Quantitative trait loci mapping results, lipid phenotypes.

| Quantitative Trait | Heritability (SD) | Chrom | Locus (cM)* | Multipoint LOD | Empirical p-value** |
|---|---|---|---|---|---|
| Total cholesterol (TC) | 71.1% (8.9%)*** | 5 | 98 | 1.28 | 0.03 |
| | | 6 | 10 | 1.28 | 0.03 |
| | | 13 | 15 | 1.19 | 0.03 |
| | | 18 | 55 | 1.32 | 0.02 |
| Low density lipoprotein (LDL) cholesterol | 67.3% (9.7%)*** | 6 | 164 | 1.65 | <0.01 |
| | | 16 | 0 | 1.41 | |
| | | 19 | 52 | 1.25 | |
| | | 21 | 16 | 1.39 | |
| High density lipoprotein (HDL) cholesterol | 67.7% (11.9%)*** | 3 | 87 | 2.43 | 0.002 |
| | | 7 | 156 | 1.73 | <0.01 |
| | | 15 | 103 | 1.79 | 0.004 |
| Triglycerides | 63.7% (12.5%)*** | 4 | 119 | 1.30 | |
| | | 7 | 80 | 1.35 | |
| | | 13 | 18 | 1.55 | <0.01 |
| | | 14 | 76 | 1.22 | |
| | | 18 | 94 | 2.09 | 0.002 |
| HDL/TC ratio | 64.6% (9.8%)*** | 3 | 153 | 1.44 | <0.01 |
| | | 7 | 143 | 1.44 | <0.01 |
| | | 8 | 148 | 1.68 | |

*Kosambi map locus; cM: centimorgans;
**using 10000 simulated repetitions;
***p-value<0.00001

TABLE 7

Ordered subset analysis (OSA) results.

| Chromosome | Pos cM | Covariate | Mean covariate value (SD) in subset | Mean covariate value (SD) in others* | Max OSA LOD | Overall LOD | p-value | No. fams in subset |
|---|---|---|---|---|---|---|---|---|
| 3 | 146.9 | Low TG | 161.1 (49.3) | 372.7 (137.9) | 4.14 | 2.64 | 0.04 | 167 |
| 5 | 171.7 | High TC | 302.4 (78.9) | 192.8 (30.1) | 4.42 | 0.36 | 0.001 | 54 |
| 9 | 23.5 | Low TG | 99.3 (21.8) | 248.9 (121.0) | 2.51 | 0.12 | 0.03 | 49 |
| 10 | 127.7 | Low HDL | 24.8 (4.5) | 39.8 (8.2) | 2.49 | 0.00 | 0.007 | 44 |
| 12 | 61.0 | High HDL | 50.6 (8.2) | 34.3 (5.6) | 2.43 | 0.35 | 0.03 | 80 |
| 14 | 0.0 | High LDL | 225.5 (36.1) | 113.0 (32.0) | 2.63 | 0.66 | 0.03 | 22 |
| 17 | 120.6 | High TG | 340.9 (133.8) | 152.1 (44.0) | 2.10 | 0.19 | 0.04 | 77 |
| 22 | 0.0 | High LDL | 225.5 (36.1) | 113.0 (32.0) | 2.52 | 0.001 | 0.02 | 22 |

*mean value of OSA covariate in families not included in the subset;

TABLE 8

Phenotypic characteristics of families in OSA subsets.

| Chromosome | No. families in subset | Phenotypic characteristics of subset* | Lipid phenotypes of subset* |
|---|---|---|---|
| 3 | 167 | Older at time of exam, older age of onset<br>Less metabolic syndrome, diabetes<br>Lower BMI<br>Lower waist circumference and weight | Lower TC<br>Lower LDL<br>Higher HDL |
| 5 | 54 | Younger age of onset | Higher LDL<br>Higher TG |
| 9 | 49 | Less diabetes<br>Lower weight, waist circumference, BMI<br>Less metabolic syndrome<br>Fewer pack-years smoked | Lower TC<br>Higher HDL |
| 10 | 44 | More metabolic syndrome<br>More pack-years smoked<br>More diabetes<br>More male<br>Higher height, weight, waist circumference | Higher TG |
| 12 | 80 | Lower waist, weight, BMI<br>Older at time of exam, older age of onset<br>Less metabolic syndrome<br>More female | Higher TC<br>Lower TG |
| 14 | 22 | Younger at time of exam, younger age of onset | Higher TC |
| 17 | 77 | More metabolic syndrome | Lower LDL<br>Lower HDL |
| 22 | 22 | Younger at time of exam, younger age of onset | Higher TC |

*when compared to family means of affected individuals in families not within the OSA subset; all comparisons statistically significant at p < 0.05. BMI: body-mass index

TABLE 9

Genetic Markers in Chromosome 3*

| Chr | SNP/Polymorphism id | Basepair location on Ch 3 | Basepair location on SEQ ID NO: 1 |
|---|---|---|---|
| 3 | rs2927275 | 118666759 | 166759 |
| 3 | rs1698042 | 118667838 | 167838 |
| 3 | rs1501881 | 118672530 | 172530 |
| 3 | rs1698041 | 118682441 | 182441 |
| 3 | 3M0238 | 118690772 to 118690975 | 190772 to 190975 |
| 3 | rs2055426 | 118703034 | 203034 |
| 3 | rs2937675 | 118706580 | 206580 |
| 3 | 27 bp Insertion | 118711341 to 118711342 | 211341 to 211342 |
| 3 | rs1875518 | 118712470 | 212470 |
| 3 | rs2937673 | 118715077 | 215077 |
| 3 | rs1676232 | 118717529 | 217529 |
| 3 | 3I0320 | 118719088 | 219088 |
| 3 | 3I0311 | 118719132 to 118719133 | 219132 to 219133 |
| 3 | rs1381801 | 118723585 | 223585 |
| 3 | rs2937666 | 118729388 | 229388 |
| 3 | rs1910044 | 118733409 | 233409 |
| 3 | rs6778437 | 118726628 | 226628 |
| 3 | rs6795971 | 118751683 | 251683 |
| 3 | rs1466416 | 118753496 | 253496 |
| 3 | rs6795971 | 118751683 | 251683 |
| 3 | rs2937673 | 118715077 | 215077 |
| 3 | rs1698041 | 118682441 | 182441 |
| 3 | rs4356827 | 118661434 | 161434 |
| 3 | rs6790819 | 118659480 | 159480 |
| 3 | rs7427839 | 118648013 | 148013 |
| 3 | rs725154 | 117992940 | |
| 3 | rs1875516 | 118805109 | |
| 3 | rs1501882 | 118774319 | |
| 3 | rs1401951 | 119708716 | |
| 3 | rs1968010 | 119551910 | |
| 3 | rs1486336 | 119386693 | |
| 3 | rs843855 | 119239225 | |
| 3 | rs1456186 | 119110095 | |
| 3 | rs553070 | 119637627 | |
| 3 | rs1499989 | 119483894 | |
| 3 | rs39688 | 120225538 | |
| 3 | rs812824 | 120037336 | |
| 3 | rs705233 | 119952613 | |
| 3 | rs483349 | 120827383 | |
| 3 | rs2282171 | 120665288 | |
| 3 | rs834855 | 82731159 | |
| 3 | rs4404477 | 118857458 | |

*SNP basepair location on Ch 3 is based on the NCBI build 35 sequence of human chromosome 3.

TABLE 10

Additional Nucleotide Polymorphisms*

| SEQ ID NO: | Flanking Sequence (polymorphism in brackets) | Polymorphism basepair position on Ch 3** | Polymorphism basepair position on SEQ ID NO: 1 |
|---|---|---|---|
| 2 | TGCGCGTGT[G/T]TGGTGTGTG | 118664719 | 164719 |
| 3 | AAATAAATTAAC[G/A]TTTATCATCA | 118670801 | 170801 |
| 4 | ATTTCTC[G/A]TTAAAATTT | 118673682 | 173682 |
| 5 | ATTTCATATCT[-/A]GGAAAAAAC | 118673698 to 118673699 | 173698 to 173699 |
| 6 | CCACCTAG[T/C]TTTTTTAATGAACA | 118699111 | 199111 |
| 7 | ATCTTGATT[C/A]TATTTATGACTGC | 118699690 | 199690 |
| 8 | GCTTAGTTGG[T/A]TAGACCAGCT | 118708380 | 208380 |
| 9 | CCTCACTCT[A/C]TTCTCCTCCTT | 118708990 | 208990 |
| 10 | GGTGCAG[T/A]GGCATGAGCC | 118713130 | 213130 |
| 11 | AACCCTCCTCAATTGT[A/G]GAAAGATGGAACA | 118717982 | 217982 |
| 12 | GGAACAGCAACATTCTTA[A/G]ATGCTCATGTACC | 118718008 | 218008 |
| 13 | ATTCTTAAATGCTCATGTA[C/A]CTTTATTAAAGTAT | 118718020 | 218020 |
| 14 | ATGTGCATTTCTACA[T/A]TCATTCAAATAGTCTTTG | 118718327 | 218327 |
| 15 | AATGATAAAAT[A/-]TTTTTTAAAG (3I0320) | 118719088 | 219088 |
| 16 | TCCCACCG[T/G]ACCCAGCCCT | 118720122 | 220122 |
| 17 | TTATATCAA[T/G]GCCTCCAAC | 118720142 | 220142 |
| 18 | ACTTGCAGAA[A/G]TTTTATATC | 118720154 | 220154 |
| 19 | GGTTGACTAG[T/A]CCATGCCTT | 118720228 | 220228 |
| 20* | AACAGAACTKA[A/G**]CACTCT | 118720249 | 220249 |
| 21 | GTCCAAAACA[T/C]ATGCTAAAGA | 118722980 | 222980 |
| 22 | TTATTTAC[A/G]TGAAGTTGT | 118722998 | 222998 |
| 23 | ACATCTT[A/G]TGAAATT | 118723379 | 223379 |
| 24 | TTGTTGGGG[G/A]ACTATAGTAATC | 118727468 | 227468 |
| 25 | GACCCTCCAACAAA[T/G]GCCATTT | 118728575 | 228575 |
| 26 | AGTTTGGA[G/A]TTTCCTCA | 118730282 | 230282 |
| 27 | TCAGAGAAATG[C/A]AAATCAA | 118730459 | 230459 |
| 28 | CTGGAGGAGATAATCATTAAGTGGGAATTTGAATATTATAACAGATCCT[-------------------------/GGGAATTTGAATATTATAACAGATCCT]GTAATCACCTGACCACTGCACAGA (27 bp duplication) | 118711341 to 118711341 | 211341 to 211342 |

TABLE 10-continued

Additional Nucleotide Polymorphisms*

| SEQ ID NO: | Flanking Sequence (polymorphism in brackets) | Polymorphism basepair position on Ch 3** | Polymorphism basepair position on SEQ ID NO: 1 |
|---|---|---|---|
| 29 | ATAAGCAAGTATAAAAA[---/CAA]TTTCCAGTAGATG (3I0311) | 118719132 to 118719133 | 219132 to 219133 |

*The polymorphism is indicated in bold text. The first nucleotide/sequence listed of the polymorphism is the nucleotide/sequence present in the NCBI build 35 sequence of human chromosome 3, the second nucleotide/sequence listed is the variant.
**SNP basepair position on Ch 3 is based on the NCBI build 35 sequence of human chromosome 3.
***K in SEQ ID NO: 20 represents a G/T polymorphism.

TABLE 11

SNPs in HAPIP and MLCK*

| Ch | SNP id | Gene | SNP basepair location |
|---|---|---|---|
| 3 | rs2272486 | HAPIP | 125470729 |
| 3 | HCV1602689 | MLCK | 125024094 |

*SNP basepair location is based on the NCBI build 35 sequence of human chromosome 3.

TABLE 12

Clinical characteristics of patient datasets

| | Initial Dataset | | | Validation Dataset | | |
|---|---|---|---|---|---|---|
| | Old Affected | Left Main Case | Control | Left Main Case | Control | Alzheimer Control |
| Number of individuals | 167 | 102 | 149 | 141 | 215 | 255 |
| Age-at-catheterization, mean (SD) | 66.1 (10.5)* | 66.1 (10.7)* | 70.9 (7.2) | 68.5 (9.6) | 69.9 (6.6) | 73.8 (6.0)† |
| Age-of-onset, mean (SD) | 60.5 (8.9) | 56.8 (12.1) | N/A | 59.1 (10.8) | N/A | N/A |
| CAD index, mean (SD) | 72.1 (19.2)* | 89.1 (8.8)* | 10.9 (10.9) | 88.5 (8.7)* | 8.8 (10.7) | N/A |
| Gender: Male, % | 83.8%* | 74.51%* | 47.7% | 85.8%* | 44.7% | 28.7% |
| BMI, Mean (SD) | 29.2 (6.6)* | 28.9 (5.8) | 27.6 (5.9) | 28.4 (5.9) | 28.4 (5.9) | N/A |
| Ever-smoked, % | 59.3%* | 57.8%* | 43.6% | 62.4%* | 40.0% | N/A |
| Diabetes, % | 32.9%* | 31.4%* | 11.4% | 26.2% | 21.9% | 0.0% |
| Hypertension, % | 73.7% | 82.4%* | 66.4% | 68.8% | 67.4% | 46.4% |
| Dyslipidemia, % | 73.1%* | 77.5%* | 40.3% | 74.5%* | 54.9% | 43.8% |

*P < 0.05 for the comparison of cases with controls.
Chi-square tests were performed for categorical variables and t-tests were performed for continuous variables.
BMI, body mass index.
N/A, not applicable.

TABLE 13

Promising SNP association with left main CAD in the initial, validation, and combined datasets

| SNP | Chr | Location (NCBI35) | Initial Dataset Basic Model# | | Validation Dataset Basic Model | | Combined Dataset* Basic Model | | Combined Dataset Full Model# | |
|---|---|---|---|---|---|---|---|---|---|---|
| | | | p value | OR | p value | OR | p value | OR | p value | OR |
| rs10934326 | 3 | 117,469,033 | 0.012 | 2.2 | 0.707 | 0.9 | 0.226 | 1.2 | 0.256 | 1.2 |
| rs1106851 | 3 | 117,943,999 | 0.088 | 1.6 | 0.673 | 1.1 | 0.125 | 1.3 | 0.208 | 1.3 |
| rs1513172 | 3 | 118,494,578 | 0.092 | 1.4 | 0.754 | 0.9 | 0.291 | 1.2 | 0.932 | 1.0 |
| rs4075039 | 3 | 118,645,474 | 0.057 | 1.8 | 0.342 | 0.8 | 0.675 | 1.1 | 0.923 | 1.0 |

TABLE 13-continued

Promising SNP association with left main CAD in the initial, validation, and combined datasets

| SNP | Chr | Location (NCBI35) | Initial Dataset Basic Model[#] | | Validation Dataset Basic Model | | Combined Dataset* Basic Model | | Combined Dataset Full Model[#] | |
|---|---|---|---|---|---|---|---|---|---|---|
| | | | p value | OR | p value | OR | p value | OR | p value | OR |
| rs6790819 | 3 | 118,659,480 | 0.098 | 6.8 | 0.726 | 1.8 | 0.068 | 5.1 | 0.071 | 5.6 |
| rs1910040 | 3 | 118,673,682 | 0.100 | 1.5 | 0.061 | 1.5 | 0.013 | 1.5 | 0.034 | 1.4 |
| ss70458782 | 3 | 118,709,990 | 0.091 | 1.6 | 0.083 | 1.5 | 0.015 | 1.5 | 0.044 | 1.4 |
| rs1875518 | 3 | 118,712,470 | 0.008 | 1.8 | 0.168 | 1.3 | 0.005 | 1.5 | 0.057 | 1.3 |
| rs1676232 | 3 | 118,717,529 | 0.022 | 1.7 | 0.315 | 1.2 | 0.022 | 1.4 | 0.110 | 1.3 |
| rs4404477 | 3 | 118,857,458 | 0.106 | 1.6 | 0.039 | 1.7 | 0.007 | 1.7 | 0.021 | 1.6 |

Subset analysis in the initial dataset identified ten promising LSAMP SNPs that displayed evidence for association with left main CAD. These SNPs were further examined in the validation dataset composed of left main affected and control. Logistic regression analysis was performed to evaluate SNP association with left main CAD using genotype case-control statistic provided by SAS 9.0. OR, odds ratio estimates. P-values less than 0.05 are shown in bold.

*The "combined dataset" consists of both the initial and validation datasets.

[#]In the basic model, gender was included as covariable; in the full model, gender, age, hypertension, diabetes mellitus, body mass index, dyslipidemia, and smoking history were included as covariable.

TABLE 14

Association of five "significant" SNPs in multiple additional datasets

| SNP | Allele | Combined Left Main Case* (N = 243) Freq | Third Control (N = 255) | | | All Control* (N = 619) | | | GENECARD Dataset (N = 2954) | | | | |
|---|---|---|---|---|---|---|---|---|---|---|---|---|---|
| | | | Freq | P value | OR | Freq | P value | OR | Affected | Unaffected | APL Freq P value | PDT P value | GenoPDT P value |
| rs1910040 | A | 78% | 74% | 0.539 | 1.1 | 72% | 0.033 | 1.4 | 76% | | 0.225 | 0.333 | 0.488 |
| ss70458782 | A | 85% | 81% | 0.243 | 1.3 | 80% | 0.017 | 1.5 | 81% | | 0.624 | 0.476 | 0.690 |
| rs1875518 | G | 63% | 56% | 0.062 | 1.4 | 54% | 0.005 | 1.4 | 55% | | 0.468 | 0.435 | 0.607 |
| rs1676232 | A | 68% | 64% | 0.633 | 1.1 | 61% | 0.083 | 1.3 | 61% | | 0.020 | 0.087 | 0.285 |
| rs4404477 | A | 87% | 82% | 0.006 | 1.9 | 82% | 0.003 | 1.7 | 85% | | 0.091 | 0.012 | 0.044 |

Evaluation of promising SNPs in the validation dataset identified five LSAMP SNPs as significant SNPs. These SNPs were further examined in multiple additional datasets.

*"Combined Left Main Case" comprises all of the left main CAD cases in the initial and validation datasets; "All Control" denotes all of the controls reported in this study (from the initial, validation, and third control datasets). Freq, frequency of the displayed allele. OR, odds ratio estimates for the displayed allele. Logistic regression analyses were performed adjusting for gender for the case-control dataset using genotype case-control statistic provided by SAS 9.0. APL, PDT, and GenoPDT were performed for the family-based GENECARD samples. P values less than 0.05 are shown in bold.

TABLE 15

Association of HAP L with left main CAD in multiple independent datasets

| Haplotype | | Initial Dataset | | | Validation Dataset | | | Combined | | | Initial, Validation datasets and Third Control | | | | |
|---|---|---|---|---|---|---|---|---|---|---|---|---|---|---|---|
| | | Left Main Case (N = 102) | Control (N = 149) | | Left Main Case (N = 141) | Control (N = 215) | | Left Main Case* (N = 243) | Combined Control* (N = 364) | | Third Control (N = 255) | | All Control* (N = 619) | |
| ss70458782 | rs4404477 | Freq | Freq | P value | Freq | Freq | P value | Freq | Freq | P value | Freq | P value | Freq | P value |
| A | A | 77% | 67% | 0.0205 | 76% | 64% | 0.0012 | 77% | 65% | 0.0001 | 65% | 0.0022 | 65% | 4.00E−05 |
| A | G | 8% | 12% | 0.1384 | 10% | 16% | 0.0297 | 9% | 14% | 0.0095 | 16% | 0.0032 | 15% | 0.0026 |
| C | A | 10% | 17% | 0.1284 | 11% | 17% | 0.0601 | 11% | 17% | 0.0299 | 17% | 0.2736 | 17% | 0.0302 |
| C | G | 5% | 4% | 0.5311 | 3% | 3% | 0.4239 | 4% | 3% | 0.2348 | 2% | 0.685 | 3% | 0.2765 |

*"Combined Left Main Case" comprises all of the left main CAD cases in the initial and validation datasets; "Combined Control" denotes all of the controls from both the initial and validation datasets; "All Control" denotes all of the controls reported in this study (from the initial, validation, and third control datasets). Freq, frequency of the displayed haplotype. Haplotype association tests were performed adjusting for gender. LSAMP haplotype ss70458782A_rs4404477A was designated as HAP L. P-values less than 0.05 are shown in bold.

TABLE 16

Definition of the coronary artery disease index (CADi)[21]

| Extent of CAD | CADi |
|---|---|
| No CAD ≧ 50% | 0 |
| One-VD 50% to 74% | 19 |
| One-VD 75% | 23 |
| One-VD ≧ 95% | 32 |
| Two-VD | 37 |
| Two-VD (both ≧ 95%) | 42 |
| One-VD ≧ 95%, proximal (LAD) | 48 |
| Two-VD ≧ 95% LAD | 48 |
| Two-VD ≧ 95% proximal LAD | 56 |
| Three-VD | 56 |
| Three-VD ≧ 95% in at least one vessel | 63 |
| Three-VD 75% proximal LAD | 67 |
| Three-VD ≧ 95% proximal LAD | 74 |
| Left main (75%) | 82 |
| Left main (≧95%) | 100 |

CAD = coronary artery disease;
LAD = left anterior descending coronary artery;
VD = vessel disease.

TABLE 17

Association tests in the initial dataset

| | | | Old Affected | | Left Main Case | |
|---|---|---|---|---|---|---|
| SNP | Chr | NCBI35 | p value | OR | p value | OR |
| rs9822311 | 3 | 117,021,341 | 0.623 | 1.1 | 0.509 | 1.2 |
| rs3821560 | 3 | 117,054,054 | 0.062 | 0.5 | 0.390 | 0.7 |
| rs11719516 | 3 | 117,067,985 | 0.252 | 0.7 | 0.886 | 1.0 |
| rs10511352 | 3 | 117,125,967 | 0.886 | 1.0 | 0.530 | 0.8 |
| rs9872913 | 3 | 117,183,885 | 0.389 | 1.2 | 0.360 | 1.2 |
| rs1920384 | 3 | 117,250,752 | 0.270 | 1.3 | 0.274 | 1.3 |
| rs9866658 | 3 | 117,331,906 | 0.703 | 1.1 | 0.952 | 1.0 |
| rs7641464 | 3 | 117,368,960 | 0.047 | 1.5 | 0.112 | 1.4 |
| rs10934326 | 3 | 117,469,033 | 0.130 | 1.6 | 0.012 | 2.2 |
| rs1461131 | 3 | 117,483,362 | 0.280 | 1.3 | 0.850 | 1.0 |
| rs9809878 | 3 | 117,515,131 | 0.254 | 0.8 | 0.580 | 0.9 |
| rs2033406 | 3 | 117,547,823 | 0.506 | 0.9 | 0.382 | 1.2 |
| rs9822445 | 3 | 117,644,224 | 0.501 | 1.2 | 0.229 | 1.3 |
| rs10934345 | 3 | 117,692,305 | 0.721 | 1.1 | 0.912 | 1.0 |
| rs9834065 | 3 | 117,730,574 | 0.184 | 1.3 | 0.259 | 1.3 |
| rs1795293 | 3 | 117,761,199 | 0.474 | 1.2 | 0.805 | 1.1 |
| rs1467213 | 3 | 117,805,164 | 0.424 | 1.2 | 0.288 | 1.2 |
| rs9847048 | 3 | 117,838,700 | 0.709 | 1.1 | 0.838 | 0.9 |
| rs10934364 | 3 | 117,896,600 | 0.598 | 1.1 | 0.981 | 1.0 |
| rs1106851 | 3 | 117,943,999 | 0.919 | 1.0 | 0.088 | 0.6 |
| rs1835856 | 3 | 117,974,362 | 0.682 | 0.9 | 0.936 | 1.0 |
| rs6785331 | 3 | 117,990,316 | 0.784 | 1.1 | 0.415 | 0.8 |
| rs7433070 | 3 | 118,042,925 | 0.644 | 0.9 | 0.199 | 0.8 |
| rs6438359 | 3 | 118,071,957 | 0.933 | 1.0 | 0.985 | 1.0 |
| rs2037009 | 3 | 118,110,689 | 0.185 | 0.8 | 0.149 | 0.7 |
| rs1133603 | 3 | 118,133,470 | 0.777 | 0.9 | 0.327 | 1.3 |
| rs1589182 | 3 | 118,186,282 | 0.751 | 0.9 | 0.688 | 0.9 |
| rs1518898 | 3 | 118,211,238 | 0.389 | 1.2 | 0.492 | 0.8 |
| rs4855909 | 3 | 118,212,508 | 0.717 | 1.1 | 0.743 | 0.9 |
| rs938115 | 3 | 118,257,964 | 0.928 | 1.0 | 0.495 | 1.1 |
| rs1850719 | 3 | 118,284,215 | 0.967 | 1.0 | 0.538 | 1.1 |
| rs7633227 | 3 | 118,313,302 | 0.357 | 1.2 | 0.818 | 1.1 |
| rs733527 | 3 | 118,347,424 | 0.306 | 1.2 | 0.822 | 1.0 |
| rs6788787 | 3 | 118,353,538 | 0.767 | 1.1 | 0.745 | 1.1 |
| rs1915585 | 3 | 118,391,522 | 0.432 | 0.8 | 0.396 | 0.8 |
| rs1462845 | 3 | 118,425,700 | 0.619 | 0.9 | 0.136 | 0.7 |
| rs4855900 | 3 | 118,477,957 | 0.331 | 0.8 | 0.247 | 0.7 |
| rs1513172 | 3 | 118,494,578 | 0.700 | 1.1 | 0.092 | 1.4 |
| rs6438389 | 3 | 118,532,507 | 0.548 | 0.9 | 0.788 | 0.9 |
| rs1513156 | 3 | 118,549,311 | 0.345 | 0.8 | 0.254 | 0.7 |
| rs11716267 | 3 | 118,586,537 | 0.603 | 1.1 | 0.312 | 1.3 |
| rs1398626 | 3 | 118,616,293 | 0.178 | 1.3 | 0.544 | 1.1 |
| rs1513162 | 3 | 118,617,776 | 0.519 | 1.1 | 0.669 | 1.1 |
| rs4075039 | 3 | 118,645,474 | 0.361 | 0.8 | 0.057 | 0.5 |
| rs7427839 | 3 | 118,648,013 | 0.218 | 1.3 | 0.245 | 1.3 |
| rs6790819 | 3 | 118,659,480 | 0.073 | 7.6 | 0.098 | 6.8 |
| rs4356827 | 3 | 118,661,434 | 0.284 | 0.8 | 0.314 | 0.8 |
| rs2927275 | 3 | 118,666,759 | 0.421 | 0.8 | 0.851 | 1.0 |
| rs1698042 | 3 | 118,667,838 | 0.110 | 0.5 | 0.433 | 0.7 |
| rs1910040 | 3 | 118,673,682 | 0.203 | 0.7 | 0.100 | 0.7 |
| rs11713954 | 3 | 118,699,690 | 0.580 | 0.8 | 0.117 | 0.5 |
| ss70458782 | 3 | 118,709,990 | 0.062 | 0.6 | 0.091 | 0.6 |
| rs1875518 | 3 | 118,712,470 | 0.079 | 1.4 | 0.008 | 1.8 |
| rs1676232 | 3 | 118,717,529 | 0.044 | 0.7 | 0.022 | 0.6 |
| rs4855952 | 3 | 118,717,715 | 0.506 | 1.5 | 0.410 | 1.6 |
| rs1501874 | 3 | 118,720,007 | 0.501 | 0.8 | 0.426 | 0.7 |
| rs2937670 | 3 | 118,720,251 | 0.844 | 1.1 | 0.122 | 0.6 |
| rs1979868 | 3 | 118,722,031 | 0.744 | 1.1 | 0.760 | 1.1 |
| rs1381801 | 3 | 118,723,585 | 0.750 | 0.9 | 0.929 | 1.0 |
| rs2937666 | 3 | 118,729,388 | 0.231 | 1.3 | 0.910 | 1.0 |
| rs1910044 | 3 | 118,733,409 | 0.504 | 1.2 | 0.917 | 1.0 |
| rs4855955 | 3 | 118,738,784 | 0.434 | 0.8 | 0.399 | 0.8 |
| rs6778437 | 3 | 118,746,628 | 0.552 | 2.3 | 0.534 | 2.4 |
| rs6795971 | 3 | 118,751,683 | 0.552 | 2.3 | 0.534 | 2.4 |
| rs1393192 | 3 | 118,752,560 | 0.418 | 0.8 | 0.581 | 0.9 |
| rs1466416 | 3 | 118,753,496 | 0.979 | 0.0 | 0.175 | 0.2 |
| rs2869787 | 3 | 118,791,508 | 0.645 | 1.1 | 0.738 | 1.1 |
| rs869851 | 3 | 118,804,008 | 0.998 | 1.0 | 0.707 | 1.1 |
| rs2904196 | 3 | 118,829,308 | 0.524 | 0.9 | 0.968 | 1.0 |
| rs6774738 | 3 | 118,849,617 | 0.291 | 0.8 | 0.165 | 0.7 |
| rs4234669 | 3 | 118,851,827 | 0.583 | 0.9 | 0.448 | 0.9 |
| rs4290831 | 3 | 118,856,228 | 0.447 | 0.7 | 0.731 | 0.9 |
| rs4404477 | 3 | 118,857,458 | 0.206 | 0.7 | 0.106 | 0.6 |
| rs9877923 | 3 | 118,862,230 | 0.635 | 1.1 | 0.522 | 1.2 |
| rs4440150 | 3 | 118,863,334 | 0.843 | 1.0 | 0.635 | 1.1 |
| rs6784348 | 3 | 118,892,675 | 0.499 | 0.9 | 0.719 | 0.9 |
| rs7646668 | 3 | 118,914,350 | 0.075 | 1.4 | 0.290 | 1.2 |
| rs6438404 | 3 | 118,918,128 | 0.449 | 0.8 | 0.634 | 0.9 |
| rs4367097 | 3 | 118,922,408 | 0.207 | 0.4 | 0.255 | 0.5 |
| rs9861188 | 3 | 118,932,645 | 0.023 | 1.6 | 0.111 | 1.4 |
| rs7647501 | 3 | 118,939,388 | 0.212 | 0.8 | 0.556 | 0.9 |
| rs4687991 | 3 | 118,947,921 | 0.246 | 0.8 | 0.339 | 0.8 |
| rs4687996 | 3 | 118,956,667 | 0.186 | 0.8 | 0.356 | 0.8 |
| rs6796552 | 3 | 118,967,152 | 0.281 | 0.8 | 0.378 | 0.8 |
| rs4687889 | 3 | 119,020,129 | 0.295 | 1.2 | 0.586 | 1.1 |
| rs7427162 | 3 | 119,069,371 | 0.191 | 1.3 | 0.285 | 1.3 |
| rs1378834 | 3 | 119,102,092 | 0.149 | 0.5 | 0.575 | 0.8 |
| rs1456186 | 3 | 119,110,095 | 0.763 | 0.9 | 0.715 | 1.1 |
| rs817508 | 3 | 119,168,266 | 0.978 | 1.0 | 0.571 | 1.2 |
| rs17723301 | 3 | 119,198,278 | 0.452 | 1.2 | 0.569 | 1.1 |

Logistic regression analyses were performed adjusting for gender using genotype case-control statistics provided by SAS 9.0.
OR = odds ratio estimates.
P-values less than 0.05 are shown in bold.

That which is claimed is:

1. A method of identifying a human subject having an increased risk of developing coronary artery disease, comprising detecting in a nucleic acid sample of the subject a haplotype in the LSAMP gene of the subject comprising an A allele at single nucleotide polymorphism ss70458782 and an A allele at single nucleotide polymorphism rs4404477, wherein the detection of said haplotype identifies the subject as having an increased risk of developing coronary artery disease.

2. The method of claim 1, wherein detecting is carried out by a hybridization reaction.

3. The method of claim 2, wherein the hybridization reaction is carried out with hybridization probes in a microarray.

4. The method of claim 1, wherein detecting is carried out by electrophoresis.

5. The method of claim 1, wherein detecting is carried out by restriction endonuclease digestion analysis.

6. The method of claim 1, wherein detecting is carried out by an amplification reaction.

7. The method of claim 6, wherein the amplification reaction is a polymerase chain reaction.

* * * * *

SEQUENCE LISTING

<160> NUMBER OF SEQ ID NOS: 39

<210> SEQ ID NO 1
<211> LENGTH: 261789

```
<212> TYPE: DNA
<213> ORGANISM: Homo sapiens

<400> SEQUENCE: 1
tttctaacaa tttctcttcc ttcctttctt tggagtgtta tctcactgag cagtcatcta    60
cagatattga cagtcatgtt ttatcttttt agtgttgctg tgtgttggct tccaatcaat   120
gacataaatt atgctgctat ttatgtatag ttagaatgac ttaattgccc tattaaatat   180
caacattttt atcttttcat tttaagcta  ccaatttaca agaatatttg taagtggctg   240
ccactgtctt aaattttaga ataattaaca gtgacttttc cagatctaaa tatttgatag   300
ataccttaag attccacact tcctaactta cgtggaagct aagggaaaca agttttttgag  360 cacatatgaa aagataaatt gcaacaaaat agagttcaag gagactggag atgtgtcaga   420
gtgcacaact gcagaagtca atattcagtt gttctaacta accctgaagg tctcagaacc   480
tactatcatc ctggtgttaa cataggttta tgagtatctt cctttttggtt ttctcctgat   540 ttggggaaca tttgcttcat cttcagtatc agaacgtttt cctcttctct ttttcccgc    600 cccctgtctg aagaggttcc atagtctgga ctgcaagtct cccttatatg tttctcaaat   660
ccattactcc ttatgtctgt agcccctata tttagctttg gcttgtagaa cacagataac   720
taaatcctct tcaaattcct aacactcctc tgctccaccc accttgacct cttctgtcat   780
gtaatgcata catggaacat gaaagacatt cttgccactt tatcctcttc ctcatgcctg   840
gtcatgttat aagaacaaat aatatttcaa aaataggagg aagtttcagt acatgacctt   900
gactctcctg ctctgagatt aaaacattta atttgtgata tcatcaccag ctttaaattc   960
tattcttaat ctgttgcctt gaatttattc aacattatac ctctcatcta caacaactat  1020
aatgcccatt gtagattttt attttttatt cagttaccac atactgctct atattgttac  1080
catagctcat gtatgtcaca cttgaaaatc cattaagggt agatttttagt tgacactgct  1140 gcactgacag ttattaaaaa aatacttatc tcccccctct aatttcctgc tatcttaacc  1200
ttatatatgt catttttattt ttttctagag agttcataat ctactctgtc cttttttttt  1260 cttttgaagcc acttcccatt acatattaaa cctattatgc ttttattctt tttcatcaaa  1320
gtgcctatcc aacttcacat cctccaagga acctttcttg ttaaggaaga aagacaggaa  1380
ttttattacc ccagatagat acaacaaact actcttttgt gataaaacat acacataaac  1440
acaaacacac aaccccctcc ccaccagtat gaatataagt gtaaatgttt ctctttctac  1500
attcctagaa tggggagaga acatcctct atgattcata atatgccact ctaacaacat   1560
gaacatctaa tgcacaacac ataatgtctc tgatgataat agaatagcaa gtaacttctt  1620
aaacataaaa tggtattgtc aagtcaaata ctcctaaatc taatccatat taaaaatatt   1680
tataaccctg aaatatatgg gtgtttatct aagtagaatc tccaactttc aggaaactca  1740
tttatttctt acgttttgcc tctgcagagg aggcaatttg ttaggaaagt ttctgcagct  1800
gctgaggctg ccataccatt ggtactttcc agataaagaa ctgcagcctc tagggcagtc  1860
caaatagcac cctcctccaa tgttaatctc acttcattat cccatttat aaaaggtcac   1920 aactcttttt atgtcacact ttggtttggg cacattttct tacatttaat ttgacacaat  1980
ataagaaata catgattatt cagagaactc tttcaagcct gtctcaaaca agtataattt  2040
attgtcttaa ttactgaaga atgggagaat gggtgtgcat gaaacacaca atgtttgttc  2100
acacaaagtg aactatcact ttgttctccc ggagttctg ataggtctcc ttacatagaa   2160
cgtagagcag aaaaaagggg gccctaaata gtattagaat ttaaaagttt caaaaatatg  2220
```

```
tcagatatcc aaagaaggag gcataaccaa tgtcttatga atctatgaag cgagacgtgc    2280
taagttcaca gacatcttct gagcagctgc cacatgtgag aacataaag aagtaaaaca    2340
tgcttgttca caaaaaagca tacagcctag ttcagaccgt gaataatcat aagaaagata    2400
acactattca acatgcagtc ttcaaaatgt tttacctgtt ttaatggatt taatcctcac    2460
agaatcctaa ttatgttggt atgtactgct cttatcccaa ttttacctgt gaggaaactg    2520
aggcaggttg agacaataat tcgctgacag tcacatgtat agatagtact gaagacaaaa    2580
ttcagaccta gagagatggg ctctggagcc aatattatta atcactacaa tgattggggt    2640
tccaaaggat gctgcactct gggtttcata gtttggactg gtatagttag cgcatgtaga    2700
acagtgtact aatgagaata tgtaaaagtc aatgttatat aagttctatt gtgtttggct    2760
cattatctca ctgttgggaa ctttgctaaa gtagagtagg catccacctt ttgggaggag    2820
ttaagcaatt ctaccttttg cctgctacta ctcccatagg aagatctttt gaacccatgt    2880
ttgatatatt tccattgata gctcatttgt ttgcattaaa actagcaatc ctgtccttag    2940
gtgtttcttt ctaaaatagg tgtgttatag tactgaacta gttaacgcat atgccctctt    3000
gctcataagt gcaatagccc agaaaaggca atcattacat atttgttaaa tgaataaaaa    3060
cagaaatgcg acaagaaagt atgtatagaa tagatatcac ctctactaga ttagtaaata    3120
aatgtatgaa agagacatat ctggtttaca tttatacgct aaggaccatc atattccatc    3180
atcttacata ggtggaaatg ctgaaaaaag acgatttcac tatataaagg gacttttcct    3240
aaagaaggca aatctggaaa tggtatgatg gtggggggcat agaatactgg atgaaaaccg    3300
tagacccgca ccaaaagtat gggtgcaaga ggacagcaac agcctagagt aaaccaaagc    3360
aaagccaaag gcaaagtatt actagtaaaa gacaattcat attagtccac tgattctagg    3420
taacctctcg actccgtagt cctggatgat cttcaactgc attccagttt tacttcctgt    3480
acttgactaa ccccaatctc agtgttcccc agacagccat ctgaagaaag tacctgttat    3540
gaaccctatc gccttgaatg ccacatggga ttttgggcac tgttgcgtag atgacagaca    3600
ggatgtggat acccttttgtt caactggcag acaggatgcg gatactgttt gttcaactgg    3660
ttagaccaag agacaaatca ggcataagtc ttaattacta catatatctg cgtttatttc    3720
tagggacata gattataatg ctaactgatc atttagaata catgcttgaa gcttttccta    3780
tactcaagct ggcaagttca gttatgtttg tacattattt ggccccactt catgtgtctc    3840
accttcaaat atgtgcccct gttttgctct ctgtgtagaa tcaatatggc tacttcctac    3900
attagtttca actctgtttg gagatatata atttccctct ctttagaaac tttgattagc    3960
atgacggttg tagaaggctg tacctcttta tgtaggataa ttatgatgcc acatattctc    4020
tattcctttt atcttgtacg ttagcagtct ctatagtaca tatggaaact cactttgtgt    4080
cgcagcacca gagaatgaag gcatggttgc cgagtaagtg aagaataaaa gtgtgttgtt    4140
catctgcaaa tatgtgccct accctccaat gtttaactga aatttcctgt gttcgttttg    4200
gatagtctcc cagaaagagc actgcatttg ttttcagac caatctatcg acccttcat    4260
tgtctcttct aactcatttc ccgcaactgt aacagagaca gtcagttcct ctaagaactg    4320
aggattccca accttagagt ttttcactag ccatttattt ttactgctga ataaatattg    4380
gttctggtat tttatactcc ttcactaaat tataaaaatt tatattcctc tccagggatt    4440
ataaatattc ttaataggtc tgaaggcata ggtgggtcca atgattgcat tgttagcca    4500
aaaatcctgt atattcattg tttaaatata aaaaattaaa tatttgcaga taaataaatc    4560
actgaaaaga acagaagata gtttgtaaat taaatcagag aataccaagt atgcaacaga    4620
```

```
acctaagtta ttatgtgtaa aggtacaaaa atagccattt taggtagtgg ttctgaaatt    4680
tatttataca tcaaaatcac ctgacaggct atacaaagtt acagattctt ggatcccatc    4740
cttaggtaca ctgattctga aattcagtgg gaagtaataa gaaatctccc ttttaaaggg    4800
catgtgatgt aattctaatg cagaattgtg tttagcaatc actactctaa agaagttttg    4860
tgattctctg atttgcctgt ggaatatctg tagcagggag cataaagctt cccagataga    4920
gtggggaaga acaaaattct aagaagctac agattacctg caaagaactg gtttccaagg    4980
aaaggggagg taaagccaaa atgagagaaa agattttctc agattacatt tgggcacaaa    5040 ggaattttc ttaaaatgca atttcctggc ttacattaag agtgtcctat aaagttaaga    5100
gacattcata aaggcttata ttccaactga agatattagt cactgactgt ggcgtattgt    5160
gctatgactg gaagagctga gtaagcaatc attgagaagg aagggctgcc atggaagatc    5220
tgctgttatc aaaatataag ccattcagca gcagaatatt gaggaaatgc tttgcaaagc    5280
cttagagtgt cacttcaaaa cataatccta aaccaggtcc ctgggatcag tcaaatcttg    5340
ttgaaatagg ctgtcaacaa gggaatattt gtttgctgtt agaatgttct cattgctaaa    5400
attctcaatt ttttacccaa agccttcatt tacattatgc aatccataat gtgtaagaaa    5460
tgaaaaaaaa taatctcaag actccaaaga tcctaaacaa gaggaagaac cattattagt    5520
tgaagagcta atcctacaca aaataacaaa tatgagcctt ctacaatcat taggaaaaaa    5580
atgggaagtc agtaacgatg tgattactca acaagtagtt gtacccagaa gcaaatatgt    5640
ttaagagaca tttcaaatgg gacaaagtta ttctgtcact aagaggagcc attcaaacct    5700
gggtatcaag ataatctgaa actataagtt tgaagaagtt actgtacagg gaagaaattt    5760
tgaaaaatca ggactttgct actctgacat tgatttatac ccttcaaata aaaaatactc    5820
cattaattac ccaatagaac acagccaaat aaaagcctca tgaaatgttg cttgaaataa    5880
tcatgaagag tagcaacaac tgagaaattt gggagaaatt tctttgcttc tttgagcatg    5940
tcaaggggag aaaaataatc atttgtttct gtacttgtca ttaagaacta tagacagtag    6000 ttaagttta ataagtaagt agttaacatt tatgcaatga ttcatttctg ttaaaatatg    6060
catcaactgc tcctttatta cttatcattg tcttcacaac agaaaatgag gctgagtggc    6120
cagaattgcc attgttttt aaatattact ttgattttca ctacccagat cttaaataaa    6180
caattatttt ctgcatagga aaaatcatga tgatgaatta acattggcct tgcctacttg    6240
cacactccac atgaactaag cttcaaatat cagcttctgt acttagaaaa acacagagta    6300
cagtgtgttg gttgggactg agaggatcat aataatgaaa acaaacggtc tgatcactcc    6360
agtttttttt tttgccactg cctattcaca gatatttgta agatggccaa tttgtatctc    6420
ctgactttct gttttatttt caatatgacc atgctaagtt actcaaatac gttactaaaa    6480
atgaaagagg attactaaat aacattgtga aattcaggat tgtttttat ttaattttt    6540 tgaggtgtca agaaattaag gtcttcacct tttctatatt atttgcttaa ttgataggag    6600
ttcataggtt tttatttggg attgtaattt acctactgtt gctaatgcta aatatttaca    6660
tggcatgttc aagttttta ttttacctgg ctcaataaca tagtacaata ctttgagcat    6720
catcatatta tgatgtgata tcactgggaa tttaagccaa gatctgtaga tgtgtcaaaa    6780
cgtatgtgaa ggtgttcagt gtggactgca tcctgacact gtgagccata tgcctgcctg    6840
gtagaaacaa ccctcgatta gaatccgagc ggactgcatt taaagcatgg tttgtatttt    6900
acaggggatt tggacaagtc acttaacctc tctatattta agttccctca tgtgaaaaag    6960
```

```
ggagatgata atgcctacat cagagacttg ctatgaggat taagtgaaag tgttttgtaa    7020
accatcaatg gccatataaa tacaaggaat ttttatttag taaggcatta gggtaaatgt    7080 attttagtt aattatgaaa ctccctgttt cccagataca ggtatatatt ttactacccc     7140
aacaatatct tttctgggaa aactaggtct tgggaagaaa tcagttgata gagtcccta     7200 actcaagaac tagtggcaat aacccctctt cagctcctga ggacaaatag gtccatgttt    7260 cattttccc tctgacacaa cacagccttt tcaactctca gatgaatttc ccagaaagtg     7320
tgccagaatc ttagaacaca actgctaaag acatgaagca attaaatatg taaatcaagg    7380
aaattacact gcactgatga cattcagcac tgtgtctgcc cccaccttct cctccttttc    7440
ctctctgctt ctattcccat caggactgag gctagagtga gagctccttc ttccactctg    7500
ctccgtgcta aatgtttttt attctcaacc acctgcccca ggccttctca tcaattatta    7560
atcaagttct atgaatatgt ataaaagcct gttactgggt tttattaaat taaaaaatat    7620
atataagaac attttctgtg ccatgataga taaattatta tatggttgaa gagaaaagga    7680
agaagaaata ataagtgtgg ctttttgttt tcattccact gatgatggca caaacatatt    7740
gagaccactg attatgcagg ttttttgtt tcaagtttaa tatcaaatgt gtctctaagt      7800
tcatattttt aaaggtttac attctggaca atggactatt ctggaatctg ctttcatttg    7860
atagacagga ttcttgtga ctgagagggc ataatgttgg ctagggagtg actggacagg     7920
ttactttgat atcactctag aaataagcct tcttactttc atgtgcttct ctctcattcc    7980
aaaactgtca ccaaccgcat gatgccctga ggcaggtagg tgatggggta aattcatgag    8040
ccctggagcc ctgtctactc tgtgaggtca ttggctcaaa tcactaatga ttttcacttc    8100 ccaatttct acttaggtg aaccttcctt tccaaagaga aacaatgtct cctctcatgt      8160
actatgaaga aggatatgtc tgtgaacagt attatggctt ttatcttatc agataggcct    8220
tccctgatca ccttctctca tgtggcacac ccttaacctg ctgttcttta tatgatatta    8280
tacttaccca tcctgacata cataaggatt tgtttaatgc atcttatttc ctgtaccttc    8340
tctaccatga atgtaaggtt aataagagca ggaattttgc cttctttatc caatgccaca    8400
caaaaattgt tttaaataga taaatgaata caaactataa agataccatt aaaaaattat    8460
tctcctacta gtaacatgag cttcggggac aaacaacttc tgtgtcctag caaactaatt    8520
aactatgata ggaccagtga aattatcacc acctcaccca atgttccttt actcccactc    8580
cctgtgtcct ataagtggct ttactgtaca tggacaggtg atcctggtgc acatgagctc    8640
tcaatccata tctcaatagt taagaaatta tgtgtcctaa taaaagggta cttaaaaatg    8700 ggatttatt ttgttttgct tgttgctat ttgttcttac ccatgtaata gtcatacatt      8760
tatataatat aaatttattt agtcaaaagt gtaggtaaaa aaaatagttg tggtttgtat    8820
tatctgtggt tttggtcatg tggcttgaat aaagatttaa gccatatgac accttcctcc    8880
cacacatctt cctgtcttcc tgcctctcat gtccttggtat ctcagccact tagcatttct   8940
aagcctcaga tattgttcc atacataaat taaagtgtcc agattagatg aacttcaagg     9000
attaatcaac aacaaaatct aactctatgg aagcaaccca ggaagaaaac agaattttaa    9060
aattattttc ttgctcacaa ctctcagttt ttgtttgttg ttattaaagt taatgtcaaa    9120
tcaatactta cattttttgt ttggaatatt ctgcttatt gcactattta ttcttcattc     9180
taaagaattt taaattaac ctccagaata gtgtattcgc ctaatgtgtt attaaaaaat     9240
ctaattttat agagtgccat ttaaacagaa atgccaattt tcagtaataa gggtcactat    9300
aacaatgttt aatgcctcag tgactttta tcagctaaaa tccccttaa acatatacgc      9360
```

-continued

| | | | | | |
|---|---|---|---|---|---|
| ttcctttatt | tcaaattcaa | gaatgaatca | ttacactttg | atgagcattc | catcacatca | 9420 |
| gacgtagtag | ttaaatttc | ttgttcaaca | gtctcattaa | tttatcactg | ctttcctggc | 9480 |
| ctccctgat | gtactcattc | agtagcggcc | attgtgaaaa | caaacagcga | tggatacaaa | 9540 |
| gctctaagtt | aggtgctgtt | cagtcttgga | agttgtacaa | cctctcatgg | ggtcgacagt | 9600 |
| atagaaaaat | aagtaggatc | tgcagaaaaa | tcactatact | atgaaataga | atgttccagt | 9660 |
| gccacatgag | aggtgcaaag | gaagtactat | catagagcta | ggaaagtaga | atcccttct | 9720 |
| gcccagagtg | attgggaagg | tatcaaagag | aaggtctgag | agaatgggga | aagatataaa | 9780 |
| aacgtataac | cataggccag | gccagctgaa | gcacagctgt | attcatgttg | tcttggatga | 9840 |
| tatgaatggg | agggatgagg | aaggcagatg | agaaagcttc | ccacacatct | tcctgtcttt | 9900 |
| ctgcctctcg | tatctaccat | aagtggtcaa | aaatgttaag | agattaagaa | tattgagaag | 9960 |
| gtgatggaga | gagagaggaa | gtgagatcat | ttggataaga | gagtgaagtc | gtaaatattc | 10020 |
| tctcccatgg | tttaaagagg | gtctgaatta | ggccctagag | actgaatttg | tcccagatct | 10080 |
| cctaggaaga | gcactatagt | cctccaaaga | acaattccac | agtctcctaa | gcccaagatt | 10140 |
| aactactgca | tagatcagaa | agcttatgca | atagaaagtt | ttcttagagc | aaattgcgaa | 10200 |
| tacatttaaa | agaaaatctt | gcttcctcta | catgaccttt | gactcaatcc | actgttgtat | 10260 |
| gtgtgtttgg | atgtgtgtat | gtctgtaaaa | taattctact | tcacagctac | acatgtatat | 10320 |
| aaacccacat | ttcaggcagt | agatagcttt | aggtaatggg | aatatttta | ataaatcaaa | 10380 |
| tttatgaata | aatcattgcc | aattccttgg | ggattactgt | gtgcacatgg | aactggtctg | 10440 |
| accctgagt | gtgagatttg | tcatcagcag | tggaaatggg | cctgaaagca | ggaaggcagc | 10500 |
| atagccttac | agagcacaat | gagaaatgag | gcaaagggc | ttcgaacatg | cagttgccca | 10560 |
| aagcagtcaa | gagagatgat | ttttcaatct | gacataatgg | aagtccctag | agagatccat | 10620 |
| ttttcattct | gacatgacta | agataataag | tcaaagtta | aaatacatag | tataaggccc | 10680 |
| aacacaaaga | aaacgatttc | tattttggaa | atggcaaagt | acaccctgat | atgtattggg | 10740 |
| ttaaatggac | attctttttc | tgagagaagc | agcccggtga | ctgtagctca | aaaaaataat | 10800 |
| ttttaagagt | agaagtcatc | aaaaaggaac | aagcaaaaaa | gtgctataag | aagtttgatt | 10860 |
| ctttgtggat | acttggagat | aatccttccc | tttgtgaaat | atgttcaatt | aaaaaaaaag | 10920 |
| atgattgaag | aaattcaaca | aacaaaaatc | tttgtggtga | tataagaaga | cctttatttt | 10980 |
| attatttatt | tatttatta | ttttgagatg | cagtcttgct | ctgtagccca | tgctggagtg | 11040 |
| cagtggcatg | atctccgctc | actgcaaact | ccactaccca | agttcaagct | attgtcagtc | 11100 |
| tcccccgagt | agctgggatt | acaggtgctc | accaccaagc | ctagctaatt | tttgtatttt | 11160 |
| tagtagagat | ggggtttcat | catgttggct | aggctggtct | caaactcctg | acctcaagtg | 11220 |
| atctgcctgt | cttggcctcc | caaagtgctg | ggattacagc | tgttcacaca | gttccatgtg | 11280 |
| cacacagtaa | tccccaagca | atgtgcaatg | attaattcat | aaatttgatt | tactaatcaa | 11340 |
| atttgggctg | ggaagaactt | tattttaagg | ttaggcttta | catttcatga | tcttttttgct | 11400 |
| agccaacaga | tgagagaatt | gtaagtgata | tcaatttatt | aaagtcatag | tagaccaagt | 11460 |
| tcaggataat | ttaattttt | tttttttt | ttttttttga | gacggagtct | cgctctgtcg | 11520 |
| cccaggccgg | actgcggact | gcagtggcgc | aatctcggct | cactgcaagc | tccgcttccc | 11580 |
| gggttcacgc | cattctcctg | cctcagcctc | ccgagtagct | gggactacag | gcgcccgcca | 11640 |
| ccgcgcccgg | ctaattttt | gtattttag | tagagacggg | gtttcacctt | gttagccagg | 11700 |

```
atggtctcga tctcctgacc tcatgatcca cccgcctcgg cctcccaaag tgctgggatt    11760
acaggcgtga gccaccgcgc ccggccagga taatttaatt ttgatactta tgaaccaaat    11820
atagaacaaa caaaatttgg tataataaaa tgcaataata agtcatgaga aatgtaattt    11880
tatattattt attttattga gaccactata gaaataaagg tgggaattgg aagagtatta    11940
tgaatatcat gactaaaggg agattttaaa agaattcttt aaaaagctga cacagtaaag    12000
ccctggacta cattcttatc tgagatgttt ggatctgagc cagattaatg aacattattc    12060
tggatgatga cataacctgt cctactacac ataatggctt tggggttatt gggttcacct    12120
cttagctaaa ttgatcttag tgtggtaata aataaaggt tgcctaaaat ttctataaaa     12180
aactcaaatt attataaatc tttaaattcc caattgatct gacaggaagg agtcaacata    12240
accatctatg agtagcttcc caaatcagca cctgttgcag acattttga gttttactt      12300 tttctctggg actcagctta gatcacagtg acaatcttat agtcccctcc tacatgtaac    12360
ttgtggaaca aagttcctcg gttgagggtt taacaagaca tcagatagat aagaacagat    12420
atttcctgtt gcatattaac ttgagaatcc tctacatata ctttgaaact ctcttcaaga    12480
acatgcataa tattcaccaa gcacatcttc cattatacta caacatgatt tctttagact    12540
atttaaaatt attaattctg actcattttt taataggatt tgtttatttc tacctctctg    12600
tttctgcatc tgcttatctg taaccttgt gggattat tttctccttt ctgtgacatc       12660
aggcctctct tccactcaga acacaattta agttcaggtc aacaaggaag tcttagcctg    12720
cttaactcat ctactactcc agctgttttt cattttatc ttctcaactc ttcatcattt     12780
tggtaaaaca caaatttgta tgggattttg tgtgtgctta agttatttg tgtgtgtgtg     12840 tgtattaaac accctataga tccccttctt tttgtatcat ccatgtgttc tacaagtcta    12900
tggctactca atatctaatt gaatgaagac agatagaaac accacacttc cgcttttata    12960
ccactcttta gaaacttaca gtcatctcta ttattattat atttgcctaa gaatgaaatt    13020
tctattgata ttttgttgat caattattca gtcagccctc tattgcagac ttttttttat    13080
gaacccagaa gctatagagt ttgtcccagg ctcagcatca cagaggtcat atactttccc    13140
tccattattt tactctgcta ccattagact tctagttaac acaaaaaatc tctcctgaga    13200
tccagtattg actacaatga tcttctgtat ccttagggtc tttctgagat gaaaggtcag    13260
ggagaattaa aacaggtgga tgtatccagg atcggagact ggaatgggtt agaactgagg    13320
gaagaagtgc ctccctctgc cacccatcca tacatggagg gatattctcg tgtagtcagt    13380
gatgtgaagg tgaaatcctg gcagagtttg tgtcctattt accttgacaa agggcagaaa    13440
aataaagatt cgtctctact gtgatcaaga gaaaatcccc tctttctac cctgtgagtt     13500 actcccactt attaaaaaaa aaaaaaaaca cataataggt acccaatatg tcccagaatc    13560
tataccctac aatgtaaaca gcaaatgtcc tcattgccct caggatgaat gtaaggattg    13620
catggaaggg tgctgtgata ctctggattt cagtgtggcc tcagtcaagt gtgaatggcc    13680
atccttgcca ctattcctcc accctgcaga catgctggtg aaagatgttc attttgtaaa    13740
aagtctgcaa agcttcagaa caacactaca ggcacttaaa taatatttat tttttatttg    13800
aaattgtgac aacaaaaatg agtgataaca ttttctgata gctagcagat acttccactg    13860
ttagtggtaa aaaaaagtgt tattttctgt tggggcagtg gtaagcatgt agaccacaaa    13920
gtttgaggtc tagaaggaaa ctgaatataa atctccttat agatggaaaa atgaaggccc    13980
tgaaagacag tgatttaccc aaggtcaaaa gaatggttag tgatagagtt cttttttggcc   14040 tctgtgttgc tgctccccag cccagtgttc tttcactaaa ataaccactg tcttttttgaa   14100
```

```
tatttattgc aggccagaca tactgcttta tgtatattac ctagataatt cttctcccca   14160
caaaagatag gaaaatagag accattactg ttttttaaag atgtggaaac tgagagtttg   14220
aaagatgaaa cttgcttaag gttacatatc atttaaaagc ccaaagcaga atttgatttg   14280
aggtcaacag accccaaagc cctaaattcg tgaaactagg ttacctgctc tgtatcagcc   14340
tattgagttt tggcttttttg agtacaatca acaagtcttg aaagaggcat catagactga   14400
cattttaaca tagttgtcta ggaaaaaatt acaggacagt ttagctataa gaaaaatagg   14460
atgtctctaa ttcctttctc actaaaggag ctatgtggat gctaatgtta tggactttgt   14520
atattgtttc ctcacagtca tttagtatgt tttactgtgg caggtaagga gttcttaact   14580
ctctctgcat ctaaaatatt ctacatacag aagagtgaac aaaactacaa tagtgaagcc   14640
atgcacattt tctaaaatca ttcaataatc ctttgctctt aatacaattt gttgcaaatt   14700
aggctttaca acttttccct ctgagtgact ctaactcact agtgtcaggt tggcatgtaa   14760
gtattatgtg cctgtgtgtg tatgtgtcat tttgagcatg tctaaaaggt gaccttgaat   14820
ttgatattct ttaaaatata ttattttgaa gttgcttggt tttgctcttt tggtccaagt   14880
ctgcatattc tcccaataag catttaattt atgttctaga ggaataattt ttttctggca   14940
cttctcactt atccctcaag attctcacaa cccttcctga ttctacatgg ttcttcctct   15000
catacaataa aacccacaac tttgttttgc agacaccact aactcttcag atccatgagt   15060 cattttggg tcctaatccc accttggaaa atattaccat aaggctttgg ctcagagggt   15120
cattgtgtct tttaaactgt tttttttttt tttttttcaa gacagggtct cacttttgaa   15180
ctattttacc aggcagctat ttccaaagac cttgtgtgtc tgcaaatcat ttttcagatg   15240
ctctcatttg tcatagaagt cacttttattc ttattgtagg cttgctttca gatactttct   15300
tatttctctg taatgtcatt ctatcgaatt ctcaaaaata cacaatgacc cactggaaaa   15360
taatagtgct aactcaaacc gctctctgcc actcaccatc tttcctatct accttaagtt   15420
gctttattta tggaatactc tgtcattagc tttcagggct tttaagatat gacaacccctt   15480 tgaaaaagat tttacattca gcaatttcta tcattctcat acaaaagtgg gaagtgactg   15540
tggagatatt gaggcagaat gggccagtga caaaacaagt agattctgga gtcagaccaa   15600
ctcctggtgc aagtacatta gccattagac tgtaaagcaa aaacaaaatt ctaagccccc   15660
caactgactg gataggcccc tactgtcagt caagggattc caaagaaacc tgaaaaacta   15720
gttcaggcca tgatgggaag aggaggttgg acatgcctta ttatactttc ctcccttttgg   15780 aatttaggca caactgacta ccattaacat taaaactgag atcataagac tgacaaaaca   15840
gactctttgt agcaataaga taccaaattc taacctgact ctagtataac attacatgac   15900
agagtaggcc ctgaaagaaa taaaaagatt ttactgcaaa aaatatttat ttgacctgca   15960
aagccatctc ttgtggggaa aatttacact gtgtagacaa tccccatctc tttccaggtc   16020 ttttttctaat cctgaagaga ttagcttagg gtctagcatg gtttaaaggt ctgaacagga   16080
aacatttgcc atctgttttc tctaagggtg gccacctaca agatgtcatc tacatgatag   16140
gaaccttggt ctctacaacc ccttatctta aaccagatac cctttctgtc ccatctattg   16200
cctctaaggg tggctaccta tgagacttca tctacataat aggaactttg gtctctacaa   16260
cctcttatct taatccagac actcctttcc actgattcca ggtctttaaa taataactta   16320
actctttcaa tcaattgcca atcagaaaat ctttaaatcc ccctatgact tgtaaacccc   16380
ttgctacaac tcgccccacc tttctggacc aaaccaatgt atgccttaca tgtattgatt   16440
```

```
gatatctatg tcttcctaaa acatacaaaa ccaagctgta acccaaccac ctgatacgcc   16500
tgagcacatg ttctcagggc ctcttgaggt tctgtcatgg gtcatagtcc tcacatttgg   16560
ctcagaataa atctcttcac attctttaga gtttggcttt tttcatcaat aagaccttgg   16620
accatttagc taacctctca gaatttcact atctgtaaaa tgagaagaat atcttcactt   16680
cctatagttc ttgggataat aatgtgcaca aaccaccagc agctcttgtc ccatatgaac   16740
tctcagttca tcattaatag cctgttttc  taattcagat aacatttgaa aaatgtgcaa   16800
actattgttg catgtgacta tagttcattc atattgactg ctagctatat actatagttt   16860
attcttcagc tctcaatata ataggaaact tggatgtttc tagattttta attatgatga   16920
acactcatat acacacacac acacacacac acacacacat atctgtatgt acatatgcat   16980
gaattctctt agttacttgg aggttgggtt attgagtcat caggtatgta aatgttcaat   17040
tttacaatat aaagctgact tctttttga  agtggttaca ctagttcaaa tgcccaatga   17100
caatatctaa aagatctaat agatcatatc cagtacgtga tgttatcaaa ctctcaaatg   17160
tttgccattt gaataggttt aaagtggcat atattatcat ggtcttcaat tgcatttctt   17220
caatcattaa tatttaatat atttattttc catagcattt cctcttttgt gaaatgctgt   17280
tgtgtttcat tttaacccag ttttttcttt aatgatatgc cttgtgtggc agatgtctaa   17340
aaatttgact attttggca  tagcactttg aaatctggga gttatttta  tggagaaaaa   17400 ttttcaaaga agcattatga aggcattcac tgaaactgtg tttgtaataa caaaatgcag   17460
taaataggct aaatgtgaaa taatgaaaa  ttatttaaat attttatgca aataaagagg   17520
aatactgaca tataatacat tcaattataa tggtggttat atatatggag ccaaagaaag   17580
atgctcacaa tatgatccta agagaaaaaa aaaagctggt aattaatagg ttttgtctct   17640
gaataaatga atttaaagtg gcattttaaa aaatctattt ttgttatttt actaaactaa   17700
atttaattat gaagacattg aagataaatc tatactatag attttaaag  acagaaaaat   17760 cttagataat ttatctaaag gcacatagct aatgataagt agaacagcag ggtttagaac   17820
ccaaacatcc ccagagtacc ggactctaag catttatctt ttattcagtt cgctggggtc   17880
ctgcttcaag aatgttggta tctgtgtcct gatcaattgt taacctttga aatggtggta   17940
agagtggcct cttcctgctt gtcagtgata actggatgta tgggcaagaa ggaatatcat   18000
ggaatgataa taaattaggg gttagggtgg atgagaagca atctattact gtgcatatac   18060
ttaatctaaa atgaagggtt aatgtacagc caatctagga aaagggactc tttcttgcag   18120
tcctcagata ttttctgata taagaaaga  tttgatatta gcataattat aaaggtcatt   18180
gctccatatg gtattttta  gtagtctgat tagtaagact atcattaacc tagtatttgg   18240
atcacatgac tgggtgtaaa acaaccactg gaataataaa catccaggtg ctttaatttc   18300
aatgtcatta aattaaattt tactgttttt tactatttt  tcgttattta ttctcatcag   18360
tctctattct tcatgtcctc ctcctttctc ttaattgtac ataaaattct aactttggtt   18420
taaaatattc ccctgataac tcctgattaa aacacaataa aggccattta agggtgagca   18480
gaatgtaaag gtgactaggt aaccaaagga gcattaatct atcctcagtt aaaactgtta   18540
agcctattga aaacaatttc tcaaacctag cagaaccttg gattacagaa tagtaagggc   18600
aagaggagtc aaagtttatt tttaagccag gacctaaata ttgtctgagt caaggtagac   18660
ccaaggagtt gaagggacat aaagggaaga cagctggaat gtcatgcaga gtgtagaatt   18720
taaataccga caactactat gagctcttcc tatggtccca attttcctat tattatttct   18780
atatcttctt agtttatctc cttaatttta gcagtggcaa tggccggaac cctcatggct   18840
```

-continued

```
tctgccactg ctgctgcata taaactaaat atttggtctt tttctaatac atacacaaca    18900
attgtctatt cataaataac tgaggacaaa gtaggatgca tccttataga ctctatttaa    18960
taaaaaatat gttaaaaaca tgtagctctt ataagccatg tagaaagtat ctagaagact    19020
tcaaaagcat tgtgttttca caggcctaaa tatttgtcga caactaattc cttactaaat    19080
tgtccttggt ttttcttgct agaattgaat gacttaagca catttgttgc ttacttttat    19140
caagatcttt taatgattaa ctaagtcttc tcctcatcac tgaaaaccc caagcccatc     19200 tatctatctt tgcctataat tgcccatgtt tagagcaaac cctcagcaac ctgtttacta    19260
tattcatgag ctcaaaggac tgaccacttt taggtcagac taattttgtg ttttaaaatg    19320
agactgtcct gctgggatat caaaaaatgt tagtgaaggg aagaaggata gcagaaagat    19380
ggcagaaata ggaagcccca accttcgttc ttccacggac ttaacagcaa tatataaacc    19440
aaaatgcctc catgaagact ctagaagcca gttaagaagt ctcagtaccc aaatgagcac    19500
aaggccaaga acagctacat taagatgtat aagaaaaagt catttattc tacctatgat      19560 tgccctcct ccaaactggc acagtttggc atgattgaga aaaagtaccc aattttcagc      19620
ccctccaggt ggaaacagaa tagtagaaca tgcattcagt gttttggttt tatggggagc    19680
tgagtgaggg agtaatttct gtcttctctg actcagggtg ctgatggaaa tgccatactt    19740
tggatgcctg agtgctgctg aaaaccttg atatggaaga gtgacctctt cctgtatatc      19800
agtgataact ggatgtatgg gcaaaaaaca atcatagaat gataataaat tagggagtgg    19860
gtagatgaga agtagttttg ctgtaactgt tcatgtcctt actctaaaat gaagagttca    19920
tgtacagcta atctagggaa acctgaagaa ccgcagacag acaccagagg aagcaaaaga    19980
ttatgagctc ctgaaaaaga aaatggcaaa catctctcat tggataggag ataaagtaga    20040
tgttaagtcg gaaactgtca cagatgcaga gaagggcatt acataatgac aaaaagacca    20100
attaaccaag aagatataac aatcataaat atatatacac caacatcaac atcagacacc    20160
catatatatt gaccaaacat tcacaaaatt gaagggaaaa atagagagta acatggtaat    20220
agtaagagat ttcaatactt cactttcaat aatagataaa caaccagta agaagaaaca     20280 taaaagaaag gaaaggaatt gagcagcact gtagaccaat tggatccaac aaacacatac    20340
agagcactcc agccaacaac agtagaatac acattttcct taagagcaca cagaacacta    20400
tcaggataga tcacattagg acaaaaacgt gtcttaagaa atgtaggatt aagttagatt    20460
aaaatcattc caactatatt ttataatcac aatggaatac aaacacaata gagtaccatt    20520
cagccataaa aagaatgaga tccagtcatt tgcaacaaca tggatggaat tggagatcat    20580
tacattaaat gaaatgagcc aggcacagaa agacagacat cacatgttct catttatttg    20640
tgggatctaa aaatcaaaac aattgaattc atagacatag agaatagaag gatggttatc    20700
agagtctggg aagcatagtg gggagctgtg gtgggtggag tgggaatggt taatgggtac    20760
aaaaagtaga aagaatgaat aagacttact ctttgatagc acaacagggt gactgtaatc    20820
aataataact ttactgtaca ttttttaaata acttagagtg taactgtaac tgaactgttt    20880
gtaactgaaa ggatacaggc ttgcagggat ggatatctca tcctccatat atatatatat    20940
atatataaaa tatatatgta tatatataca tatgtatatg tatatatata cacacatata    21000
gtagatatat atgtatctac tatgtatgca caaaaaaata gaaattaaaa ttttttaaaa    21060
aatgaatagc aaaagcaaaa ctggaaaatc cataaatatg tagaaactag acaatatgct    21120
cttgaacagt taatggatga aagacaaagt catgaagaaa attagaaaat atcttgagac    21180
```

```
taatgaaaac aaaaacataa catactaaca ctcctgggat gcagcaaaag tagtactaag   21240
agagacattt agagcagtaa acacctacct taaataggca gaaggatctc aaatcaacaa   21300
tgtaaattta cacctctaga aagtaggtaa agaaggacag actaaaccaa aagttagcaa   21360
aaggaaggaa ataataaata tgagagcaga aagcaacaaa atagagaaca gaagaataga   21420
aaacatcaat gaaattaaaa gttagtgttc ttaaatcaac aaaattgaca aacttttaat   21480
gaaactaatt ttattttatt tttgagatag agtcttgttc tgtcacccaa gccggagtgc   21540
agtagcacca tcttggctca ctgcaacttc tgcctcccgg gttctggcaa ttctcctgcc   21600
tcaacctctc aagtagctgg gactacaggt gcacgccacc acttccagct aattttgtg   21660 tttttagtag agacagggtt ttacgatgtt ggccaggctg gtctcaaact cctgacctca   21720
agtgatccac ctgcctcagc ctcccaaaat gttggaatta caggcatgag ccactgcacc   21780
tggcttaaac taactttaaa aatatagaga gaagatgtaa caaaaatcag aaattacaaa   21840
aaaaatcaca actggtgcca aataagtaaa aagagaaaa gagtactgtg aatatatgcc   21900
aacaatgtgg ataacctgta aataatggat aaattcctag aaacaaagtg gaaaacctga   21960
accaacctat attaagtaag gaggttgaat cagtaatcaa aatctcccaa tgagaaaatg   22020
ttcaggccca gatggcttcc ctggataact ctaccaaaca tgataaacta ttaattcatt   22080
aactcattaa ttcattccat ggatatattg ttctattcat aaggcagagt cctcatgatt   22140
ctatcacctc ttaaaggcct acgtcttgat actgccacac gggggattaa gtttcaacat   22200
gaggtttgga gaggacatcc aatctatagc agaggccaaa gatttgtacc ctgaaaacta   22260
caaaattcta aaccaatta aataatacac aaatgaatga aaagacattt tgtgatcatg   22320
gattggaaga cttaatattg ctaaaatgtc catactactc aaggtaatct acagattcaa   22380
tgaaatttct atcaaaatct caatggcatt tttgttttgc taaaatagaa gaatacaccc   22440
taaaatttat atggaatctc aaatgaattc aagtagctaa aaataaaaat atcctaagaa   22500
agaataaagc tggaagtctc acacttgctg atatataaaa aaaagactac gaaagaagaa   22560
agatggagtt ctcacacttg ctgatatcaa aatatattac aaagcttcag taatcaaaac   22620
agtatggtac ttgcataaag acagacatac agactgatac agaatagaga accaataaat   22680
aaatccacac atttaaagtc aattgatatt ctataaaggc atcagaaaga cacaacagga   22740
aaacggtagt gtcttcaata aatggtacaa ggaaactaga tattcataag aaaaatccaa   22800
acataagacc tgaaaccaca aaacttctaa aagaaaacat aaaggaaagt tttataacgt   22860
tggataaggc aatgattttt tggatatgac accaacagca caggcaacaa aagcaaaact   22920
agacaaattt taaatatca aacttaaaac ttcctgtgca gcacagaaag aaaaatattt   22980
catgatctca cttacatgtg gaatctaaaa aaataaaata atatacaaag ataaataaca   23040
aaattttggc taccagggac agggtgggaa ggtgcaaaat gaggagaggt aatccagaga   23100
atacaaggta gcagatatgt aggatgaata attctaagat ctaatgtaca acatgaaaat   23160
ataggtaata aaattgtact gtatatgaga ttcacactaa attagtagat tttagatatt   23220
ctcgccacaa aaacagacaa aaagaaatgg ataactatgt gagatgatgg atatgttaat   23280
ttgcttcatt atggtaacct ttttactatt catatgtatc ccataacatc atgccatata   23340
ccttaaatat ccataatgag aattttttaaa aaaatacttc tatgtagcag aggatataat   23400
caacagacag aaaaggcaac ctacagattg ggagaaatta tttgtgaact atatacctca   23460
taaggggtta atatccaaat taaataaaga acaactgtaa ctgttggtaa gtatgtaaaa   23520
tggtgcagct gttatggaaa acagtatgta ggttcctgaa gatattaaag ctagaaatac   23580
```

```
catatgacct agcaattcca cttttttggta tatatcaaaa aaacctgaaa gtagaatctt    23640
gaagagatat ttgcacccttc atgtttactg cagcattact cataacagcc aagagatgga    23700
agcaacctaa ttgtccatca atgtatgaac agataaagaa aatgtgatat atacatacaa    23760
tgtaatatta ttctgcccta agaaagaagg aaatcatgtt ttctgctaca acatggatga    23820
aacttgggga cattatatta ggtgaattaa gccagtcaca aaaataacta cataattacc    23880
cttatatcag gtatctaaag tagtcaaact cacagtgaca gaaaatagaa tgtgggcact    23940
agtgggtagg ggaaaggtag caatgagtag ttattttttaa tgtctacagg gcttcagttt    24000
gcaaggtaaa aagtttctag agatctgttg cacaacaatg tgcatatagt taatattaca    24060
gtattctaca ctgaaaagtg gttaagatag taattttatg agttttttcaa cataataaaa    24120 aatgttatag gagaagaatg ttagcatagt gattatgagc aaaagttttg gattctgata    24180
aacatggctt aagtttggat acagtctcat actagccata gggcccacaa gtcacttaac    24240
ctcgtagcca ggcttcctat ttggcaaaat ggggataata actgttccta cctttactat    24300
tataattttt ttagataagt gtgaaacatt gagctcagtg ctaggcactt ggcaagcact    24360
caatcaacag cagttaaatg gtgtgatgag tattccagga agatggagta taaatgaagg    24420
actggggatg aagactggtg agttcctgac agctttgggg ttggtggaaa tgatgagtaa    24480
gtgaatattt gaagacttgt tacattcaca ttattgttga gcccagacct taggatgaac    24540
acctcaagct aacatcagat ccagagccca ggagtactgc ccaaagctat ctacatgtta    24600
ctatccatgg tgctgaatta tcttgggact atgccctctt gacttttttca taaacatcac    24660 agaacctgat cattctattc caaaatgcaa tttacaaaag ttcataacct attttttagaa    24720 acaaacggaa aaatgatgct tacagaaatc ccattttttgt tcccatatat catctgtaaa    24780
atttatttct gtggaaaaac ataacccagt gcactaaagt taggagagtg aaacaataaa    24840
gatatttatc gtgatccaat taatactggt tatgagaagg taagtacatg aatagatcta    24900
ctcatatcct cataatcaat tagccttctt aataaggcag acgtgttttt cagagaaatc    24960
agaaatcaaa tcagagtttg tattggtatc ttaggaaaaa gcatttcaag aataaatctt    25020
ccaaaaggca cacactttct cagttctact gataaaacaa aaacaaggat atgtaaagag    25080
gctttgctgc tcccttacaa actctcccag tttatactcc caaggaaaat aaagtctgcc    25140
ttatttcttt gcccacctgc ggtgaacttt aatgtttgtc tatatgtatt gaagaacctt    25200
aagttcattt cccccctggga tgaattcagc atatggtctg ttcctaaggc aaacatttat    25260
ttaaacttta aatctaaaag gaattctttc attttatttc tagttttgtt tcctttgatc    25320
ctgaaagtaa ttaactttca ctggcagcta attataagtg aagagaaatc agagtctata    25380
tggtcgtttg tttggtgcag tcctggcaaa atgttttcta attggaaagt ctctttgctc    25440
aatgcattcc aatccatttt gcactgtatt tattatccag gattcatatt ataaccatga    25500
cctttcatct aatcacagaa tctcacacag agaaaaaata attattttaa caaagagcca    25560
ccgtggctat aaaaagtgag agaggctggg agggagtaga atatgacagg agaagaacca    25620
catccaaaat ctcttcctgc tcttcactat cacagtccca tgacaacccc cttgtactga    25680
aaaacatata ccccacattt ggattaggaa attatcttct tcaaacttat acagaaatca    25740
gctcctgaaa aataatacag aaaagaagag agccataggt aaaaataatt gaggtcagag    25800
gtgctgctta ctgttccgtg ttaatactaa tcatcagaag catggaaaaa tttgaaagtt    25860
aatgaaccgc cagtcaaatg acccttacca taactcccat ttccctgaaa atgacccttg    25920
```

```
caagaactga caaatctttt tgtcatcaat tttttccttt tcaaaagaaa aaccaggcat    25980
ttaaaaaaat atattcattg tctgtttgaa ataaatatgt tacaaggatt taaaaaaaac    26040
acactgaata caatgaggga atttaaactg tattttggaa agaggactct aaacatcttt    26100
gcctttctaa acaactcctt aaccaaccaa aaacaatcag cattacagga aagcaacact    26160
cttaaacaga gataaatctt gacctgactg ctcttcttgt atgacatctt ttcatactgc    26220
tactgttaag aactggtgtg ataaagataa tctaaggggc atattatcca ccatcttcta    26280
caaatttgca tcaaattaga gcatcagaaa acaatatgcc cataccctcat tagcttgcat    26340 ccatgcagaa taacacctgt gagttatttc tatagatctg gcttaatcta gagtcaatgc    26400
atatgatggt aatctcccac atcttacaaa attattggta aaagcaataa tttccatatt    26460
tttaaataac caacataaaa atttccttcc aagtagagta catacaattt tgcttcttcg    26520
gaagaattga ataatataa acttcctgat ccattgcatt tgcttttct ctttttttt    26580 tttctttctt tttgagacag agtcttactt tgttgcccat gctggagttc agtggtgcag    26640
tctcgtctca ctgcaacctc cgcctcttgg gttcaagaga ttctcctgcc tcagcctcgc    26700
gagtagctgg gcttacaggc acccaccacc atgcctggct aattttttta tttttaatgg    26760
agacgaggtt tcgccatgtt ggccaggctg ttttgaactc ctcacctcag gtgatctgcc    26820
cgcctcagcc tctcaaaatg ctgggcttac aggtgtgagc caccagggcc ccccagccac    26880
atttgctttt attgtgctgc tgctaggaag cgcagggtaa agacattatt caatcacaat    26940
gactaagtga gcctagataa attgtatatt tacccaagct cttctagatg aatttaatt    27000 tttgagttgt attttaatag gttttgttgt gtagatttaa ttccccattt tgtgagaaac    27060
tatactgtaa aacaatcttt aatattcatt actggcttga gaatttaata aaatgaaaat    27120
gttttctact tttacttgga atttcatagg tgcatcttta aagatactga caccactcta    27180
cctccacttt taaggaattc attaaagtgc tgatcattag ctgaaagtat gataaagagg    27240
tgaaaagttt tgcacatgtt gcaagtgaga aaatgtcaca ctaatgaggc aaacatcata    27300
cattataagc ccctatgtgg gctactccat tattgagttt agatggttag cgaccttgtg    27360
aattaggcca attaatgcct aaaggttacg taagatagtc ttgatgaata agaaaacatc    27420
ctttcatact gctgggaaac taaacaaaag catatgcctt tattgggcat cgctaatact    27480
aacttcacat tccatgattt ctacttactt tcattttgtg gaagtacaag aaactgttac    27540
atagcaagtc cttatatctc tcaaaacaat ctcttccctt gaaaatgtct gcagcacttt    27600
ctcaattcca ctcagtcctc ttctatttct atctttcctt aaccatctgg agaagtcaat    27660
cctagacatc atgggatggt gttctgggat ttatattatt gcagatattt ataagaaagcc    27720 taattgatga gcctctttgt tcttatcttc tgtagcctca ctcgtaataa accgttaaga    27780
aaacagaaat tgcagaccag acaagacaca gcctttccag ccttggtaag acgtattttc    27840
tagaagagtg ccgttttct ccacaataga acttaaaag tagatccatc atttaatgtt    27900
aggaatctgt caagcatgaa ttttagcct ccatcaaaat tttcaataat taattccatg    27960
ggtttgggaa cctacatatt cccttctcaa ctatgtggaa aaaaattacc tctgaaattt    28020
gataaacatt tctatgtgca gtttattaat attaataaat tttataaagt ttaaacattt    28080
cttcatcttt atagaatgat agtatcattt taaagcttat tcttgtatga atgttaatct    28140 ggctcatttta caaattccct tcagttggat ttcttgctca agagaatttg tatgaaagat    28200
ggtgctgata tccaccagat tttgttctta ttttattga ttgttactt gttttgcata    28260 atgataggtt atgtgcagaa tagttcaggt tctttttctt aggttttttt ttttgccatg    28320
```

```
tacatgtcca gttgaaatat acatgctcac ttttatgtag tccatcctct tctatattga    28380
gctaaacgtg agttcatact gctgtcttca attctgatcc attaccacaa aggtcattat    28440
aacccctcc tccttatttt ctcacccttt caatgagttt gtttcataca tttataaat    28500
acttagaata tcttttcaca ttctgtattc catcctggaa ttttccaacc ttctaaagga    28560
cattttttaa aaaaccttaa aaagaagct tcacttttg tgttgtaaaa cactgtaggt    28620
tttgataaat gcttaatgtc ttctgtccat gattacagta ttgcatagaa tagtttttac    28680
cctaaaaaat tccctgcact tcatctattc aaccctcctc tgccctacta ctccagcttc    28740
tggtatccac taatttgttt cctatagttt tgccatttcc agaatgtcat atagttgaaa    28800
tcatatagta tatagcccttt tcagatagct tctttcactt aacaatttc atgtaagatt    28860
tattcatttc tctgtctctc tctctctctc tctctctctg tctgtgtgtg tgtgtgtgtg    28920
tgtgtgtgtg tgagagagag agagagagag acttgacagc tcatttattt taatcactga    28980
ataatgttgt aggtctggat ataccacagt ttttatccat tctcctttaa agaatattct    29040
ggttgctttc agttttttgga aactatgaat aaagctacta taaatactca catgcaggtt    29100
tcatatggtc ataaattttt taatcagttg ggtagtacct aggagagtga tcaggcccat    29160
gtggtatgac tctgtttagt ttttttaagaa acttgtcttc caaagtggtt gtatcattgc    29220
gaatttctat cagcagtgaa tgagagttcc tgttgttcca tgtcctcaac aatatttaat    29280
attgacaaat ttttgtcttt tagccatttt aaaaggtata atatgtacct attaaattaa    29340
atatttaatt aaatatttgg tatctcattg tcattttaat ttgcaactct ctcttgacaa    29400
attatgttga gcatcgtttc acattatttt ccccctgcat atttcatttg gtgaggcatc    29460
tgttttatgg tgtattttt tcattttaa attgagttgt tttcttatca ttgagtgtta    29520
tttgtatatt ttgaatacaa ttccttcaac aggaatgtgt ttcacaaatg ctttctccca    29580
gtctgtgact tccattttaa atttttaac agtgtattat ttaaagcatg ttttattta    29640
atatataacc atttaatata aaaataacaa ttctttcatg gatcattcta ttgatgtatt    29700
taaatacaca aggtgatata tattttagcc tatgttata ataatgtttt atatttat    29760
tactttacat tcaaatctat gatgcatttt gaagaaaaag gttcagctttt tcaccactaa    29820
gtatgatgtt agttgtaggt tttatgtaag tgttcttttt caaattgaga aagttccct    29880
ttattcctac ttcactgaga gttttgtca taaagaata ttgaatttt taagtgtttt    29940
ttctgtgtct attgacataa tgatatgaac gttcctttt catctgcagt gaattatatt    30000
gattttcaa tgttgaacta gtattggcat atctgaaata aacctcactt ggtaattata    30060
cttggttgaa tagtgtccc acaaaattca tgttcactta ggatctcaga atgtgtactt    30120
atttggaaat aggaactttg caaatgtaat caagttaaga taagatcata ctgaattagg    30180
gtgaccctga atccagtga ctctccttct aaggagagaa atatttgaaa acacacacaa    30240
aaggaagaag gctatgtcac agcacaggca gcattctggc tctgttctag agtaaggcag    30300
ctgcaagcca aggaatgcca atgattgttg acaaacacca aaatctaaag aaaggcaagg    30360
aaaatttctt tcctagaggt ttcagaggga acatgtccct cgtgacatca tggcttctat    30420
tctcggaaac tgtgggagaa taaatttta ttgttttaag ccactcagta tttaataatt    30480
tttaaaggca gtcttaagaa actaatacat ttctggtgta taattccttt atacattgtt    30540
ggattcaatt tgctaatatt ttgttgagga ttttgcatct atattcatga tatatattgg    30600
cctgtagttt ttcttacttg taatgtccgt atatggtttt agtattagaa taatgctgat    30660
```

```
ctcatagaat gagctaggaa gtgttccccc ttttctattt actagaaaga gattgtggag    30720
aattggtata atttctccct taaatatttg ggaaaattca ccagtgaaac catctggtca    30780
tgatgacttc attattggaa agttattaat tattaattca attcatttaa tagataaagg    30840
acacttcaag tcatttttc  tccttgtgtg agttttagta gttcatagct ttcaaagact    30900
tggcccattt catctaaatt gccaaatttg ggggcataga gttgctcata gtatttgttt    30960 attgccttt  ctaatgccca taggatcagc aatgatgact tctttttat  tcctggtatc    31020 agtaatttgt attttatat  atatatatta tatatataac atatatatat ataatatata    31080
catatatgtg ttatatataa tatatacata tatatgttat atataacata tatataatat    31140
atacatatat atgtatatat tatatatgta tatatgttat atacatatat attatatatg    31200
tataatatgt tatatatatt atgtatatgt tatacatata tgtacatata tgtacataac    31260
atatatgtta tgtatatgtt atatatatta tatatgttat atatataata tatatgtaat    31320
atacacataa aaacacacat atatacacat aaatatatat cttttttggtt agcatggtta   31380 gaggcttatc aaatttatta agcttttaaa agaaacagct ttagatttca ctgattttct    31440
tactgttttc ctgtttctga ttttattgat ttctgttcta atacatattg atgttctaga    31500
catattgata tcttttattc tgcttgcttt aggtttaaat tacaaatttt tccccagttt    31560
tctaaagtgg aaacttaaag tattgatttt agatctttct tgttttttaa tacagtcatt    31620
taattctata aatatccttc ttagtgaata tcacaaactt tcataattta tattttcata    31680
taaattgaat tcaattgttt ttaaaatttc tcttgagatc acctctttag attatgtgtt    31740
atttcaaagt ttgttgttta atttccaaat gtatggggat tttcaattaa ttttagttca    31800
attccattat gatccaagaa catacttttat ttgatttcta ttattttgca tttgttaagg    31860
tgtattttat cacccaaaat gtgatttatg ttggtgaatg ttccatgtga actagaggag    31920
tgtgattatt ctattgttga atgaactagt caacaaatat taatgagatc aagttgatttt   31980 ttagtgttgt ttaggtcaac tatattcttt ctcactttct tcctgcttga tctattaatt    32040
actgtcaggg aatgttgaaa tcttcaactc tattcgtgga tttgtgtgtt tttccttttca   32100 gttctatcag ttttggtctt gtgtatttt  atgtgttgtt tctgcctgca tacatattta    32160
ggcttgatat ttcttcttgg agaattgacc cgtttgccat tattattaat gatatactcc    32220
tttattacta gtaatttgtc tccttccaaa gtctggtttg tctgaaatta atatggctac    32280 tccagttttcc tttcaatgaa tgctagcatg gttgctttat ctatccctttt attttttaacc   32340 tattagaaac tttatttta  aagtgggatt ttgtagacaa catacagttg ggtcttattt    32400
gtttgtctac tctgaaaata tctgtctttt aattggttta tacagaccat tgacatttca    32460
agtaattatt gatatatttg ttttctgttt tgttttgttt ttgttgctgt cgttgttgtt    32520
tttggtgggg agggacaggg tctcgctctg ttactaacct agagtgccat ggtgcaaaca    32580
tggctcactg taatcttgac ctgggctcaa gcaatccttc tgcctttagcc tcccacgtag    32640 ctgggacaag agacatgtgc caccacactc agctgttttt ttttcatttt tattattatt    32700
tcattattat tatgattatt attttgtaga gacagggtcc cactttgttg cccaggctgt    32760
gcttgaaatc ctgggcataa gcgatcctcc caccttggcc tcccaaagcg ttgagattac    32820
aggcatgagg caccatggcc agccaattat tgatgcattt ggattaatat gaactattct    32880
tgtaattgtt ttcatttatt gccagataat ttttccctcg tgatacctct ggttttaatt    32940
tcagttatac ttaaaaaaaa aaagattttt tagtggtttc cctagagttt acaacataca    33000
tttctaacta cttttaatttt accttcaaac aacattattc tgcttatagc tccagttcct    33060
```

```
ccttctcatc ttttgtgaca ctgctatcat acatttcact tatccatatg ctataatcac   33120
ccaatacatt attagtatta ttactttaag cagttatcca tatgctataa tccatacgct   33180
ataatccata tgctataatc acccaacata ttattagtat tattacttta aagttaccct   33240
ttagatcaat taaaataaga aaaaataaat aatttcattt tgtcttcatt tattccttct   33300
ctaatgttct tcttttcttt atgtctatcc aagtttctaa cctacatcct ttttgttctg   33360
cctgaagaaa atcttttagc atttcttgta aagaactggc aatgaatttt ctgttttttgt  33420 ttgtttgaaa aaataggcca ggcatggtgg cttatacctg taattccagc aactgaagcc   33480
aaggttggag gattgcttga gccaggagtt caagaccagc ctgggtaaca tagggagacc   33540
ccatctctac aaaatatttt ttttaaaagg ttagctgggc atggtggcat gtgaagattg   33600
cttgagatct gggaggtcaa ggcttcagtg agccatgact gtgccactgc attccagtgt   33660
gggcaaaaga aggagactct gtctcaaaag aaaaaaaaaa aaacaaaaaa accaaaaaaa   33720
aaaacaagga aaagtatgta ctttctttca cttttaatga atattttcac tggatataga   33780
attctaggtt gatgttcttt tcttttcaata ttttagatat ttccctctgt gatcttattt   33840
gcatggtgtc tgattagaaa tgtactgtaa ttcttatgct tgttccttat aatttgtata   33900
tgttgtttta tctttctctg tattatttca atattttctc ttttctttga ttttatgaag   33960
tttaaatatg ctaggcctca gggttgattt tagaaattta ttctgcctgg ggttctctgg   34020
gcttctggat ctgtggtttg tgtctctga taaattttttg aaagctctta gtcattatta    34080
ctttaaatat ttcttctgct tcattcatgc tttcttatcc ctccagttgt ccaattgcat   34140 gtattttta tactgtccca tagtcttgga tgttctgttg tgttgttttg ttttatttta   34200
ttttcccatc cttttcttta catttctctt tggaaatcct caagctctct aaatctttcc   34260
tcagtcacac aagtctacta atgtgttcat caaaaatatt cttcatttct ctcccagtgt   34320
tttttatttc tagtatttcc ttttgattct ttttcagaat tgcagtctct ctgattacat   34380
tacctatatg ttcttggatt ttgcctgctt tctccattag ctaccttaac atattaatca   34440
caattattta aaactctctg cacaattatt tcaacacata tgtcatatat aactctggtt   34500
ctgaaacttg ctttgtcttg ttaggctgtg ttttttttct tgatctttgc ataccttgta   34560
atttgtttgt tgaaagccag acacattgca caatagagat tgatgtaaac aggtctctag   34620
tgtgagtatt gatgttaatc tggctaggag ttgagatttt tttaatgttt tctatagctg   34680
taggatccag aggtttcaaa ttcctctgat gaccttgttt ttgttttccc ttttgatttt   34740
gggcttacta aaattaatat tcctcctcag aaagtttgtg tctcatagct cttctggcgt   34800
aattactata actcattatt agaatgccat agcctcttgg tgtggtggtg aggtggggaa   34860
tggggcacat cccatagtct cagtctttta gaaggccgta tttctgccct atgacttaca   34920
caagtgtttc ttcctgtata gcttcttctc cactccgcct tacatatgga gaggactgta   34980
gtgagaggaa taatttcccc tcacaccttt gggataaaac tctggtagtc ttcctactct   35040
agaggaagcc attttttatgg agaaggcttc ggggtcattt ctcaaggatt actcttttcc   35100 tcccctacc agagccacaa aggggtctt tcttaactct ttattgtgag aatctggcgg   35160
tttgctgggg taaattctgt gaaagacaga gtgtcttcct aagactacag cccctaggac   35220
tttctcactg tggtagtaat gcacattcaa cctctagaaa tttgtcaaaa ttcccattta   35280
attgttccta tcagttaatg gctgcagtgg cttctgctcc acgtaaacag atctcaatta   35340
tatctctctg gattctcctg tctttccaat tgttggagtg gaaatttatc ctgcaaactc   35400
```

```
agttttctaa tccgtccaag aaaagtcatt gattttcatt ttgtccagct ttgttttgtt    35460
gttaaaataa tggaagtgac catttccaag ctccttgtac gttgaagcta taactggaat    35520
ttaagctagg attttaaaac atctaatttt actacatgct tatgtgccag tggctttgaa    35580
agggatactt gaagagatac atgtccaatt caagtctgtc tctcaggaag ttttgttact    35640
ttctagagca tattgaaat actttgcact cctaccaatt tctataaatg gatcttgaaa     35700
ctgaatgcag gaaaaatgat cccttgaaac tagagaaggg tatgggcttg tgaccaatat    35760
aagcttaaaa gagagaaaac atgcgtctaa taggatttag tcttctgatt tttcctagct    35820
gcttttaatt ttatcagctg ttttatagca gttttatgtt attatattct ccctatattt    35880
tttattatct ttttcaaaa agagttgttg ctgattctcg taatttaaat gtgttatcat     35940
ttttgatgat tagaagaaac ataacacaaa acatgttttt atttatattt tcaaattttc    36000
ttatatcact agatttacga aaatacatct ttcaaaaaag ccattcattt attcattctt    36060
tatttattta ccaatcaaga atccagagta cctattatgt gcacagcttt aagtacattg    36120
gggaatgaaa agatgaatag ttttcaagca aaatctttat tgctgatata ttttaagaat    36180 tataaccta atgagaaaca taagacatgt attttttgtc ttataaggtt ttttcttta     36240 aaaaatacat tatagatcac cttaaaagga gaaaaatatt aatgcagtaa atcagtttta   36300
acgttgctag cctaatgttt acattattat tcttggtata attaaaaat actaacaaat    36360 attaacaaag attaaacaaa aatgaactta tctagatcta aggaagtaaa tggttcttga   36420
ctatttaggg ctttcagtga agtgtgcgca gcttggcttt ttcgaagaga atgcattca    36480 aatatggtat aaaaatatct gatttcaccc aactcatctg tgagaatcta gaaatgactg    36540
ctatctaaca aggcctacat aacatcttca ggaatctgtt acagcttaat tctcttttt    36600 tttctttcat tttctttttt ttattattat tattatagtt taagttttag ggtacatgtg    36660
cacattgtgc aggttagtta catatgtata catgtgccat gctggtgctc tgcacccact    36720
aactcgtcat ctagcattag gtatatctcc caatgctatc cctccctcct cccccaccc    36780 cacaacagtc cccagagtgt gatgttcccc ttcctgtgtc catgtgttct cattgttcaa    36840
ttcccaccta tgagtgagaa tatgcagtgt ctggttttt gttcttgcga tagtttactg    36900
agaatgatga tttccaattt catccatgtc cctacaaagg acatgaactc atcatttttt    36960
acggctgcat agtattccat ggtgtatatg tgccacattt tcttaatcca gtctatcatt    37020
gttggacatt tgggttggtt ccaagtcttt gctattgtga ataatgccgc aataaacata    37080
cgtgtgcatg tgtctttata gcagcatgat ttatagtcct ttgggtatat acccagtaat    37140
gggatggctg ggtcaaatgg tatttctagt tccagatccc tgaggaatcg ccacactgac    37200
ttccacaatg gttgaactag tttacagtcc caccaacagt gtaaaagtgt tcctatttct    37260
ccacatcctc tccggcacct gttgtttcct gacttttaa tgattgccat tctaactggt     37320
gtgagatgat atctcattgt ggttttgata tgcatttctg tgatggccgg tgatgatgag    37380 cattttcat gtgttttttg gctgcataaa tatcttcttt tgagaagtgt ctgttcatgt     37440
ccttcgccca ctttttgatg gggttgtttg ttttttctt gtaaatttgt ttgagttcat    37500
tgtagattct ggatattagc cctttgccag atgagtacgt tgcaaaaatt ttctcccatt    37560
ttgtaggttg cctgttcact ctgatggtag tttcttttgc tgtgcagaag ctctttagtt    37620
taattagatc ccatttgtca attttgtctt ttgttgccat tgcttattc aattcgaaaa    37680 gaggaagtca aattgtccct gtttgcagac aacatgattg tatatctaga aaccccatt     37740 gtctcagccc aaaatctcct taagctggta agcaacttca gcaaagtctc aggatacaaa   37800
```

```
atcaatgtac aaaaatcaca agcattctta tacaccaaca acagacaaac agagagccaa   37860
atcatgagtg aactcccatt cacaattgct tcaaggagaa taaaatacct aggaatccaa   37920
cttacaaggg acgtgaagga cctcttcaag gagaactaca aaccactgct caaggaaata   37980
aaagaggata caaacaaatc gaagaacatt ccatgctcat gggtaggaag aatcaatatc   38040
gtgaaaatgg ccatactgcc caaggtaatt tatagattca atgtcatccc catcaagcta   38100
ccaatgcctt tcttcacaga attggaaaaa aactacttta aagttcatat ggaaccaaaa   38160
aagagcccgc atcgccaagt caatcctaag ccaaaagaac aaagctggag gcatcatact   38220
acctgacttc aaactatact acaaggctac agtaaccaaa acagcatggt actgctacca   38280
aaacagagat atagatcaat ggaacagaac agagccctca gaaataacgc cgcatatcta   38340
caactatctg atctttgaca aacctgagaa aaacaagcaa tggggaaagg attccctatt   38400
taataaatgg tgctgggaaa actggctagc catatgtaga aagctgaaac tggatccctt   38460
ccttacacat tacacaaaaa ccaattcaaa atggattaaa gacttaaacg ttagacctaa   38520
aaccataaaa accctagaag aaaacctagg cattaccact caggacatag gcatgggcaa   38580
ggacttcatg tctaaaacac caaaagcaat ggcaacaaaa gacaaaacag cttaattctc   38640
taagcagtgg aggtttacat tttaaaagaa acaacaaact ttgttttttcg cagtggcaac   38700 cttgaacgct tttgaattaa aacctgggga tcctgtttat tggctttgag atttttttgct   38760 acaccactcc aggggggcact aagcacattt tctaatctcc ataaattaaa aaaaaattaa   38820
aataacacat ttctttttta ccttgaaaaa acaatttcca tcaacacaac aatttccatt   38880
caatttcctg gatacaaact gttaatagaa gtagggaagg aaaggaaagt gataattatt   38940
taaacatgtt aaagtgaaca attcatggtt taataattgc tgtgttttca caagaaagtt   39000
attctttgaa attggctttc acatgtgaaa taaaccacct ttagatgctc tatcttcatg   39060
cacggttttc ttacatttaa tcatttcatc tttaaaacaa aaatgacatc agaaataaaa   39120
cacagtctca gtactgttct tcagttatac ttaatgaaca tacaaaatat agacagggggc   39180 agaagagagg cataaaaatg atgataatat gatactttta tgtaccattt ctagtaataa   39240
gtttgttagc tcaggtaatt tggatctaac agaagaaata gtagcagctg ccatagcccc   39300
atctcaacgt ctcctggaag ggttgacata aaagactctt ggccatggtg gttagttatg   39360
ggacagaatg agccaagttc attaaaccat tccaaggaag ggaaagagaa tcactttcaa   39420
catacacata aatacgtgtg tatacacaca cacacacaca cactatatat attatatata   39480
tatattataa ttaacaagat gaggtagatt tttatcaatt tatttcttgg cttatcagca   39540
tctatcaccc tagttcaagt accagacgtt tgaggattct accccttttc attttttatcc   39600 ctgaatttgg gtgggctcca cttacccccct gatactagaa gtaaagcatc tatcttagac   39660
ctaagtttat tagttcattg cattctccct agagacaagt acgtgacaga aacacagcca   39720
gtgagatgca atggatcttt agctggaact accaccagag tgattctcat tttgcttttt   39780
ccagggcatt tgagaatgag tttatagaaa ctaagagacc aactcagaag ccacacattt   39840
gagaggttga gacaaagtaa ccaggtcctg atgagttatt tgagcatttg cctaaagttg   39900
tgcctgaagc caggcctatc cctagacttt ttagttacat gacccacac atccccctt   39960 tgcttgaacc agtttgcatc gaattttctg ttacttgaac cagaaagagg cctaaatagt   40020
actgaaaaaa tatatatata tctgaggaag agattatctt atcatggatg taagcagaca   40080
attttataag aattcaagag agctaaaaaa cagaacaaac attccagtga attttttgatt   40140
```

```
ttcctactca aagtttcatg tagagaaata tatacatcat ctggtgattt ttatttaatt    40200
gcattactgg aagctgttat aacaaaatat atgtgacttg atgacataat tacatgtaat    40260
atggatacca tggcctagca tctaaatgct aagattttaa aaactctttt taaaaaagaa    40320
ttctagctaa aagtttgtgc attgaaatct ctcttattct gtttctcatg gcctcaacca    40380
aatatccttt atgtgcttgt tattttgttt tgatgccatc aaatgaaggt tcaacctcat    40440
gagaaaatct tttgaaatgg tctcctgaaa caacacagaa tatgattcta gtatgagtat    40500
aattatgtac aacacagcag tggaaccaag gacataaaat aaaatagctg acaacactaa    40560
gaagtcataa tttcagcttg ttatacacac tctcatctta aggaagatga atcaaaattc    40620
tttgcaactt gcgtcatttc tgaatatgaa ggactgcaat atacaaagct aaatttatcc    40680
ttcctttaat ggaccatgca gctaattcca gcagatgaag actgcaatcc caatatccct    40740
ccttctgaag cactaaacaa aacaggcagg ttttgtgaac ttttgctgct tattttcact    40800
atgacttttc acatttcctt tggcagcttt ggcatggaat accttaagaa aaggttttag    40860
tatctaacat cgctggaatc atatttacct gcaaggttct aaaatgtgat gttcaaaaat    40920
gaaagctcct ttaactcccc aaaccagtca tatgccatct gtaatctgtg accggccaaa    40980
gctcaacatc tatgagaagc tgaacagctt ctctctaata cacccaccag cagactctca    41040
attctttggg gtgtcttaag aacaacactc tgaaaaccca aagtaggaaa aaatccatca    41100
atgtatcaaa caaaatttcc acctcactca tggctcatga ccaatatttt ttagtgataa    41160
tggataaagg ccaagaaatt ggccgatatg aaatccagct taaaaaaaaa aaagactttc    41220
tttgcactag gaaaataaag ccatattaca gaatgaattg acttaccatt ttaccatttt    41280
gttaaaagac attctgatga gatttagaaa gcagcaagac ttacctagaa gaaaaaagag    41340
gaaaaaaagg agaagatatt aaaacaataa ataagaaagg ataatagtga agacattttt    41400
aaatggattc taagatgaca aaaagtgagc acagaccacc tacataggag taagtcagta    41460
aaggagaaag ggggaaaata aacttcttta agttgttatt acctttatcg cacgaaagga    41520
taaaatacac aggaatcgag tgtttatgtt atataaggtg tgtaacagag cccttcatat    41580
tagcacaatt cataaggaaa ttacatgatt ttaatgttac ctcttagtcc ctgagaaatt    41640 gaaagtgac ttcacattac atacatttta aaaatattgg tgtactgggc atcagccata    41700
aagatcatca aattgtttta aaacccagg caatatgcag atgacaggga agaaataat    41760 ctccctacaa gcttggagtg gtcattccag gactttttgt tttgtttgtt aatcaagtct    41820
ctgtactctc ttaccattgt aataggctag acaagtataa acctttaagt ccgctgacag    41880
ggttccctgt ttccccaaag tggatgaagg gagaaaaagg aacaaagaat tgagtttcac    41940
ctctaaagag atcatatgat gtgaggtcag tttatgaag ttttgctgct agaagcatat    42000
gtggaatttc ctagccacct agacagttgt taccagcttt gtcctatctt ttgcagggag    42060
actgaggcaa cctcatacat ttttatattt tatgtttata ttaaatttcc atgttctctt    42120
tcattccctc cacctagagg gacttatctc ttcctaaatt ccctcttcta ctgggcaaag    42180
aagtaagaga agaatcagaa atgcatacag aaaagttaca ggctactttt ttcttgtttc    42240
ttcaaactga cctaaatttc taggtgttcc ggggatatac atatgcttac ctttcacatc    42300
acttcatatt aacatagtaa ctggtgcaag tggctaaccc ctaccccat aaagaccctc    42360 tttttctgaa ctacagttga gtgagtatta aaataaggac taaatcccca acatatttt    42420 ttaatcccag aaaacatatg tattactaat ttataatcaa agcccaggac atagcaaaat    42480
gcattgcgta aatgaatgtg ggcagggcta ggagaatacc taggactttg gatgcctaat    42540
```

```
ctagtaactg agtacacgtc gacacagtgc ttttctttta atcctgagta ttttctatat    42600 tcgttttag gaatgtttc aaaagtattt tggcatgatt tttaaaattc actacataac     42660
attttaacaa atattctttt ttttttaac gtcgaagtcg tcacctgaca tttgttatag    42720
tcaatcagta gggcaaacct ccaagtaccc ctgccatctt ataggaactg acaacagaga    42780
tttctgcagt cttattaaac agtccttttg caattacagg tacatcactc caggttagtg    42840
actgggaggt gcggtacggc agatctattc acgtaattat ctctctatga gactgtaaac    42900
acatgacatt tcttttcagt ctaaaatact gaaagcgcat tgttttagta acaacatcat    42960
gcagtttttc tgttggttag caagggcttc acctgctgtg aaattcctag atcataagtg    43020
aaagtctaac tcagagccat cagggccatg agtagcgatt tcattttag ttcatacagt     43080 taaattagtt atttacttac atgtctgtgt atgcctgatt cttaaaaact acggttattt    43140
gaatgttatt tagtcttgag cgacatacag taattggtac atgtatttgt tggtggggag    43200
agagataagg atcattctgt ccttccctaa ctttgaaaaa cacataatat caaaatttat    43260
ttctatactt tcagggtaaa taaatagtta tgcatttaa gccagtagga gaaggtttat     43320
tttcaagctt gtgttaagac atttggtaat aattattgga gaagtggata aatacttttt    43380
tccagatgat aattttatgg cagaaaattt ctctcagtgg ctactgctat cttgaatatt    43440
ttatatttta gtgctcaaaa ttcacgattt tggtacatca tagcgtgcaa catagtaatc    43500
atcacaaatc accaattgtt taagagtggg cactttaatt gctcattaat tccctaatta    43560
attgacacaa gccaatgtta atgttattta aagattagta tcagtcctag gggtttattt    43620
gggcttgccc tggggaatta attaggcaga tagctcaaat tatgttttct ctccaacttt    43680
ctcaggcacc agtaggctg ctgactgaca ctttgttctc tcatccagtg tacgtcgggc     43740
aggggaagaa tctaactaac acacagagta ccccacttca gagccaccat actcttctca    43800
caccaccaac agttccttgt catccacttc atgaagtcaa atctctactc tgtggatttc    43860
aaggcctgat ctgtcttggt ctatgactct caaatacatc cttctctctt gtgtctgatc    43920
tgggtcgtct attccacaca gcttaattta cacaactatg taaccatcac ttttccacag    43980
ccaggatttt tttctttcc tttgttttgt ttttgtgatg gagttttcac tcttgttgcc      44040
taggctggaa tgcaatagcg cgatctcacc tcactacaac ctctgcctcc taggttcaag    44100
cgattctcct gcgctttagc ctcccaagta gctgggatta taggtgccca tcaccgcgcc    44160
cagctatttt ttgtgttttt agtagagacg tgttttcacc atgttggcca ggctggtctc    44220
aaactcctga cctcaggtga tccacccacc ttggcctccc aaagtgctgg gattacaggt    44280
gtgagccact gcgcccggca ggttttttc aagtagttct ctatagtctt ccttctccat     44340
tcggcctttc tacatcccctt tcactcattg tgaatttcat tcttatcctt ctctaaagat    44400
actttgctct agccagatcc caatccacat cagctgcccc actctggcca ctcccagggc    44460
ttcagcctca tctcctgtca cttcctgcca cattcttcc tttcttccag gttcacagaa      44520
ctatttgcag ttcccaaaat ataccttgcg ctttgatgtc tatgtgtttt gcttataccc    44580
tttttgaaac tcaaaagtaa agtttattga ttttccaaag ttaatttagg catttattct    44640 ctattttcc ttaacttttg atgccttaat tttaaccttt atagcatttt ataataaata     44700
ctagtatcta gcatctcaga ctcctagaaa attgcctgat gcatagacag cattcagtaa    44760
atgtagagag aattaaatca gacataatcc ctattagatt ttgagttcct aagaggagga    44820
gctaagtctt attcattttt ggatcttggg tatacagcac agttcttggt ccagagctgg    44880
```

```
tataagatga gtggataatc aggaaaaagg aagggattat tggaaggacg gaaggaaagt    44940
ctttcatttt tggtacactt caataaatat ctgtcatttc taaattctgt agcttttaga    45000
gattcggtcc atgcttgttt gctttctgac tgagtatgtt gacaacaaat tatttaatag    45060
gaaaataggc acatctgcca aaagaatgga aggctggata tctcaggcat tgctaaagat    45120
ttctagggta gatgtagttg ttgaaaataa agacataaat aaagttgtcc tatttgtcac    45180
tggctcctca cattgttttt gtttacagta gattgaccgt aaaaataaac taacacccttt   45240 cagagctatg cactaccttt tttgctaaaa ttatctcaga gaattgagaa gatttgtttt    45300
gaatatatac attcccaaac tcttcacata actaccaaca tcttcatttc acatcataca    45360
gtaccatgca aaaaaagca aattcttttg attcttgatg tgaagtgctt tcaaatacat     45420
ttcctcaatc taaaaattac tctagaatca aaaacaaaga aaacaactgc ttaaagaaaa    45480
ggaagtgctg caaaaatgag aaatatgttt tattatatct tgattacaat aattagcagg    45540 attcaaaatag tggttttgct tttgtgtctt cttacgtttg tgtaagtcaa ccctccccac   45600
ttctttctct ctctctcctt tctctcttct aattctattt attgcaaaag tataaaatat    45660
gaggtgtaca taatgcatta gtagccacat gatgaactat ttggaactct gatttcatac    45720
tttcttggcc ttttaaacat cagtgacttt tttttccttt aaaaataact gaaagacaca    45780
atcccacaca cagtgggttt tgttatgaag aatagatcta cctccaaggt cttaatatta    45840
tagttttatc tcttttctca ccttctcatc tccctctctt actctttgcc atctcttgaa    45900
tccactctct gccctactcc tgagccagac tctatcaaac cccgacaatc ctcagaaact    45960
catcggttct tctccagctt tgctttccta tgaacacatt cttgtgccaa gcatggattg    46020
gtcttttcaa tattgtttgc tgtgtagcca aagtgcagag taacagtttt tgcaagtgta    46080
ttctacagga aaaataatga tcaaaatatt aataggtgtt ttcagaggaa aaataagttc    46140
tgtatatgtt ttagctaaat agtattattt ttgtcatatt cccaaattgg aagtcccagt    46200
acatattagc ctattacaat tctaagttat ttgcagtaaa gaatatagat gaagctggtc    46260
tcatttctat tttccaagtt tttggggcc atagtgattt ttttttaacc tgacaacacc     46320
tcaggaaatt tatggtttac agagcacaac attgtaaatt atggcaaagt aaaaaagaaa    46380
acactgaatt tcaacttgga aaatcagaat gctgttgcta atagtattag tagcaaatat    46440
attaagtatg tcaaatatgt caaatgctgt tgtaagtgat ttacatatat tagtacattt    46500
aatctcacat aaagcaaatt aagtaatatc attagctcca ttctacagat ataaagaccg    46560
agactcaggt aaattaaggt actcacccaa atttacatag cagaactgaa attcaaactt    46620
atgcaattag tctccagtct aagattttaa ctgcactgtt attctgtcgc tgttacctac    46680
taattgggta acctgtggca agctatttta cctctctaag tcaagctgtt tattgatcag    46740
acagattaat gttatctgat gtggctgtca taaggaatca gtatttaaca gagtcaaatg    46800
cagtgcctga aatatgcagt tggtactcat aatacttatt tattaaatga gactcaagaa    46860
ctctagattt ggttatcctc ctagctgtgt acacacagct atttgttacc tatcgttatt    46920
agaggaacag gcataaagct gtgctgagct gcttgacgga aaattcccac tctagaactt    46980
caactggatc tttagaacta atcattaatc ttggatttac ccaggttgat tgcccattgc    47040
aactcatacc acaggcattt cacgtactgt atgcattcct caaaccaggg caggggatc     47100 aggaaatgat ttaaacccgt caactgagga gccccaggag gaccatgcac tggctgccct    47160
gacattttac caaatgtggc tgtcctgtca tgatcttttc ttaagaatcc ctacgtaatt    47220
ccaaagctaa tattaaaata tacgtaaata cctctatctt cactctgtat cccttcactt    47280
```

```
ctaggctctg gctccatcaa ccattccatc atccttttga gtttccctgt tcctttcctc   47340
tctctctccc tccctctttt tccctttcac acacacagaa cactctgctc ccaaactaca   47400
tctgtgctac aactatgctg cccacctatg ccaatgtaca cagcaaagta cgaatttgtc   47460
tttactctat cagatgattc ctgcttcttc tatatttttt ccccttaaaa ccaaactttt   47520
tcaaataatc tacttatcat atttatttct ccaccaaaca ctgtcttcaa cctctgcaac   47580
tcagctacat tctcatgatc tctaaaaacc atgtttctca agacaacag catcttccaa    47640 ctagatgaat gcaatggact tgctcagtc ttgattctct ttggcccctc agaaactttg    47700
ttatgcccat atcctgctgg aacctctctt cttaatcaga tttcagtcac tacagtgatc   47760
gtctttccat catttcagcc attttgcatt tatctctctc actggctttc cctctatttt   47820
gtattttaaa catggagtga cccctgtggc tctgacctcc accttctgct ctttccatat   47880
tactctttca ctaggacatt atgtactcta tggctctaac aaccatttta tgcaaacggt   47940
gtgagaagct actaaattgt aactgtgagg aaagggatta tgtcattcat ctttctaatt   48000
tccaagctgt ttagcatacc accttacata taacaagtgt gtgtgtgtac atatacatac   48060
acagaaataa aagaacaaat ttttatcaaa atattacctt caggcatgga acatttatta   48120
actgaaaatg ctgaagcaaa tgccaggaaa tttatgttct acttaaggac tgtttggttg   48180
gttcatgttg ttctctttgg gaaaatattt gtgacaaaac tttataagat taaaaataat   48240
tgtccttcat tttgtttcct ctccacatgc ccttgcatct ttcaacttt taaaataact    48300 ccaggttgtt aattccatct atgtaattgt gggtgcaatc taaatgaaac taaactctac   48360
ccaaaatgag atagttaggg ttatcaatgt tggagatgca agaagagga atacaaatct    48420 gtggtatcat agaatggaaa ataagcttta aaagtcatcc acatgaaaaa catgaggtcc   48480
tccacaccat ggaataaaat atgtacactt ttgctattat tgtgagagaa caggaagtag   48540
cagtagttac aaaaggaaag tgggtcagag gagggtcaa tttcattttc tttctctcat    48600
gttccaagcc tagagtatct tactttggaa tatagcgaca tctggatttg ctccacttct   48660
atccaatcag taactaagtg gcactcattg caacactctc attaaagga cctgactgtg    48720 catttcccaa cacattcgta aagtaaaaag aaattcaaaa agttcctctt ttttttgac    48780 aaggtctcac tttgttaccc aggctggagt gcagtggcgt gattacagct cactgcagcc   48840
tcaacctcct gggctcaagt gattctccca cctcagcccc ttgagtagct ggaactacag   48900
gtgtgtgtta ccatgccagc tgcttaaaa cattttttg tagaggctgg gtctcattat     48960
gttgcccagg ctgctcttga actcctaggc tcaagtgatc ctccctcctt ggcctcccaa   49020
agtgctggga ttacagatgt gagccacggt gcctggccac atttcaaaaa atttatatca   49080
agaaacagtt ttaaaattta atagagtgct cgggcacagc taccatcatt tagcacttaa   49140
gcaactatta gtactagggt gggatgcact aatatttagc acagtaaaga attaaaacaa   49200
aaacctagaa cttcaggctg catgttaata agtagactat ctttatgtag aattgcttga   49260
aagttcagca agaaatttcc taatgtccca gaaaaagtgc tcattcaca cactcattga    49320 tttgcctcat tgtcacttag tttcagagaa aaaataggca tccactaaat atttagtttc   49380 tgtcttttcct cccttcccca gaacatgaga taagagtgct tcacaaggag gccatttttg  49440
tacaccagca tggaattcct catattgacc ctatggctga tcatacggct ttataaatgg   49500
gctcataact tgtcattgcc ttgcctcata attatttcta gaactttgta gagtcagtac   49560
cattagcctc ccttgaagaa aaaggaaagt tttaggaaag ttaaacaact tgcctaaagt   49620
```

```
cacatggctg attgatttgc aagggataat catgtttata ccaaatattc cattttgggc  49680
ttcttcccca aatcctggaa ttgttctagg tttccaaagt ggcaagatcc aagataccct  49740
gggcaagcct gaatatatat gcaaacagcc tcacacgtac tgtcacactc agtgcagaaa  49800
ctcttatggt agtaatagca gacaccaata taatgtatca aaatgttcac cttagaaaat  49860
atttgtcagt gttttttcac ttatgcgcaa atgaattaaa cttagtagct atgatttata  49920
agaaaagaac aagattgcat gcccataaag aaaaggaaat atacaggaga gtgtcttaca  49980
acttaccaag atacaggtat aatcaatgta ttagaaaaat tcaaatgata taccttgtc   50040
ttcaatacac actggtaggc acctccaact ggtacctgtt ctatcctcta agctcagggc  50100
agttggagaa ctatcactaa tggaagtgtg ggtgcatgag aagtaagtaa gacaacagct  50160
ccagtagagt ttgaagttat ctgagttttc tgattaaaca agtatttggt gagggcctac  50220
tacatgctat acattatgct aattattggt gacaaatgcc agtgaataaa ggccaaggaa  50280
cacaaccaat caaagacaga agcatattaa aaatcaatat ataaatttga tagagttgtt  50340
atgagagttg tgtatacaga aataagaggg aatgcacagg gatgagtgag ggaaagatac  50400
cacttggagt tggaagacct ggaagtgtaa tcctagagga aatgactggt ggagagaaaa  50460
gaagaagtaa atgaaataaa gataagggaa attgtaggaa gagcaaaagg agtatttggc  50520
taggagaaga ggcaggtggt agtgtttggc tagtgaagag aagggagaaa agaaagcaag  50580
tgcttacgtg tcagaggcct tgaagctcct ttgcaaatga tcacatgtcc ccatgtgtca  50640
aatgtgtcac actcagatag cattgcctgt cctcaaaaga ccactgatgc actctgaata  50700
aattcatgta attcccagaa atctgtctct ttgtcaagat atttggtcaa gctgtgacta  50760
aaaacattaa gtaatggaaa aaagaagagt ggtttagcca gcattgcaag ggagtctatt  50820
caaaaggttt attatcttat gagcagagaa gggtaaaaaa aaaatgaaaa aagacatcca  50880
aacttctgct aaatttgcac tcttaatcct ttaaactcca tttcacttat atctatatgt  50940
ggtagaaaag aggtactgag aggacagggt ggcaagacct tttatttgaa catttgctaa  51000
atcctcaatt atatttcact tctaatcctg tgtcattatg agcaaaatgg cacatttgga  51060
gaccatttag atatgaatgc ctgaagcctt cctatcagac ctgctgactc tttcttct   51120
tctcactctc ttttagtcac tacagccaat tatgttgaga tatgattttt ggccaggcaa  51180
tctagctctg gcatcagggg tcccacaata gcctggttgg agaccttcat ggcctctaat  51240
attattattt tttgggcagg gtcattgtga caatcataac tgggaacaaa tatccttatt  51300
cagcaaaaag agaaaaacaa aacagagcaa aacaaaacaa atccctatga tctaacattt  51360
agataagcct acaaatgtaa cacaaatcca aaaagaggaa gcttacgtaa ttaaaagtta  51420
aagttaattc ttgaaattgg tgaggataat taaagaatga aagaggccaa ctgtttgaaa  51480
ttactgagtc agatctaatc tttcactggg ctccatatac acattgcatt atgtatagtt  51540
taatgtgcaa gtcagtgata ccgttcacaa ttttactgt ggctcagctt acaatgtgcc   51600
atttggacct aggttatctt tcatctgtat ttttaagtgg aacctgtaac taacaatgag  51660
ccaagtgtcc tacattcctt gttctaagtt tgagtttctc ttgggcctat gcttctttct  51720
tcagcttcag ggatagaatt cagtgtaatg agaaacgctt tgtctacttt caaagtctga  51780
gagtccttag aaactaactt acgctggcaa ttcacagaga gctaattttc aatacatata  51840
tttgtgccca ataccagaag tcacaattaa atggtatctc tccatattct gtccccatcc  51900
tcaacacaca cagacatttg cagcagaggt tgtttagttg aatgacagaa gcagtccatt  51960
tgtatctatc tgtctagtgg tataattcat tttccgctca tactctaact aaccccaacc  52020
```

```
taacttaaga aaaaaaaaaa agaaagaaag aaaagaaagc agagcctaga tgctgttggc    52080
tagaatccag aatcctcgga ttagaaaaaa gggtgaaccg gggcacagta cagcctaata    52140
aggctggcag ccaacattat gcaaagctca ctggaaggaa gcaaagcctc cttggcaaaa    52200
cagtgataaa gaattagaat tttctgaaaa tagtaataag aactcaatac aaagacctga    52260
ccaattctag cacacatgga aggggtcaag aagaaggtgt tccatactaa ggatatgcaa    52320
aacctaaata atagaaggaa ccaagaatgg accagagggg caattaatct cttgctcatt    52380
tctgtttacg agttttaagc actgtgtata actagctgta tatataagct atctatgtga    52440
taaactgtgt gcacttctca ttacatgtat aggttgagtc tttcacaact actatatttg    52500
gtgttgtcac gaagtcctcc aataaagtat attttcagtt gggtgcagtg gctcatgcct    52560
gtaatcctag cactttggga ggctgaggca ggcggatcac cagaggtcag gagttcgaga    52620
ccagcctgag caacatggag aaaccctgtc tctactaaaa atatgaaatt agccaagcat    52680
cgtggtgcat gcctactcag gaaggctgag gcaggagaat tgcttgaacc cgggaggcag    52740
aggttgcagt gagccaagat cgcgccattg cactccagcc tcggcaacaa gaacaaaact    52800
ctgtctcagc aaaaaaaaaa aaaaaaaaaa aaagtatact ttcaggtgct gttatgggca    52860
gatacttagg ctgggtggaa ctttgtcaat agcagtaaag attctagtgc ccagagcagc    52920
aaaaccaggg ctgtaatgcc ttctacacaa cagataaagc cctaacaatt cctggctggg    52980
ttggtgtgta tgtgcttcta caaatatatg ttaaattgcc agtagaaagg aaaggtgtaa    53040
agttgaaaag aatgtcatat aatatttct gtgaacttca ctaagaaaat tggctttatt    53100
gccaagaaaa cacaccttat tattgatcga ttagaaaaca cctcttcaaa atctaaagct    53160
gatattaccc ttaggtggat aaaaagttta ggacaacatt attattttaa aaaaattgtt    53220
gtctagtatg aaaatagtta tgcccaagaa aattagatgg aaatataaag ctgtaagacc    53280
aagtgctaaa ttacgggctc acaatctatc taaaaatatt tattgattcc ttattctatg    53340
caagggacag ggcaatcctc atgtaacaca ggctttatac tctaagaaag ctggcaatat    53400
tagtgaggag atatgagaca catccaaaca taatgaatt gaagaaggaa agagattggg    53460
aggaggaaaa aaggtaaatt tagtgtggtg ccagtgagag ccatcgaagg cttttgagca    53520
agataaggat ataatgaaat gcctttagtt agattaatat ggaaagccac ttaagagaga    53580
atcactactc tagtcaaggg agggttggtt gtatagggac ttttttttt ttctatcaac    53640 caggtagcca catttgaagt ctgcatactt aaagtggagc ctcagcccag ggctgttctc    53700 acactttaa gccaaagcca atgctcttcc tcctctttct acttcagtct tcctgtgttc    53760
tccatcttaa tgttttccc ttcctggttg acttcaaaac acaacaataa aggactgttt    53820
gtgttaaact tgaggaaagg aatggcattc cataagtgtc atggcagccc ataaaataca    53880
gattctctac cttggattaa gatctgtgga atccttagag gtagagacgg tggctctatc    53940
ttcttgttgt tctttaatct tcagattcca gaacagagtt cggaacatgg tagggctaga    54000
atatatttgt gacagtcaac tagattcatc atatatttgg aaaaccaaaa agaaatatgt    54060
tggcatggaa taattggtaa ctgatgggcc catgctgacc tcacctgttt ttataaaaac    54120
ttatttcatt tttatcagaa aatttttacaa ttttgaact aagaagagcc tcagaaactt    54180
tcaggttatt tgttaaattt aattctcaaa atctacctgt agaagaaata gtatctttat    54240
tttccatatg gagaaactga gactacggaa ggttatgcaa ctcccttaag gcaagctagt    54300
aaatgataga actaggctgg aactcagcaa tccttttggt aagttttttt ttattattat    54360
```

```
atgtcatgat attttatat gatgtgtggg acattatata attaaggctg tttgagactt    54420
tctataattt gggagactct gaaataatgt aaaagataca aaattgtctt agctggatat    54480
gtaagcattt tttaaataat gtgatatggg tctggttcta gggttatagt ttatatcagc    54540
aaaagtatag ataaaatttc catgaaacct ctatccgtcc atcttggtaa tgccttctag    54600
gaaattttta ggttatctat ggaaatatcc tatgtccaca agttcttcct tttttaatat    54660
gctttgccaa ttttctatac atcctccttc atgattgcat ctcctttgaa aaattactcc    54720
tattaaacta aatttctctg tcactgcaag agacataaaa ttaaaaacta tctgtcttta    54780
atcatgccag gcttcttcct tgtctcctgg gctccattaa tcaataatta atatataaag    54840
aagactgaaa tccatttcaa tttcaaaggc ccaaacgttt cgctgattaa taaaaaattg    54900
tgctcacaaa gatggacgga tatgccatgg tgaaatgatg gaggacacag cattaccagg    54960
gaatagattt gcaggaccac atgtgctgtg tggcctacct gtacaagaaa taagccatgt    55020
ggaggaacaa ttctgcagaa tacctcccac caagcctgac atctctgcat gtaagaattc    55080
ttatccacaa ttatcatctt agtctatttg atttaccatt ctacccagag tcttataagt    55140
ggaataaaag ggttaactca tactctaaga atctactccc tgggcttaca aatatatcta    55200
gtttactgaa caattaatat tcttgttatt atatacacag aactgtagat actatacatt    55260
atgggttggt gaaaaccata gatatgaggc ttgagagaat aatatctggt ttctactaac    55320
tttctgatct acccagttta tgccgttgcc agctctctta acattctggt gccgtttgct    55380
gtcagcattg gcttctctat ttaaggagtt ttagcactaa ttgctgggaa ttcagtcact    55440
cttcaagcat cccagttcta cacaagtggg acctttccat ctgtgcaagg cctaaggtct    55500
atccttgcac agaaccatta atacagaagg ctcactctcc tattcttacg tcctacaata    55560
cctactgcag tttattccca agaactgact agagttctag tctctctgtt ttgagagatt    55620
cactttggt ctctccgtga tgtgtagcaa tgagaagaat tcttttagcc agtatctttg    55680
atagtataaa gcagtttcaa gtaaagaaat ctaccaggga actaaagagc atacaggtaa    55740
aaatggatag atatagaact ccttcttcag aaaagtccta aaagtgagtg aactcttaac    55800
actcctcata caaattctta gaggaagagt gtttcaccta cctcactggt tttacctcat    55860
aaggcctttc tctcatctgg ctgccattgt tgagtttaat tccacatgga gtgctcaaaa    55920
tcccagtgta ctcgtgcata gatttttctt cctatttaat taatccgagg ttctttcctt    55980
tattgtttct accatagcta gaattcaaat ctattgccta ccttgtatat aagtagagaa    56040
ttgaggaaac aagatatttc aggtcaggat tatggaatga gacatacata ttcacatagg    56100
tatttatgc tttttttgac ctagcctcaa acacaaaata tcgaagattt agggaactac     56160
aagagccttc aaggagaaaa tgatagcaca ttcctattga ggctcaacag gatgaataat    56220
aatcatatct aacatttaat acaaactttc ttggtacaag cgttttcata ggcatttaat    56280
atacattatc tcatgaaatc tatgacagat ctatgagcca gtactattac tttccacttt    56340
ttatgaatga ggaaatcaag tattagagga attaaaacat tttcccatgg atcacttgct    56400
cataagtggt acatctggga cttgaactca ggcagtaggg ctccagcaca catatccttt    56460
accagtgctc tcaacatcaa gtgaacccttt ataagggta gagctacaca gagccacagg    56520
ctccagatac caccctttgcc tctaccatcc aaagtgcttc tcctgtgcat acatagatta    56580
cattctccca aattaaaatc aacaagacag acactgatgg aatccaaagt aaaaattgca    56640
gaatctatgg gacatttgg tcattgatgt agagagtaaa taaaaatgtt tgaaaccaag     56700
acagatcttc atacttatat catgtgaggt aaaatgtaac tattggctga tctgaggctt    56760
```

```
cattctactg actacatgtc ctcttgattg atataatggc actaatttta gaaatgaaaa    56820
agggtcacat agatgcagag tattcaaata taactgttca agtaaatttt aaaggctgag    56880
catatgtgac aggcctgtgt tattctttt gccatctctt ccctcttgcc tgcactgtga    56940
agcttcaaaa acactgccaa tgcaacggca accctgctgc cgaggcccaa gacaaacaac    57000
ggcaaagatg gtagatgagc cagtgattac aagtcaataa caattttgca attatacatt    57060
ctataaccaa attagaaaca atgtcattaa gcctcaatgg caaaaaaatt aattaattta    57120
atataaaaaa atcttccttg tttgtccaaa gtaaataccc tgggaaatag cactatgtca    57180
tttggtaatt actacagaac aatataggaa tagatcatga ctggtgtcta gaaaaacagc    57240
aatcacattt tgccttctaa ttatggcagc actctcaaga aacacaggga gcagtgcacc    57300
ctgctgttac accacagcaa taacactcat taccccagta aatactatgg aaatgtgcag    57360
taacacacag gggcctccct gctgtgaggc tgtggcagaa tcactcatca ggctgggaag    57420
tatcactcga tcgtctttaa ttacttccaa aatatatgat aacctgccca cagttagaat    57480
gcggtgatat cactcgttac ttctccctcc ctgctcccct tttttttttt ttttttttgta    57540 acttactaag aaaccctgca gtagccttac tatagtggtg atgtattgta acttataccca    57600 atttaatcac atagatttgt gtgcttttgg ccaacatatg ctcccaatgt gaaatgagca    57660
caagaaaaat atgctcaaat actgttatct ttctagcaag atcccttttc tcacgttatt    57720
gagttgtggc aacactgttg taatcctttc ttttttattct ggaaattaga gtgataatta    57780
caccgtagtc cctggaatc cagagtactt gtaattatat ccagttacct aggaaaacag    57840
caatttcaaa cctattaccc acaggtatca tttatgttta ttgccctatt tgtgaagccg    57900
cttttactct gaattccaag tggcaggatg tttcactgag gtacttgtgc tccggaggaa    57960
gggagaaagg acagagggag gggacaatag gaagaggcct ctactccttt tcaggaggct    58020
taggtctgat ctctattaga aagggtttgt tcaggcccctt ttcaaatgga taaggcagat    58080
tatgggacta tgttttcctc acacagtttg gagacagggc tcaaagtttc agggttttgt    58140
gtttgacacc tcccattgtg ctcacttgtc tcaatgtgcc acaaatgcct gcagtaaggc    58200
taaactaatt cttgattatg actcaccctg gcaggtgaat aatagctttt taggacagca    58260
gtttcaaaaa taattaaacc taggtgttgc tattttcata agaaagaaga aaataactgt    58320
tatgccacag cattcatcac tttgatttgg acaatttatt ctaaacatca gtacttactt    58380
aagagaggtt ttgcatgtag ttattcagta agccattcgt attccaaaag agggagtgat    58440
ggatgtaggt ttccttctct tgctaatttt tggagtgatt tgtaagatta aatttttata    58500
aggaagacct aatcttagac ttacaaataa taatattgtg tactgaatat ttaagtcaag    58560
tactagttag ctgtaacaat aactcaacac aagaacgtta ttgaccccat gtatagataa    58620
agaaattaag cctctgagag gttaagtaat gtgctcatga ttattcagtt agaaaacagt    58680
acagccagga tttgatctca gttcattcaa gcctccgatc ttgtcctttt gctatactat    58740
cacactactc catcaggtgc tgcatctatt tctattggct tcaagttctg taatgcttct    58800
tgacatataa aaagaaaact tgctcagaat gtttaaatta tgaaaaaact tccccacaaa    58860
atgtatttcc cttatgaggg agaaagactc aggtactttt aagctgaaag tattagtagt    58920
tgtctgtctt ttcctttacc ctgtgttaac agccacttga agacatacga agccttcatt    58980
ttcaccccaa attgggcttt gggtcttatt caccatttat cacaaactat tctgaagaat    59040
gaaacagcat tggagaaaat gaaaacttgg gacttctaaa gtttaacttg ggagtctatt    59100
```

```
actgaattca agtattaaac cgggcaaagt cttcttgccc gaacgattaa ttaattaaag    59160
tcaagcattc attcatttt gtaaaataac attttatatg tatttttatt tttactgttt    59220
attttcacat accttttta tagaggtttg gtaatagctc cttttttgc actgatagag     59280 aaataagttc aacttcagta tgatccactt agtttctcaa acatgatat tagaagcata    59340 aatccaatgt attttaataa gaaaaaaaca acataaatgt gaacatatta cacacatttg   59400
tctgaaatct attgaggtac agtaaaaagt gtaattccag agttaaacac acagagttgt   59460
tttaaattac tttcatttaa aacacttact gcatgcacaa catgatttaa ctacagataa   59520
tagtactaaa atgatttctc taaggtatct tcagagatag agattgtgta aagatcacaa   59580
atctaggaaa gtgtctctac tttaccaaaa cagcattggt catgatatca ggtcatccac   59640
tggcaattgt gacatgggca ttttgaaagc agagcttggc attcagcagt taccagcttg   59700
ctagtcagag ggcatgtcat acagtctaag agagctgcat tcatttctgg tcaggccaca   59760
gatgcaggtt accaagcaaa tgtttcattg tcccctaggg taagcaaact gaacctccca   59820
ggaagatacg tctctattat tctgagaagg ctattattga aattagttaa gaaaaccact   59880
tatctcccta ttattaaaa atctgtcaat gtaaagatgg atggcattac tcagaatcag   59940
aaaatttgaa ttccaacact tgattatgaa acttggtagc tgtgggggc ggggcaaaga    60000 tggctgacta gaagcagctg cattcagagg cgccaatggg aaaaaaacat aaaaagcctg   60060
tgaatcctca caggcaacca aggtatccag gttctctcat caaaattgtc tagaaggttg   60120
atgtgaccca cgaagagaag gaagagcggt gttgtgccgc agcccaccatg agagcaggca  60180 aggggagctg cctccccca gccaagggag gcggtgagtg agcacactac cagggaaact    60240
gtgctttttc cttggaactg ggcaacccat ggatcggaag atcccacttg caaacccacg   60300
ccaccgggtc ctagaatccc gaaccctgaa tgcagattct tacagcctct cagctggagt   60360
ctgcttaagc ctatccaact tccccgcagg gaggggtgac cagcatgggc tgcctgacac   60420
tgccctgtgt ctaagctgtt tgagctcctt ggggagggg cagcatccag cactgggact    60480
cacaactacc taacaccacc cacgttaagc tccctgggtg ggggaagagc ggcacccatt   60540
tctatagctc caggttgcgc tttccctg ctggagccag aggggctgga tggcttggtc     60600
tcaagagttg tctccacagc ccaacacact ggctgcggca gtctgtggcc agagtgcctc   60660
ttcaggccca accccgaccc atccttcttc agtgggcagg gcttccctgt aggatctcca   60720
ataactccag ccaggggctc atggacagaa tttggatctg ccaggactga gcccctagtg   60780
ggaggggtgg ccacagaatt tgtggaccag cagacttagc ctgtcctcct ggtagttctg   60840
aggaatctgg gcagcccaga tgagtgaagt tctccccagc aaagagacaa agtgcttcat   60900
taaatgggtc cttctccccg ggccaccaa ctgggtgaga ccgtccaaca gaggttgtca    60960 gacacccat gcagaagcaa tcctactgac atcaggctgc tgccctacaa gatcagaggt    61020
cccagaagaa ggagcaggca cccatacttt gctgcttcc atcctccttg aatgacatct    61080
ccagggcgcg aatcagatgg atagggcctg aagcgaatcc acagcaaact gcagcagccc   61140 cacagaaagag ggaccgtact attgaaagaa aacgaacaa gcagaaattg acagtaacag   61200
catcaacaac aacaacaaca agaacaaaaa ggcctccaca aaaaccccat ccaagggtca   61260
gcagcctcaa agaccgaaac tagacaaact cacaaagatg agaaagaatc aacaacaaaa   61320
aaatgctgaa aacccaaaag gccagagtgc ctcttcttct ccaagtgata gcaacatctc   61380
ttcatcaagg gtgcagaact ggatggagga tcagatggat gaattgacag aagtaggctt   61440
cagaagatgg gtaataaaaa actctgctga gctaaaggag catgttctaa cccaatgcaa   61500
```

```
agaagataag aaccttgata aaagtttaga ggaattacta actagaatga ccaattcaga    61560
gaggaacaca cgtgacctaa tggagctgaa aaatacagca caagaacttt gtgaagtata    61620
cacaagtatc aacagccaaa tcgagtaagc agaagaaagg atattagagt ttgaagacca    61680
ccttactgaa ataagatatg cagaaaagca tagagaaaaa aaaaataatg aaaaggaatg    61740
aacaaagcct ccatgaaata tgggacttca taaaaagacc gaacctatga ttaattggag    61800
taccagaagg agatggggag aatggaaaca agctggaaaa cacacttcag gatattatcc    61860
aggagaactt ccccaaccta gtaagacagg ccaacatgca aattcaagaa atgcagagaa    61920
cactattaag atacgccaca agaagatcaa ctcctaaaca cataataatc agattctgca    61980
aggtcaaaat gaaagaaaaa ctattaaggg cagccagtga gaaaggccag gtcacctgaa    62040
aagggaagcc catcagacta acagcagacc tctcagcagg aactctataa gccagaagag    62100
actgggggcc aatattcaac attcttaaag aaaagaatct ttgacccaga atttcatatc    62160
cagccaaact aagcttcata gtaaaggag aaataaaatt ctttccagac aagcaaatgc    62220
tgagggattt tattaccact aggcctgccc tgcaagagct cctcaaagaa gaactaaata    62280
taaaaaggaa aaaccagtac tagccactgc aaaaacacac caaaatataa agaccaatga    62340
cactatgaag aaagtgcatc aactactgtg caaaataacc aaatagcatc atgatgacag    62400
gatcagattt acacataaca atactaacct taaatgtaaa tgcaccaaac acccctgtta    62460
aaagacacag actggcaaat tggataagga gtcaagacct atcagtgtgc tgtattcagg    62520
agacccatct tacgtgcaaa gacacacaca ggctcaaaat aaagaaatgg aggaaaattt    62580
accaagagaa tggaaagcca aaaggcagg ggctgcaatc cagtctcaga caaaacagac    62640
tttaaaccaa caagtatcaa aaaagacaaa gaagggtatt acataatggt aaagggaaca    62700
attcaacaag aagagctaac tattctaaat atatatgcac ctgatacagg agcaccgaga    62760
ttcataaaac aagttctcag agacctacaa agagacttag tctcctacac aataatagtg    62820 ggagactta acacttcgtt gttagtatta gacatatcaa cgagacagaa aattaacaac    62880
aatattcagg tcttgaactc agctctggat caagtggact tagtagacat ctacagaact    62940 ctctaccca gatcaacaga atatacatta ttctccgtcc cacatggcac ttattctaaa    63000
atcaaccaca taattggaag taaaacactc cccagcaaat gcaaagaac tgaaatcata    63060 acaaacagtc tctcagacca cactgcaatc aaattagaac tcaggataaa gaagctcact    63120
caaaaccaca caatttcatg gaaattgaac aacctattcc tgaatgactc ctgggtaaat    63180
aatgaagtta aaacagaaat caagaagttc tttgaaacaa atgagaacaa agagacaatg    63240
tgccagaatt tctgggacat agctaaagca gtgtttagag ggaaatttgt agcactaaat    63300
gcccacatca gaaagcttga aagatctcaa atcaacatcc taatatcaca attaaaagag    63360
caagagaggc aagaacaaac taatccaaaa gacagcagaa gacaagaaat aactaagatc    63420
agagaagaaa tgaaggagat agagatacga aaaccctcc aaaaaatcaa tgaatccaga    63480
agctggcttt ttgaaaaaaa taacaaaata gatcgctagc tagatgaata agaagatga    63540 tgaaaagaat cagatagaca caataaaaaa tgataaaggg gatgtcacca atgacccac    63600 agaaatacaa actaccatta gagaatacta taaacagctc tacacatata acggtaaaa    63660 tctagaagaa atggataaat tcctggatgc atacacccta ccaagactaa accaggaaga    63720
agtcgaatcc ttgaatagac caataataag ctctgaaatt gaggcagtaa ttaatagcct    63780
accaaccaaa aaaagcccag gaccagacaa attcacagct gaattctacc agaaatacaa    63840
```

```
tgaggagctg gtaccattcc ttctgaaact attccaaaca attgaaaagg aaggactcct    63900
ccctaactca aataaaaaaa aaaagagag agaaaactttt aggccaatat ccctgatgaa    63960
catcgatgca aaaatcctga ataaaatact ggcaaagcga atccagcagc acctcaacaa    64020
agttacccat cacgatcaag tcagcttcat ccctgggatg caagtttggt tcaacatatg    64080
caaatcaata agcataatcc atcacataaa cagagtcaaa gacaaaaacc acgtcattat    64140
atcaatagat gcagaaaagg cctttgaata aattcaacat cccttcacat ttaaaaactc    64200
tcaataaact aggtattgat ggaacatatc tcaaaataac aagagctatt tattacaaac    64260
ccacagccaa tatcattttg aatggtcaaa agctggaagc attccctctg aaaaccagta    64320
cgagacaagg atgccctctc tcatcattcc tattcaacat agtattggaa gttctggcca    64380
gggcaatcag acaagagaaa gaaataatgg gtattcaaat agaaagagag gaagtcaagt    64440
tgtctctgtt tgcagatgat atgattttat atttagataa ccccatcatc tcatcccaga    64500
aacttcttga attgataagc agcttcagca aagtctcagg atacaaaatc aatatgcaaa    64560
aaatcacgag catgcatttta caccaacaac agagagccaa atcatgattg aactcccatt    64620
cacaattgct acaaagagaa taaaatacct aggaatacag ctagcgagca atgtgaagga    64680
cctcttcaag aaggactatg aaacactgct caaggaaata atagaggaca caaacaaatg    64740
gaaaaacatt ccatcctcat ggatagcaag aatcaatatc atgaaaatgg ccatactgcc    64800
caaagtaatt tatagattca atgctattcc catcaaacta ccattgacat tcttcacaga    64860
attagaaaaa aaaactactt taaattgcat atggaatcaa agaagacccc atgtagccaa    64920
gacaatccta agcaaaaaga acaaagctgg aggcatcatg ttacctgacc tcaaactata    64980
ctacaaggct acagtaacca aaacagcatg gtactggtac caaaacagac atatagacca    65040
atagagcaga acagagacct cagaaataac accacacatt tacatccatc tgatcttcaa    65100
caaacctgac aaaaacaagc aatggggaaa ggatctccta ttcagtaaat ggtaccaaga    65160
aaactggcta gccgtatgca gaaaactgaa actggaacac ttccttacac cttatacaaa    65220
aattaactca agatggatta aagacttaat tgtaaaaccc aaagccataa aaaccctaga    65280
agaaaaccta ggcaatacca ttcaggacat aggcaaaggc aaagacttta tgaccaaaac    65340
accaaaagca attgcaacaa aagccaaaat tgacaaatgg gatctaatta agctaaagag    65400
cttctgcaca gcaaaggaaa ctagcatcag agtgaacaga caacttacag aatgggagaa    65460 aattttttgca atctacccat ctgacaaagg tctactatcc agaatttaca aaaaacttta    65520
aacatattta caagaaaaaa aaaaacaac cacatcaaaa agtgaacaaa ggatagaaca    65580 gacactttc aaaagaagac actttcaaa agaagacatt tacgcagcca acaaacatat    65640
gaagaaaagc tcaatgtcac tgatcatcag agaaatgcaa atcaaaacca cagtgagata    65700
ccttctcaca ccagtcagaa tggtgattat taaaagtca ggaaacaaca gatgttggca    65760
aggctgtgga gaaataggaa cacttttaca ctgttggtgg aatgtaaat tagttcaacc    65820 attgtggaag acagtatgac aattcctcaa ggatctagaa ccagaaatac catttaaccc    65880
agcaatctca ttactgggta tacccaaa gggttataaa tcattctact ataaagacac    65940
atgcacactt atgtttattg aagcactact tacaatagct aagatatgga accaacccaa    66000
atgcccatca atgataggct ggataaagaa aatgtggtac atatacacga aggaatacta    66060
tgcagccata aaaagaatt agatcgtgtc tttttcaggg acatggatga agatggaagc    66120
catcatcctc agcaaactaa tacaggaaca gaaaaccaaa caccacatgt tctcactcat    66180
aagtgagagt tggacattga gaacacatgg acacagagca ggaacaacac atactagggc    66240
```

```
ctaatggagg ttggagggtg aagggaggga acttagagga tgagtcaata ggtgcagcaa    66300
accaccatgg cacacgtata cctatgtaac aaacctgtgc attctgcacg tttcctgttt    66360
tgttttgttt tgttttttctt tagaagaaat aaagaaaaaa aaaacttggt agctgtatct   66420
ccttgacaca tgtctaggca ttgctgcttc atccttaagg tgataataat accctgaaca    66480
cctaaaatcg taaggctaaa gtagataaag gattgaggtt tagcagtttc atgtttcaaa    66540
cttttcctgg aaaaagtaca catttatctg acactaatga aatatgattt tggttcttcc    66600
ctacgctaca ccccatgaat tatatatatc aaaccacttc tgtaagttta attaatgaat    66660
tgcattatta atttatttt ttggtttgaa tgcttggtcc tctcaaagaa aagctgattt     66720
gaacccattg tactttgact cttaagtgtc aaaaataata ttcgtttgag tgttttcatt    66780
ttgactgtga gatgagagcc aatataagta tctctttcct ccacctcagt cccaccaatc    66840 ttcattttt aagtgaggtg ctgctatagt aagtttagaa cctcaccaat atttgctaat     66900
aattttaaga tcttcagggc attttaaata ctaatagttt ggggctagat gtttagtatt    66960
tatgtccaca gggtacaaag tctttttttag ctcattaaat tttgctttaa ttaatcctgc   67020
cacggcttta taagaaggt gcactctgct tcaggttaaa gcatgctgcc taggattat      67080 acgcccttc cttaggccat ggcatttgta cctattatcc atttcaggcc ccatttaac      67140 atagctagaa aaatgaaggg agaaaggaaa agtttagttg cttagttaca ttttatcaaa    67200
ataatacttt atttagttag ttagttagtt tgttttttttg aaacagagtt tcactcttgt   67260
tgcccagggt ggagtgcaat ggcgcgattt tggctcaccg cagcctccgc ctcccgggtt    67320
caagcaattc tcctgcctca gcctcccgag tagctgggat tacaggcatg tgccaccatg    67380
ccctgctaat tttgtatcgt ttttagtaga cacagagttt ctccatgttg gtcaggctgg    67440
tctcaaactt ctgacctcag gtgatctgcc tacctcggcc tcccaaagtg ctgggattac    67500
aggtgtgagc caccgcgccc agcctaaaaa taatacttta aaacaccatc acttccagca    67560
atatcctcac taccaccaag tcaaataaag agacaaaaat ttgtatccaa tcaaaattga    67620
ctctccaaat aataggcagt tgattcaatc tctaatagtc tatattaagg aacaataata    67680
acaattaact ttttaataga tttcaccatc tcaaaggctc acagcaagtc tcaaacatta    67740
tctcaattct tatattgatc ctatgaaata ggtaacgtac actatgccca ttttaaagat    67800 gaaaaaaat tgtggttcag aggaattaag tgacttgcct atggtttata caaagactaa    67860
ataaagagat acaatataaa tctaaatatc ccaatttcaa ctttaaatgt ctactaccta    67920
aaccgccccc caccccacag aaatggctgg aagtagatta atggaagtta cttgaccttc    67980
atttgattaa aaagaacata aaatactttg atagaaaggc ctaacactat tcccaaaccc    68040
aatgttccat ggtcttctaa aagaactttc tcaagtcact agcagggaat caatacttat    68100
tttctaaggt ctccaggcat tcccaagact aggttcttac atgctttcct gattgttgaa    68160
aggctatgct gtcttttgcc tcttctgcag tactttctta cataacatcc tctactttac    68220
tacatgtatg gtcaggtttt gatgcttgtt ctcctacagt gagtgcatgg agatcttgag    68280
taatgcagtc tataccacag gtggaaaact acatgtatag tacaatgatt tactttgtca    68340
ctactcaatg taatagtgtg gtttttaatg gacatctcta ttttcacttt ctgtgaaact    68400
aaatgtattt ttgtcagatt tctcaaacca aactcaagga agtaagcttt tcctgtctgt    68460
cttccatctc tccttatcag ctataatcaa acatccacta tatacaactc tggcttgttt    68520
attgatctta ttcaagtcat tacaatctct tgtaaagagc atctttcatg tgcaagggca    68580
```

```
gatgaccaag agagacatgc actagacatg ttaagagtac ccagaaagag aagatgggt      68640 gaaagactgt ttgtagaata aaagtgtgca tacagagata aaaactagag atagtcatca      68700
tagttaaagg aaagaaaaaa aatctatgac tgtagcaaat gatatttgtg taagaaaaca      68760
attataaaga aatgtgcatc actaaaggaa tttaatactt tgaaatgaaa ctgttgtcta      68820
ggaaataaag ctaggtttta acagtaacaa atggcaaata gtataaaata gaatgagtta      68880
tacattagaa aaatgtttcc tgatatgcaa tcttttaaaa agacaccagt ggaatcattt      68940
tctatggaaa aaatttaaaa gaaggcagca tttcatgaac tctgtcttga gttttttggaa     69000 atatctctta ctaattatga cctctatggt ctatatggca aatgcctctc acctggtagg      69060
gtcaaaacac tttgagggtt ccctaatctt gaaaatgatt ggaaatcctc acattttagg      69120 cctgaacac tcagcattga tgcatgcttc tgccaggcaa tggcagcaga gatactaatg       69180
aaagcagcag cttagtacgg tgctctgatt agatcctcag gttggggaaa gggcaggaaa      69240
gatgagaaga ggaaagactt tcactgaaac tctgatgaga gattctagaa gtaacacatt      69300
ttaattaagc ttcctccaaa tcagcaggga gtgaaaattc agctagtatt ttatttttcca     69360 atttatttct tcagggaaca tacctaaaaa ctgttttgag ggtgggctat tatgtaactg      69420
aaggacacaa tttcattatg aacaggcaga aacttgtgaa atatcaattt ttagtataca      69480
tattttggga gcacctacca aggaccttac aaaattttac gaaacattat ctaactcaac      69540
catgagtcac ctggtatttc aagtcactgt ttctcaggga aagctaagta ttttcttaag     69600
cttataaaaa cataattctt ctcagtttct tcttgtagac atctagtcag cttctatcac      69660
cctgtacaca cacgcacaca cacacacaca cgtgcacaca cacacacaca cacacacaca      69720
cactgcagag ttagttcttt atgttccagg ctcctcatgt gtaaaatgta gataacaata      69780
actgcatgat ttcaggatga gtgctgagag gtaatgtatg tgttgagggc tccacagaag      69840
taggatggac ctcatacca aaatttggtc caaatgttga gactgatgat gctacacata       69900
ccccaatgga gtacgaaaag gtttattatt cacataagga ggcccttgga aggagtagca     69960
taggctacca agtaggtcca aaaaaatggc tagagatcag ggagggccc ctggcttggg       70020 gtgttatgtt ggttagggag tgaggctgag gaacagattg tccagcatag accagggctt     70080
gcatcgtttg aaccccctgc aggtaccaaa ggagggagcc cctggaattt cttattagct      70140
tgcccagata tggggcagaa gggtaaaggg aagtggtggg gcttgaaagt tgtcagcagt      70200
tgaacataaa aatgaactca gactctttac taacctatac aaagaattta gcacagtgta      70260
cttggtagat gtgcaataaa tggtagcttt tttattattg ctgttaacac aattattata      70320
cctatgtttg tgcctcccac tgcttggctg gcatgatgaa aacagaattt tagaacatgg      70380
atctaaaagg taatcagtat gaatagaaca gaatttgagt aattgcttat gtggtccaaa     70440
tattatacca cagtagcagc ttaaagtgtt atgtttaaca tcataggtaa agtgtactgg      70500
acttggattc acaaaaccca ggcttacatc tcagctttat tccttaagaa ctacatgatt      70560
ctcaacagtg gcttacatgc cttcaaactt atctgttcaa tacaggtaat accaccaatt      70620
ccactgggtt gttatgaaca ataactggaa gataataaac agactagcat atagcaattg      70680
cccagtactt caaagatgct cggggaacaa caattgaata tgattctgaa tataacccat      70740
taagtcactt taattctctg agactgattc cccttattta caatacaagg ataatagtta      70800
tcttacttat tatacaggat gtgataagaa tcaaaatcag cagcagacca tggatctgat      70860 ggcacttttct aaagggaaat gtaaagcatt tgtaaggaaa tgtaaataat gtaagacatt     70920
attattaaat acctcactta tcacataagc attgcagagg aaacattgcg gacgtgctag      70980
```

-continued

```
aatcttgaca ccactcaagc acatatggtc ccctcatggt ctcaacttca gggaagaatt    71040
cctaaatcag gtccactttt catcgtattt gctaatcaca ttacatgttg aacattctct    71100
aaagccctga cattttcaaa cagggccaaa aaagattgat atgcctgagg aacccagata    71160
tttacttcct ctcagccaag aatccccatc tgttggtatc agttgacatt tgagataact    71220
tgcccccagt aaacatgcat tttaaatcct gacttcagaa aacagactca gaagattcat    71280
cactcaagtt ttcaacaaga gaaataattg aataagaatg aagaagaaag aattgtattg    71340
gaaagcaggg aagcaaaaat ataagtggac aaaagttaga gaagtgcttt tgggaaataa    71400
ataagaatgg tgaacaagga tgagaaacat ctaccacact gattagattc actccaagaa    71460
gtcaagatta ttagtgaaac ctcttagggg agacaaaaca cagccatttt ctctttcctt    71520
cttcttttcc cttgtcttca tgcctcccca gcacaaaaac tgtataacag agatattcat    71580
gccaagtatg gattgctttc tagagccagc actctaactt ttgtcataag aaaatgatgc    71640
acacagaagc aacctatatg ctgtgctctg ttatctactg atgcctgtgt tctcctcaac    71700
actgtggcag tcaactatct ggagggatat ggagcttagt gggaagctgc cacatcttca    71760
cttttgcttc aataaggtaa ggggatcatg ctgtatatct tcacacctct cttctgcctt    71820
gttatgccaa atggtatatt cagccaggca tctggtagtc acatgtttac cgcaccaaag    71880
aaaattttag gcgcttacag aaaataactg ctcagaatac atacagcttt attcaattgt    71940
aagataaaga tgtatctatt tatattcatt ctttcataat atttgcgaaa cccgtaagta    72000
tggcacatga tatagaaacc tagtagtaaa actcttgtca ctacacaatg tccttggctt    72060
taacccacca gtttatattt ttattcaagg ataaaccatc ttctggtatt attattattt    72120
tgagacagag tcttgttctg ttgcccaggc tggagggcag tggcatgatg tcagctcact    72180
gcaatctctc cctttcgggt taaagcgatt ctcatgtctc agcctcccga gtagctagga    72240
tgcgcaacca agtccagcta atttttgtat tttagtagag acggtgtttc gccatgttg    72300
gccaggctgg tcttgaactc ctggcctcaa gggatcgccc acctcagcct cccaaagtgc    72360
tgagattaca ggcatgagtc actgtgcctg gccattcag gtattttata ttcactgttt    72420
ttcttctcat aaaacttggt taatgctgaa gatctcctta attagttgga taaattacac    72480
cttcccacat ggaaaaattc cttggggggat gcatcaacat ttttcttctg tacttcctca    72540
aagcacaagt tatggtttca gtgtatacaa ggttttcaag aaatattgcc atcagattga    72600
ttaaatgact gactgcatag cttttttattt ttcttaacag ttaaatagca tttatatttc    72660
aataaggggt ttttactctg taaatcacag attccaaatc acaatttgca atagcagagc    72720
tcacctgcca aaacaacttc aaattaaata gcaacctttg ttacagtatt ttgcagccat    72780
atctgggaaa tgcaattgac actggcatgg agtagaaata gtttccacaa ggcaagaaaa    72840
ggcatattga ctggcaggag catgctctgt gccttgaca cacaagcaag aattcggccc    72900
caatctgttg gagtctcaag gctcacaaac ctgccagatt gccatctttg tgctgaatgc    72960
aaaataatca cagtggctaa aaatgataac ttgtggatgg ctgggatggg aagcaacata    73020
tttaatcaat ctctccttt cactctgcag gttctaacca tgaaaactgc actccaacta    73080
gagagaataa tttccattct caaactctgg aggtaagaat atgtcattcc acgatccctg    73140
agtaatctta cttacagctt ccctagaaaa tgcacattta gatttagctt gttgatgaga    73200
ttcaaataat aggcttcatt gactcccaag agactatgaa gtatcaattt tttagctctt    73260
tgatttctta aaccctttcc agtctggtct cctcctacag accaacctat tcctggacta    73320
```

```
gttctcagag tttaggaatg ttgaaggaac agttgttatt tttgtaacaa aatttaatct   73380
acctgtgcaa ttattagttc tcaacacagc tattgtatac ctgttaccat ttttctgatg   73440
tcatctatat agaaagcacc aagtattttc atggtagatc tttcagaata tatcttctaa   73500
agagttgatt ctcttttttct tttcttttct ttttttcttt ttttctttttt tttttgagac   73560
agagtctcgt tctgtcaccc aggctagagt gcagtggcgt gatttcggct cactgcaatc   73620
tctgcctccc gggctcgagg aattctcatg cctcagcctc cctggtagct gggattacag   73680
gcatgcacca ccatgcctgg caaattttt tgtattttca gtagagatgt gggttcctcc   73740
atgttggcca ggctggtctc gaacttctgg catcaagtga tcctccagcc ttagtctccc   73800
aaagtgctgg gattacaggt gtgagccact gctcccagcc aaagttgat tttttgtagg   73860
caattctgaa ctttaaaatt ttattttctg agtcctattt caaatattta tgttgtaatt   73920
tttttattta tcaacatata tccctattgt ctctcatgct tttatttctt taaataccat   73980
aaatgaaaat aatatctta aaaagcataa tagttttga ttttgaataa ggatgaatag   74040
acttcatcat gacatttcag atatttagaa ctgaaaggaa tatcaagatg tttaggtaga   74100
tactgataat gacaactgaa agtagtaggg gagtcacact agtgatgttt aaactggttg   74160
ccacagtttt cccaaatcct ggtagattgc tggtgtttct gagttgtggt cacaactcca   74220
aggtggtagt tcttgcctac ttctctaaga gcttcactac agagagaaaa aaaaatttct   74280
ccagaactgg aaacctcaag tatttaggat aaagaaaagt atcttttcct ttaatatgga   74340
gtcttgagct gaatgcagct tgcatcgtat gttgacattt ttaagttgac gatgcaaata   74400
tctctcttgg tagcctggtt gtcattataa ttactttta tgtcaatgag gctacaggct   74460
taaaagcctt ttgtttctag aagatacaca ggacaattga tctgcacatt tttcatagca   74520
atccttttat aaagtggagg aggcatttttc tagtcttctt ttcctcaggg acactattct   74580
agtttttact attctttatg atctcttttc tctactccta ttttgtttgg ttttattttt   74640
attttttatt tttatagagt tggggataca agcgcagttt ttttacgtgg agatattgta   74700
tagcggtgaa atctgagctt ttagtgtatt cattgcgcaa ataatatata gtacccatta   74760
agtaatctct cattcctcac caccctctac cttctgagta tccaatgtct attatcccac   74820
tctctgtatc tatgtgtaca tagtatttag ctcccattta taagtgagaa catgtggtat   74880
ttgactgttt ctgagttatt tctcttacgc taaaaacctc taattccatc catgttgcta   74940
ggaaatgcat catttcattc ttttttcatgg ctgtttactc ctattttaaa tcatgctctt   75000
cagtatgcat tctatttttt tatacatcct tttgttttta ataatactgg agatgaaatt   75060
tagatacatg ttactgaata gtatagcttc atctgaatgc tttacattcc attatatact   75120
tcggtggata taaatgataa tagtcctaga ggtgagaagt tgcggttgct gttgttgtta   75180
tgtcagttta gttagtttct gacttctctc tgaaagcttc catcagttag ccaatccata   75240
tcagtactga tttagtcatg taggcatcag ttattatttt atcttatttg taaggattgt   75300
tttcacaaaa tgataaggat tattacctgt atcctaaaaa taaatctttc agtaatcaat   75360
atatgaaaaa gaaaattatc attccaagaa aatttacatt ttcttttctc cataaatgca   75420
agtaactttt tgcatttttg gcaggaagtg aaaatttcat aacaaatgca gcaaaattaa   75480
gcattgagca gagaaaggtg tcagaacatt gcacgatatt cagctgagag ttacaaagta   75540
tcatcagcca gataaggaag agagagaggt gttgtaatac taaattctcc agttttgaaa   75600
ttttccataa agaatcgatg ggtccagagt ctgggttaaa aacaaacaat atgaaatgag   75660
gcttgtttct agaactctgg ccattgtgac ccagggcctg attgtcacca tgccactgta   75720
```

```
ctcaacaata gttttcaggt ttttagatac ttctgcagac atatacaaat cagtgaaaag    75780
aagaaaggga tattgtacag ataaaaccac gtatttgtat acatattagt caatgcatag    75840
atactgagca tcttctatgt acaggggtta taccatgatg aaacacatgc atgatttgca    75900
ctcattgcag tttgtacact tgaagtcata ctccgtttgt atgcctgcct ccccattagg    75960
gtgtattctc ttttaggacc aaaaacaaat tatttcattc tgtttctcca gtcccaacta    76020
acatactaga tgactgatat actagatgac tgactgccaa ttaaatgaat ggcttaaaaa    76080
taaacaaatg catcatgaat gcatgtgtag cctatgattt tgggtggagt tttccacctc    76140
tttgtgctct gtgtcctcct tgtgatatg tcaagcaaga tggattaaga agtatgcatg    76200
ttggccgggc atggtggctc acgcctataa tcacagcact tggggggcc gaggcaggca    76260 gatcacttga gaccaggagt tgagacctg cctggccaac atggtgaaac cccatctcta    76320
ctaaaaatgg aataattagc caggcgtggt ggtacatgcc tgtaatccca gctacttggg    76380
aggctgaagc aggagaatca cttgaatctg ggaggcggag gttgcagtga gctgagatcg    76440
tgccactgca ctccagcctg ggcaacagag tgagactctg tctcaaaaaa aaaagaaaga    76500
aagaaagaaa gaaagtatgc atgtttgtgt gctcaattgt gtcatgtgct tcaggattca    76560
acttggacat tgcatttcct ttagaagttt gcgatgaaat aaaaaataaa gttaagatgg    76620
tcttcaaaac agttacgatc tgaacagaaa tctactttat gtctgaatat ttttcactt    76680 tgtgcttacg gcttccatct tagctttttc acctatgctg caacactatt aaatgaggtc    76740
attttacatg agtaactttg atatctgttt gttgattcac agcttctcta acttggaggc    76800
aggaaaaaca agctaatgac aaagatattt gtataccaac tttcaccta gaaattatag    76860 tttccaaata ctcacaagta aaataccac aaacttaat gacttaatta agccagtggt    76920
aaaacacaat atatctagga gggtgttagt tacaatagca gggaaattat atggttttca    76980
gcaaggtgga ctagaagaat caggctttgg aaccaaaaac tagactcaaa atctgattgt    77040 tcccttaat gaggcttcgc tgtagcttac tctttctgca agttaatttt ctcatgtaaa    77100
atggtgataa tatgacatat tttgagagag aattcagact ttgcaaatct tccaacacca    77160
tgctagtttc ttttctctca cctttgctaa tatgagaaag acagactgat aaaaccgtgt    77220
ggggtcaaca cccactaaaa taataaatgc tcccatatgt cactgagtca taaaaatcat    77280
aaactgagct gttcttcctg atgcatcttt aactttaggg agtattattt acttttacca    77340
tttttgagta agcaattaaa gtatgtattt tacgtaattg aaggaatcag tatctccatt    77400
gatagtaaaa tattaccagg ccaattgtta tttgtatatt tttttaaaaac cttttaaaag    77460 aatagtgcat ttgcttgcaa agcaaaagat gctgtgactt accaacaaga tctggctgcc    77520
ttttctgtgt tacttattat tgtggcaaaa gaggttgtaa gtgtgacaag aaaatataac    77580
ataagaacat gaataaacaa ataagggcag ttgttatgaa aactgattct tccagaatga    77640
ggagttaaat gagctctctc cttagtacct tcttcctgtt tcccaatttt taggctaaag    77700
aagcacaaaa cacttaggca gttacaagag tcctttaaaa tcctccatgg tattttaaa    77760 aatctctaca attctcttgt attttgagta aaagctaaat tggagctgta ttgttttatt    77820
tcctgagtct tcttttatt gaattattta cagtggacat gattgctggt gatgatcaca    77880
gccttagtct tcatattcta gggacaaatc tgtcctaaac ttctgtcatt gaactttcat    77940
ggatggagct aacagttaat gattggtgta taacaaaagg cagtatccct ctaggtagct    78000
aatgtgggcc accaaagggt caagaaaaaa gttataggcc aggcatgatg gctaacacct    78060
```

```
gtaatcccag cacactgaga ggctgaggca ggcagatcac ttgaggtcag gagtttgaga    78120
ccagcctggc caacatggtg aaaccttgtc tctactaaaa aatacaaaac ttagctgggc    78180
atggtagtgc acgcctgtaa tcccagctac ttgggaggcc gaggcaggag aatcacatga    78240
acccgggagg cagaggttgc agtgagccga gatcgtgcca ctgcactctg gcctgggtga    78300
cagaactaga ctctgtctca aaaaaaaaaa aaaaaaaaa aaagttatag tagaataatt    78360
aaagtatttc taaacctagg ttataagatt taaaagaat ggttttagt ttctagtttc    78420 ctgcagtatc taagatgtct acaaggcaac attgggaact ggagtcaaaa agttgatgct    78480
tcacagctcc ttggacacta cagatagaca gtgaaaaac agtcaattgt tgtcacatcc    78540
caagaacagc aggggattcc agttaatttt atgtagcgac attgagcctc tggattttaa    78600
ggaccttgct gaactctcaa ctggtcttct tccctatctg tatctcatgg tggcagcagc    78660
ctctctgtat taatgggaaa acagagacct gaactcagat gtgttataaa ctgaacttct    78720
gtttattgtt atcaaatatc tttacaagct ttctaccact ctggacagac gacagataga    78780
aggcaagctt gacttcttac tgtgcaaatg gagcccaacc aacctaaagg gtaagccacc    78840
taagagaggt tcctcttttg gtcctacact agctactagc acatatcagg aggggatatg    78900
ctgcattaag aatgcaaata tcactttgtc taagggtgtc ttcagatgat gccagtaatt    78960
cataagtgtt ctcccaccat ccagaaaggg catcattcag agagtcctca tctctctacc    79020
atcactttca gggtccatcg ctagtactca actctccctc ttaccttgca ggtggtaaac    79080
aaaagggaag actattaaat ttatcaccta tatatttcag aaatgtttct tttctctcaa    79140
tatcatcact tttaggttat ctgcttaaca aagctcctac ccttctcaga gtctaaggat    79200
caaatctttc tgtgattcat ttcaagaagc ttttgtcgaa gcactgttat ataatgttat    79260
gaatcaaatg gacaatcaat acatattgga tgatgatgga taaagtttaa gccacagagt    79320
aaagactgtg ttgttgagct aaaagagttc agttttatc aagcacaata ataataatt    79380 ttattttatg tgcagattc tgatggtcag atcattgtac agtagagcat aattgaaagc    79440
aaattccctc agaggccact gaccactggt aaatgttcaa atatataata cagttcaata    79500
cgactgtact aaacaggtaa taaaatgttg gcctttgacc tcccgtgact actagtttca    79560
gctacttcat taccccatga ggcatgtcct caggtatgtg catctctggg tgggcagcta    79620
ttctcttgca ttttccagca gtcgtttgcc atcagtaggc ctgtcagagt caatgcttca    79680
gtttcataac tgtaattgga ttgtctgact tcctattcaa ttggtacatg tttcttctta    79740
tttctgtttc ttttaaaaaa tcaataaatg gtttgtgatg cctcaaatag agagaaatca    79800
ggttttacca cattatggaa ttgacatttt caacatttat ttctcaaaga ggaccattgg    79860
gtatgtcaga ttcaacgcat aagttttgga ttaattgaat tgtttggtcc cagggatata    79920
taataacgtg aacacatttc atgatggaaa ccaaagagct ctatcatgcc ccaaacttta    79980
tgcatatgag tagaaacaat ttttctctt tttcttgtct ttctttcctc cactcataaa    80040
acccaccact cataataaag ttatagaaag cataaatagc tttatgttta aactggaggc    80100
tgatattgaa accactaaaa cattatgggt gtgaatggaa tgtgcacata tatttatatg    80160
tatatataaa gtccaaattt tatatacata tatggacttt atacatagct acatatatct    80220
acacatacat atatgacacg aagagctgaa tcagttaata tatctctgca tttaagagta    80280
aatcatattt gatgcaattc tgcaagtaca tcttggctcc ataaaactgt gatagtggat    80340
gaagttgcaa aggtgagtaa gacagagtat ccaccaccaa aagtcctgac gtagaatgaa    80400
aatcttccaa aaagaattag taagttcata tcgtttcgct tttgtttaat agcttggctc    80460
```

```
ctattaggat caggtttgca ccattgatcg tgtattgact tgaataaaaa tacatttcaa    80520
aataatgtac agtattgact aaagatggga ctacctgctt aaaatcagat tcattccaca    80580
tttcattgct atctctaagt attcattctg caggaggaag agattttttcc actgcataga   80640 gaacattatc aaatgtttcc atcttccttt gaagcattca ctattaactg ctgttagagg    80700
aaggattcta gactgagtgg gccattggtt tgttctggta ggacagttcc tgagttttaa    80760
tggatatata cagtttggaa gaaaaaagaa aaaactacca gagacaaact ttaatatttt    80820
gagtggcact tagctgatat ggtaggtaga atttaccaat tccttttaaa atttaatttc    80880
ttgttaaacg tgaaagcttg aagttcagta atatgaaaat aataacattt ttcaggtcat    80940
gaatatttgc tttttaaaat agtttacttt actctacttg caagccagat ttccctattt    81000
ttaagtgagt ttattgtggg agtgggagga gttgaattag aacaagactc tctacagggt    81060
cacaacctct tcagggcttc agtgcaagga agggatgaac agatattgac agaccaactg    81120
tcttataacc tgagattccc actcgtttgt tattctgtat ggctatattt gctttcaacc    81180
tcaataggct tcattcatct gcaaacttcc tgtggccctt gatcaaaaag ctacaaaaa     81240 ataccatgtc ctcatgtgcc aagtaaaaat ttgtgactat gcagcttaaa agtcggtcat    81300
ggagaaaatg tttcttaaca acgctttgaa ctatttaaat tagagcttta ttttagaaaa    81360
tttactagac agtggtctac ttcattttat tatactaatt atctttagtt gcaagaacaa    81420
tggccatttt gtgagttgtt agttcaacca tacgttgtta tatttgtgag acaaaaatag    81480
ccaactgtga gcaattttat atggcttgac ctaatataaa attttgtgtg ctttgaatgt    81540
ctgtgataaa cacagagatg tattcccatg gaaaccatgc cccatgcatg gtgaagcagc    81600
caatatggtg gtaaggatta cactggcatg actgtctata gtccaggaaa gtattataaa    81660
gatgttgctt ggagttctgt gcaaaagaaa agtccacgtt taatcaatgt ataggtatat    81720
taagaaggaa atcctcctat ttatgattca ccatgaccaa tgtcatagta aaggctttga    81780
aaaattctgc agcaaattac atcatttagt caaataaatt ccatagggta tgctgtgctg    81840
ggccataaaa taccttttct gatcaaatgc ctatcagcat tttataggaa agcaatgttt    81900
cataattctc tgtaattcaa tttgagaaac caacacctga ctgaaaactt gacacttgta    81960
tgttcctgta ccttcagggg ttaatgcagt gccttatcca tataaggtta accttacaaa    82020
ccaaaaaaat gacagcttta gactcacagt ttgtaatcta gctctcatat ggtgcatgct    82080 gtttaaagg aaattatatc tactctcctc atccagcaaa ctggcatttc ataagataag    82140
ctatgcactc tgagtttaaa taaattcaga tatttttctt tgaatacatt tcacagccag    82200
ggcataacat tctgaacact gtgacattat ccttccttaa aacgtgtatg tctgttttct    82260
catgttaaac ttccttttg ttctatctgt atctgtaata attgcctgtg atttctggaa    82320
tgggtctcat gagggagtcc attttttctc ccttagcctc tctctaagca cccaatatgg    82380
aagctgcagc ccatggtgca tccatgaata ttatcggaga agatcaataa atctaagtcc    82440
acagccaaca gtaattactt tctttattct ggcagagatg gtggcattat ttagacacag    82500
ttgtagagca agtgacaaac aaggcacctt tttgcagact caaatttctg ggatacattt    82560
acaacagtgg tgaaaaatta cagagggatg gcaggtatat gtgaacaggg ctgcaactaa    82620
tttggccttg ggaggtgaga ttgtcaggca tgtcaaaagc taagcctcat tcagaatcct    82680
ccccactcca gcacttctca gatctgtttg caccacctct tttctccctc tcctctagct    82740
tcaaacttac cctctctatt ggcttcatcc tctcggaata taaatatact tgagaatctc    82800
```

```
ttctcttgaa aaagaatcca ccctcacttc caccttcctg ttttctctct ccctctcttt    82860
cgtggagaag ctacttgaat gaatacccta cattcccttc tccacttcct gacctcccat    82920
gtgtgactcc atccttcata gtaggtaaac attcttgaga agattctcat ctgttgtgaa    82980
gtcttccctt acccccact ctacttctcc cacatctcgt tttagatttg gatgttaccc     83040
tcaccatgga ctcctactgt accttgaatg cttctcgatt cagtcttacc attcaagaat    83100
gtaatgtttt ttattttgtt tctgttgata agaggtagag cttgtgtctt catcatcttt    83160
gtatccggtg tccagggtat tgcctgaggg caattatagg gacttaataa cgcccaaaca    83220
catccaacct ttttcgatca aatttgtttc taaagcgaga atacaaaaaa aaaagaaaga    83280
aagaaataga aaagctccct gtttgcaaat gtgctgtgta ttttgtgctg taagcctctg    83340
ataaatgcag tggtgttatc caattaactt tccagtactc aggagagagc cttacaggtt    83400
ctgccaactt accatcgact aatcttaatt gtcttttgac ctatgctagc tgcatggagg    83460 gtaggggat tagtagtaat gtagaacttt taaatattaa cattatgtac tatgtatatt     83520
atataaggaa atttgacctc tttcagaaaa aagtagcaca agttcatata gtatgggcag    83580
taggactttg ctatttaaat cagtaccaca aaatgttttt atatggaatg ttattctaac    83640
tttctggaca aacctgaata atatgtttaa agtttcatat tacaggatcc ttatttataa    83700
tacctaaata acattttcat ccttccatag cctgaacaat attaaatcaa tatataaaat    83760
cacagtaatc ataaaattag agtttcacta tgtacactga ggtccttcag tgattaccaa    83820
gtgctgccaa ataacacaat cctacatcag ctgtcagtcc tcagttctaa ctcctaggct    83880
ctggctactt tgagatgcta tttccaaaaa gtcctcttct ctggctactc atgtcacctt    83940
gaggggcaca gctcactcgg aaaagctact cttgtagaag cctcactatc tgagacccct    84000
aacaactcat tatcatccct cctcccaaca acttaaagaa catgtattcc acaacacagg    84060
tcttatgagg gcagggcaga atgggtggc cctctctcca aaatcaatat gtgagttgag     84120
aaaaaaatga gacattttgt tctcatcaag aaatctatag acagcagtga tcctagggtc    84180
cccaactgga accaagaata tactgaccca gagacacatg aggtaaaagt tttattcttc    84240 agattttac aactatgcca ctaaggtatt cattcagtca tccttttga gctggcaagg      84300 aaaattaaac caaatgtttt taaggcttac catatcatgc taaattccac caaacttta     84360 aagaagaaca aacatgaatt cttttccaac aattctaaaa aaattaaagg ggatggaatt    84420
ttccaaactc attctacaag gtctgcatta ctctgacaac aaaccagaaa aggacacaac    84480
aataaataaa gaaaactact agccaatatc actgataaac acagatgcaa aaatcctcag    84540
caatgtacta atgatatgga agaggagaag ggaagtgctg gatagaggag ggcatggtcc    84600
ctggctgggg ctccactcct gggcctgtgc ccatgtacca ggtgaggaca ggcattcatg    84660
ttttcctgcc taaatgttgc atttcccaag acaaccctgg cctgccacaa ccccatcctg    84720
tgcctataaa acccccaaga ccctagcagg ccgacacaca ggtggctgga catcgagagg    84780
agaacatcag cagaggacac atgggccgct ggatttcgag aggaacacac caacaggcac    84840
tggcactcca gcaggtcacc aactggcaga acaactgagt gtttggccag ggcagtcaga    84900
gaagagtcgg gccaccaaga ggcccaattc ctgggagaac catctcccctt ctggctccct   84960 catctgctga gagctacttc cggtcaatac aactttgcac tccttctcca agcccatgta    85020
tgatccaatt cttctggtac accaaggcaa gaatcccagg atacagaaag ccctctgtcc    85080
ttgtctaatt gagctgacca caagtcacct atggacagct aaactaaaag agcacccgtt    85140
aacacacacc cactgggggct tcagctgtaa acattcaccc ccagacactg ccatggagtt   85200
```

```
ggagtcccac agcctgcctg cctgtatgct tccctagagg atagagcagt ggggcactga    85260
agaagtgagc cacaccctca ccacatcccc tgtgagggg acaagggaaa ttttcccatt    85320
tcactaacaa accaaaacca acagcacatc aaaaagatta tatactatga ttaagcagaa    85380
tttatcctag ggatgcaagt aagtttcaac atatgtaaat caataaatgt atgctactat    85440
atcaacagaa tgaagaacaa aaccatatga tcatctcagt agatgcagaa aatagcatgt    85500
gataaaattc aacatctttt cattgtaaaa actcccaaaa aatcagataa agaagaaata    85560
cacctcaaca aaatacaggc tatatttgac aaatccatgg ctaatctcat aatgaatgag    85620
gaaaaattaa aagcttttcc tctaagaact ggaagaaaac atggatactc attctcacta    85680
ctcttactca acatagtact ggaagtccta ggaagaacaa ttaggccaga gaagaaaata    85740
aagggcatct aaattggaaa agagaaagtc agtttgtctc tgtttgcaga ttacataaac    85800
ttatttatag aaaaacatag acactccacc aaaaaattct tagaactgat aaattcagta    85860
aagttgtgag atacaaaatc aacatacaac aacagtagca catctttgta ccaggaaagg    85920
aaatcagtat gtcaaaattc taatgaatga actaagaaag aaatcaagaa acaatctta    85980 tttataatag ttataaattt taaaaaaccc taaaaataaa tgtaaccatg gagttgaaag    86040
atttctacat tgaaagctat aaaacactga tgaaagaaac tgaagagaac acacacacag    86100
gaagataacc catgctcatg gattggaaga ataaatattg ttacaatggc cataccaccc    86160
aaagtgatct acagatttag tgcaatctct ataaaaatac caatggcatt caacacagaa    86220
atagaaaaaa caatcttagc attcatatgc aaccacaaaa gacccccagat agccaacata    86280 atcctgaaca aaaagaacaa agctgaaggc atcaatctat ctgacttcaa aatatattgc    86340
aaagatatgg taaccaaaaa agcatggtat tgccataaaa acaggcagat acaacaatgg    86400
aacagaatag ggaacccaga agtaaatcca catatttaca gccaactgat ttttgacaaa    86460
aatcctaaga acatacatag gggaaaggtc tcttcaataa atggcactgg acacactgaa    86520
tatctgcgtg cagaaggtta aatacccatc tttcacgtta tacaaaaacc aactcaaaat    86580
ggattaaaga cttacatgta aaacccaaat ctatgaaagc actagaagaa aacttagggg    86640
aagcacttag ggatattggt atgggaaaat attatgaata agattttaaa agcacaggca    86700
aataaaacaa aactagacaa aagggattaa gtcaaactaa aaagattctg cacagcaaag    86760
gaaaaaaaaa atcaatggaa tgaagagaca acctacagaa tgggcaaaaa tataaattat    86820
ttatttaaca aagcttaata tctagaatat acaaggaatt caacagcaaa ataaataaat    86880
aatttgattt ttaaaataga caaatgatct agatagatag ttctctaagg aagacacaca    86940
aatggccaat aagtatgtgt aaaatgctca gtatcactaa tcaccaggga gatatcaaaa    87000
ccacaatgag atgtgatctt actccagtta gaatgtctat tgtcaaaaag acaaaaataa    87060
gaaatgccgg tgaggatgca gagaaaaggt aactcataaa ctgtttgtga aaatgtaaat    87120
taatacagcc attgtggaaa acagtctgga gatccctcaa aaaactgaaa atagaattat    87180
catatgatct cacaattcca ctatgggta aatatttaaa gaaaataaaa taaatatgtc    87240
aaagagatat ctacattccc atgtttactg caacattatt cacaatagcc aagatatgga    87300
atcaagccaa gtatccacca gcagatgaat ggataaagaa aatgcacatt tacacaatgg    87360
aatactattc tgccaataaa aagagtgaaa ttggcgtggc acggtggctc acgcctgcaa    87420
tcccagcact ttgggaggct gaggtgggca gatcacgagg tcgagagatc aagaccatcc    87480
tggccatcct ggtggaaccc agtctctact aaaaatacaa aaattagct gggcatggtg    87540
```

```
gcacacgcct gtagtcccag ctacttgggg ggctgaggca ggagaatcgc ttgaacccag   87600
gaggcagggg ttgcagtgag ctaagaccac gccactgcac tccagcctgg cgacagagcg   87660
agactccatc tcaaaaaaaa aaaaggggg ggggtgaaat cctgtcattt gttacaaaac    87720
aacattgttg taactggagg acattatgtt acctgaaata ggccaggcat ggaaagataa   87780
ataccacatg ttctcactca tatattgaag ctaaaaaagt tgatctccta gaagtggaga   87840
gtacaatagt ggttactaga ggctgagatg ggtagaggaa agaggagaat agggagaggc   87900
tggttaacag atacaaaatt acaattcaat tggagcaata atttctagtg ttctatacca   87960
cagtaaggtg actgtagtta acaataattt attgtatatt ttcaaatagc tagaagagga   88020
gattctgaat gtccacaaaa caaagacatg ctaaatattc gaggtgaagg atatgctgat   88080
tatctcagtt tgatcaatac acattgcatt catgtatcaa atatcctac tgtatcccat    88140 aaatatgtac cattattgtg tcaattaaca ttttttaaaa tgtctactgt aagaaaaaaa   88200
actaaactaa acaaagccca cttaccatat cagatagatt ttcataagca atagtcagcc   88260
cagttttctg gcctatagag ctaggaatct atttgtcatg aattacgaag gaagccctct   88320
gagagtttat gtcagcaggc aaacttgcct accatctcct gctatagtat tctaaggtgc   88380
tgaatggaaa aactgggcta atgatgtttt cgtttgtatt ttacatggaa aagctcaata   88440
gagatgactg atttcatgac atgagagggc ttttttcagaa tgaaataatg aattgcattc   88500
ttaatattgt aaatgccctg cctagatttt ctctaaatca ttacaatgag aggcaattcc   88560
ccaatgtaga agggtgtgac tgtctccaga gaagtggaga gtcaatgcat cacccgtgta   88620
atttaggaaa accacccact ttatttcaag tgcttttttca gatgatcatg cttttttggac  88680 ttaaattctc tggataattt ctccacttct cttccctgtt atgtgtacat caaagcataa   88740
cgacttggcc ttggacaact gaaaaattaa taaccgaagc aagagtttaa gaaatccata   88800
gtaatgacac aaatgagacc tatcaaatta gaaaatcaaa atgaaaacac actaaacact   88860
tcaaaattta attagaaaaa gttccaagtt cagaccacac tgaggccatt atgcaccaga   88920
agcactctat attgaaacct gaaaggagag tcattttggg tgaaatgtga ccttgggaag   88980
gaggtaagat cgctcactgc ttcttttact ttatctgctt tttaaggctc accccttaac   89040
gttttatgaa aggcagatcc aaggcaagca tctcttcaat ttaaccttca caagagacac   89100
aattcagtct tttatttttc ccaatgatac tgcaatcaac ttgagactgc tcaccatgaa   89160
ccatttgaaa atattttca aattaataca caaattatga agcatacgtt ggctgctgat    89220
ccctgtgaac cattcccatt gacttttaag tccaatgctg tatatcaggt aaggatgatt   89280
ttctcccttg caacttaatg ggatgagagg gaggcttgtg ggttatatat gtttagaatg   89340
aatcatcttt cttttctgcc gcccttttca tacaaattgt atatcctcca acatttttat   89400
agacttctat aacataggag agtataaaga atatattaca agaggcagga gaatagacaa   89460
gcttccaatc ctatgtgaag tttatatggt acctatcttt aaaggcttta tatattttgc   89520
cttactacct cacatcttag aattaaaccc actttattat gcatttagtt ctcaagttat   89580
ctctgtttga tgagcagcat tgccaccaac cacattttta tcaataataa agctgagaca   89640
aactgaggtt cctacaaggt cacacaataa gtatagtgac taaagactag tactcaagtc   89700
tcatatgagc catttaagac aaccctgaag ttaagcactg ggtgactttg ggaggtgtgt   89760
gtgacagggt tgagttatta caaaacacag catactcaca ttccccccaa accaacttcg   89820
ttatttgtat agtttctgaa cagaaatata tatttgcaaa tagttataga aaaatttggg   89880
atgcatttct attaagaact gcatgtgtat ttccattaaa gtcagtgtgt atcctgaacc   89940
```

```
aagcctgctg cagccttgtg gccatctgtc atttagattc tcctttcttg actatccttg   90000
gaagcttctt tttcactttt tccttggctg atcaaaagct tttacctctc actactggtt   90060
gttagttctc attcctccat ttcataatat ccttcaaaag tttagtttgg taatagaccc   90120
tcatttcaat atccctcaga aaaagcatag gaattttta aatactgctc attgtcttct    90180
tctttctttt cttttgaagc aactgacttg cttgacctag gtggttgtgt ttctttgatg   90240
tatgccagct ttcaatgtgt tgagaggtgg gagtccaagt accttattgc tgggctcctg   90300
tgctcatatt ttaccatcat agacaaggtg acaatttggg atgggaggc actgcttaag    90360 caggcatggg gagtggagtg agggccaaca tgggctgtct gaaaaaggtc aaagcactag   90420
gtctgtccat gaatctggga atacttgctc tgttcaggga aaaaaggctc ttctacaggg   90480
caagtgcagg tatcataatg tcaagaactg ccatttcatg aatagtgcca ggccctcttc   90540
tgagatataa taccaagaga atattatct gtgccatttc cagataaaga acctcagctt    90600
cttttagaaa aatttacggt tatctgaagg agccagaatt ttccacaatt tcttccagga   90660
ttatgtgtat aagcaaacct ttatcactta catacaaaca cacactcata cacagttttc   90720
taagggaaag caaaattttg gtgacatgga tgtggctaat acatgagtag ataaaatact   90780
acacataact ctttatatat tattgagtag aaacaaatta cggtgtattt ttagtgagtt   90840
atttcaggca caaaaacatg cctcatggag aatacaacag ttgtagtagt gtattataat   90900
tcaatagtgg tttaaatgca aatgatccac aggtggaatg tccacttctt cccagcttag   90960
ctgtaagaca ctagcttttt atttatgtca taactcaaag aaaaagagaa agattggggt   91020
agctccagag agcccaatta ctaatatggc ttgaaggacc aatggaaggc accatttttt   91080
aaaacagttc accagcctgg ccagcatggt gaaacccat ctctactaaa actacaaaaa    91140
tcagccaggc atgatggtac atgcctgtaa tcccagctac tcaggaggct gaggcatgag   91200
aatcacttga acctcggtgg cagaggttac agtgagtcga gaacacacca ctgcactcca   91260
gtctgggtga caggtggaga ctgtatctca gaaaaacaa aaacagaaca gttcataacc    91320
ccagggctgg gcatgcattt tctctctgtg atcaacccct ctgtctgggt agtgaactga   91380
aactaaagtc ctcagaccag caaggatgct agttgtgcta ggctattatt gcattgctat   91440
aaagaaattc cggagcctag gtaatttata agaaatgagg ttcaactggc tcatggttct   91500
gcaggaagca cagcactggt atctgcttct gggggcagcc tcaggaggct tacaatcatg   91560
gtggaaggct aagtgggatc aggcacctca catggaaaaa gcagtagaga gaaagagagg   91620
gagacagaga gagagagaga gacagagaga gaaagtagca ggatgctaca cacttttaaa   91680
tgaccaggtc tcgtgagaat tccctatcat gaagatagca ctgagctatg aggatatacc   91740
ctcatgaccc aaacacctcc caccaggccc cacctccagc actagggatt acaattcaac   91800
atgagatttg agcagggaca aatatacaaa ctatatcact aggtatctct gagggcccct   91860
ctgatgctga ccagaagcca ggatgtgtgc tacaaagacc caggaaagcc aggggtggt    91920 gctgatagag ccaaataccte tcaggataa caaggatagg gtttccagat ttgatataat    91980
acagaacaac ttcttccatt tccagctttt cctccaccaa atcaaaaggc atcaaattaa   92040
tgaagctgtg gcttgttgac attaaagttg attacaaaaa gacatgtttg agtgacaggt   92100
aaacaatagc aaaggaatga gtttccataa atacttattt atatatgaag agtatatggt   92160
ttgtagaata aataaacctg tagtcattgt ttcttatttg aagtttgtaa cctgtcatca   92220
taggttaaat aactgtcagg aaagctcata cttgtgatat tttaaatagg agctgaaatt   92280
```

```
ggtgtttccc taaggtaaat ggatgtttct aaacattgat agttcttcct tttctacaaa    92340
aaggtatatg taaatataca aaatgagaag tcaaaatatg tattccatgc acagaaagag    92400
atcaagaggt ggaatggagt tggggtgtga acagaggaag gttgatttat gttatatggt    92460
tgctctcttt ttgtagctat ttttatatct tttcagcttc ctccagatta ctctagttta    92520
tttcctattg tttcttacta ttgactttta attgttccct gacaataaac tgttttattt    92580
aatccatctt tgaaaatttc acataaccat atttagggac aaggctttga gcatctttta    92640
tttcttccac taacatattg taccctaaat aagtttccct cccaggctca tttactacct    92700
ccatttgctt tgtattttg ttgttgttgt ctccctatct tctttgtcct cttctgtaat    92760
ccattcctct ctctttcttt ctttttttt tttttaagat aagagtgttg ctctgtcacc    92820
caggctgagt gaagtggcac gatctcagct tactgcaacc tctgcctcct gagttcaagt    92880
gattctcctg cctcagcccc ctaagtagct aggactacag gcacataccg tcgcacccag    92940
ctaatttttg tatttttaat agagacaggg ttccattttg ttggccaggc tggtctcaaa    93000
ctcctgacct caggcgatcc atccgcctca gcctcccaaa gctctctatt tttataatag    93060
ttatgttgac ttgttcttct ggctgcagct gcagctttt ccagttgtct cttcctgttg    93120
tcacaataaa aaatctctt ctttatttcc tgtctatatg tgttttgttt tcattttttt    93180
gctttccaca tttatccttc ccattcctgt atcttcatga acttgtaaat tcttaggaaa    93240 gcaaaaaaa tataaagctt gaaagtttca aagtcaaagg aaaagagaaa actcaagctt    93300
gcctcagaag agattgtgtc ccatttctgc agtagagttc atggaatttg tgcaaaaagt    93360
gagaagatat aagggaagct gtgctggctt gtgtgtcatt taaattagag agcttggatg    93420
ttgatattac accactgata aaggaaatga gacagtttcc acttttaatg aaaagaagtg    93480
cagtggcaaa gttgtctcac accacaagat aagcaagatt caaggaagg ggacagtcat    93540 tctggtgtta tcattccaat tctatccagc ttatttacat aggcctgaaa atgagatgat    93600
cccaggatat ccatttgatg taaaaaaaaa aaaaatctt aacagcccca aaaagggata    93660
atttagttgt gctacacaca tgggtgcgtg cacacacaca cacacgca cacacacaca    93720 cacacgcatc ccaagaatga cacacctatt gatgagagtt gaaaacccat cagatatcca    93780
aatgagtatg tatctagagt tgtctatact atgcgttata tgactgaacc attttcagat    93840
ttttttctag tttgggaaga tatctgatgc cgtgtagata cagacactat cttgtgggaa    93900
acccatagtt tccagtctga acataaccaa ataaggatct catttctctc tgtctctgtc    93960
tgtctctcct tctttctctc tctgttgctc tctctctctc tctctctcat cttatagcag    94020
caatgcctaa agagaacatt tatacattct acccaaatcc cctttacaca ctggcatata    94080
tctttagtgt gcatatgtgt gtgtctgtgt gcatgtgcag ttgcacattt tgttaagcag    94140
aaaagctcta gtgaagtatc atcgccttta gaaggaaaga aggactaatt tgattttct    94200 gattccaata catggtgcta tcaatgagtg gagatagcac tgagataata tagaacatga    94260
taaacagcca gtggaatggc agcattccat aataatgcca atgcttgctg tcccatcact    94320
cccattgctc cgtgggaagg atctcgtaac tgataaacca atagtagcag gcatttggga    94380
tgtttcctgg agaagcagag ggaagcctca ttggacatag tttcttgcat tttgctgtaa    94440
tttatggaac acgtggattt ttaaatctac aggtaattac gtaaataaaa tattgaataa    94500
gacacaaacc tctaggttcc cccaatctct gtcgcaagcc aaccagctgc ccttcccact    94560
ctacttcttc tccacacaaa gcacagaacc gaccaacact ggaaaagaac tgtgttatca    94620 catttctca tagttggatg gccattctgt tactctgatt ttgagaaaat caaaagcatt    94680
```

-continued

```
accctttgagg aacaattaac atctatttcc agtccattat tccttttcag gacaaagggc   94740
tgtatttcac aggcttttaa acaggatatg aatatcccat caaatatcag tggtctgagc   94800
tacagctctg gcaccaggca cactgccaaa aatgtgacca agtttaaaat gattgatgct   94860
aaatcacatt cctcttaagc atagtctagg ccgagtgagg catacctact catacactca   94920
gtcctcctat ctgggaaatt catggttctc tcccaacatg agaattatgg ttttgttcac   94980
aatgtgtgga aactagaaag gcactgaaca tctgaggtaa aatggaaaca atttagttct   95040
gttgaatgtc accctctgtt gttgattcca cacatctgtg catctttcc ttatccaaaa   95100 ctcatttaaa tgtgctagtt tctcctggag atgtggcaga taatgtcatg agccctcact   95160
gcattctttt ttttaataga tgagggatta aaatttgctg tacatagagt tacctcttgt   95220
ttgaaagtcc acgtacagtc agataacgtg tttatgcttt ccttgtaact aaaaaccaac   95280
tattttggct tggaaattcc ccactttcca aagaccattg cttctttgcc atggttaacc   95340
agaacctagc tcacacatcc actgggaaga aaataaaggc tctaatggct gaatgtagcc   95400
aatgcagcac agaagctcag acctcctagg gaagcctgaa aatggtgata cccttctcca   95460
tttgctgctt gctaatgagg ccaaggtgtg tcccctgta aatcctgaca acctaagagg   95520
ggtgtgcgat tcatctcagc tcccttccca gatgacaagc aagttgtaaa ttgtattcca   95580
ttccactctc cactgtttat ctgccctgac agtccactgc agctcttgtg tagctggaag   95640
cccacagggc atgtgtgact tttctcaagc tcttcccagc tgtcttaagt gtctctgtcc   95700
ttcttgtatt tttctatctg ttgcttcttt ttagaggtcc ctcttcctct ttccttgatt   95760
ttcagttttt ctcgctatat gcatctctct ctctctccct cagattgcct gtgtcttgca   95820
gttttgttac cttacaaact gctacttcgt tttatccctg actttctttt ctttgaaata   95880
catttttcat ctttctttta tagtttattt gtatttttc tgtttggttt ttggcaaagg   95940
agctcagcaa ctgacccagt aagctaacac tttcagaaaa tgttgagtga tggaaaagca   96000 aattttaaa aatctctatt actttcctat cttctttctt acttgctgct cattctagat   96060
gtcctcatgt ctatttcatc gtctgctttt atactaagct ttctcctctt aagcattgct   96120
ttccctacac ttatctgcta tttcagatct ttaaatatcc tacagtagtc agaatgggac   96180
tgagtactga cctgtgagat gcttaccacc agaaatattt tgcaagttca ggcttttgaa   96240
agaaacaaca gaactatata ttatgtttta tatgtccatt cgggaaactt aagacatatg   96300
ggggcttggc agaaacatca tcaacattgg agtagtgctc agtcatttcc acagagaaca   96360
gtcttacaac ctatcaccgt cttctagtaa atgggtacca atgctgatgg aaaataaatg   96420
ggaacaagaa agatttagga aatgttccca agtcttttga ggaagactga attaataaaa   96480
actgtgagat tattggagta aggttgtcta ttcttgtgtt ctaatatacc attgaaccat   96540
gacctttcca atgcactacc tgtaaaatata aggtatatt taatagaaga aatttttctg   96600
atattcaggg cttaaaggct caaatttgcc tttaaaattt ttttctccca atactggcag   96660
gaacaacatt tttagatctc attctttacc ttaaaatatg attttcagcc cagaaagctt   96720
tactctaatc caaaataaaa tttctgtgct acagaacaca ggagcaaaga ttagattcaa   96780
ctcatctttg gcaatcaatt cagggagcta ttttgcactc cctccttttt ccatacctgc   96840
caacacactt cctatggatg cttttcttct cttaactcta gagaaaaact ggaggtgaga   96900
aagtctgtat tcaatgaata tggtaggttt tattaatgta gtcacagaga tgttgcataa   96960
attaaaaaat agtacatagt tatctttgca ttattttttt ccttttaaga tgactttgtg   97020
```

```
tatttaccac ttaattttat aaaaccctaa agaactttt aaaaatcgca tcagataaaa    97080
taaatattct tatctaaatg gagttttgga tcttctccac ttgccaataa ttattttaaa    97140
atgaatttat ggtctagaag tctcaaagac ctagttattc ttgaatttgt tgttattgac    97200
tagagtcaaa tgctagtagt taaatattta gcaaattctt atgaagctag aaaagccatg    97260
cataagcagt aaaaactgta agagatttcc ccttgggtta agaataaga aagtaaaaag    97320 accagttcac ctgaatcaga accctgatgt ccaatggctc ttgctgacac tctacatgct    97380
gacggaagtt tcttgttcct ttttttccag ttcttttgt ctccctattt tttctctgta    97440
ttgaaaatga tgctcatttt gcttctaagt gatgaaggag aaagaaatgc ctgtttcaca    97500
gatcaaaagc aggcactgct ttagagcaac actggctgaa tgtcttacat cataactctc    97560
tctggcttta tccatcatcg ccaacatttt ctcttttgca gctttgaggg tgatggggat    97620
aggtcatata ttattagtgg aatacaaaga aacacaaggg tgtataagaa gccctggttt    97680
cagaacctca gtgtgccaat acccaaacta acccatagac actcgtagtc ttctaagagt    97740
atttatttac ttgcaagtac ttattgagtt tctattatct tacctctaga ttattgaaac    97800
agtctcctaa ttagtctctc agcttctgtt ctagcccttc ttcagtctat tctcaactca    97860
gcagtcagaa tgatcctgtt acaaactaag tcattcattc aatcctcttc tccaaggctc    97920
ctcagttcat gcagagtaaa agcataggtc ctcatacatt gccacacatg atcctccagc    97980
atctcttgaa cccatcctca tttagtctcc tctcacttgc tctactatac ctcaaagatt    98040
tcctccttat ttttcaaagc caccaggtaa gctcccacct cagagcctct gtggctgccc    98100
ttctctccac cggtttctcc cctccttccc ctaggcacag taagacctct cctggagtcc    98160
ctatctaaaa ttgcagcccc tcccctatg ttccctgtcc cttttcttg ctttcttgtt    98220 cccccttagca cttaccaata tgtaccatac tatatatttt tcttatttgt ttatttta    98280 tgtttccaac taaactgtaa cctccatgaa ggcagggatt gtttgtttgt ttgtttcatt    98340
cttatatcta atggtgccta ggaaagtgtc tggcattaag taaaccctaa attaatatac    98400
tctgggttaa tgaactggtg aaggaaatcc aatagttaat aagacagaca tggtcactgc    98460
ccacaaagct atcacaatca actgggaaag accatacgca tttaaagaaa taaacaatca    98520
ttttaaactt tggcaggtac tataaacaat gaacaagata ctgaggcaga ggatagcagg    98580
aaagccgatg tagcttagac tcaatggtca ggaaaggccc tcctctgggt aagatttgaa    98640
ggatgagata aaactgaaca tgagatggtg ttgggatggg ggcagtgagc aatcaaagaa    98700
ccgtcggaat agagggcaca gcaagtgaaa agaccttggt gtcctgagat agagaaaacc    98760
ttgctgtatt gaaagaatga aaaagacttg tgaggctgga tctaagttgt ccgaagagga    98820
ataacatcat tgttcacatg tatggggcta tactaagatg ccagacactg ttctgagagc    98880
tatttctaga tctgctcatt aactctcctg ataatcctat gcagtggata gtatcacatt    98940
atccatttta taggaggaaa cagggtacat ggcttgtaag tggtggggct ggagttccag    99000
aaatattcca tgcataagca cagagtgctt aaacacactt ccttggatcc ccgacacacc    99060
cacttaagtg tagaattgaa gcgtagaatg ggtgtgttga ggatccaagg aagtgtgttt    99120
aagcgctatg tgcttatgca taggatattt aaagatcagg caatatagtt gccagaattt    99180
atagtccata gtcctttcac ctgtgaaaaa aaaaatgaa gtgaggagag caatatatta    99240
tcttgacctc acagggagga agattggcgg tacaacttt acacaattac agagacaaac    99300
aagtgcagtg caagaatgaa aacctatctt gccttagact ccacaggtta tctgccctgg    99360
atcaatcagg gatgcccctg cacactcaca ggccagggtc cgcatgctct ggatgcaggg    99420
```

```
ggctgtgtgc acacaggcac acacgtatct tattctcagc cacttccttg aaataaccag   99480
gaatacaatc caaaaggagt gctttgtgtt tctgagaacc ctcaaagaag ctttgaaaga   99540
cttgaagaga aatgatctta acaaaagaac aaaaaaaaaa aaaaaagaaa gaaacttgaa   99600
agtgaacaga agttctgaag tgtgtggggg tggaagaagc tttcttggag aggaacagta   99660
aggagatagc taactcaaag cgaccagaat agcttagcga gctgagaatt gagaattttg   99720
tgactcggtg gttctgctcc atagggacac tgccggctcc cggggagaat gcatcttact   99780
ctgcccccta ggcaggtcca gtttctggac ttccctggcc acacagctgg agatttccac   99840
atcatatatt ctgcttgtct tagaaaactg aaggactgat tttctgggcc ttctgactga   99900
ccagagagcg ttctttgtga gagacacaat agctatctat tcctttgtgc agtgtgcttt   99960
gccaagttcc atgagggcag cggtccctgc tatctttgtg taattctggg cagtctgagt  100020
cccacaaatt ggatttacac agcacctgcg agttctcaca caagcccct tgttggtaat   100080
atcatttggc atatgtagca agcattcatt tttatcatag tgttaattgt tagccatggc  100140
agtaacaagc cagaaaaaag cacaggcaga aaaaaagcca cgtctgctca attaaagggg  100200
gtaaatggct tggcggcacg gcagggtgct gcggacacaa agagcaggta aaggaagtga  100260
cctgtggtgt tgaagtttat ttgtttgaac agctgagaat tatctcctga cctaagtcac  100320
ctccataaca ggtggccctt tctgtctgag tcccacagca cttggcttga gagagtgtcc  100380
aatctcattc atgtggaaaa gatcaactct ttttccccc tgtaaggaaa aaaaaaagg    100440
aatgtgactg gctgttcaat tgtaatcatt tctttgagtg cctctgtgtg gaaaggatgc  100500
tgcctcacct attcctcagt ttccacatct gtaaaatatg gaaactacta cttgctctat  100560
ttcccttcga gggcttttg ggaaatccat acagtaacaa aaaaaaaaa aaaaaaaaa    100620
aagacaacac attaccaatg ctaagtgcaa agtcacaaag tcatgttaca aatgtctaca  100680
ggagcaaaac tacagtcaag aacaatgtca taagatattt taaaattcat ggctgtggat  100740
tatttgttga gcacttgttt tgctgtagct cctggtgact gggggataca cactccttgt  100800
gaagggctct aggtgtggca tagacagata cctctgcttc catagcagcc ttcttctgaa  100860
ccccatgcta ttacctgctg gacagtcagc agtggggcac catcactgtg gcaggtgaag  100920
cactctaccc caaagagaga gaaaagctgc ctttcattgc aagcctcctc tccagacaca  100980
ctctggagtc acagcagttt ttgtctgtgt ggccttgtcc taaaattgct ggctgttctc  101040
ctcatcttcc tttctcttgg atcagagtta gcactgggag aaccctacag ggtgattgtc  101100
agaccacagg catgttctgg ctctgtggtc tgataggctg tctgtgggcc ttctctgtgt  101160
acccaagcca tctctgatta cacacagagt gccagagaaa aacaaaacac tttcagttta  101220
ggcaaagttg agaaacccat caaaataaac actgttgatg gtcacagatt taaaaaagaa  101280
tatgtagaga gataataggt aaaatgcatt gacagtcaca gacataggct gcgtggctgg  101340
ctgcccctac tgcttaaagc actgtgtgtc cggagatcta agtgtcatta gtggtattta  101400
cgaatccatc aaatgtgcag atttttactt tgcagatcaa gtaaataag gagagaggac   101460
gagaggcatg ctgagactcc atgctgcttg aagagaaaaa ccctcatttg tattcctaag  101520
cccttgcca tgaactgctg atgtccccaa acaaaagaa agctcgtggt ttctgttctg    101580
gtaaattaaa aagcccttta gcttaacagc aaagcatctg tctaccttgt tatacatatg  101640
gcatctaatc agaatgcagg aggtcagggc agaggggagt aaagaaagtg aagatattgg  101700
ggtagaaagc taaggaaagt attaaaccta agatttgggg agtaaattag taaggaaatg  101760
```

```
aattttacaa aagaaagagg agaatagcaa atgagaatca gggaaggtaa caaaaagata 101820
acatccaaaa gaggagcaag aaagaataaa cgggaaaggt gtgtaaaact gaaatgaagt 101880
tggttgacga tgggaaaaag agaaggatcg tccagcagca gataaagagc agctggggag 101940
aacgtaacag attctgatcg atcgtgatgt ctggatgagc tcagtttcag ggctgtgata 102000
atctttacaa tggactgagc tttgctctcg gggtttatga tcctggaaga accacttgat 102060
tgactcatga ttctccaatt gatcacttca tatcagcaat ctttgcttct atgactcatc 102120
accactcaga acctctcaca aagaagctgt tgtgtcttga aactttggt gatattaatt 102180
attttttaaa gagtatatta aaacttagat agcccctgtt gacattccac aaggagaaaa 102240
atgccctaaa taccaatagc tgcctgtgat atcctgtgat agaaaagtaa taaaacaaag 102300
taaaaattag gaggcatgct agactgtgct tctatttcct tgctgaacta agtcgcagct 102360
ttgttaagaa ttatatagca gttggcatgt ccagttgata tttacttgca aaatcatcat 102420
tggctcttat acagctcatt cttgactctg atacgccaac gttccaatct acataaaggt 102480
ctttggggta gtatgacatg cagtgattct gagtatgctt tagaagtctt taggcagtat 102540
agacctgact tcaatctagc tagaaaggtg aagacaaaa ctcttttttca gctgaggctc 102600
tttctcagaa cagaggcctt tcctcctctt cctacacaca aaaaaatact cagcctgggt 102660
aggaggagct ggctctagcc caatagagca gattatttac cagtttcaat tatctgcact 102720
aatgctcccc ttcattggtg agggtaattg agagttgaat gtatttacaa ggacagggct 102780
ataaagctga aacaatttta caaggtgtgg tgcagaaatg aaaaggtaga aaaagagctg 102840
gtctagacaa tgcttttttga aaacatattt cacataactc tagcaagatt gctaggtcct 102900
gaggggagga tgggtatttc agaagagcta ttagaagtgc tattaggttt taggagattt 102960
ttgtggagtt attggacatt tcatattta agttaggatg agggtattat ctctgaatcc 103020
aattcctttc tctcctttta tttccaaacc cactctggtc ttcatcctgc tgtggtgtgc 103080
ttgttcccag gagcaatcta gcatcccagt ggaaagtggc cgacctaaat gtggctctcc 103140
aaagacaaaa aatttattct gggtattgta tgatgaccca gatacagtat gatataaaat 103200
agaatatatt actgtgggtc tgataatgtc gatttcaagt ttcctaacct agtatctact 103260
tatagtatta ttattttttag gtccggcttc tcccttttaca aggagtaatg actatgtgtg 103320
gccaacatat ttggctttat tactttaact ctcaatattc tgatttctct ttagatcata 103380
taaatctttt gcctttctca ttaactctca aaatgagaag ccaaaaagtt ttgttgctgt 103440
tatagtttga ttttttaaag tatacaaatg acatctgctt tcaaaaatat tgaaaccact 103500
gggtttataa cttcttgaaa taccagttag tttggtgata aaagttaaac gagacaagca 103560
tgaacttatc gaaattacaa ctccttattt gcagcaggat agttttttgat gataatgtcc 103620
actgataaca atgatgaaat aaactacatg catttcccct caaggcctct gcacatgctc 103680
tggggcctct cctctgtgtg tggctggctc ctctcatgct ctggatctca ccttgaagtc 103740
acctcttcag ggaagccttc tttgactctc ctgcctaaat gacattattc tctacctcag 103800
cactcagcct gtcctttata gtacttgcca ctgtttctag ttgttttatt tatttgctga 103860
tttaaaatga gtcgatctca tgactacact gtaaattacc taagttgagg agatcatgtt 103920
tctcacgttc acttttttcat cctagtgcta gcaatgacct gacatgccac atagtagatg 103980
tacaactaac atctacttaa gtgaatgcac caatgaatga tgcctgggtt atcaatgtga 104040
tgtacacctc ttcattcact attacctgct ctgaatccca taagtaatta gaggttacta 104100
ggttttttatc agagaaaaga gaaaactctt aactttcata aacacttgaa atatttcttt 104160
```

```
tcctttggta ctactgctga taatacctat gactgctgag tggttggtgt tttccaggca 104220
acttgcttta tgagcattcc tctatttaat attcgcaaca aacctataac gggtacttt  104280 attatcccac tttacaggta aagacacaga gagttggcga ggttaatgaa tttgcccata 104340
taggctatta atcaaggaca gactgtaatt taaaactcaag cctatctggt gccaaagctc 104400
actgtcttac ccattgctat ctatggtaaa ttaaaatt  agtgttgtaa ctatctaatt 104460
atatgtatca tacatattta ctactagata taaagtatta tcagaaaaaa agggcttatt 104520
ccttctcatt ttttatcttc ccattcctcc ccacattttt attaatctat taacatatgt 104580
atttaattct tatagaacct agtatagtaa tctgctatgt gaatgctcat caataaatgg 104640
ttctttgagt gagacctcca aagcagcata tgacatggta catgttaacc tttaggtgag 104700 gaaaaagcc  aaattcccta atttatcttg ctgctaacgg caaggttgaa caccaccaca 104760
gagtatgtat ataagaggt  gcagttagct gacgccctcc tctgttccca aaaatgttta 104820
ggtaagtttt tatccgggaa tagtaaaagc tccaaaaata agaaaaatca tcctggaaac 104880
tatatttatt atttatttat tttaaaatta agtaaaatta attaaatgtg aacccattca 104940
cggaccctaa ggaaaacaag ataacatttt tgggggcat  taggttttca ctgggaattc 105000
ttctcaaggg ccctgtagct ctaaacagta tcgttaataa ctccattgga tctcatggca 105060
cactccctca caatttcatc tgccaaatac ataaaattt  tgacaagtta aagtatattt 105120
cctcacctag aatatagaaa ttgaaatatt tgctgaccat caagctctca gaaatttaac 105180
aagagtcctc atgtcctgga tttctttgta gtatgtctca tgcacagcac gcaataaggc 105240
tctgtacaca atcaggcaga ggaaatgttt gctgaatgga atttctgtaa ggagggattc 105300
atgtcatagc aggatttcca ctgcaagcct atttaagac  agaaaatatt tatcctgtct 105360
aatcaaccaa aagatcaggg tctgaatgtt ttttaaatct acacctattt ctactaggag 105420
gcaccataga gcatttgtca aatcttcttt tactttgctt gggtttatta acacaagcaa 105480
aataaaagaa gatttgacaa atgctatatg gtgaaatcta accaaatagt ccaacagaat 105540 aatgggcct  gaaaattctc ttttgcacaa tagtctaatt tttgcccaaa ttaccgattt 105600
ttgctctgaa tagtacacat taaatgacta gaagaaacag tttgaagaca taactgtc  105660 ctactgttca aattaactgc tgatacagtc attgcaataa ttgctcccat tctgaaagtg 105720
tctctgcaaa cattcttacc acaaaaaaga catttaagaa aaaaaataca ctaaaatatt 105780
ctcaatacaa atatgtatgt gtgtacattc ttaaatatta cagaatggta ctgcattctt 105840
acccaaatga tactattact tatctaagga acagggtgat ataatacata aggttaattg 105900
tgaaataatt atgattcata cagtgatctg gacagttcaa aacaatggct taatattttc 105960
ctgtgaagta acttttaaat aatgaagtta ttaatattta cttgatttct ggcctgcatt 106020
tgccaaaaaa aaatttaaaa cttaatttt  aagaggagag gttgcaataa actgaaagat 106080
aaaatctttt caagggaga  agtgatcgtg tttcatagtt tttcaatagt ataagttaac 106140
aaactaacta aaacttaagc ttataaacag gatggcagtg agctaccaaa tataaaaatg 106200
tagttatcct gcactgaaag ggttatttct tatattactt aattgttttg agcttactgt 106260
ttcttaccta aaagttttgt ttatttatgt actcaatact gaatcagatc tccttccaca 106320
cttcagtgat caggccattt acaactgaaa tatttttatg catatggact cgaagaggca 106380
gttactgaaa acgcatactt tcctggcaag aaataatgca ataactgttg aaaataatgc 106440
tggcaactag tgttttcctt tgctgctaaa tggcatgacc agtgtcatag gagaagataa 106500
```

```
atagtgtgtg ctcattcact tgacattttt agcacctgct ctgatctaaa ctgggtgccc    106560
tatctgggga tttcattttg ctaatgtctg cattaatcaa cacagtctca cacacacagg    106620
cacacaggta caccacaaaa aaaaggaaga gagctctgga agtagagcta aaatgaatta    106680
tttggggaca aacatatttc taacttcaga aactctgtct ttcttttgaa atgtccaaag    106740
cgaatggtat attgattttt gcagcacact ctgcactttt cactgattgg tatcaggatt    106800
gtgaaggcat ccattaagtg agctcaaaat gctctcctag tataaacaaa atccacagtt    106860
ttaatcaaat ttaatgtact ctgacctata tgtgttttgt gaaagtcaga gtggactatg    106920
gcaacagaat tgaaagcata tattacaaag tccttcacct ttcagatctc ctgaaaggaa    106980
ggattgtcag aggtattgtc tatgtattct tttaagtcac ctctgaggag gcagcagggg    107040
catggggaat gagatttgca tttcagagct ggagccaacg tcaggttatg agatatgat    107100 gaattaaaat acatctgcat ctgaaggaca atgagatcct gtggcccagg gcttcatttc    107160
ttagtgtaag aagagcaaga gtttcaggta ttcacatctc aaggtcccat ctcagaaggt    107220
tcccagcaat gaggtaaaat gctgcctgaa tactgataaa ttctccttgt ccaaaagtga    107280
ccaagatctt attcctaaca caaatattgt taatggcact caagcagtat tgcttgtttg    107340
tttctcaaat tcacggagtg ctaaggctct ggcagtttta ctgaacacac tttactagta    107400
aacttaatac tgttagagaa tgtttcagtg taattacttt tagttcattt atgaaaaata    107460
aatgtatttt agtacacaac cattaacttt ccctagaact tttactgata ataatgtcta    107520
ctgccataga caagaaaagg gtcaaatatt gtcaacagga ttacataggg agaatcagtg    107580
aaaagaatag taagtattca ggtaagagga aggaattttg gagttaattc aagaatgatg    107640
gggatatggc acaggatcag gggaaagaaa cttttttgttt tgtttttttga gagagagtct    107700 cattcttgtt gcctaggctg gagtgcagtg gcacgatctt ggctcactgc acctccacct    107760
cctgtgttca aatgattctc ctgcctcagc ctcccaagta actgggatta caggcaccta    107820
ccaccatgtc tggctaattt ttgtattttt aggagggacg gggtttcacc atgttggcca    107880
agctgatctc gaactcctga cctcaggtga tctgccccact tcagcctccc aaagtgctgg    107940
gattacaggc gtgagccact gctcctggcc tatatattaa cctttatgt aacccaaggc    108000 aacacatgca aactcacatt attctcagtt ttcttatcta ttaaacttgg atgattatat    108060
atctgttcaa cagttaccat gagaagtttg ttaataatta ttttttatgat gatgtttcct    108120 gttatctata caaaatttta aggtactcaa aatatttttct cttattagca ctatgctaac    108180
cctatgatct agtaaatact ggggagaata gtgttcccag aagacacccc tttcctctag    108240
aaactgttag acagtcatgc agtacttgtg aaggaacaga gtagacaacc aggtttggta    108300
tcctaaaatc acattggctt acagctattc atatgtcatg ataatctctt agttggagaa    108360
ggaaaataaa atgagaaaca gtttcttctt cctgtttcaa ggggaacaca atagtcttat    108420
ctttacattc agctaccttg ggtataagta tcagcttttc gtattttgcc tttactttc    108480 cgcccatgca gattaatgtt gagatattct taacctaaca cacacatgca cgcacacaaa    108540
cacaccaaca cgcatattgc actcatccat acaaacgttt gggcttatca aggtcaattt    108600
aagttttttt aaaaatgtca taatatttat gttatctgta tttttatgtg tctgtctttc    108660
tccccctttg gaatgtaagc ttgacaaagg cattggtgag atctgaattt gtccattccc    108720
ttttatataa ctattttcatt tcatgtatat ttttatctc aattaacata cttggcttct    108780
tatagatatc tctatgaatg tccatctgac ccttttcatttt ttagattctt cagagcagag    108840
attatacctt tttcaattat tcaatctgaa aaccaagaac agtatcttat atataatgta    108900
```

```
cacataataa acatgtctat gattgaattc tatatattga atcactacat aataactgat   108960
tctttgcaca gtgatttgca tacacaataa ggatataatg attatattta cctgcctaga   109020
ctttacagta ccaaacttga ggtatagatg gcagtgctgg gcacacactg gttaaatgtg   109080
ttgatgagaa ccctagctca agaaagccat tgttcccttt atctttctgc ctggtcaaac   109140
aactttgtca aaatctggcc ctgagctctc cctggctttc atttagaggt aaaatcaaac   109200
actttgttca agattttcta ggataatttt cattttaag gtgaagatat tgagacacat    109260 tcgttcttc aagacaaagt tattgacaga cattcccagt gagaccaagc cgactagcag    109320
ggttgtaccc atacaaatcc tccttccttt atcctcctct ccttaagccc actttcatcc   109380
acagaccaca gatacaagga ctaagacgag ggaaggaaag ggctgataaa tcacagaaca   109440
aatggtatac aatgaatgga aataaaatgc tgatttccta atgagaaaca tatggttatg   109500
actacgtaat aaacatcaga aaatgctctt tcatggctcc caatagtcat aaagtttctg   109560
gaataaagag gaaggaaaga tgcaatttaa tcctataacc taaatgtctg aggatctacc   109620
tttctcaatg gggctgtctt gttaatgaac tagaccaggt ttctttgtgt agctttcacc   109680
tgattctacg taaggctttc tgccaattgc taaacatagg ccgctgaaag atgaataagg   109740
agggaatcat cagctgttcc accaggtcag aagcatgatc tttaactaaa gggccagatg   109800
gcttttataa attaagcaca aaaatctctc atttatgcct ttttaaagta aagaggttag   109860
gagttatgtc ttatacttct tttttaatttt taactctatt atatcccttg caccaatgat   109920
tgagagttat tcagttataa taaattatat acttatcttt agttaggcta tcagactctg   109980
tttatacagt agtgacaggt gttaaggtcc agagaaaaaa tttagggttc tggagcctag   110040
ggtttgccta cacattgggc tccttcttca ttggttcaca tatgctcctg tctacggctt   110100
attatttggt atgactctaa aactcattcc ttgtactcac ataccatgtt tactttacag   110160
aaaaaaatgt taggacttaa tacacatggg ccctatgaag atgaaaaagc tgcttttaaa   110220
tgtttgttgt tgtttctatg aaaactacca cgctgttatg ttctagttca catataaaga   110280
gttcattctg tttaaataag tggaacaact cacatttata ttccacactc aggacccata   110340
tgcttggcct tgtgctggta actaggaata taagataaca agacaattcc cttgctttca   110400
aggaaatcac actttataaa actttgaatt cttgaaatgg gtttcagagg ttccaaggtc   110460
aaattcaaga ataagagttt aagaagaaaa agactatgag aaaggaagtg ttgacccat    110520 ttgcatttaa atagcaggaa tagtctcaat ctactcattg gggaaaaatg tatgttgcat   110580 attttgaga tattgcaact tgctctctct ctttgccacc ccaccctttg tcatgctctg    110640
tttttgtgtt gaattggcaa gaaaaatggc tggagggctg gaagaagttg gacccttctt   110700
ccttcttcct tcttccttct ttcttcttct tcttcttctt cttcttcttc ttcttcttct   110760
tcttcttctt cttcttcttc ttcttcttcc tcctcttcct cttcttcctc ttcctcttcc   110820
tcttcctctt cttcttcttt cttcgggggc attgggagct taggaggttt gggtggtaaa   110880
gaaagggtta atcctggggg atgtgggtaa agggtgcact ggagctgcct tgggaaaaa    110940 tgtggtctcc cactttccat ggacactttg ttcatagaaa ggacaactgc taggaatgaa   111000
caaaaatgaa caattagatt cattgtacac cttctagtac atttgaggct ctgtgatccc   111060
agatgcttac atcatttaat cctcataatg accatatgat agatccattt tacaaatggg   111120
gaaattgaag tttatcctgg aaatttgttg agattaatct ctatttgatt acaaaattta   111180
tcttcttctt gcagttttgg tgacttggaa atcaccccat tatcttgaaa aataacccag   111240
```

```
atatttaacg tattctataa atccctggaa aatacaaaag agttgcccaa tgtagtgcat   111300
actctctggt atcatgagat actgacagtt caaacatggg aagctagcct aattaggaaa   111360
ctctccttaa ataggtgacc agggttttct tctaaaggaa gaacaccatg tcaacattaa   111420
ggagttcaat atttgctgat gaatgcagta atccaaagca acaaaaagtt cctgtggaag   111480
aaaaatatac agtttgaatg ggtctcaaaa atgtgaaaat ggaacactgg gatattttta   111540
aggaaatttt ctttcaacat agtgcaccca tgagagtgat tcattgtcat ctggaatcaa   111600
ggatgaacgc aaacttgccc tttcactgaa ttagtctgac atacatctac aaagagttca   111660
agccctcctc tgggttatgg tggagcagcc accctcagag gaaattctca aggctgtttg   111720
taattgcaaa ggtcctgctg tgggactgga aggataccac tgaaggcaag cctcagcagg   111780
gctttgggag gcattcttct gtggtatata caagctgctc tccagggtct atgagaaaca   111840
aagcccaggg attgaagctc taggagctga aagggagttc attctttgtg cagttacctt   111900
aggtaaaaac aatagttcct tctcttttcc actgttccca tgaagctgtt aagctaaatg   111960
tccacagagg gatacaagtt tgtatcctac tccgtgctct gtgtattcat aaatgattag   112020
atggcatcac caatgtcctt ccagctcatc agcctttcca aaatagtcct gaggagcata   112080
ggagaagaaa tagagacaaa aatttggatc ctcaggtcta caacctggct gggccaggat   112140
gtcttttcag ggatcattag ttagaataca cagttataca tttgcataat tctgagatga   112200
gaaagacttt cctcagaatg acaccaaggt cgaaaaataa gattagaaaa caagattagg   112260
aaaaatggaa aagaataaaa catttaaaac ataaatatgt aagctttcat aatagtaaaa   112320
tataaataac aaattgggaa aagcagtcat atgaacagac tttataagaa aaatatgtac   112380
tgctaaagca aattaaaagt aaaatataca aattggaata agttgactat ttttctcatt   112440
aaatcttaat gataaaagca aatgattttc cttatgttga taaaggtttt gccagaactg   112500
taaattggta caagtttcct gaggcagatg tggtaatact tatcaaaagt ttcaaaaata   112560
ggtgtaacat ttgggtgaag taatttctat ttctaaaaaa ttataataaa gaagcaatta   112620
agaatgttca caaagaatta gttgtgagaa tgttctttgt actgttgttt ataatgtagt   112680
gggggcagaa agtgaaccta aatgtcaaac aatagaattt gagtaaataa gttttgtttt   112740
gttctaagag atggagtctc actgaagtgc aatagcatga tcatagctca ctgcagcctt   112800
gaactcttga gctcaagtga tcctcccacc tgagtctccc cagtagctgg cattacaggt   112860
gcatgcctgg ttaaatacat ttttttcagg tccctgtaaa gtctgggatg attaaataca   112920
ttttacagac atctttacaa cagcatactc tggagctatt aaaagacagt gctgtagatg   112980
tatatctatt cacatacaat tgttatgtta attacataat attaaatgaa aaaacccatt   113040
tgcaaaattc tgtatatggc aatttagttt atgaatatgt actaaacatg aaaaaataca   113100
caccataatt ttcacactag ctgtctatgg ctcgtggaat cagagccatt attttttggga   113160 aggggagttc tctttttatt caaatgcatt tcctaatatt tctttaacat gtatatatta   113220 cttattttt ttaaaatatt gaaagtaaaa ttctttagga tttagtctgg aaagaaaatc   113280
cacaacagtg aaattttttt ttcccctgct ggccttatag aagcataagt ctttatgtgc   113340
ttctgcagag gaaaaaaaaa cagaagcaaa gtctaacttc tagcagctct aattagaatg   113400
aataaaaccc tacagttgaa gcataaccag gtcacagatt tgcatcctta taagagcag   113460 gcactttaga gacataatgt cctgggtcta gcctctgtgc cttgcttata tgaaaacttg   113520
aaaaagtaac agaaattctc tgaggcttat tttctacaaa tgtgataaga agataataac   113580
gcttatggca cagggcagtg agaattaaat ggtaatgtgt taggaaacat ctgttatgta   113640
```

```
gtaggtgctc aaaacagttt tagcttcctt ccctttttcc cttgcagtct tgtttaaggt    113700
atcaaaatta gagcagaaca ttgccactgc catgtgggcg gggggagact gattcctcgt    113760
ggactgaggg aggttctact aaggagtggg gtgagtgctg tgaggcccag gacaaagatc    113820
tgtctcgctg caaccctccc ctcccccagc acaccaattc ctgtatcagc atttgctagg    113880
ttgctctaat tttccttttt atatgttctt ttctgtctga tgtccttgaa tgttgggaga    113940
cagaaattgc cctgggactt ctatgtaatg aaaagagagt aacagtgagg atgctgatgc    114000
tggatggagc ttgggatggc cataggctaa gaatcctaga agagcctaga caaagaatcc    114060
ttggaaattt cgtataatat gcaaggttca gggaagcacc agtaaatatt aacttccaat    114120
cctctctctc tctctctctt tctctctcag cttgttttcc tcttcttttt ctttatattt    114180 tcttcccccct cccctttttc tcctttccct tctccttctt cctcttctcc ttctccttct    114240
tctccttctt catcctcttt tcctcttcct tctctctttc cctcttctct cccttctcct    114300
ctcctcctcc tcatgctcct tcatattctt cttcaatata gggggtaatt ttatttggat    114360
aaaagaaaat tatcagatta ttctatactt agggcctact gtcatcttcc caaactctgc    114420
taggcaacat tctctacaac aatcgcttgt ctcatacttc ttgctttact tagaaaacac    114480
attcatttcc caaaggctaa ttaaagaaat ataaaagtta gagttacagt ttgtatattc    114540
tcattagcaa atcaccaacc caggggacaa gaacaagtta ggagcatctc taccaaaaat    114600
ctaaggaatt gcaatccatg taaagacact acgttaagtg ttgcgtgtgt taccttcttt    114660
acaaattaga gtcctcactg ctggattgag gctggcctaa tgaagttgta aaatgaagat    114720
atattaattc tttacctggt gcttttatta aggaaagtta tctaaatcat ttaatgaaaa    114780
tcaactaaat gtattacctc ctacattagg aatacagtga cacagaagaa gaaaacaac     114840 tcttggataa tgactctggg cagaaaaggg agatgagatt gcaaacaaaa tatcccaaaa    114900 taggttttgga gagaaaatga gaaagaaaga gtcttggtga ttgaagggaa ttagaaatga   114960
tagaagaagg ggagatacat agctctctct tggttgatta tcttgcactg aggaatttct    115020
atgagaacgg atctagggaa gtacaactta gtccaggtta gatgactttc agaggcaatt    115080
tctgcataga actagattcc tcagtattca gaagaagtat ggtagaagtt tgcccggatg    115140
gcacaaactg gaatgcctgt atgagctgat ttaccctgac tgacgttcag attgactgat    115200
cggtaggatt ttgctgttat tcacccacat ctccagtttg tactagccta gaaaccttct    115260
atttgatgac ttatttgtcc catttttgtct caaatacata gaaggggcga aaacattat    115320 tctagtggga ggtttctgtc acttttgttc attctgaatt tgtacagaag gtaacacaca    115380
caacacttag gtggcatcta tatggttgtt atttcattag atttctagta gagatgcctc    115440
tgacctgttc ctgttccctg ccaaaccaat tctgagagcc tgattaaggc aacagggtct    115500
tgaggtcaag attccacaag ccaccgttga ctaattaaat atcacaacgt aacagctaaa    115560
cttcctcttt gtagcttcag agactccata gcacaaatct tcccctaaa tcatataaac     115620 ttgataaata aagcagcatg catataactg agcatatatt ttgaaatgct tctaaaaagt    115680
agaacatcaa tttaaagcat taaaaaaatg ttagacttct ttctttttt ttttttttt      115740 tttgagatgg agtctcgctc tgttgccgag actggagtac agtggtgcaa tctcggctca    115800
ctgcaagctc tgcctcccgg gttcacgcca ttctcctgcc tcagcctccc tagtagctgg    115860
gactacaggt gcctgccacc acgccccgct aattttttgta ttttttagtag agacgggggtt   115920 tcaccttgtt agccaggatg gtctcgatct cctgacctcg tgatccgcct gcctcggcct     115980
```

```
cccaaagtgc tgggattata ggcgtgagcc accgcgccca gcctagactt cttaatacgt  116040
atgcctctga tagactgcca cttttctcctt taatgataag tttctatttg cctcacccccc  116100 cccaggagtt gtttgctctt gagtaggacc tatgcttaaa tttgtacctg ccactgctga  116160
cactactacc aaatcaattg ttcttactaa gttagtatct tatccgagaa agaggcactg  116220
ggttttcttc atcattcaat caatctctag aggcagcttt cagtgtctct caaattctat  116280
cagtaaattg aagtttctcc tgcctgaact gcaccctgac ctcacccctt ggtgagggtg  116340
ccccatatct catccatcca tgctcagaca aatgtcacag atctctaatt caactcttat  116400
tatgtcatcg taatggatga acaaatgaag tgaatttaca dacagcaatc ctgggcttcc  116460
cgtctttgac tctcgatgta tgggcccctc ctgctgcata tttacataca attagcaata  116520
aagtagggtt ctcacagtta ttttgtttct ttgtacataa ggcaatttta gtgcctttat  116580
atatctagta tgttcttaca ctctcattca ctcattcatt taaaaataat tttgctcaaa  116640
agctgaagat gcaatattta tgatcgagga gatttattag gacaggagaa aatatcagat  116700
gaaagttgga tgactggtac aaagtgctgc agaaattttg aagaaagaaa gaatataaca  116760
tacaactgag aaacaattta ggaaatgcta ctttcaagta cttaatttca ttatgggtgc  116820
ctgtctcttt tgctatcata agacaaatat agacccaaag cacaggacac aagcattagt  116880
gaacaacttg ggaaagcagc attttccaga gtgtgctcca cagaaatcct acaatgtatt  116940
tcatcgaaaa agattccatg ccactaaat ttgggaagtg ccacctaagc aaccctctct  117000
cttgtgggtc acagtaacca tcagtatatt aaagactctg aagttgtgca cttaaaacaa  117060
aataaaacac acacacactc acatacacac acaaccagaa aactgttttcc ttccttcctt  117120 ccttcttccc ttcctccctt cctccccctt cttcttccct tccttcccct ttctctttct  117180 tttgacagt ctcaccctgt tgccaggctg gaatgcaatg gcacgatctc ggctcactgc  117240
aagctccaac tccctggttc aagtgattct cctgcctcag cctcccaagt agctggaaat  117300
acaggtatgc gccaccacac ccagctaatt tctgtatttt tagtagagac agggtttcac  117360
cctgttggcc aggatggtct caatctcctg accttgtgat ccacccgcct tggcctccca  117420
aaagtgctgg gattacagac gtgagccaac atgcttggcc aaaaaatttc ctatgtttaa  117480
ttttgatttt tcttcccttt tgaaacgaat gcatatagta ttactcttag gagtactatt  117540 tacttgtttta attcatttat tgccatttct acatatcact gtgctggtga ctctgtgcat  117600
gtatatgcag ggcagaatat gcattaaaat cttggaagtg caagttggcg gaggatgaat  117660
agaatatgtg ctattggaat ccaccacagg atttttaacc ttcttcctgt accaacccat  117720
tgtaaatgcc ttatacagag taatagcaga acactatggc aaggggagtg ctccaataaa  117780
tatctgacgg gaatgatctt ccttcacagt tagtattaat atttgtttca ttgtctttat  117840
tttaattatt ttccattacc tttctatgaa agataaagaa gagacatttg tatatctgta  117900
accttcacca aatgccacct gcctggtaaa tgtcagcagt ccccagggct tgtcctggg  117960 tccctcctca tttgcatcct cactgaggaa catttgtctc cttccaagtc ttcatttagt  118020
acctcattct cttggcattc tatcacaagc cctacacacc agtggccagg aatagggcag  118080
ctcaaaccag cacacacaca catatttctg tgacttact catgtttcta catcatcaga  118140
gttgccctgg ttctcactca tcacctgtca aaataacttt catctttcaa ggtcgacaga  118200
gccgtattaa catagcggtc aagaacgtgt ccaacctaga ctgggttcaa atacagactc  118260
tagataataa ccttggaata atgttggtac ctagctcagg ttgaataaca tttaacacaa  118320
ataaaataaa acaaaagaaa atatacttcc aaaaaccttt ctctcataaa tttattagag  118380
```

-continued

```
ttattaggtt ggtgcaaaag tcattgcagt ttttgtcatt acttttaatg gaataaaaaa 118440
acgcaattac ttttgcacgg accaaattgt tcttctttgg caatcccta gcaaatcaat 118500 tcaacttctg ttattcactg acaacattgt tttttctact ggctgcagct tttcacaagt 118560
ctgtgccctc tcttcactgc tataaattgt gagcgcacca aggagaagac tgtcaagttt 118620
acctttttgc tcatattgaa agtatgtggc aataactggc ttccacaatc tgtgtgttga 118680
tttggaaaat gaagattgag gtacaagcaa aaaaaatcag tgaagcacca tttaatacag 118740
aggggaacag ggcatatttg gaagtgaaca tttatttctg aatccaacat cagtattatc 118800
tagttggcta acttttttaaa tttttttattt aacaaatgta caacatattt aatattgtga 118860
tgtggacttg gccctgtcat ctagaaaggc cttagcacag gtagtttaat gaagtgtcag 118920
gtgagaagct gtcccatccc ctattaagca atgtattgtc taaatgagtt taattaccat 118980
gcaaattact aggagctcat atgcccaagg cctacaacat atcagatggc aggtctaaga 119040
gaaattcagt aggctgtgcc tctctttgta gtaatgcttt tacgtaatat agaaaaaatg 119100
tcaatgtaac aagaataaaa tgctatgatt cttggcaaat ttttaagtca gtgaaatcac 119160
tggtaaaaat tgtagtggac ttataagata gttgatataa gcaagtcact ttcaagaata 119220
gctattaact tatttgttct cctttctcta aaaacatact ggaagtgact aaatgtctga 119280
atcctgcttc tacacaacca tgaatatttt ggaaaaggct acaccactca tgtttatggg 119340
gaaggccttg gggtgtgggc atggactgga tctgaaaata aaaggtttat atcctgggtc 119400
agcttactaa atgtgatctt gaacaggtca ctcaacatct cagagtttcc attttctctt 119460
ctgtaataaa gactagtgat gccatcttta agatatagac taaatgattt aaagtatttt 119520
caaaactcat gcaaacatag gtattatgcc atagacaatt tttaaaagtg aaacaaaaga 119580
tatattcctg ttttcagcct ctatccatag acagagtttg ggtctgtcaa aatgttaacc 119640
gcagtataag accaatctga agtgctgtca gactaatggc atctttacct atcctgaact 119700
gcatggttct ttcacacaca caggcctgac acaaaacagt atatcttgta agtgctaaat 119760
aaatatgaac aagatgagac tgaagtttta ttactactac tcatttgaac atctttccaa 119820
atactgacca aattacaatg taatagaatg tgaccgtctg ttatctagga aaaaaaaaa 119880 atcacctaat gctttaactt ttacaatatg tctaatctat tcagagccaa gaataacctg 119940
ggagataagc acatgaattc agattggatt tctaagagat ttttagcaaa gtcttcacca 120000
aatgtgccta gaataagtca tatcttctga gcaataaccc aaagagggat gattctacaa 120060
gagtttccaa actttcttga ctgcaaccct cagcaataaa cactgattta taggtaatga 120120
gatggaaaca tggcttatta cttatataca taaataaaac aaaaatattt tactatttgc 120180
aatgcactct gatattttct atcctatcct acataacatt caaacaaaat gttatatttt 120240
agtttactta aaaagtatgt ggttgacaaa ctgttgatga attctacatc atcagggttg 120300
ccctggctct cactcatcac ctgtcaaaat agctttcatc tttcaaggtc gacagggctg 120360
tattaacata gtggtcaaga atgtgtccaa cctagactgg gttcaaatcc agactctaga 120420
taataacctt gtttgggaaa caccgtgttg tggatccagc actgtgtagg catataacta 120480
tttcatagtc catttgctta tttggagaga tgagaaaatc aggcctaggt gttcatgaaa 120540
tgcatccttc aaagactgag tgagagttgt cagtggtaaa atggcacttt gcagattaca 120600
aaatccagca tgaaccatga cttcaataaa gagtatttgt tgcattttgt aatagttgta 120660
tgcaaggtca aaaggactaa tattgtgctt gattttctcc tttgcctctg caataactga 120720
```

```
aaaacaggta tacacatggg taaaagaaat attaatatgg tgtttcaata acagctcaat   120780
aatttgattc agtacactgt attggattct tttctgttta gttggaacta atgggtgcaa   120840
cttaaagaca gttaaatata tatactttt  aatttgaagg aaaaactttt tcttttttat   120900
ttaaaggcat tgaactgagg aatgtgctgt cttatggcct agtgtttctt atctgcctgt   120960
gtcaaagcag tgcctgaaaa aggatttgca agagctttaa tggagaaggt tccagcactg   121020
ggtcatggag tagaagaaat atctaaacct gcactgattc cagttctgta gcaattagtc   121080
acatgtggct attgagcact tgaaatgtgg ctagtgtaac ctgaggaact aaattttcag   121140
gttttaattg tatgtaaatg taaacttaaa tagccatatg tgattagtcc ttaccacagt   121200
gtactataca gatctagagg aatcaatgta ttggctattt gctaagtaaa tgtgacaatt   121260
tttgatacct catattatca taatttataa tgcatcccac atactaaaaa gtgatctggg   121320
atccatgaaa agcagaaatt acaggattca tatatttaaa atagaactat tttgagacta   121380
gagacaaacg tattgccagc tttgggtttt agtttttaca tctctcaatg acaaataggt   121440
ttcttctgat tctccagaga gactgctgac tgcactgact cttattagtg gccttcaaga   121500
agtcctgctc caaatttcag ccactgcttg tatatacaat tttagacatt gaaaagaaaa   121560
ttctgctagt tccttgaaaa tggggctgtt tatccatttg gattgacaca agaaattaag   121620
acagggaatg tttttgtgaa gttggtcatg tagtatttgt atgatgggac tcttctaata   121680
agttcattta atcttaaaaa taatatgcaa taggctgggc atgatggctc atgcctgtag   121740
tcccagcatt ttgggaggct gaggtggtca gattgcttga gctaaggagt ttgagaccag   121800
tgtaggcaac atggcaaagc ccaatctcta caaaaaaga  aaaaaaaat  aagctgggca   121860 tggtggcatg tgcctgtaag tcccagctaa cttggaaggc tgaggtggga ggattgcctg   121920
agcccaggag tttcaggctg cagtgagttg tcatcctgcc actgcactac aacaagggtg   121980
acagagtgag gaccagtctc aaaaaaaaaa aaaaaaaaaa gataagataa aagaaaaaaa   122040
atgcaacaaa actaaaaaga ataatgatct aaaatttgtc aaacacagca aaacaactga   122100
ccttttaata ataatttggt tgcatccaat tttctccata ttccaagaaa ctcttgatta   122160
tatggcagtt ttattgactt acgagaaaaa cccactccgg atataataag caatttgtga   122220
tatgcacaga atagaggtga atgcacaagg ataaactgta tgctttagca attaaatcca   122280
gggcatttaa gggaacagct acactaaagt atagataatc aaattgaact aaggaatggg   122340
gtctttccat gatattccca gtgagcaaca gaacgtcatg gaaaactcca atcagtattt   122400
cagtacctct ttccttgcatg caaacaaatc actaaacggc aaatttgatg tcttttacat   122460
cctggaactc caggctagag acacccctgt aaattccctg tgaggtggga aattttgcct   122520
gagttgcagt caactctggg gtttgagtat tcatgggaca ggctgttatt taataggttc   122580
aggagaagaa tttgagggaa ttccaagaat tatggatttt acaggcgcgg gaggcaccta   122640
aggataattg tgtagaattc actgaggact aggaaatgat gttgacctct gagaatcaaa   122700
gtaggtggat gcagagataa tgtgtgtcca acagccacct ctagaaaaaa gccaggttat   122760
gatatttata aaggtgagaa caaaaaggtt tgagaattct atataacttt catcaagatg   122820
aactaaggaa agcaatgcag cagtttgatt gaaatgtaat gaactggact ccaggcaatt   122880
attgtgtatc ctgtctagtg aaaaactgaa caaagtgaaa aagattagct tggactgtag   122940
aaaagggaaa ccaaagggcc agaatttggt agagtattga acactggctg agagaagata   123000
gtctctgtac caggaacttg cccaattcct gtgatagcta tgtatacatt atagcaaagt   123060
gtttaaaagc taggatctac tgccagatta ctaattcctt aaccttggag aacttatttt   123120
```

-continued

```
catctctgtg actcaatttc atcttctgta agtgattata atagcatcca tcattaggtt    123180
tattgtataa ataattgagt taatatgtac taaccatttg aaatagcact ctcaataaat    123240
gtttattatt atcacccag agatagatac attagacatg ttaatatata tgcaactcat    123300
acaactaatt atctctattt taggttcaag gatgctaagt aattcttcga ccccctgaaga   123360 ttggcctata aggagggatg caccagttag gcagatatca gcattgggat acttatatca    123420
ctctaaattt gcatcttggc attttggctc atagttcagt cttttgtgag ttttattatc    123480
attagtcagc ctcctaaatc caataactct agacactgat aagtgacatt tggaccattg    123540
aggctgagag ctagacccag aactggtaaa ttcactaaca gtatgctaaa ggtaaaatct    123600
gttggcaaat agctaaaaag ccatctgctg tagaccttga tctatcttct ttcaaatatc    123660
agtaattcac taccaagatt ttaccaaatg ccaagtagtt tcaaattccc cccaaaataa    123720
aaaggaatag attatcttag agatatttag agttacagaa gggttacact taaacaaaac    123780
atatcaatca ttaagatttg ccctgtcttg tctaatactt gagggttttg ccactacctg    123840
aagactaagt cctgaattga tacacacaaa acagtacaca aaggaatcag tgattttttag   123900 tccagtgata cctagctcgt gattcaagtc aacttatcag tgtgctaaag catactcacc    123960
tatcccagta accactatct ctccactatc tctatttatg aacagaaatg caacaatcta    124020
tatttttaga gtatgggcct aggaatttgt gatacagaat tttttaaag aaagaaaaat     124080 atcatatata tacttccatt gcaggtctgg cagcagatag ctgttttgcc actttctgga    124140
aaaactaatg gcttttgata taccctccac tatgtagtat atttgtgaaa attccagagt    124200
ctcaaatgca atttccaaga ctgttctggg ccttatgcta ctaaccatgc aaatatccct    124260
cagctgaaaa attttaaaca catcctgggg ttgggtttat gttggagaag ctctcacagg    124320
actatcggcc caggattata ttgtagcccc taagtaggaa aggttttgtt tatgttgcct    124380
ctatttacat gggattttct ttttttgaat aactcaaacc caattataaa ggagcagaac    124440
tgagcctgtg agatatgacc aggctgccaa agaggaaatc gacaaagact ccacaaacta    124500
aggagacaag agcagctgtt attctggcaa ggagatgcaa cttgccaacc ttctgcccag    124560
cggtgccaca ccagtggtct gaacaataag ttgagtttac agcctcccct gtgactatgc    124620
cagtcacatt caagaacatc tgccacagcc ttaatgacag agcctatggg aacttaatga    124680
gtaccccata cacctgtgcg gttctacgag acagctgttt cccactccgc cacctccttt    124740
ctcagtcctt cccatcacgt gtgctcactg ccccatcttc cccataggat acagctgact    124800
ctcataccgg ggtctgtgct tttgtgagga tttcatttat ctccatttac atggcactta    124860
taggcagtag agataaaaag cataatatct ttcacactgc tcaagcttca cagttttgcta   124920 tgcaagaggg tgagtgctgg agactgagaa agtcaatcag aagaatcaat ggtctaagag    124980 ataagggggac aagaaggaag aagatgagaa gtgctgctac ttttttctttg ccaacaactc   125040 tcagacacaa attagaaatt cacaaagcca tggaaacact tcacagttta cctctgtagg    125100
tatctatgaa attgctttgg tcaaagcatt ttctggttga gaaagctgcc tagtggaaga    125160
cctaacaaaa caaaaaacac aaaacaaaat gcaagacaaa acaacttact aaaaatactt    125220
ttaaaattct gagaattcta attacatgga aagtgcacaa tgttagtata gtgcatgata    125280
gaaagaatct caaaaactgt atgacctttg gcaagttatt taacacctct gagtttccat    125340
ttttttagtt tgttaaatta ggataattac ttagatttgg taaaaccaca ataaataaat    125400
tatatatgtt atataaagtg ttttacataa taactagcac aaccaagtgc ttgataaaca    125460
```

```
ttattattat tatcattatt attattgcca catcaagccc atttcttatg gctttactgt   125520
aaccactaaa aaatgtgttc ttgttccata ttttacagaa taaatcattc ttttaatgac   125580
aaaaaaggtg aaatatcccc tagagagaaa aacctaaaaa taatgatctc atttgttatg   125640
taaatcaaaa ggtatgagct tgaattttgt agatatatga ctaacagaat gtagaaattc   125700
ttcagtcatt catttcggac tgtttacata tcagaagcat tatatgttct atgataaagg   125760
ccacgtggca tggcaaaact atgacaatat tagtagttta tgttaaaaag aaatagtccc   125820
ccatatcact agactgcact gtccaatatg gtagccacta accgaatatg gtagccacta   125880
accgaatatg gtagccacta accgaatgtg tctattgaac atttgaaatg tatctgctcc   125940
aaattgatat gtgctgtaag tataaagtac acactagatt tctaagattt agcatgtaaa   126000
aaagaattta aaacaactta ttaacaattt tatatgaatt acatgttgaa atgataatat   126060
tgggttaaat aaactatatt atggaaataa attttatcta tttcttgttt gttttaattt   126120
gtctactaga agatttaaaa ttaactgtct ttctcctatc atatttcttt tgggcagtgc   126180
tgctcgggac taatgattct caatggttct tatatatgca gtaatatttt gtttataaat   126240
gtcacacaag gagcttgaaa aaaatttaaa cccctggtct ttcagtgatt ctgactccaa   126300
tggccaagga atttgcattt tcaataagaa actggatatt tcaaatgcag atggtcactg   126360
gaccacattt tgagaaacac tgctatagac taaggtttct ttagttgaaa catgatgtta   126420
tgaaacacag atatgattgg ggggatgttt atggacagca tctagactaa tatgaaggca   126480
gaaaaagaga gggagaatca agatggtaga agatgcccat taacctgctt tcaggatctt   126540
ctccctaata agtagtaaat ataagtctgt tactttttcc catattctag tgccagtggg   126600
gatggaggag taaagtctgc actgggccag gtacggtggc tcacacctgt aatctcagca   126660
ctttgggagg ctgaggcagg aggattgctt gagcacagga gtttgagacg aacgtgggca   126720
atatagtgag accttatctc tctggaaaaa aaaagtctgc actgcgagga cctctcacca   126780
gtaaatttta agatttgaag gcaaggttta caaggctgtg gtgaataaaa gtgatgacat   126840
aattattttc agtggtaact aataacattc ttctcattta acactgtcac ttccattact   126900
actgcaaatc ggctggtggt gagaggtata agtggtatag atcaaatctg gagaaagaga   126960
aatattccat atagcctcca tgtcccactt ctttcatgat ataccttagc cactgtccac   127020
atagcaatta cattccaggc actgggcaac aaaatcacaa tcattcatgg ttgctgcaga   127080
gacacagagc ctctcctgcc atgtccagca taagaggctc tttcttggct gacacacaaa   127140
aaacctttca aatataaaga aggagagact ctgagggaaa caactcattc atcaaaccaa   127200
cctcatccgc cattaacatc acaccttttt ttgagattct tctattacca atgcccttt    127260 atttccttcc taccaacttg atgtgttttgc ctcaacaagt actctttcct cacagtttgc   127320
tttgccgtta tgttattgta tcttttgatg cctttttttt ttcgtccagc ttacactaga   127380
tgcaaaactg ataagttgt gctgattgga tggtgactgc ccaatcccag aaggacatcc    127440
ctcccacaat tgccttttcaa agttgtcacc ctcctatatg acgaaactat ggcagtagct   127500
gggaattttt ttttgcagtc aggtttaatc ttcattttgc tgaccaagcc accagggcaa   127560
gcacctctta cattgagggt ggtgtgctct tacagtgaga gcactactac agttatcagt   127620
gatgaaacag gaattcctga tgcagtaaat tgccttttgg aaataaatgg tagcatactt   127680
tcaggcttaa gttgacaatt taggtcattc ccccaaatct aaaacttcct atcacaaaaa   127740
cctgcaaaga aatcacacaa ttgttgaagt tagctgctat actgaggtca tttagtccaa   127800
tttttaatgc aaaataccctc ctaattggat gtcactcttc ctgaaatata aacagtaaca   127860
```

```
attgattaag tttcagatat tcttgctaga agttttcttg acttaaccca cttaaccctc   127920
agtagaggta ttactagctc cctccctccc tttacaggtg ataaaacaga gatccagaga   127980
aactgagtca cttgcccaag attacaaatt aaaggtgtga gctggttttg aactccagtg   128040
atccatttct aattcctaag gaggactatg ccttaagaca attcatctgc attttctaga   128100
caccatggcc acagttttag gcaaataaga gttaggcctg ggactcttta ggaaatgact   128160
gagaaagaga agcccttcct tcctttacca ctggggtttc taaaaggcta gatagtaact   128220
gtggaatttt gcaaccatga tggcactgta agtggtgagc cagagatggc gtggtcctga   128280
gctctgatga tctggaattt actgcttttct ctgaaatgtg agccaataga ttccttttct   128340
ttaagccagg ttgagttgtg ctgtcacttg aaaacagtta agtccttaag gagtgaacaa   128400
ctaagtaatt gacataaagc tccaagtttg taatgcttaa gccaatatct tgcacatatt   128460
agatattcaa taaatattag ttttttattct tccacaatgt tcaggagcaa tgattacgct   128520
tctctatttt gcacagagcc taaaaagggc tgaaacataa aaaataaata cattgaatac   128580
atgtctgcag atcaacagac atgttgagaa ctatacccag gagagattag acagtcagac   128640
tgtacccact catcatttcc acttctggct ctaagtagga gccagggaag gaaagtgctc   128700
tcagcatggc tcacagggga gactttccca acaggattct acagattgga cttgactcat   128760
agtcataatg tgccagactc accccagtgc cacctggtta atcaaagggc cagaaggtat   128820
ctgtggaaga aagacttaag gaagccgggg aagtagatag cagttcactg aagttcctgg   128880
catttgcctg agggcacagc tggggacatt aataatcatt tttctcatca gactgctgaa   128940
aatgagagca aagtgagaaa gggaaaaaaa caagtgtttt gctgcctcct gtttgaatta   129000
atctcttctg acaactgctg atttgggttt gtgattcgat cttccatatg tctagctcca   129060
ttggtcaatt aagtgtcgag ggtgattggg ggaagcagtg acactcagcc tgattagagg   129120
aagaagcatc acaaggcatt tagaacatgc aaagcagccc actgagcctg cttaaacag   129180
agccaagcag agcaagggtg gtgtctggta ctgccaggag ggtcagggaa gagtcgaacc   129240
tcagcactca gagcactaat caagtaagga ggacatcaaa gtcagtttcc tgtgagcagc   129300
gagtaagctc tggagagttt tggagggatc taaggctcat gcaaagttaa gcccccgtca   129360
acccattcaa atcttattct tctagactgt ccaactaatg aactactttc aacaaagtat   129420
cataaacttg agaacagaaa ataaagtcat gtctaacttg gagagttcaa tttatacatt   129480
tgaaggaatc ctctgaaatc aagaaatggg atagcagaac acttaagtta gacaaaaaca   129540
atgcagaagc agtagtgctc acacattact atgcagtaat aaaaacattg aggaactatg   129600
agttctagtc ctacctcagt taatggcttg ttggttactt tgcagcaaga tgcttctttt   129660
cttcattgtc acttccccat tttttttttt tctttgagaa agaatctcac tctgttgcta   129720
ggctggagtg cagtggtgca atctcggctc actgcaacct ctgccttctg agtgcaagtg   129780
attctcctgc ctcagcctcc tgagtagctg gcactacagg ctcacaccac catgcccagc   129840
taatttctc atttttagta aagacaaggt ttcaccatgt tggccaggat ggtcttgatc   129900
tcttgacctc atgatccact aaggctcagc ctcccaaagt gctgggatga caggcctgag   129960
ccaccatgcc cagcctactt ccccattttt aaggaggctg atggaggaag tgggggcact   130020
tgtacgctcc taaataaaac tgaaacttga tctaacagct gaagagaatg ttttgactgg   130080
agcaatggca gcctaaagtc tttttatgagt taaatgctaa agtacttcat gtgactgttt   130140
aaaagaatag ctaataaaaa cgattgtacg ctattttttt ataaagatcc atatcaatgc   130200
```

```
tcaacaatca tcatagaagg caacaggctc ctttaaaagt aacattatgt caaaaaagca 130260
cctatgattt cttggatgta gtcacagttt tgttgttcaa atttaatgaa aatagaacaa 130320
atgtggcagt tgttaaaaat aaatggaaaa actttggctg gattgcaaac tagttaagta 130380
tgatcttaat agaataacca tctaagcatg taaacatgtg gatttatatc actctgaagg 130440
aaaaactaat agcctagcaa agcctccatt caatgcttta tctcattcaa catatttatt 130500
gatgactgac atgggtaaaa tatacttaaa tagagagatt atcaacttac ttccccaaat 130560
ttaaggagaa aagctaaggc ataataaaag cagggtacaa aatgaactag atctgctcta 130620
ttccacagtt gtcattgtaa agatcaaata cagatcaatg ccacaacatt aaagatataa 130680
caaattttag gtcaagtgaa gaggacgtgt gatggtgaag aagacttggg cactgtcagt 130740
caaagaaaaa ttgaaggaaa tggatcaaga gagagcatgt ttgagggaaa caatggcaaa 130800
ataatcagtc tattttaaag gcttttaat ggggaaaaga tttagattta ttctgagtgg 130860
atccacaagc aaaatacttt agagagatag attttgacac aaatgaagag atttttttaa 130920
ataagtaaaa tgactttcct aataaatagt gagttctctg atgggagatg gggctcaaaa 130980
gaaaccaggg aaagactctc ccggtaaaag agattcacat gtcaagtaag catctagact 131040
gcatgacttc tgagatactt gtagttctaa aactccttga ttctattacc atagaagaat 131100
tctacagcta tttattttac atatagaaaa agcatgttaa gtcttgagaa atatgtattt 131160
cttagttaac tgtcatgatg ggaaaataga acattaatag acttaaatat ctgaatatac 131220
gtgtccctcc aaaattccta tgttggaact tagtgaagtg atggtattga gaggtgggac 131280
ctttgggagg tgattaggcc tcagggtgga actagtgccc ttagaaagag ctctagagag 131340
caaatatgtt ccttgttgac ccctgctacc tgtgaggact cacagaaggt gctgtccatg 131400
agaaacacgc ccttaccaca cacacatctg ccagaacctt gaccttggcc ttcctagcct 131460
ccacaactat gataaaataa aattctttt ttttaaatca atctaaggta ttttgttaca 131520
gcaccccaaa cagactaaga caaatgtaaa ttctgtaaat tcttaagcat acagtagaag 131580
gaataaaatc taacactaac aaatggtaga gttttagag aatgaataat ctatgaaaga 131640
aggcatacat attgactact atgaaaagac cgcacgtgac agaattgtag ggagtgatgt 131700
ttaagagcac aagctctagg ttagctgttt tcattcaaat cctggctctg ccacttgcta 131760
gatgtataac cttggacatg ccacagtttc tgcatctgag acatgaacat aacaatatat 131820
ctatcatata aagttttac aatttaaatg agtttaatat atataaagat tttgtaatag 131880
ttcttaaaac acagtaaaca ctatacgagt actcgttatt ttaccagctc tttaaaaatt 131940
ttcagaaaaa caggactaga gatattcaag tgaaggtgga tgtgctttca acatccctct 132000
taataaaaat aggtaaatta gttaatagac aatagaggtc agcttttttaa atttcattat 132060 tttatttatt tacttggtat tagccttctg gaatagctat atgtgaaaaa ttgattttca 132120
tcctgttgtc ttgccattac tgatgacgga atatatagca cagaaaattt taaaccactg 132180 attttatct attacataac ttttgcaaaa gctgaaatat aacaacctgg ggtaagcatc 132240
tcccatgcct ttttcctttc ttgtaccta aggaagtggt atcaatgaat ggccaaaga 132300 tgaaaagtaa taaggcagcc catctaatta ttgaattgtg taaatagctc ctgaataaat 132360
gaaagttgat tgtatgtata aattacaggt tatctaaaaa tggataagtg tatttttaaaa 132420 ataacaacat tcaacctagg tgatctgatg agatgaaaat aaactatgaa agtcaaaata 132480
tttaaacaaa caatgtcaat aacaacaaat attttgaaca tttagcatca atttattaac 132540
ttcctagtta atgtggcaaa aatggcagag tatttttacac atcgttcata acgtgggaat 132600
```

```
tctaacagaa atgttttctt gattcagaac caagatgtct acccttttt  gtctccttgg  132660 tctgtccaga ctgaagcaca atcaacggca aatgggagat atgagaaaag atgacatatt  132720
tgaataaatt ccatgggaaa aaattctcac atctttagat aatacatcta aactcttttt  132780 ttttctttg  accttcagaa aaatcctaaa tgtcagcagc ctgatttaga aaaaaaaaat  132840
gtctttggca gatttctctt cctttgttt  tctttactgc ttttaatgaa atgctaatga  132900
taccatttta ttcagcaatt ctacttctag gaatttggaa gtagaagtgc ctatagctga  132960
gaatgtggcc ttagattcaa gttctagttc caatgttgtc tagctgcatg accttgagaa  133020
aatggattaa cctctctaaa cctcactatc gttatctgta aaacaaggac ataaagtctt  133080
tagcatacat acaggtattc taagttcctt ctttatatca aaataagtca gtcattggaa  133140
cattattagt tttagacaaa cataacttaa tccttctcaa atctaccagt ctatatttta  133200
atgatcttct ctgagagttt actgagggca aatataagaa gctcttaaat aaagcatttt  133260
tttatttgct ataacgctgt taaaggcatc atctttaaaa gtacccgctc tttaaaattc  133320
cataaagtaa attcatttca gcatgtacta tcacgaacac tatctttctt aaataattag  133380
tatgtgttct tctactcatt aatgaaaata taaataaact tctattttag atgccaggaa  133440
actcagagta aatttctcat tcatatttat ttcatccttt tttgtaaaat cattttttcc  133500
attataaata ttatattgta taaacatgtt aataagcaga ctcaaatatt tcataatgga  133560
acccagagaa ctgattactt ttataaagta taatgtgact acaatttagc ctgcatcaaa  133620
aaataattaa aacatgtttt atattttat  attaaatctg cattaaaatt acattagata  133680
atacattcaa aaaccataac caaaggatat ttctcactgc tgatgcaggt gtggagagaa  133740
agcatcttgg aatagttcct aatgatagtg aaaatgtcca tgaaaggctt ggtaaatctt  133800
tacaaatagc cataaaaatg tcaacataat tcaaaaaaat ttgcttctag aaatctatga  133860
tttctaagaa aataatcatg aataaggata aaaatgtatg tatgaatgta ttcattacag  133920
tactcacctt gtaaaaatat tttatgaaaa aatcccaagc taaggaaatc atgaactaat  133980
gaaatacatg taatttcaac ttgttgtata tttaagtgaa ttattttact caaagaatg   134040 atattaggta ggaaaaaagg ccaacaaaga gtagattctt ctcaaaatta tgttgaaaaa  134100
ttattactgt tcagatatta tttccaagac tagaagaaaa tacaacaaag tgttatattg  134160
cttaaatatt ggtaatagga tcaccaatgg tctttgtatt ttcttttgat tttcatgtgt  134220
tttcttgttt tctacaatga atatcacatt aatcagaaaa agtaaaaaca aaataaattt  134280
gtgaaagaat ctaatatgaa aagggaaaat ataagacttt ttatattatt ctaataaggt  134340
agttttatta gaaaacatgt ctattctaaa ggaatgtact atttcacttt attataccat  134400
gaagtatgat tctgagctct gatataatgt atattgtcca aaatgtcctc aattccacaa  134460
agcactaaaa attatggaag taataattgg gagcgaactt gacaatcatg gttaaccata  134520
ttaattataa aactttcaaa gtgttggcac accgtgtctt ctgttgaatt gattattgca  134580
gcactctgca aggtaagcag atcatatatt aatgctttcc ttattcaaag gggttgaatg  134640
actcactcaa ggtcactcag agcttccata tacacaatct ggactctaat tcaagtcttt  134700
agatctaaat tccttggaat tttataggtc tagagacggg ttttttgttt gtttgtttgt  134760
tttaatactc tcttctctg  tctctctctc ccctactatt acttacttct atgcaaagca  134820
gttagactag tgcttgggac acattgcaca ggcatataag tattcattga ataaataaaa  134880
gtgggacttt tcatactggc ttgaaggaaa tatgcctttg gatcttcttt tggaagaagc  134940
```

```
tgtgttcatt ttccttgatg aaaaaaaaat gtaatctaat aattagtctc acttacaggt    135000
gaaaaacagg attattctac tcataatagt agaggctcac atgcccctca cttcattgct    135060
gttagtcatg ctgctgaaag ccaaacagaa gccaggtact gactggctgt gtacagggca    135120
cattctgcaa tcccatgtac tttgtgctag caccaccgca gcaggccttc aaaaattggc    135180
cctgtcactt taaatataat agacaataaa tcatccctct gagacagccc taaggaaaa     135240 caggggaaaa aaaatagaaa tagcatttaa aagcccttt  ctattacaat gcctctaggg    135300
agcttttaaa attggaactc ttttgaagtg aattttatgc tttttggggc ttttaaaaat    135360
gcttctagaa ttaatcttgc aattctagga ccaaatcctc catgagatcc tttaatttgg    135420
gggtctttat tatgctagta ttatcatatt tgctcatctt ctctgtgctg ctttccctgg    135480
tattccataa ccaatcaacc cctttctca tgctctttgt aatttcttta ttcctcgttc     135540
ctccctatcc atgtttctgc cagtatattt cttgcttggt cttttctttc tttttttct    135600 tttttttcctt catcaaatct agtttagtt acttctcctc taagatacc  tttgttcttt    135660 tgcaccttgg atgcagataa tcctaattag gctaccatgc agataatcca gaattttcta    135720 cttttcctcct cctatagcag aattttctta gacacagttg aaccacaact gcctctgttt    135780
cataagcctc cccttctctt gttcttgtga ctgttcctag ttgataagag aaaaacatca    135840
aaatagcaaa gaaagttaat ttagtttagt ctgaaaaaaa tcttagtcaa atcctgaaaa    135900
aaataaatgg taaggtgtga acatataaag cacagattat acaaagggtt agggtttaca    135960
ttaagaaaga gagattcaat atcagcctga ctctcatgta accagtactc agctatgatc    136020
atttaagtca tatagcatta tgtggcccaa taaaacagtt atggctcaat ggcctttatt    136080
attcttacaa attaaaaatc tatactgaac aaaaacacagt tcatcttaat attgaaaaac    136140
atacacactc agtgtaaata acaggacaac agcaactgtt tcttgacact acattacatg    136200
tcttcttaga cccctgatc  tgtgaaggaa ggcaggagaa attcaacttg atattgagct    136260
ggtgtctttt gataaattgg gaggccaaag tatgaagcaa aaagcagtga aagagatta    136320 ttctgacacc ttttagattt atagacttcc cagcctactt aatggccatt catctcatct    136380
ggcctgccat agtcactcca gccaccctct gggtgagtgc ttattaccaa caaggcagca    136440
atcaaattat tgcagggaat ttactgagtg agataaataa aagctgccta agtcagtgat    136500
tctcagtgct ttctctggaa cataagtctc ataagaagct ctaaaaatgt cccacagaca    136560
cataagtgtt gtcaacacta catacccta  ccctctgca gagtaatggg aagtatatta    136620
gcatagtaaa agcactgaca aaagaaagct gtctggcttt gtttaaccca gcatgtaccc    136680
aaagcatggg acatgctgtt ttactttttt tttttttaag aaatggggat ctggctatgt    136740
tgcccaggct gcaatgcagt ggctattcac agatgcaatc atagtgtgtg cactacagcc    136800
ttgcattctt acttaagtaa aacttatgaa aattctttgg aaactttgga aaagcctaga    136860
ttaagtactt gcctaaaaga agatctggga caactatctt gaaggtaatg atgactgtta    136920
aatgaaatga ttagatgaag aaaaatagga agaaatactg aaggtttgta ttaatgatta    136980
ctatcaccaa aggagagaaa tgtaccagca gatcacagtc attaaaaatg acccatcagt    137040
ggacagcaaa ttacatactt gggaaccaat gctggagaaa aatcaaagag ggagaggtca    137100
tgttttattc cacttgtaga gcttttcaaa ttcagtccta accaaacctg attaaagtaa    137160
atcccttttt tacaggctgt ggagtctata agattatggt gttaatggaa gtgctattcg    137220
atccgtcagt aatggtgcat gtcgggaccc tggcgcctct gacaagtcca ttttttaaga    137280
cgtatttatt gttttgtttt ttttttctcc cttctgttct ctgcattgcg gggtttaatt    137340
```

```
gaacagttta aagtgattct tcttcaaggc ccattaattg attttatttg tgtattctcc   137400
agggtcaagg aaaaggggga aaaaaaaaac caataaaatt gcagctctgg ttttcactgt   137460
catattctcc ctggaaattc atagctctga attttgtttc ttttctctgc ctcaagaggc   137520
cattttatga ttttgcaag gtgcattttt ttttgtttta tattactgat ttattcaatt   137580
ccgataggga ttcgccatta agaaaatagt aaaatgtgcc caatctgacc aaccatgtag   137640
tatctagggg ttcctcatga taaacccaat taaagaggaa atacttcggt gaaacagtca   137700
tgaaactgta cattctcatg acaaagcatc catagcggtt tctttctatc ataatgggac   137760
aaagtctctt gaggtttgat gttgtgacat gcctacacat atataatcac agtgtgttca   137820
tatttattca tttaacccag cactgcccct gaatggtctt atgtctgtga agtaagaatg   137880
aagatgctac ctggattgca aaacagtata ttcaggggga ggaaactgta gagtgaaact   137940
gagattctgc caagggcaga agctatacat atgtgtgtac atacatattg gcatcacacc   138000
acaagaggct ctgtcctgtc atgtcatagt gccctatgat gtcacattat tatgtcacct   138060
aatataattt gtaccatttc ttaatgcttt tttctatcag gaagtagcta atcctcacac   138120
tgaacttatg aagcaggtat tactatcacc attgaatcgt caaagtctga aactcagatg   138180
tgaagtaatc ttccaaagat ataaataagg tttaaatatg catctgattt actccaatgc   138240
ctctactttt ctgttccttg gatatactgt tgccttggag acttagtttg caatggcttt   138300
tatttcacta aagatgaaaa tataataaag tcatttaaag gtggataact tttttttctac  138360
ctctgcttcc ccagagtagg ccccaaacaa atactagttg aataatgaa taagattcct    138420
gccccttttgc tatcacatca ttcctgcttt gagcttcact ctaagaccag tcctttatgg  138480
gcattgtaat aacaaggcca gggtaaaaga taagaaaggg acagggccat aaacaccaat   138540
ctggattcta tcatgtggac aagctaattc tagcctcttg gttttttga catatccatc    138600
tcttcattca tttctttgtc ccttccttat tcaaattccc ttgatgaagt ccccaataac   138660
acataaagct taggtctttc attgaaatgc aggtcaaatt tgtcttttgc atacactagt   138720
aaaactatgc cactggcttc tggttcctga ttatcttccc ctgaatgttt taagagagat   138780
tgagagttta aagctaatac taagattgaa agaaaaagca gcagggggaag ggagggatc   138840
atatagaagg aagtattttt ttgcttgctt gatttactgt aatcaatagc tgagaggaga   138900
aagcgacaag ttcgaaattt acttccagcg gatgaacaga tcatcgtcaa ggacaagaca   138960
catatattta agaatgtgtc agtcaactga aaatctcaca aaggcaacct tctcgcggaa   139020
ggggtgcact ctctgcacgt tacggtcaca cagttcagag gaaattctat gctatcttgc   139080
atctgcacct ctatgtccat cttctctttc tcgacttaag aaaatcagct tcctggaccc   139140
cctttacctc cattcacctt tcacaacttt cactcgtttt gtgagacagt tcaattatca   139200
cttttcaggat tgtgtctgtt tcctgataga tttaatagta aaatccttcc aagggccaga   139260
aagaatgaat ggcgaggaga ggtgtcccag tctgaagcca ggtgtagtga ataggaatag   139320
ttagtaggag tgagtacaaa atcctcaact agtagtcgca ggtggtgacc actacaaagg   139380
aaatgaaaac acgttaactt tttggatatt actccaagaa aagagaatat gcctgcagac   139440
ctttctctaa gcaataagac acactggtgt acaaaaagac ccacactcct ccccatgctg   139500
agatacgtgt cctcctgtgg attcccagaa catgaaaatc actatatcaa aatatgtgtc   139560
acacactacc ctaagctttg gtttgcatgg atctcccctc gaaactgaat caagtcacgt   139620
tcatctctat ctctagtttc tccttcagta cctggcgtat aagagatgct caatacatat   139680
```

```
ttcctagcat aaatgaaaga atgaataaga aggaattttc ttgtaagtac taatataaaa 139740
ttgtgatgca attacaaatt ttggagatag tggggccaaa acaaagtggg gctaaataac 139800
tggtccagaa aaaaaagaca gggataaact ttgaattttg cattattaag gttaaaaaca 139860
gctcttatct ggccagaaag agaacagttt ttgtgtaaaa taattttttc aaatttcaga 139920
aaaaaatatg cttatgaaag aagctttaga atgcaacctg cactgttcat gaccaaacat 139980
gtatcagtat agagggcatg agagcagaaa taaacagaaa taaatattca cctccacagg 140040
gtagccctaa ggatcctatg cccagataac tagcttgtga gttattcact cctggaattg 140100
cctgttacca ttgttccctg cttaagacaa ccatgttgtg agtatatgtg tgtatagtga 140160
ggtacaggga aagataaaac agtgtcctca aaagcccatg gacaagatgg tcatatttta 140220
cttgggagga tgtgaatatg aactaataca ctcctcttgt taagatatta gtacagggta 140280
gcatgttaat gttcatcaga atgcttgtca ggtggttgca gtgtcaagga ttccttccaa 140340
tatgagggta tgtagaaaat gcagccctcc acttttgaca ctgcttacaa actttgaatc 140400
agagaagaca gttgtaaagg gaggtggtgt tcttcttttc acaaactttt cacaaactgt 140460
ctttattttt attcttctaa ttttctcctg agatatcaac atcgaagtag catataacct 140520
tcctggaagc aatctaactc cagaaaaagc acatacaggc acagaaaaaa aataaccaaa 140580
ttcattttta cataagaata gcagttgcag gtggcattac tttggtctga ttttatgatt 140640
agtggaaact gatgccttct gtattgctac cagagtacat aacctcttag gcctaagtct 140700
ccattgacaa ataattggga taacaagcac ttttcactgc atttgtgagt aatctcagtg 140760
aacagtcttc tttctgtctt gtacttaata tccttcaatg atcaaatttg taagcaggtt 140820
gagcagctac acttattcct ccaaattaag gacttcccat cagctgctca ttaacatctg 140880
tatggatatt gcctaaattt gttttaaaac tctgtgtgag ggtacacttt gatctgctca 140940
actgacttca ttctagctat taaataattt caacacaacc ttgatctgtc taatccaaca 141000
aaaccaaagg caacttctta gtactttctg ccatgtaaaa atacatcata gtctttcaag 141060
ccaatatatt gttatgaatc atacatgcac aaactcagca aagttaaact tccttaataa 141120
tagagtgggt gctatagtac ctgtacacca ccttcaatcc actgctgtga gcgaaaatca 141180
ggcagcagca ctagtagtta actcaatatc agctgcatta ataagggtaa atgaataag 141240 tgtgcctgga ttttctccc ttgatgactt taggtccaga tttatcttat tttagcttta 141300
gtcttgaatg attgtcaaag atgtgcaccg gcctctgaga tagccactgt caagctaaca 141360
tgtatggaac cagatcggaa gaaattgccc aacagatttg cagggcttgt caaggcctgg 141420
aaatggtgga agtcagatga ttatatttgc attgcataat tggcggagct tgtcacaaca 141480
ctgctggagc cagcagctgc tctctgctga gagctaattc cacctgatct atttaatatt 141540
ataatgaatt taatcctctc cacattcatc caggagccaa agagcacagt ttatggctaa 141600
acctgcattt gcagacagat gacaagggac ccctctggtg gtaggaatta atttgggaa 141660 gtatgctgac agaattgccc aatcatttgt ttcggttgag attttttcc ttttccagag 141720 agcagtcttc agtatggtct gaattttccc ttctctcctt aagaagaact cttggaagtc 141780
agaaatgaac ttagatattg tttagagctg aaatgtgctc cccctcactc acccactcaa 141840
attcatatgt tgaagcctaa acccctagtt cctcagaatg tgactgtctt tagatatagg 141900
gctgtcaaag aggtgattaa attaaaatga ggctgttagg gtgggtccta attcaatctg 141960
actggtgtcc ttataataag agaatacaga gagagatatg aggatatgag taatgcatgc 142020
acagtgggag aaccatgtga ggaaccaatg gccatctgca agctggagag gcttcagagg 142080
```

```
aaaccaaacc tgccaacacc tttattttgg actttcagta tccagaactg tgagaaaaaa   142140
aaaattcaat ggcttaagcc acctagtctg agtggtattt tgttatggca gtcctaccaa   142200
attaatacag ctattatcta gtgtaactca atgtaagttt cttctctaca gaatatcata   142260 atttttttt ttccagagga acgggaagag gaacacctct cttatacaac gcaactgtta   142320
gcattaaaag aagatcattt tatcagaaac ttctgtgtac tgaggcggga tgttcctcct   142380
tatgactgcc accttactgt cccacttctg tactctggtt cggaaccaaa taagatgtct   142440
tacagggcag ccctttaatt agatgcaggc agccgttgta tgtccatgct cctttttaa    142500 accttctctt tttagttaaa cctttcttga tgccttcaga tactccctat atgccactgt   142560
tctgagtgca ttctctcatg tttgttctgc tttgaacccct ttctactggg caattgtttc   142620
tattaaaatg agatatagct aaagtcacta actcagatgt tatccagcac tgcagtgtgc   142680
tttaggactc ttagccctct tgctttcact accatatttt agggtcctcc ccattaagaa   142740
agaataaaac aaaatgatct ttaagccctg gtatggaatg agtatgtggt aagctcttga   142800
gggtaccatg ataccttttca tatgtgacac aggggaactg agacttactg atggattttc   142860
tatcagctga gtattttgga aaacattatt tttaaaagtt gttaagaaat gttcttagta   142920
ttacatttga ttttactgat atatatatat atatatataa tatatatgta tagatgtata   142980
atacacatcc agattcaagc agctttactt gtatctattc acataattat aaaaatataa   143040
atatattagg cattttttttc cctcaaatac ttagaaatcc taaaatgcaa aaaccaaaca   143100
cctgggtata ataattgtat ctccaggagg gaacaagttt ccatagcaca ctaaggatag   143160
agattactgt aaatatccat taaacttaaa tatgccactc aattgagtct gcaatttgca   143220
acttaggaga aaatggccag aaatgatgaa gccctgggc atcagtacat gaacagttat    143280
aaaaatagaa gaaaatagtg tatatttttg gcttctattt gctgatgtat gtattgtaag   143340
gcaatagcta acttcaaagg ttttcatgct tgcccaatag ctattgaaaa caggacataa   143400
ttaaaagcct tttcccctaa acaccatgac tccttaaaat gtagaatgca agacctagcc   143460
gacatggaaa caggatacag gtatactgca gtctgtcata ttgactctct acagttttcc   143520
tattatatga acatatcaaa aatacctgga ggctgaggca ggactacaaa atgttttgc    143580 acatgcgagg gaatttgaga gctagcctag gggcagagta aatatcagaa acattagtta   143640
tgtccgttac cggaaaagga gtgaccaatg ccttatcact ccatggcact tatttttttcc   143700 ctctctactt taagaataat ctctctagag aattagctct ggtatagctg aacactttct   143760
tagaaattaa gtaacaatat gataatatct ttcaaattcc atcctaaaga gagagatcta   143820
tttttttaat gactacagaa tgtcctcccc ttaaccctaa attactttgc atttagcatt   143880
ttagctgcca gaaggtactg tcaaaacaga cagaccgctt aatggaaaag aaaagttaat   143940
gaactaacaa gggaacaata aatattccac aaatcaagga aaagatggaa cgatttccaa   144000
gggggaagtg gatgtatcga aatattttg ctagaaactc aaagcaatgt gttttaaaga    144060
ttgaaatttg gggtgaggga atgatgtaat ggttgattag tgcattacta ccaataatct   144120
caaaacaatt atataacatt gtttatccga gtagaggaga agcaacagga aagaaagac    144180 aagaaggacc agttccttttt attaagtgaa tggcatttct gccatatggt attagataat   144240
gcaaagataa tgccagtgac tgggagacca tcatgtgggc ttttttggaag gaagcatgta   144300 tgcctgacac ctgtcacata gctcaaatgt gatgctggca tatttgcaac taaattagaa   144360
taatttaacc ttcattaacc ccttcctgtg tttatgaaag tagagcgtaa ttgacaaaat   144420
```

```
tctgggggaa gggtggctcc ttgacttaga ttcggtggaa ttttttgtgag tagacgcaaa   144480 tactgttgtg tcatacttct atgctatcag gctttctgcc caggattcca tttatttgga   144540
gactgtgaac ctgaagtcaa ggatatctca tgttccagtg ttttcagtag aaaaataagg   144600
cgaactgtca attgacagat ttttcatata tataaaaagg aacagtctag gatttacggg   144660
gcaaataaat attgtgccag aacagctggc aagcgtgagt aagagcacaa accgctggta   144720
tgttatctgc aacctcccac acacataccg tgagctgcaa ctcaataagt ggatgattac   144780
agaggttatg agaaaagtag aagtaaacac agtgaagttt aagaacacc tggtatgaaa   144840 gataacttgg tttccaacag atacctcagt ttcatgggaa gcattttaga gtgatggtta   144900
agagggcagg ctctaaattg gtgtaatttc atatatacca attatgagct gtgggattgt   144960
accaagtcgc tacacttctt taagcctcag tttatttata taaaaggttt ataatgttgc   145020
ctgccttata gagttacaga gagagataaa taaatcactc cacctaaatc acttatcaca   145080
gttcttaaca catgatatgt gtttaataaa tgctagctat taccattaac aatgcccatg   145140
atctagcaca ttctaattta tgatgccact attccacat ccaaatatc acctatttca   145200 actgaaggaa gaatagcatc aggtacttaa gttggtgccc atgaggaacc attatagaat   145260
atagtatggt tcgagatgtt ttaacactct aaatgaaaat atttatttgc aaaaagataa   145320
tcatgttcat gaaatggttt aaatattgcc ttatttccag gaaaaaacaa ataagtagaa   145380
attatatata aaacatatac atgatatgac tattatgcat acaaaacacg acacgagcta   145440
atgtgttttt agtttcacta ggctttcttt atacgtggtt tcactagact catgctttgt   145500
cccaggtctg tgtgaaaatt gcatttctga cttaaacttt tggaaaagga gaaaaggtta   145560
tgttaggaaa ttgcaaatta aatcattaac ttaacaagtg ccctaaaaaa caattacata   145620
gattcatata cacattgatc aacttaataa agcatattaa gaaaaccaca tctagtgatc   145680
tagttgcatc agcagttgaa agtcccatga gttcagtgtc catgcttacc actaacgcct   145740
agcaaacagc ctggcacata gtgagatgga aaagttccct tgacccctc ccaggacttg   145800 tgacagggat ggcttgttta catggcagct gtgctcaaag cccatgtggg agggggagca   145860
cgcaggtgag caggtgcagc aggtggggca agtgcctttg ggcaccaaca ggaagaaact   145920
ggcccgtggc agcaactagc ggttgcatgt gaccactgga gccccagagg gcatgtgtta   145980
caataagtgc tctttcagca tttgccatcc ttggaaggct aagtgttaaa cagctcagtg   146040
gacagtcagt gtgacagcct cttgcaccta cacccagatc cttgtctggt gctcaagagg   146100
aatgaggcca tacagactgg aaggatggtg aatgcaaagg ttgcactgag tggtggaagt   146160
agctctcagt gggatgggaa gctggaaagg gaatagagtg gaaacatagt cttctgcgtg   146220
agtttgtctg tccctggctg aacacctctc tgaccataat ctcctatgtc cagctgcctc   146280
ttctcttgat gttcagttgc ttcttctcct ctctcctctg ctgcatcgct ctgctccttt   146340
gccagtgaag cctgggggttt ttatgggcac aggataggag gcatggcaga ccaaaaggtg   146400
acattcaggt gtgaaaacag ggatgtgaac ttctcattta gggcttcagg tccaggcttg   146460
agggtggaac ccttgtcagg gacccccgccc atttctacct agtatttccc tgcctcctgt   146520
ccatatcaat agtaaatgat aaataattac tgataaatca cttatctctt tatttcctct   146580
ctgtatgtag gaaaaattta gttctcattt catcatactt aggatatgtt ctacacattt   146640
tagctctact ttaatgaaac accttatgct agaaacttta aagaaccat ccttaatcta   146700 tttttacaga tgaagaaatt aaagctcaaa catgtaagag ttagttgaat acaaggctgc   146760
acagctagga agagctagaa ccaggtgtga atcttcatat gacaatctct attcactacc   146820
```

```
ccatgacact tttcattcat acttgagctc ctttgtgcct agatgtgtga tatgaggtaa  146880
cgtgagcatc atgatctctt ctacattttc tttatctctc tgagaattag ttatgcatca  146940
gggagcacta tttcctttat cctccctatc aaataaagat tcatgcaaga tgtagcaagg  147000
ataattctta accaaataag tctattatat tcaacaagtt gtaatgagta agtgtataat  147060
ttcatacaca tttggtttta acactcttca ctcagctgtg ttagcttcac taaaagagtt  147120
aaacattact attcactaac tctgttccaa catctgccct gaaaaccaag ggttttcagc  147180
tataaagtct ttgttttcat aatcttttat cacactaagg aataatatta ataaatcact  147240
atttctctct gttggaaaaa ggccagcatt ttttggatgt acataggtaa acatccttgg  147300
gtttaagatg taagtgagga gggctttacc taccctttta attatgagga aatgtggaat  147360
tcagtggtgc agaaagccca tctgcagtat tgcccaaagg ggattctttt aagtgacttt  147420
tttagacctg gatcagacag tagtatctcc attcattttt agtcacagag aggctaaatt  147480
gaagtccatt tttctgaaac tagtcacata gtcaaaattc tcacattaag agtaataaaa  147540
tcctgtgaag ccataacttt tctgaaagag ttttctcac cataaatatt taaaagtag   147600
caaccagttt caatataaaa attagcgtat taatgatttc ccataagata aactagatat  147660
ccgaatgatt ggcttagttt aatgaatcag cacatatatt taagaaagga acttaccatt  147720
agtgaaaagt tgaaacaaaa agcataatat aaattcaaaa atagtaactg tacttattat  147780
atctttcatt tattggtagc tcactgtatg ctaaatccta tgctgagcta tttatgttta  147840
ttaactcatt tacctatact ttgaatctcc aaggcaaatg ctattcatat atagtatgaa  147900
attatgctat tgcagattaa gacagattag ggttagcaaa gtgaagcaac ttcactaagg  147960
ttgcagagtt agttggtgac acccatagta gtctgactcc agggttaaaa tacttaacct  148020
tcatgtatat taaacggcat aggccagtgg ttcagtttcc aaactcctgt cctagaacaa  148080
gtgctaattc ctaaactttt cagcagtctt ttgataaata ttctagttgc attttgtttt  148140
taaatatgtt tatttgggaa aattaaaata gtgtcaaaca aatataattg ttccatatta  148200
aaaataaaca ttttggaagt aaaagaagaa aaagattttc aagttatttc tgtgtactag  148260
ataaatctga gctgctattt acatgaggaa tccttttttt gggtgcttaa gggtgacagt  148320
gttgaagacc agaagaaggt aaccatttaa ataaataacc aaggatgtag gaaatattga  148380
ggtgaaaaga acaagtaaaa gctgttataa tcccaaatgg cttggacatt ttatagacaa  148440
agaaaactct gggggaggta atgctatttt atttgggaag atgatgggtt gcctgttaac  148500
ttacttctga acatgttgag tttgtggtga gggatttaag taggaaaata tctagcaagc  148560
aatataagga aaactgcagg tttcctgatc agacaaaaac taaattcttc aaggtaagca  148620
atgtgccagt gtgtcagtga gtctggtcag tctccaaggc atgttgaaag gaggggaag   148680
tggtcaatct ctcagccttg acactgcccc tgttggtcat cttttccttg aacacttgtc  148740
ataaatgaat attgtcacta ttgcactggc ttgagggtag aacccttgcc aggggcatcc  148800
ccactttaac actttaccat gaacctgaat gcacatgcct tcctttaatt ttccattcgg  148860
agttgacgcc aggctgtttc cgaaaggcta aagactcaga gcaacaaaag ggaaattagc  148920
acaaagtata taatgtgtaa ttagatcaat gactttaacc tcttttgggt agcactgaga  148980
atctgatgaa tctccccata tatacataca attttgcaca gcctctgaga gcctactcaa  149040
attccagacc caggggggaaa aaaaagagag acttaagcga tgcagcaagc aacttctctg  149100
gcttaaggtt tgttttcatc tgcagatgat tgacctggga aatatacatt ccctgcagtg  149160
```

```
atatttaacc tgcctctctt ctctgactaa ggggtcaagt cttagtttat gactcccaag   149220
ggtcaactac ataaaataaa catgagttta acccgggtac gagagataca catgtgtagc   149280
acgagatata attttattac agaaataacc ttcacaaaat agggcttagt gaaccccccca  149340 gtcccaaaaa ccacattact taggacacat ccaatttaaa caccaatcca catatctatt   149400
tccagaccct tgactagtgc tgtagttctc tactgaaaat tttattgagg gagtatcaaa   149460
gaagggatta aacttcgaaa tacatacagc agagatttcc tgaaattatt ccattcccac   149520
atctctctcc tcaaagctcc acacatcaca gcatttgctc aaatctgttc aaactttagt   149580
ccctgcccat ttgtcttttct cattctttaa tgtcttcttt ctttactcgt atttcctctt   149640
ccagtaccac tctttttctt ccctcagcag gtctccctaa gttcttttct gtgtagaact   149700 atttttccc tcagaaagac aactagctag cagagctaca cacaaaacta tttggaggag   149760
cagacagagg gctctttctt tattccagct gaattataca aaaacagaaa gtgtacatgt   149820
ttagttttca gtcatattct aaatgcctcc cacagtgcct gacaatactt tccaagtaaa   149880
tatttgttga ataaatgaat aaagaaatac tgattgaact tcagttagag tttaggatta   149940
aaaacattga cttggctggg cgcagtggct tacacctgta atcccagcac tttgggggct   150000
gaggtggaca gatcacaaag tcaggagatc gagaccaccc tggccaacat gatgaaaccc   150060
cgtctctact aaaaagacaa aaattagctg ggcgtggtgt tgcgtgcctg taatcccagc   150120
tacgtgggag gctgaggcag gagaatcact ggaaccaggg agtctgaggt tgcagtgagc   150180
caagatcatg cccttgcact ccagcctgtt gacagagcga gactccgtct caaacaaaa   150240 caaacaaaac aacaacaaca caaaaaaacc acagtgactt gaagggagaa gaccacagaa   150300
tgtcagaatt ataaggacca catgcaatat aacaagtgaa gccttctctg atattgctaa   150360
aagttataac taacaaaaga gatcaggtat cccagaaata gatcttggag acaggaagtt   150420
aaaatgtacc gaagaagtag caattagaaa gataatttaa aagagagaga gaaagagaga   150480
cagactataa gaaaaaaaaa taatgtaaca tcatgagtct aggagaaaag ataattatca   150540
aataaatatt caaagtcgac aacatatcac tgaagagttc ccatatacta taattcttca   150600
gctcaccatt taatgaaatc aaaaaggaag aatttttat tggccttctt aaacaaacag   150660
tttctttatc cagtatgctt tgcaaagagg taaattagta cctgaaactt ctagttgatc   150720
aaagaaaaac aatgaaaaat aatctggcct tgcttatagc cctgaggaca aaatagaata   150780
ctcaattttt atttcagagg catgtataat tctaggccat ttttggaagt aatttatttc   150840
taggttagtc tggaagagtt aattttcaag aaagaaacaa actagaaata ttctaatttt   150900
gaattaattt ttaaatagag agtataggaa ataaatctta taagataca atattcagtt   150960 tgttatgggc aaatctcatt actactaata attaacctat attatgaact aatcatctgt   151020
taaatttcaa ttaaacttcc aatttaaaat gtataaggaa atttcaacca aacaatgaac   151080 ttttttttcat tatcccatat ctttaaatga ttatctattt accatttttaa aaacctcccc   151140 ttatttctga agtactgctc aagtgaaaaa atacattagc tatttattac acttcacttt   151200
acaaaatgac gtggctgata tttcatctaa tgtcatgtgg aaagacaaag ataccctga   151260 gcatggaagg agacgtgaaa gatgaagtgt gtgtttgtgt atgtgaaagg agtggggaag   151320
tggttagtgg gaagcaggaa agaattcaag aagctctttt ctaccagatg ccaatagact   151380
aagaagtaga aatacatcct tttatttccc cttttcttct tttatcttga accaccttca   151440
gccacacctt taaaattagt agtccccctat ggtcattatc aatcacatta atttcttcag   151500
tggcatctaa ctagggtatt ctcaaacaaa tgttcacaat agtggttctc aggtgaccag   151560
```

-continued

```
atagctaaga accaagatct ttatctcagt tttctcttag tgatgagaaa gggtgaaatg   151620
gtttgattac tggttgaaca aactctaaaa tgtaaacgta ggggttcttc attcacttca   151680
gggaagattt agaaaaattt tcctaatctt gattattaca caattttag accgcttgca    151740
aagcaggaca tgttagtttc acttctacct gaagtgaatg aaatctggtt agtatgtgat   151800
tgaccaatcc aagggtttc ctcatcaggc tgcacaggga gtcagcttta ttttgtctta    151860
ttgccaaaag gtatatatat atatatatat atatatatat atacgtatat atatatatat   151920
atatatatat atatatacac gtatatatat atgtatatat atacgtatat atatatatat   151980
atacgtatat atatatatgt atatatatgt gtgtgtatat atatatatac acacacacat   152040
atatatacgt atatatatat atatatatac gtatatatat atactcttag cttgcattcc   152100
tgtaactttt caaggagact gcataagagt gtgtagatag ggcattgcaa tatagtatta   152160
cttgatagca gaaaacaac tcaaacaata tgtgggttat caataacagg tcgctggaat    152220
cattttcttg taaaaataat gtactaaata gctataggct ttatgaggcc tagaagtctt   152280
gggcaaatgt ctttaaaact gctgtgtttt ttttttggga atatttaaac tttatatagt   152340
tagtagagaa ataagatcat ttttgttttc ttacagaaga aaaaatacca gaatcattaa   152400
aaataaaaat aagacaagag gcatcttgtc tcgctctgtc atctagactg gagggcaatg   152460
gcacaatctc agctcactgc aacctccgcc tcctgggtac aggcagttct cctgcctcag   152520
cctcccaagt agctgggatt acatgtgctc accaccacac caggctaatt tttgtatttt   152580
tagtagagac ggggttttgc cacattggcc aggctggtct cgaactcctg acctcaggtg   152640
atatgcccac ctcggccttc caaagtgctg ggattacaag tgtgagccat cacgcttggc   152700
ttaaagtat tttaatataa gtacttttac taggaaaacc aattaccaga ggaattggtt    152760
tactcataaa gtatttgtca tctgccaaat gcctggtaag gttgagatct tgttccttct   152820
aactctacaa gcatttttg aggcaatact aataccttac attttaaaag tcactgtttt    152880
ccaaaattgc ctaattgtga gtacctgatt cctcaggtct taaccagaga ttgggtttag   152940
attaatctcc agttgaacaa aaacattgt cttttacaaa actgtctaaa attttatctt    153000
accatccagc aagttggaaa gcatttttaag ggagataagt ggataaatct tcccaaagta  153060
ttttagattt ttgttgtgga tagcatggat tgatattcta cattcattca atgttctttc   153120
tagcacacac cttcatataa tgccaaagtt acaacactaa aaactatatt tgcaagacct   153180
ccttgttgct agattttcag acgtaattta gagtttgcta gtcagagcac tttggttaga   153240
tttggaaagt ggaaatgagg agagatgtgg aggcatttgg ttgtttgaca gcactgtcag   153300
cagagggtcc agtgtccaat cactagcttc acgggtattg agaagcaggg tgaggaatca   153360
ttcctctgaa gcttcttcta tttgggacca tcttgttcag atgtaacacg gttttgaacc   153420
agtcagcagc aatggaaatt ttctgaatat tagagcttct agagccggtg gcctactcat   153480
catagaagag ggactgcctc ccttggtgtg atagtttaat ggtatgtcca aaacacatac   153540
tattaaactg aaaattcagt ctaaaatcta ttttttcaac ctacccatgt gattcataag   153600
cctgtatttt tctttgatag agcctttctc gcttaaatga tctagagtag atttcattct   153660
ctgcaacaaa aattggacaa atataataaa ggctaattaa aactattaat ctattctatt   153720
taacccttcc tctactgttt ccagcatctt gcctttggt gcagtggtgt ccctttttat    153780
tcaaagtta gttgacctaa ttagagattc agtttggaat ggtcttctgg gactgaggga   153840
agaaatgtcc tgccactggt aatctgatta tttaatcaat gtagaaagtt ttcaaggtat   153900
```

```
gtagacttca gttttgtccc tcaattttaa tttttattta tttgttgaag agaggtcaaa    153960
gcacacgaaa gttaaaaaga gatgaaaggt gtagaagagt atttgatgag ctaagaaatc    154020
gttcttgata tattttttcc tttcaacagc aggcagcaaa aatatatgca gaaaggattc    154080
aattttctca agacaacata tatatgtgtg cgtgtgtgtc tatgtgtgtg tgtgtgtgtg    154140
tgtgtatata tatatatata tatttgttta tttaaaaaga ctggaagatg cagccaaata    154200
ttattaacag tagttatcat taggtggtag gattgtaggt ggttttaatt ggagcatttt    154260
gccctagtaa taattctttt ttcttcttct ggagaatgct actagtgaaa ggtgatccaa    154320
tgctgtaggt tgtctttagt atagtataga tgtgtttaat ttattctata tgcaatataa    154380
aatgattcaa tgggagcatc ctgagctact gtcaccagta caatgtttaa tggtgttaac    154440
taggaagaga caaggcactg aaaaaaaaat gggggatttg ttttcagttc agacctaagc    154500
aggaagagtc tttccaccta aaggcttgaa aaattgtttt tcctaatatc agaacctgaa    154560
tacagaatgc tcttatcact gaaacaaaa ataaaagcct cagcctccac agattagagg    154620
actgagctga agctttatat agcttttcta aatgaatgag cgtatatagt tcagtactaa    154680
agaatacatt ttgaaaaagt gaacaataaa aggtttaaac tttgttatgg agccttgaga    154740
gaaaacacag catcacagta cagaaatgga aggcctggaa tcttcacttt gaatgctaac    154800
acaaagatga gtctccagat gaagcatgag aaaactctca tgtctcaaag agtggccaat    154860
tattaatttg ttttgagag agagaaaatg agacagtgtc aggcttttct ttctctgatg    154920
tggtatatac aattctgagt aaaatggggtt tcaaattctt ctaacagtca ttcttcgcaa    154980
attatttaga catttccagg tagtcccaag atgagaatct gtcttagcat tttccatata    155040
aaaataacta gcataactta atccttttct attagagtca aaattctggt attcaaacta    155100
agaaaaatca ggcaaggaac atcctctcca aatgctgtta taagaagggt tatttcgtc     155160 tgggtgtgct atgtattaca aacgcattaa ttcaagaaca ttatgtctct tggtaatctg    155220
tgatcaattc aagtgtattt tgaggcattt ggccaagata aaacgaaggg gaaaacaaca    155280
ataggaatta atacacaatg gaattaaaat attgatccca aaattataag tttcacactc    155340
tgtttaacta agctagtcag atgtgatttt ctcacataaa gtggaggttg ccatatattt    155400
ttaaattgaa taatatagac tgaaaaggtc tgagaagtac aacaatattt catctccacct   155460 ttttggggat ctaacttttt ataagaaaag tgatgaagct tggtaagaaa tgcagaagct    155520
ttcaaaactt ttagggccta caactatatt gtatatgtgt tgcatgagga agaccttaaa    155580
acttggaagt ttgaatttc ctgagacttt agaggtttct cttcctagaa ttgcttttgc     155640
ttagagatcc ctttggaccc cttagtattg aagagcccag atagatccca gaaagaaaac    155700
tagacgttgg ctgtccagaa aggaaattcc ttccttttcc atacaggtat atattaaagt    155760
ctgtgagagt taaaaacgaa gcagggattc aaagcagtct cttgcttaga aataaagaga    155820
gtgcatataa ctgaagtttt cttcaaatga tatttgacaa acaggcatag aaggttgaaa    155880
agtgaagctg cccaaatccc agttacaggc ctatgtgaag tgtcactatg caccattaaa    155940
caccaggtgg ctttctcctt ctggtgcctt atggtggttt caggatgtgg gcagtgcttc    156000
ctgatgtgat cctatgcacc ttctctgctt tctatgctct gggtaacatc tatctctcac    156060
gccccaactg gggttggatc aagccactgc caaaaacact gggcatggtg ccaatctgta    156120
agtttggttt taaaatgtaa atgacttaaa ttttcagaga aatattttat caccttacat    156180
taactgaaac tactgaaatt acaaataatg taaaatataa cactagaaga tggagacatc    156240
tacattcaga atgcttaaaa caataactac acaatgctag ataacttcta gaatagaaat    156300
```

```
gacaataata gcaaccacat tgaaaatagc aacaataact atattaatcc cctttagggt  156360
ctattctgct gcctactgtg gtagtatact gttcttttc tgaactacct cagaacattt  156420
aacccatttc acccactata taaaagcatt tactattttc aaattatcca ttcacgttgt  156480
tccttcaaaa ttcaatataa ttttccttga ttcctttgat attttctttg tatgctaatt  156540
caaaacactc taattttttt attaccaaca gaaattctga gaaacaaaaa gttcttcctc  156600
tagcactagt ggcctcacgg ccatgtcaac attgttttga tccccatagg aattttccag  156660
attacgcaac tcatagagca ctgatggagt gcaacatgtt aagttgtaaa atttggatat  156720
ctcattacct cccccccatc ttatttattt tatgattacg tctagcttcc cattattttt  156780
cctctattga ctatgttctg tagctttcat atttgtccgt tagtaacttt ctaatatatt  156840
cctctcatag ttagcttcta catccctacc ttgcagtaaa gcttctccag gttttttctt  156900
gacaattctt gcatctttcc ttgtattgtc atatctcttc ttctcctttg ctctcactca  156960
ctccttccag catattcatg ctttgctgct tcaatgtccc ccttctgttc atctccattt  157020
cctgcctgga ctcagcttca ctcacccccct gtgccagtga gctctctacg accttccaaa  157080
taaaactctt ctgaaaatga cttctgtttt agtcttgagt tatctgggga ctgcagagct  157140
aggtgggacc agttccagcc ttggaggtgg taagcccatc aagtattcca acaaggagca  157200
atgacaactg agactggttt tggtaggaac aggtaatgca aaggcagtaa gaatgcaata  157260
tgaacactac tgctcagatc acaagaagag aggcattaaa agggataaa tagacaagac  157320 acgatgcagg gtgagcacga gagaggctgt catgcctgtg ttacctggtg gttcagatca  157380
ggaagaaaga caatgtgcat gccacaagtg tctgggagca ctaccaaata tagattcagg  157440
ctgtgaaaaa tgagtagagg ggaagaacaa ctgagcttaa ctggattctt tctcggggaa  157500
gaacacgtga gtaactgcag cttacctgaa gtagtgatca cttgccaacc actgtggtta  157560
gcactttatg tacgtcatct catttaatcc tcaaagcatc cccatgaggc agacactatt  157620
ttgtaactgc attgtacagc taaaacccaa aggtctaaag aggttgaata actacattaa  157680
caacttgtga gtggtagaga taaaacctga acgcaggctc tctgactcca gagggcatac  157740
tgctagccac tactatacta tacctggtgg tagtgagcac gataggtcag tttgagacaa  157800
aataaaagca gatgagggga gagcagtaca atctgaggac actgtcgcag gggtggttgg  157860
tcccgttttt ctctggcttt ctgataattg ttgagcattt gcttcagaaa atggccaacc  157920
ttcactgact aacagaaaag cacagtgaga aaaagaatat tcttctaata agttatagag  157980
gagccagact gataatgtaa taaaattttt attgtccctt ttctcacata cctctgggat  158040
ccaaaaaatt gattgattgt gatttttatta ctttcttaaa tgagatattg tattttgta  158100 gcctttaatt acttcattaa gatgacttta aaaccatgct tgtatgattt tcaattacac  158160
tttctaatca caaaaaaaaa aaaataaaa gaactggaac tggttcagat ttaaaagaaa  158220
agtcagaaca gcctacccag tgtggccttt cagctgccta tgtgcttggc attatcttca  158280
tggactataa ctgaatttgt caccgcgttt ccaaaactat cttaagtgtg aactatctcc  158340
tcgcctttct tctcctttca tttgcaaaga agataatgtg gtgcattagc ataggataaa  158400
aaaaaaactt gtccttatac caaaatggca agtagaacaa gtgtccagag gaagaatgat  158460
gtcaacatct ttggtttttt tcaagtgctg taagtctgat tttttttttt tttcttaatc  158520
ttttgaattt gctctgtcgc ttcgttggca aattcttgtt aacaaaactg cccaagtggg  158580
gaatagaatt aacaagaagg ggaattgatg ggtcttcttt aattatcatc agaaaaagaa  158640
```

```
gtatacacat aaagagtgca gaatctggag tgattctttt ctaaatcatt gtaaccataa 158700
tcagataatg tcttaacttt ctgacagaat aacatgcatt tagtcattca acatatatta 158760
actgtgcgac tcataagcac aaggtactac tataataata tgaagatgaa tatgttctag 158820
ttttcatgct aaaggagact ggagcctggt aggagagaga aagccaagat ggcacactta 158880
ctgggaatat aagtgaaatg tcaaccaggg tgagtggagg aggattacaa gaaactgcta 158940
ggagttcata agatggtatg acaatgcaat aatactttgg ctggagtggt atagtgtagt 159000
aatgcttcat ggaagaactc attttgagc atggctttga agagtgggtt gaatttagac 159060
atgtgattat gtctaggtgt tgggaatagt gtaaaggaag acactgaggc aaggccttta 159120
acactgttga ggagcaacag ccatttagtt ttgcctgata ttccagtgtg taaggaggaa 159180
tgaaggcaga taagactgtt gaggtctgat ggggtgagtt catagcattt cttgaccta 159240 gaactaaaga aagatgatcc atcctctaac tcaggcaacc ccagtgctaa gacagttcac 159300
attacaatgc aagcgaaaac ttcccaatgc ttggattcct ctactctctg gctaggaaga 159360
cttcattaat ttaaacactt attcctaaaa ttttatttt caagagcatt ttctattgat 159420
gaaataatga ttatagaaat tatctttcag gttggtttgt acatacttcc acccaggccc 159480
tttgactgtt taatttcacc atcagcttca gtgtctttta ccctattagt agtgggatga 159540
ataagtccaa gattctaaga tacacaggaa gagttggcta ccaaatagga agtctgataa 159600
ctttatgaag cttatttcag aacatccaaa tggcaacctc tggtcactta gaaggcaaga 159660
aaaacctagc ttaaaatcaa aatatatggt tgatgactaa ggtttaatac tcataatcat 159720
aaggagtttg aaccagatgg gaccttaaag atagtcaagt cctgtggttc cagatcttta 159780
tagactccta ttttttcaaa agacctacta aggtagtgaa gaggatcata atctgtttct 159840
aatatttcaa agccctagta gaaattaagc ctctcatgga tcatgaaaat agcaaccata 159900
ttatcaaata aataacttt ttgttatctt ttctgctgtt tttgctcttt taatatatat 159960
tcaataaaaa cattcttaat gaataaaaat gaaaaaaata aattattgat tgattttcat 160020
aagccaaata tttctaaata aaatatatgg gaataagtaa taaaaagaac tccttgtgtt 160080
gaacatacca cagctacatt taattcaatt ttcaaattat atagatggag gaactgagat 160140
ctaaagaaac agagactatc catgtaacca aatgccgctt gttcctcaaa aactattgaa 160200
atagaaataa atttactgaa atttgtttta tggaccagaa tataatcaat cttgataaat 160260
gatccacgtg cacttggaaa taatatgtgt tctgttgttg ggtggagtgt tttataaatg 160320
tcaactaaat caagttgatg gttcaagtaa aaaataaata aataataat aaataaataa 160380 atacagacac ttgccaaaga tcatataatt aattagtgat tcgggtagga tgagaaccta 160440
gatcttataa atgccaaatc aacattcttt ctacaatagc atgctactag gtgaactgcc 160500
tcagaagatc ccagagtgga aggtaggaga gatttggtcc agggaccata gattgtaaga 160560
tataagatca tgtcagctat ttatttttgt gttgtagaga attttactca tcaaaaatgt 160620
aaaacaataa aataacatat ttggtttact gtttctctaa aacagtctcc aaagtagctg 160680
acatgtctga agagtctggt ttattgactt gtaataaatt agctaatata ctatttactg 160740
tttcaacata cccctaaaac acacatgaga aggacttta ctcatttat aaatattaga 160800 gccgaggtct ggaaaacagt gttttccaa aaactgtcag cagtgaggct gggattaggc 160860
catagggctc ttgaacttta ttctcaatat atattccagt ttcttggaaa ccaatttcat 160920
cagtttgact gcaagccgtt cctggaaacg gcaacaagca gttgaaggaa gtcaggagat 160980
ataagggaag tacaaagcta tataaggatt tttaacatat tatactttg ttttgaggtc 161040
```

-continued

```
ttccctccat caacttgaat aattgagacc tgtcagtgat atactctcta attcccagat    161100
gcattgtgat caatttatta gcagtcaaat gtgttggaaa ccataaggtg ccatatcagt    161160
gctgataaat attaagagag aaggataatg catatcccag acagtatagg ctccactgga    161220
actgacatca gaggcctgtg ccctttactc tgattgttat tctgatctga atgtcattaa    161280
ggagagtcta gttcaggtca atagatggcc aagagttcta actcctgtca attccaatga    161340
tggttttaga taggaaaaat actacttacc tctactgtaa taaaaataca gattttccct    161400
tcatattttc tagccatgtc aatcaatgtc tttctttaac ctttctgcat catcttatat    161460
acatccattt gtgcaacagg aggcatgcct gttacgggag actctaatat tgcgagttgg    161520
ggtgttaaag tctcccacta tttttgtgtg ggggtttata tcccttagaa ggtctccaag    161580
aacttgcttt atgcatctgg gtgctcctgt gttgggtgca tatatattta ggataattag    161640
ctttacttgt tgaattgaac ccttttccat tatgtaaagt ctttctttgt ctttttgat    161700
ctttattggt ttagcgactg ttttgtttga aactaggatt ggaacaccta ctttttttctg    161760
ttttccattt gcttggtaga tttttctcca tcccttat ttaagcctat atgtggactg    161820
acattctttg cagaactaga aaatctatt taaaaattca tatggaacca aaaagagcc    161880
agaataacca agacatatac aaaaattaac tcaagatgga ttaaagactt aaatgtaaaa    161940
cccaaaacta taaaaaccct ggaagacaac ttaggcaata ccattcagga cataggcaca    162000
ggcaaagatt tcatgacaaa acaccaaaa ataattgcaa caaaggaaa aattgacaaa    162060
tgggatctaa ttaaactaaa gagcttctgc acagaaaaag aaactatcaa cagagtaaac    162120
agacaaccta tagaatggga gaatttttt gcaaactatg catctgacaa aggtctaaca    162180
cctagcatct ataaggaact aaacaaatt tacaagaaaa aacaaaaaa gcctcagtaa    162240
aaagagggca aaggacatga acagacactt tcaaaagaa gacatacctg cagccaacaa    162300
tcttgtgaaa aaaagcttaa catcactgat cattagagaa atgcaaatca aaaccctcaat    162360
gagacaccgt ctcacactag tcagaatacc tattttaaa aagtcaaaaa ataacagatg    162420
ctggcgaagt tgtggagaaa aaggaacact tacactgttg gtaggagtgt aaattaattc    162480
aaccattgtg gaagactggc aattgctcaa agacataaag acaaaactac catttgaccc    162540
agcaatccca ttattgggta tacacccaag gaaatataaa ctgttctatt agaaagacac    162600
atacacacat acattcattg gagcacaatt cacaatagca aagacatgga accaacacaa    162660
atgcccatca gtgatagact ggataaagaa aatgtggtgc atatacacca tggaattctt    162720
ttaaatatta attagcaagt gacatgtatt tgggtcaatc aatgcttttc caaatgtgca    162780
tcaaatgcta taaggcata tttttttgtct taatcacagt atcagaataa ataggtattc    162840
atcaacgtga gaatgtggta tctgttacta tggtgaacgc tcaggagtta ggaattttta    162900
agtgtggata actatgcaaa ttgcccatgc tgtactgata agacatattc attaaaataa    162960
catatgttta ataataacac ttatctatta ataagcaata gctatgtaag tgagaacaag    163020
gtgttatgca acatgaactt ccaggcaaaa gctgccatcc ttgctactaa gtgtatctca    163080
tagacatata gactgaagga catactgaat gtaattttc atttaagaac tcaccaaact    163140
gctcccaaac atgttagggg gatagctatc agagtaaggg tattctatac tgcaactcta    163200
ctttcatatc tactcccctt taacaactgc tctttccaag gaaagttaag ctttattagt    163260
ctaatatgat ttttctttt ctttcctttt tttttttt tttttttaga tggaatcatg    163320
ctctgtcacc aggctggagt gcagtggcat gatctcggct cactgcaaca tctgcctccc    163380
```

```
acgttcaagt gattctccta cctcagcctc ctgagtagct gggactacag gtgtgcgcca    163440
ccatgcccag ataattttt gcattttagt agagacgggg gtttcactat gttggcaagg     163500
acagtcttga tttcctcacc tcgtgatccc cccacctggg cctcccaaag tgctgggatt    163560
acaggtgtga gccaccacgc ccggccatga ttttcttta acatgacttt tcttctaagc    163620
aaaagcatca atagacccaa agtagatcca ttagtatact tgcactggca acaaagttct    163680
acttttaata tttagtattt atctcttaga ttgtaaaacc caactaaaac caaggataca    163740
aagtggcttc tttactgcta tctgtacaag tttaagtaaa ctgaaaataa atttaagtaa    163800
attgggtagt gtttccatga acaaaagtca agaaaatgta taaatgagaa tgggcttttct   163860 tgaaaccaat aaaaatgtgt agcatgatga ataacatgag gtgatatgtc tactaatcct    163920
ttatcaaagt agagataaaa gtttgggcct tggagtcaga taacctgtgt tcaatcatat    163980
tttcactact tctaagctat gtgaccttga acaaattata tcacttctct aaccttcagt    164040
ttccatacct atgaagtggg aacaatggta agatctagct catagaattg ttgagaaaat    164100
tatatgtagc gatagtcata atgtactcag catagtgctt gacattgagt aagcactcct    164160
taaatattac attataagca atgtttatta gtttacatag aggtaatata gtctaaaaaa    164220
atcagtatat tcaatgttta attcccaact gtaagtgaga acaggcagta gttaggtttc    164280
tgttcctgtg ttagtttgct taggataatg gcctccagct gcatccatat tgcggcaaat    164340
gaaaccaatc tgttcttctt taatggttgc atagtattcc aaggtgtata ggtaatacca    164400
catagacact agggactgat tgaaggagga gggtggtggg agaggactgt gggttggaag    164460
gctacctatc aggtactacc ttcactacct gagtcatggg atcattcata caccaagcct    164520
cagtgatgta caattgactc atgttacaaa cctgcacatg tatccccaga acctaaaatc    164580
aaagcagaag aagaaaaaag taagaagtaa aaaaaaagaa gaaatgttta aaatactttt    164640
taagtttcta ggaatgttaa atcatttag ataagatttt aattaccagc tcagacttaa     164700
aaacacacac acacaccaca cacgcgcaca cacaaaatta accataacat ccatacatga    164760
gaacatcaga ttatataaac tgtggtgcag ctattattgc aacctttagg taattttcct    164820
tgaaaacaca ttgttctctg tgtccagata gtgaggtggc ttctcttgca tatataaaca    164880
gtaaggccaa agtatccagg agattctggg catggttcag tatccaagaa ttttgccttc    164940
caacagatga tactaatgtg gttcccaaac tgaagagttg acactaaata tctggaacac    165000
atcccataaa aacataagaa ctcatgccca gaaaatcatt gcatgtaccc ataaatatgt    165060
tgcctttggc tataataact gccacttgga aacatattaa aactttcat gggtagttat     165120 ctaaaatgtc caaatatcat tatgctttgg ggagtttaac ttgaccaagg agaaacaata    165180
ctactaaaag gaatgttttg tgatgcctaa acaaatccaa gtaactggaa ggtagggcc     165240 aaaaaaaagt agccttctgg attagtttct gcatatatgg tggtagctta aatcaaagag    165300
tagtaatttg ttgtagagag gcaattggca gaaagcactg gcagaatcat tcacaaaaaa    165360
caagcctttc ttccctctaa aataggaaag catgagcttc tcaacttgat gttttgtga     165420 cagaactcag ggattatgct gtcttatgtt tgtggggta ggaggggagg tgggtgggag     165480
gaatttctga aaagcatatc tgtgttcctt tgcagtaata gctcatgctc ttgaacaaaa    165540
tcaaatatct cccatcctgc tataaagtaa atactgacgt aagacaaaaa ggcagtatct    165600
ggagactcta aatgcctcat actttgatta aaaatgcttt tgtcaattac agattgattt    165660
tgtagctcat tacaatgatg gatgtcaggg ctggcggagg tggtatttta ccacttggcc    165720
tgagggcaca cacagttaga agaagatggt aaaattataa ttatttcca gcactcatcc     165780
```

```
atgtgcctac attgacccaa tgggtaccac tgggataatt tgaaagaata gcatcagatg    165840
gaatggccaa aaagaatagt acctcagccc ctctctagaa ggaaaacatg ttagacaaat    165900
atttctcaac aacctgctga gattcttgtc acctgataag tcacattaag ctacatcagc    165960
caggttttaa agtaagctag agtgcttagc agaggctgca gcaaagaata tgcaaatgtc    166020
tctgtgtgta ctactatgaa tattaaaagt ccctatattt atatatcata atgtaggcac    166080
attcttccac atacataaat acaaatgtac tttctccccc actttaacat tggaggttgt    166140
tagaagctgt ggggaaatca gaggatatag gtaaaagagc tgcaggggaa agaaattaat    166200
attccgtagc ggctgaaaaa aaaaaaagaa ggaaattcat gtcactttgc catacattca    166260
tatcatgctc tgaagtgacc tgtatttctg gagacactgt gtggtttcta aactctgata    166320
cccatggtta gttcacaaga cattctctaa tggtatccta tgaatgacta cattctctgt    166380
gatagctgca cggccaaaga agtaatatcc tccagacaca taacatgcaa atcttctatg    166440
tggtatacct agcacctgct gcaaaatgat ggtgactcag cattcaatta aaaatgtaag    166500
aaaatcgatg ccaagtatta tggaaaaaga tattacatga gactgatatc agcagtctta    166560
ggattaagaa aagaataaaa tcatttcaaa ttgaagatta ggaggcctgc ctacactatg    166620
actatagcaa tattggccat atatctcacc aattgctttt tataatagtc caccatgaac    166680
acaaacctat ttatggccta cttttcatggt gatatatctt cgttctgcta gttgtttaga    166740
atcccaatac tgtgaaatgg aactgtggtg acaaaaaaag taatacttca tataatgaaa    166800
tgtcaagaaa tttaagttaa agtaaggtaa tgatacatag gttcagggca taaaacctga    166860
tctatgctta taatcaaagt gaaaatggac agtggaacat cattagaaca tctggatcat    166920
tttggaaact tattatgttt ggcatcaagg accaggatga aatctcattt ttcttacctt    166980
ttgtattata gtggtggtaa agaaagagaa ggaaaatgtg ttcataaagt ctggaaaaat    167040
ataagcgggg tacatatgct ttaaaaaaac agacaataga caatcaaaaa ccaactctgg    167100
gatatctaaa gcattaaaaa cttttagata tttaaaatta gctagaattc tagttgttaa    167160
aataatatgc ttgtagatgg cttatttctg tgccaaagtg tcaatactgg agtagaagtg    167220
tgctatacaa atagtcttca ccatgaacaa tcccatgaca agtcttgctg atagggtaaa    167280
atttgaaagg agaaacaaca ggcatggtgg ctcacacctg taatcccagc attttgggag    167340
gccgaagcgg gcagatcact tgaggtcagg agtttgagac cagcctggcc aacatggtga    167400
aaccccattt ctactaaaaa tacaaaaatt atctgggcat ggtggcagat gcctgtaatc    167460
tcagctattc cggaggctga gacaagagaa tcgcttgaac ctgggaggtg gaggttgcag    167520
tgagctggga ttgcaccatt gcactccagc ctgggtgaca gagcaagact ctgtcagaaa    167580
aaaaaaaaaa agaaaagaa aaagaaaaaa taaagaaaga taaagaaaaa gtgcttaggg    167640
aagcaacaat gacttctatt ttaatggtcc caggtctttg gctccaagtg ttgcatagtg    167700
tctattccac aggtaaagat gactttaagt actatctaaa ggcaaaaagt tactatcatt    167760
ttatcatttg ggtaaaaaaa taatactcat cctagtatta taaatttgga agggaaagac    167820
tctcagtttc tcaaatcgta agttgctaaa gccaatgatc ttatctactc ttcctgcaga    167880
gagggaaaga aacatgtaga aagtagtgat actgcgcaat atttgctctt ccatatactc    167940
tggagttggc agaccatttg atggtttcat tgccttctct ctcctctgct aatattgctg    168000
ttacaattcc actaaatttt tatactcttc actcccagtt ttcactttct agacaactga    168060
atgcagatgc tattaagtgc atcaatagga gttctaagag gaatacagga gaagtttcac    168120
```

```
tgctgatcta gacctcagac ttggttacag gtaaggttaa aggaccctat actctgcctt   168180
ttgtagcacg aaaactgtca gaccatacca aatagaaaaa tgggaaataa ttttttttctt  168240 ctgtcatgat tacaacatca atagataatc taagacattt tgaattcatg gtcttagtat   168300
ccaacaacct ttctgctgct tggtcctgta agagcactta ccatgccata tttaatttct   168360
gtgtactggt ctctctctac ttcactacct gtgagctctg tggcaaatat tctatctttg   168420
tctctgtatg taagacctaa tatattattg gttcacggga agtgctcaat aaatgttaaa   168480
tgcataaact tatactcatt tgaatggcaa tttctaaggt ttttttaaacc acctaagtac  168540 ccacataacc aattagacaa gggacttaaa tctcatattt agagtatttt tttaaatttc   168600
agattttcaa gacatcttaa aatatctcct gaaatacaaa atagaaacag aatttaaagt   168660
atatagaaat ggtattaatg tcattgatga tgatgatgat gatatcatga aaatagcagc   168720
tgaaatgata taaactgtta catggtagca cagatacaat ttgacagaaa ccaagtttat   168780
aatgaaaaat gacaattctt aaactcctgc atttccttta ctatacatga atttgagata   168840
attgttccag taccagattt atgccccact aaactgagac tgtcacaaaa cctcctcagc   168900
aatagcccct ctaggtgcag taaaggttga ataagtaatg aaaagactca gactacagtt   168960
gaatacacct gtgaaattac tatataccag aagctccaac aaaccatttt cctccctcta   169020 tgtgtacccct aaagcctgat tcagaagaca agttgacaac tcttacaagt taatggcaaa  169080
tatctgccca ataaaatgac tgcttgttgg tatcactgaa gtatttgttg gggtagtttc   169140
aaactttaag accatctgac ctcatctgac agaagagctt gattatatga gcctgatgca   169200
gtgtatactg tactcaattt actatactaa tgagttggtg atacaaaata taagtccata   169260
aggaatttca ttaaatgatg taaaaaaaaa ataagaaaat cagttaaatc aaatgtgtaa   169320
acctataatt aatgtactac aatttgtaat ttagctttga aatatgcaca tcacttgaaa   169380
actatcaatt cagaaggaaa atggaaaata aggttaacct taactgaata tgttacaacc   169440
cagtgagtac actatatgtt tatgtagaca gcagaatgtg gcacttccaa gtggggtctg   169500
aaatcagatt gcttcctttc acaccttaca agatacaaga tgttgtgcca attaacattt   169560
tctacctgtg ttaccatctg taaaatacag acaatatccc ctttctcaca gaattagttg   169620
gcacctcaag aaatgtcagc cttgcccatg acgggccaag ggcaacatag tagcaggact   169680
ctcccgcagg ggctgagaat aagggggtta tttgcaaaga atttgaaaac aattgtaaaa   169740
tcaacaaaaa gttggtcaac tttttattat aaacatgtat tagttaattc aaaacagagc   169800
cagtgataaa ttactcttgt tctcagaggc agaaacttcc agcccccaac tcttagtata   169860
taccactgaa gtctcatggt aaaactgagc taagaataat catgcattaa ataaaggaca   169920
tttatatcca ttttaatttta tcagatcaac atagtttgaa ataaaagcat agacatgtgt   169980
agaagatgaa atagtctctt taggttcact attgatctcg tttaggaaag caccatcact   170040
tccatattaa ttatttcttg gccattatta aactgctatg cacccgtctt tgactctgtt   170100
ttctgtctgc caactctcat tgcaaaaatt ttctgtctag tttattgaga tgtaaagagg   170160
acagataatg ttacatttat aaattatttt caactgctaa gataaaatgt actgtataga   170220
gtacatttca agctacaaat aacaaatgca aaatagtgat tacattttct ccatgaaaat   170280
tttgacagaa ataagggcac tgtcatctat tctgtataat tctctcctct cccatctttg   170340
ccctgttaat tagtctcaag atcacttact tttacttgtt attttttaag ttgatgagat   170400
cattaaattt attagctacc caaatacatt tgaagtttat taagattctg tggtgccttt   170460
gaactggaaa tagagaagga atagaactca cttttaaaga aattaaagta ataaagcaaa   170520
```

-continued

```
atgggtacca cttcatttta agtacccatt aaccagacca taagagagaa agtcaaaatg 170580
gaaatctcag agaaataaac aggtgaaaca tatgccattc ttcccacgca agcattagtc 170640
cagcagtcag cccatccaga atacatgccg aaagcatttc acaggggaat acttaaaaag 170700
tgtattttac attttagag atagagtttc attgaaatct caatttgtgt gcaggactca 170760
ttaagagatt gagataatgc tttcatttgt tgatgataaa cgttaattta ttttctctat 170820
taagccactg caagtctttg ggttcaggat gacataaaat actttatatg aaatgatctg 170880
gttcatgaca tttttattcc ctgtacattt ggcagacaca aattttctta aactgcaaat 170940
actattcttg gtgtcatgaa gaactgtcgt tgcttctaaa tcttcaaaat ttgtttcatt 171000
taaatgtatt ggccaattgc tgcagttaat gatgatgaat aggattaaga ttaaattttt 171060
aataaactgg attgactgta gccataggca gaaactagct atctaaatga tgtcatctct 171120
gttgctagaa gttcctgca ttataaatat tttcctatta ggttttaagg tacctaaaac 171180
ttcgtttaaa attatttgtt taaaccattg gtatcataaa accacattaa gatactcatc 171240
agggagatgt tttgagatag cacttttaaca ggtattatgt ttctcaaaat ttttacagtt 171300
tttaatttta ttttttaaat tcacatatgt ttcttatgaa attctcacac cacccagtgg 171360
ttttgtataa gccaagagat gttggaaaca cggagtacta cctgagcctt aagtgagagt 171420
ctcagagttg caacctagaa ccaaggataa aggttgtgta attacagaaa aatcagacct 171480
tgaggaggct ggacctactt ctaattccct tctgaggttg gcctagataa taaactatca 171540
aggaagaaat aaaataattt aataaataat tgccttttcc ttttttgact ttttcattt 171600
tgctttattt gagatattga tagcatagtt gacctaaatg ggatgaaaat tcacttgcat 171660
aaaataaaaa atacttaaat tctgtcagaa atttggatag cacctaaggg acctgactga 171720
ggtcacaaga tcagaagtct ttatatttct gctaaaatta catttaaat gtttaaatta 171780
tataaatgcc aaatcattta ataactgaaa gtttaagaca atagattgac ctaaaccttt 171840
gcaatttatg aaactgtatt attagttcat gtgtcttatg gacatttatt tgtttctact 171900
aggataatag ctaaatttta ataacaaaca taatagcaaa aaaatcagta tcaatataac 171960
tgaaggaaat ggaaactttc ttttcaacaa gacatcttca tgtatttata agatttcagg 172020
cctggatctg gaactatgat tctgatatag gccccagtgc ttctaaatga ctgccattta 172080
actaaaacat cataactgta tagttattca taattttatt tgttagtaat attaattttt 172140
tgagattatt acttcatgca aaaccagcca gccaatcaac acaatggata caccagagac 172200
acaagtattc taattcttga agtgatctta attgtgggtt tttgcatata gagattatag 172260
atagatttag ggatcataga ctatttgcag gtttcttact taatcctcct tgagcattgg 172320
tggaaacctg tggaggcttg aatgaaggcc ttgtagcgag ggtatgcagc aaatcttgtt 172380
gggaagcagc ctctctgagc taaatgacaa gttagcatcc cctaagttag cacatctgag 172440
tgaagaaatc tgtggaaaat ttgttttcca aagatatttg atattctgcg acctatttaa 172500
aatttaaagt aactttgggg gccagtcatt aggagaaagt gtcaaatatt ctctctttga 172560
gtacacttat ttaacaaatt tagctaggca tttcttcagt ggtactctca gagacaggac 172620
actggtacgg agatatgtat gagaatttgg tagtgtagct gttttctccg tagtccttgc 172680
tctagttcta cataaagact ttggtcttca aactgcccaa cccagcctta tcccctaagt 172740
aaagagaact caataaatgt ggtcatgtaa aggaataatt tatgatgctt gggattaaaa 172800
acaaatacca aaccaaggct ggaattaggt caaaaccaag tttaatatat aacaggttat 172860
```

```
aggcatatga aatatgattg taaatgataa gcttatgtat atataactat gttaattata 172920
tttatgcaag gtatttttc ttttcaaacc aatgaactgt cttgattctt caaaagtaat 172980
gagaaaatag taattaaatc tgataattac attttctta gtgaatatat tttaatagaa 173040
aagatgcaca tttgagggga tatgaccta ttttagatga gagaggtcaa aataatcaag 173100
gtttgatggc aagagacaat tggaatatat ttctatttt gcttcacaac atctattaga 173160
tgtataaact attttatcta acaagtctcc agacacatga aaaaggcaca tttaaaaact 173220
atatttatt tcttattt ctgattccca gcagcatctg aagaaatttc tagggacctg 173280
actgaggcta caggatcaga aatctttata tttctactaa aattacattt taaatgtttt 173340
tattaaagca taatatacac aaaagtgcaa agatcataat tgtagcacct gatgaattcc 173400
cacaaatttg acatagctat ttgaattagc accagatatg gaaacagcac attacctcac 173460
tcagaagctc cctcatgttt ttttacagtc attatccttc tcttctgact tctagcagca 173520
tatattaatt ttgtcttta agccagaagt ggaagctggc ttattttgct caacattatg 173580
ttacacaatt aattcatatt attgcatgta gtcacagatt gttctcattg ttgcatagta 173640
caccattatg taaatataac ccaatttta aaaaatttct cgttaaaatt tcatatctgg 173700
aaaaaacagt cctaaaatat atctttatct atctatctat ctatctatct atctatctat 173760
ctatctagga tgctgtataa ctgaacagaa cacagataca taaatgtttc aaagttaat 173820
aatcttattt ttaaatgcca gagggttagg gagaagccac aaaagaaata tcttccaatt 173880
aataccacat gttttaaaaa agagaaaaat tcaatatcaa catcaattaa gaagtcttaa 173940
tatctgtata tactctgaaa tcagttttaa atgtgaatga gccatatcaa gttctctttg 174000
gtaaacaaat gagcaatgac atggatatta gtgacattga taagtattaa ttgataatta 174060
agttgatgat aatggggaaa atgttaagaa tcatgaattt gacctcagga ggggaagctc 174120
atcaaaatca gatcgtatct aaatgagaca tgtccttaaa atgaaaggca gctctggtct 174180
ataagaactc atagtaattc aactagtgac tactaaagta ttttcaaatt acagatctta 174240
cttgaatttg gtttgttgta tagggaagcc tcatttataa ataggagttg aatttccatt 174300
ttatgaatac gttaaaatcc ttataaacca ttttttaaat aatttacaga gcttcccta 174360
ataatcttgt ttaaagtatt aattttctaa actaattt ttttaatgtt ctggtcacaa 174420
acttgagttc tgaattaatg aaatgtgaga aatacctttg ccagacttca tatatttct 174480
ctaatgttta tatttggaaa attttatgaa agaaaacatt ttttgaccac gcagaggcac 174540
catatatgaa gcattttggt tcaacggaga gttctgtggc tatttctgca gaatctctat 174600
ccatctccca ctctttatct tgccacatct tgtacatatc ctgttaccct aattgtcctt 174660
gatatttcct gcatttattc tgtagcatat ctccataaaa ttgtccttcc tctattatat 174720
tttcacagag aaaatgaaaa atgagtctct gcccataatc atccacctca caactattag 174780
aacagaatca agagtctaaa gcatttccaa gagctgagtg tctttattat cacaaacaca 174840
caactggaac tataaattca gcaaatgcag agtttatatt gattcgatat tgcactgagg 174900
tttcatggca atagcattgt ctctcaaaag acagcaacaa atgtccaatt gcatgtaagc 174960
taatgaagaa ctcagtcaaa tggggcaact ttgtcatgtt agtaaggctt ctgtatccag 175020
gtaagcataa cagtgcaggg aaaagaaaag tagtttcatg cccagggtca ctagacttta 175080
tcaactggac agccaacact tggaggattt tcaggagaa gtagatcttt tccatgaatg 175140
aaacaaacat tcaatccaat tactagaaat gtaccataca taaatattg tgggcattcc 175200
aaaaaaacac aaaaaacaaa aaagttaac ctcgttaact tattgtaagt tgcttacaat 175260
```

-continued

```
atggtaaggc ttatattttg atgtaaacta taaatcacca caaaagtttg atagagaagt   175320
acataacagt aagaaaaaca atttctaatt ctcaaagcat agtgtctttg aacttgaatc   175380
ttgagataca atcatgtctg atgggactaa tttctgcatt ttaattatgg catttactgg   175440
aagtgctcct tgagaagaga ggacaaggaa gctcaagtgt cttttgtaga agtgtgtcca   175500
gaacaaaaat tatattggca gcaacaatca cttaatgaag gaagagaaaa atgaaaaaaa   175560
gatttcaact tgaaagctat tttataatca caggaggctt tagataatgg cctggcaata   175620
aaatggtccg ggagtagccg ccaaggggag ttattgttgt tctttgttta gttttctttg   175680
tctgaagctc agtttatgta aaaagaaggc tttgctttgc gggtagggaa aaaagatacc   175740
ataatctcac ctctgcccgg gtttaaaata tttctaggag aggaacaatg actctagaat   175800
gcctttgcct cagcttgaag ctgccactaa tggcatagca aacacaaact acaaaaaacg   175860
tctgtgttgc cggacctggg actttggtaa cctcctgctt ccaattagaa gaacaagcgg   175920
agccacagta cagccaggca agcttaagtc aggtatttgg aaggagggag agtgacagag   175980
gaaagtcaaa gcagtagctg tatggtcctg aagaagtggt ctggtagctg gaggaaccct   176040
ggagatttag ccaaggggtc atcatgagcc gccttccctg ctgtagttca tgctcaaatg   176100
ccagaatgaa ctaaatttct cacctgggaa aactgcattt tctacctgaa ttcctgatcc   176160
catcccccac ttcctctgtc ctcgtctatc aataacttgc tctttcctgc atcttcattc   176220
tgtccggttt ccctagctac tttcttttgc cttcattttc tcaaaagata aaatataaat   176280
aattatttta accccacct gactgaatga tcccactagc aggagtctaa ggcactggac   176340
aagggctgaa gtctttggtg cctggactag ttacaggtac tgaggtgtgg aattaagtga   176400
agcatggtgg atggacctaa tacaggatga ttattcctaa ttcgaaaatt ccaaatttga   176460
aatgctctaa aatcagaaac ttttgagaa ctgacatgtt caaaggaaat gctcactgga   176520
gtattttaga ttttggattc cttgattagg gaatgtttat gtgtagtgca gatattacac   176580
aatttgaaaa aatctaaaat ctgaaatatt tctgcttcca agcattttga ataaggaata   176640
ctcaacttgt aaacaggtag cacaaaatgg aacaaggtaa tttgagggat gaactgaacc   176700
acatgcagtc ccaccatggc ataaaaacac aaaaagagaa caggataaaa caaagataaa   176760
atcctctgga gcatggggta ggaggcaaag cttagagagt tctgatctcc tggcatttat   176820
tcatagtcac aatttttacg aagattggtg atccagctca ttcagggaac gtttgaactg   176880
tcatcacatt tgtgccattg cctttcacca ccaaactaga taaacatttt accaatggtt   176940
cttttttcca tttctggtca catcgcctgt aaacattcaa aaatggtgtc ttttcacttc   177000
tcctttgaga ttgcattctt caatgtcatc cgtaactcca tagtagccaa attcagtgat   177060
cctttttaa cgttcatgct ccttaatttt ctgcaacatt caattgtaat tatattgcct   177120
cttttctcaa atctcaccca taccactttg gcttccatct ttctttctgt tctctaattg   177180
ataaccttca ccaaatgaca gaaagcagaa aagagagcac acatttatga acttgcatta   177240
tgacctaaaa tgattaattc atattcttat aagtttcatt gaatcactct ggctgctctg   177300
ttgagaataa ctataggaag ccaagaacct cgttaggaag acctcacatt actacagact   177360
agtgttcata gtagctctga taaaggttat agcaataaaa gtagagagag atggtcaaat   177420
tctggacata tactgaatgg agagccacaa gatgtggtgg gctccctcac atgtagggtg   177480
tgaggggaag agaggagcca ggccattctg agatgttagg gccagacaac tggaaggaga   177540
gacttgccac caactatgat gggaacacat aaggaacgag aaagtttagg gggaagatcg   177600
```

```
ggagttcagg ttttgatatt ttaagtttga agtatttagg aagataaccc aacagagtta 177660
ttaaggaggc agtgaaatat atgaatctgg atatcagaga gaagtctcgg ctggaaattg 177720
aaatttggga ttcattggca ttttagatgg acacatgagc cagacagcaa atgtcagcat 177780
agcaagatct tggaagaatt atttcagatt cagagtcaat gaatatttat taagcaccta 177840
ccatatgcca agctctgtgc taggcacctt caaatacatt ttttcaccc ctacacaaac 177900 ccatgatgaa gttttatata agaaaagaca taatgaagaa attaagcttt gaaaaagtct 177960 ataaatttt ctaaagtagc aaaattagca tgttatgaag caaagattca aactactgct 178020
tgcttcatta cctcattttt atcactctat gggtatgtac atttgctaat cctcataggg 178080
ctcataaatc ctggatatct gaccctcaga tacttgtgtc ataaaatggg aactaaattt 178140
atccttagtg acctcaggac ctcatagatg agttgaaaca cgaggtactc aaggtggcct 178200
gcctggcatt ttgctttcag tgggcctgag cacccagtgg catggatgtg ggtctgcatc 178260
ccatgtgatg tgaatgtcct gcctgttctc aagtgctgtg aagtgcactg taaaacacta 178320
atctctctca gctgcaccca ctcaggctta ttcagaactg cacaaggctc attgccttgg 178380
aatctttgta gagaggaaaa ctcaaggcag ctagctggac cttagtatcg gggcaaatgg 178440
aggttctgac aggtaaactg gaaacagtgc cttccaaagg gaaatctgcc attttgcttt 178500
cttttggtgc cttcattttc tgcttcactg ggaatttgtg attgtagata tagaatatga 178560
attttaaaac tctcccattt gggcttccat tttaatgtct ctgagttggc aatacacgga 178620 cctttcttc tgaacttctg gacatctgct tcttcaagtc taaggtagcc ttcagactac 178680
ctcctatttc tcactctcct actccacatt cctaattccc tataatatct aaccgctggg 178740
cctagcataa tttcctaatt gttttctgta ttcacatctt tactagctcc taagttcttc 178800
aatgacaaca ctatcttaac tccttaactt cactgtgtcc ccagtaccta gcccaatacg 178860
aagcatttag tgtctcaatc atatctactg acttatttca acaacttttg caggtattga 178920
cataaccatg cactctggct cataaggtca acaatgtcct agtttctggg aacagactga 178980
ctagaaggct ccctctgcag ctatgagcaa aagcagcagc cttctagct tactgcctaa 179040 atttaaaccc caagagctta ggtttcctac cgggattctt gctgcggtgc ttccctgacc 179100
acgatgctca gactcacctg cttcacacca tgacctctgt tgtttgcctg gtactgggag 179160
tagctgccta ctctgtatgc cacctttttcc tggtgccgta tgtagattaa aaaaatgtgc 179220
ataacaaact cttctttaca gaagaggaaa ccgaggctca gaaaggttat gccattttct 179280
aagatcccac agagaacaag tggtacattg aaaaatagaa gccaagtttg gattctcctg 179340
agccattcct ctcccctgaa tttgcactgc tttggttacc taatctgacc cagcaaaata 179400
caaaacaaac tccacttccc ttgcattcta gttttgtgat atgctctcct taactggctt 179460
caacgatcac acttttctg agtgtttata tttttgttta ctgtttaca tcatattccc 179520 tcctcttcct ctacctgctc ttgtggtgta tacaccagcg ttctggaagt ctttatctct 179580
ttttacctta cgagaagatc atctttagta atgccatttg ttaccagagt tgcaactctc 179640
acctacatac tgatgctgat gattttaaaa tttgtctctt tagtcctgac ttctctcatg 179700
aattctctac cttcttactg gacctcttac ttgggtgttt cacaaacatc tcaaactgca 179760
aatatccata gctaaaataa gtgtcttttc tctcttatta ttccatcctc cagtgtttta 179820
aatttctgtc aaaaagtcgt catcctacca gtcattctag ccaggaaatc tcgagaagtc 179880
gctccttgcc tgtctctctt ttactcacaa agccagtcac caggttctct ccaaactgct 179940
tctaaaatgg ctcttgcctt tcattctcca gtcttcatcc ccgctgccat tcctgtcttt 180000
```

```
agcttagatc cacaccatca ctacaaatta gtttctctgg tttcaatctc ttccctcatc  180060
tggtgcattc tccatatgcc atcagagtta tgtttctaaa aacaatctaa tatgacatct  180120
cacgtcttaa aaaattcatt gggtaccagc taacaggaca cagcaaggat gctcagaata  180180
tggccactta gtacttttcc actattctat gaatcctcta ccatacagtg cagacacagc  180240
acttttcat tttttttctt ttctttttta taattttcc attccatgaa cgctctctac  180300
agttttcttt tgagactttt gtgacttctg atctgcagtc tttctgcctg gaccgcactc  180360
ctctaactct tcactcttga aaaaatctta catctttcaa agcccagatc cagttcattt  180420
ctgtgaagct ttccctgacc catccaagga gaattaatta ctctatattt tttgcttcta  180480
tatttttttc atccaaccat tatagcatgc atcacattct tccagagtta atttctgaga  180540
ggtctgattc actagctaga ttgctagctt cttgaaggca acagctgcag ctcattcatc  180600
tccaaagcct atacattaag cacagtactg ggcatataat aggccctcag aaaatgtttg  180660
ctgaattaaa cttaatttaa atgatacata atgggaaaaa taatatttca tatataggat  180720
tggcaaactc actttagaga caactgttta gagacatatc tattccgaaa atgagatgct  180780
tcaacaatca cagtgcaaaa ggaaataatt aggtctgcca tacacacaaa cttaacttct  180840
gtactttcaa aatgacttca aagagagata ttttcacgg aactattgat attgagcaag  180900
atgttgcttt cctttcagta agcatgacag aaaaaaaaat taagtctcta gagtgtttgt  180960
aatttgttct tgtggaggga ggtagctagt aattcctgca gcaactgttg ggtgggctac  181020
agatatcttg acataatcta gagcctataa gacatgtctg tcgccaggga tgtcattctg  181080
atccgaagct ctggagtgct gcttagaaat gtgtaaggga gactgactta gaggtttgca  181140
gggaatatct cgctaagtga ctaatgatct ataaagtcct gatacttgcc atatctgcct  181200
tttcctggga ccatggatta ttgtatctgc tagttttcag cctcaataaa agaactctgg  181260
ccaagcaggt gagaagcttt aaagtataac tttattttaa acaatgcctt ttaacaataa  181320
ctaccaaagc attaacaata atatatgtat aaaatgttat gtaaatgtta tacaaattat  181380
atatatatct aaatctatct acacatatat attatttata attctgcctt aaatttaatc  181440
tctattatag ctgcaaagtt tatatattca ttcttatatt atctcaaatg ctagcacgtc  181500
cttcattttt tgcttcgtat ctgtattttg gtttgaggct agcaatagta accagatccc  181560
ctaatcccaa atgagggggc tctctgcaaa gacttagtcc tgcccaattt cattaccatc  181620
tcagatataa tcacttacat tgcactaatc tttcctaaat cttgagcaga gggagaaaga  181680
aacaaagcac tctttttcaa ggtcatgggt agagaaagca gaaaatcaag acacagaacc  181740
cagatctgtt cttgattggg ttctcaatct agtgctttca aatacactgt gaacaaccaa  181800
acaggagtaa aaagacatat atcaaagcca acaaaagatg aaacctcaaa gggtgtgtga  181860
gtgaagggaa tcagatgaga gttgaaaata cagagttgat gagaaaagca ataaaaacaa  181920
gccactcagg tggcattagc tgcaaagaac aatcttgctg gtcaatccac cagtggtatt  181980
tgaatgctgg tgaaaggtga ttaaaggaag ggagtttcag gtgtgcagag aacacaaatg  182040
gaagatatac tagatttaa atcttaaagt gattttgaaa tctgttttat tattattatg  182100
tttctgaagc acagagggaa tctgattgag cgaacatctt agcttgtagc ctagccaggg  182160
gttcacaagg ccctgagaaa accttctgcc tgactctcac caggcctttg aggatcccac  182220
acgctcagtg gctgacagga gaggcagctg aaatatgacg agtggtgcca aggctgtcag  182280
cactggccca tttagggaga cttgtgttca ttcactgtct cagcttaagg ggcctttgtg  182340
```

```
ggaaatggca attcacagtg tgaatttcaa tagaatcttt aagtctctca gagattttc   182400
tctttgccaa gaaaatttcc cactgccaaa cacttgtaga ttgacagctc tgcaggtatc   182460
tctctaatat agctgttcct ttcttacttt ttactgtacc tagggccttg tttcctaaag   182520
gttttgtgt gtgtgtatat atatttttaa tattattttg atggatcttt cttttctaa    182580
ctggcatgag ccttaagtta aaatgaattg gatgctggca tcatatagaa atattgtttt   182640
tacaggtttc tcaaagtaag atgtattaaa gaagacatat caagtttcca gggcttgtgt   182700
tgccatagca accagtatag gcctagtttg gagaatggga actggggct aacaagagac    182760
tactagacat gttttcctcg accataaaag ctctgaatga attagattcc cactgtcttt   182820
gtggttttaa gatgtagaac aagcagaaaa taggtaggtg ggcaaattta ggttataggt   182880
ataggtacag gcagagagta agttataaat gagcgcaaaa ctgccccgac gtgcttcatg   182940
gaatcatcaa atatcagagt ttggaacaca tgaggaagtt gaggctcaga gaggttaagt   183000
gacctagcca gcaagcaagg gcaggtctga tacaggaaat aaactatctt gcctctccac   183060
taaataatgc aattgtgtcc caaatgcata gggaggactg tctcctttca gcagccagaa   183120
gttctttgaa gagatattga cccaatggaa tgacaacccc catctagcat gaaaagaca    183180
acaataacac acaaacataa tcttatttcg gcacagtaaa aaccctctaa cgtaggaagc   183240
agaaactgga ggtggaatta cttgctggac tttcctttca cctttgtgga gatgcccagt   183300
gcagtaggaa aggaacgagg ctcactttca tcctcttcga tgtagttcac tatgggcctg   183360
gagctggtga aagtgtgttt tcactaaatt aggtctgtat gataacagtg aggaaattta   183420
tttccacact accaccaagc tagaagcttg ccctaaccaa atccacaaca ggaatgttct   183480
gattctcttt aactccatca tttgcttatg acctttcatg gagttctatg cttagaactg   183540
catgtctagc ccaatactct ccaattggaa tataatgcaa gcaatgaatg agacggacat   183600
atgtaatttt taagacccta gtaaacacat ttttaaaaag taaaaataag caggtaagtt   183660
aattttcata agcctatttt acttagtgta tataaaatat tatttcaata tataattaat   183720
acaaaaacat taatgagata ttttacattt tcataccagt tgcagaaatg gtacgcattt   183780
tacagttaca gtacatctca gctggactaa tcacatttca agagcccatt agtcacatgt   183840
agcaagtgac tgtcatattg ggcagtgggc atctagagtg tggggacata atgtctgtgg   183900
gacttgagag gaagaggaag aaaagatgaa atgttctatt ttttttttc ttttgaaaca    183960
gggtctcact ctgtcgccca ggctggagtg cagtggtgcc atcttggctc actgcaacct   184020
ccgcctccca ggctcaagcg attctcctat ctcagcctcc caagtagctg ggattactgg   184080
cgcacaccac tacccccag ctaattttt tgttattttt tttttaata gagacggggt      184140
ttcatcatgt tggccaagct ggtcttgaac tcctgacctc aactgatcca cccgccttgg   184200
cctcccaaag tgctgggact acaggcgtga gccaccatgc ccagccaaga cgaactgttg   184260
ttacacccta aaatttcccc accctactat aagattatct ctgccaactt tttacataaa   184320
taatcttcaa atcacagaga ataatttatc atctcattag tagttcttcc ttaccaaatt   184380
ttattgcttc taaactaagt gtatgaaata caaacccaaa attttaagtt taaaatacaa   184440
atgcgtatag atatatagat taatgtgtgt atgtatgcct atatatatat atatatat     184500
atataaagct tagtttcata aaattttgat tatttacttt ttgcttttgc ttgcctaatc   184560
agataattac cttggttttt attctaaatc ttctgtagaa caaggtggac tgtaaataaa   184620
taataacttt atttatatat ctcatttcc ccctgtagtc atagcattca tgtaaaaact    184680
cttatctacc caataaaata tttcatcaga atgtgaatgc cttgttttat cagagggaat   184740
```

-continued

```
ttcttttagc caaaacacct tgtgaccttc tgttattgaa ccatatatta atcatatgaa 184800
aagttataaa gagaaaattt gaatcagtgg ataatgaatg tctttctttt tttttattt  184860
ttatttttat tttttctttt ttttatcata ctttaagttt tagggtacac actagactca 184920
ggctcgcagt ctctctcact acccgaggca tgagtgtgag ggaggctgtt tgtattctat 184980
gctaatgctt ttttttcaat gctcaattcc cctcccccg cctttttttg ttttaactgt  185040
ctcacatttc aacatttcca tataaccagc taatctgata aacccatact tgacatacgg 185100
aaaaagtcaa gaaaagccta tttgtgggct atctttgtct ttctaggttc taagtgtcaa 185160
acgatattta agagtgtttg tttgtttgtt gtggagccat tttcgttgct tttgtgatat 185220
aatagaaaaa tgggaagtga gctaagcacc gtggctcacg cctgtaatcc cagcactttg 185280
tgagacctga gtggatagat catttgagcc caggagttca ataccaacct gggcaacatg 185340
gtgagaccct gtctctacaa aacatacaaa aattagctgg gcatggtggt gcgcacgtgt 185400
agttccagca ccgtgggagg ctgaggtgtg agaatcacct aagcctggga agtcagggga 185460
agtcagtgca gtaagccttg cgccactgca ctctggcctg ggaaacagag caagaggctg 185520
tctcaaaaaa aaggaaaaga aaagaaaaa agggaagtgc ctctttctgg cttctggcct  185580
agaggctgtg cttccatgac tgtgagaatg gccaccctgc aggctgcaac cctttgtaag 185640
aaataaagct ctcctttcca aatttataaa cctcatcact cttcagttga tgtgattaaa 185700
aaaaagtta tgctaaatga aaactttaca ttaagaacag agaaaagttg cattaagata   185760
ggcaataaat ggaaggattt aggacagtct tgtttgaaca cagggtgtgt gtatctgtgt 185820
gtctctgcat gcatgtgtgt atgtgtgttt gtgtatgttt atgtctagtt tgtgtatgtg 185880
tgtttgtgta tatgtcttgt gtatattatg tctgcatgca tgtgtgtatg tgtgtttgta 185940
tatgtttgtg tatgattatt tggttgtttc accaaatctc taccagaatg tcaaatgtga 186000
cttatttta cgtagaatat atataaactc tgaatcatta tatttagctt agttgctaag  186060
gcaagtgtaa tttatttcct gcttttatct tttacttata aatataaaat taaataaagg 186120
agaatgtttt gtaataatcc acaaataact ctcaatattt tataaaatag ttacaaatac 186180
catggaagtt gtttattgga atgtggcttt acagtccctc atagaagtaa ttttataaga 186240
gcatgattga taataatggt tactattcac taaatttcaa catatgtatg gcatatcatc 186300
tcttttgtc ataacagtac tgcagggaaa ttattattat ctccatttta tgaatgagaa  186360
aacttaacat tacatgactt tctttttttt tttttccttt tgagacagaa tctcactcta 186420
ttgcccaggc tggagtgcaa tggcgcaatc tcggctcacc gcaacctccg cctcccaggc 186480
tcaagcaatt ctcttgcctt tgcctcccaa gtagctggga ttacaggtac ctgccaccat 186540
gccaggttaa ttttttgctaa aaatacgtga ctttcttaac gttgtataac caaacattga 186600
cagagtcagc atttaaaagg aagtctctca ggtttaacag gtgttttatac acacatgcat 186660
gcagacataa catacataag acaaaacaca ggtgtgtgtt ttgtccacca aaccagaggc 186720
ttccttgggg ttgcagttgt acccatacaa tctgatttat ctccctaata tcgtattact 186780
aagttataat atttataaaa taataagccc taaagccaag tgtatcgtat ttattcgata 186840
tcaaactcat tctcagttct agctacagtg acaggaacac atctaccctt gatgcaattc 186900
tggctacact taagtaacag agaagaaagg ggaaaaagga agggaagaaa ggggatagct 186960
gtggcaggga agaaagcaaa tgtgaaattc cagtagaatc aaaaatggta agagcatctt 187020
cagctatagt gaggaggaac caggccacca gggctgcagc tttatacact aaggggccgt 187080
```

```
tcttactaaa gagatctttg taagaaaatt ggcaattaat gagtcagaaa ccgcttatga   187140
tttcctactg tagaaatgca ccaaatgact tgccacaaac ttgaactcac aatacttgtt   187200
cattcagatc acttctctga ttcaataaaa attgtaattc aactttacaa agcattagct   187260
attcagccca ttttgctgcc agcatagaac cttttccctt aggtctcagg aaggccagga   187320
accatctagg tcaatagtta tcaacctggt aagcatttcc aagttatata gccttccctt   187380
cttagtgata cttcacttgg ggaagaatac aagaatggat cacagagatt ccaggtggga   187440
gaaacaggca ttctacctaa tgttatagga tcctcagatg actaatatgc aagatctctt   187500
atgccattct caccagtttc cctgcttgtt gaaaacacta agctagtcat cccctgctgt   187560
ggccaaagac ctgaacctag actgtctaac atctaaccca gtaaacctct ctgtgctttc   187620
atttcctggc ttgtaaaata tgggtaatag aatatattca taacattata gagaggtaac   187680
taattaacat aaacaaagta cagatggcct gacttatgat ggtttgactt aggattttc    187740 aacttggtta tagtgcaaaa gtgatatgca ttcagtaaaa ctgtactttg aattttgacc   187800
ttttcctaaa ctaccagtat gcagtacaat actgtcttgc catgctgtgc agcagcagtg   187860
agccacagct cccagctatg tgatctgagt atatttaagg taggcgaggc tcagatatga   187920
tgttcagtat gttaggtcta ttacatgcac ttgcaactta caacatgttg aacttacatc   187980
aggatgtaac accattgtaa gttgagaagc atctgtactt cgaacggcat ctgacacata   188040
gaaagtttgt tgttgttgtt gtcattatta ttttatagtg agaaactgag ggctggatag   188100
accaaatgac ttatcttact taactaaggg ttcagaatag aatgcagatt acctaagttg   188160
aaatctagtg cttttcatg acaccagttg actctcaaac tgaagttaat acatgtgttt    188220
ctcattttct tagcctgttt gtatctaccc gaagttatgc atttaaaagg atcttcacca   188280
acattactgg gaggcagtaa ttatttaact aatttaagaa atttaaacca ttttagtttg   188340
tacctcataa tattttagga ttttttccct caacagaaca atcgagaaca ttaaaagaga   188400
gcaagctcca cgtcactcaa ctgatgctac cacccaggac agaaatcagc agtttctgtt   188460
tttctactga ccagctttgc attaaacact gcaaatggga gagctagtcc actgaactca   188520
tgcaagcatt catttattta tccacaaaaa gcaaatatg gcaaggggaa tttgggagga    188580
gtgaaataag ggttgtcaga ctaacagtga caaatgggat gcaattgttc tccaaaagct   188640
tggagcagag aagtcttccc ttttcccctc cccttaatcc ccactgattc caccctgcct   188700
gcacacagag aaggtggtta acagaggaaa gccccgtgaa taagctatga cagccctaca   188760
ttcagaaact gatgtcattt ccctaaatac tgtttgtaaa atggtaatta tctgccaagc   188820
aatgacagct ggcacttagc atagacacac agagagacag aaaaagagag aatgagaaaa   188880
aagggtccct gcataattta ccaaagggct gaaagagaga gggaaacata atcagaaaaa   188940
taaaatgatt accagtgtgt gatggggtga aaattgcttt gggcattttt ttttccttt    189000 agagagcaca ggattgaatt ggaagaatga agctggagct ccacgatgca cactggaaga   189060
gaggaggttg tgttaaggtg gcggtaaaag gagaaataca ccaatggtgc tgggctgtgg   189120
caaagcagca ggaaaactct gtgcacacct agccctcaa acaggaacca ctcagcccag    189180
caatacttaa taatacaccc aagattgttt cctttagttc atttgggttc aagatataat   189240
atattaagta cctcttgccc ccttccttgt tatttatgtg atggtcggtt ttatgtgtta   189300
acttggctag gctgtagtga tcaactatcc aatgacacat tactctaggt gttgctgtaa   189360
aagtattttg taggtatgct tgatgtctac aatcagttgg cttatgtaa aggagttgat    189420 cctggatgat ctgggtgagc ctgttctaat cagttcaaaa gtcttaagaa cagaactgat   189480
```

```
gtttccctga ggaagaaaaa atctccctg tggattgtgg catcagctcc tgcccaagtc   189540
tttccaaatt gtccttctga tggcctaccc tgtggatttt ggacttgcct agttagccct   189600
cacaatcaca ttacgatccc ttgcaacaaa tcgaactctc ctgtctctct tcactcacac   189660
atgcgtgcat gcgcgcgcgc gcacacacac acacacacac acacacacac acacacacac   189720
cccaacttgt tcaatttctc tggtggtacc ctgactgtta aacttgtcaa gtacctgtgc   189780
agtgatttgc tcagctaagt gaatatgtta tgggttgatt tgtcataatc ccctcaaaat   189840
ccgtaagttg aatccttaac ctccagtacc tcagaatata accttatttg aaagtagtat   189900
cattataaat ataattaatt aagataaagt cattagaatg ggctcaaatc ctacatgatt   189960
ggtgtcctta taaaagggga aggtttggag acacaaacac acaaaggag  aatgccatgt   190020
gaagatgaag gcagagatca cagcgatgtt ctacaagcca aggcacacac cagagatcgt   190080
tagcaaacca caggaagaaa aagagaggca tagaacagat tctccctccc agccctcaga   190140
aggaaccaag cgtgctgcca ccttgatctt gggcattgag cctctaaaac tgtgggagag   190200
taagtttcta ttgttttagc cactcagtct gtggtacttt gttacagcag ccctaaaaaa   190260
cgaatgcagc acattaccag gaaaatcgag acagttgaat tggggaaagt taagaaacat   190320
acaaagttac aaaattttct gagtattaca gaaagctcca tttccttact gcttttgaaa   190380
tacaaactta ttcccttta tgcataacgg ttttactgcc aatagctacc caagaaaaga    190440
cctggatgat taaactgaca attacagaga tgtacaaatg ttccagaaat ttttcaaagt   190500
agttctttta aattcctgga atctggtctc ttttggata  acagatgttg tagaaccttc   190560
tataactatt catctctcta tttgtgtcct cctggagtgt agctcttcag ttctgtctta   190620
caggaaaagc taacaatcac cacctggtgt cccttcccct cttctagcaa gtgaagctaa   190680
tagatattct gtaaaggaa  aaaacaacgg ccgagcatgg tggcgcattc ctgtagtccc   190740
agctactcgg gaggctgagt catgagaatt gcttgcacct gggaggtaga ggttgcactg   190800
agcctagatc gcgccagcct gggcaacaga acgagactct gtcttcatag atagatagat   190860
agatagatag atagatagat agatagatag atagatagat agatggatga tagatagata   190920
gatagataga tagatagata gatagataga tataaatgga aaagcaacag ttgtgcccaa   190980
tcttccacaa ataacttgca accaggcaga acatagaacc caggtctttt gatgccagtc   191040
acatccagct gtccttccaa gacattgttt ctatgcaggt gttgagtcag caggccagat   191100
aattcctccc aacgtttatc taaatacagg tgtttttct  aaaatgcagg aatgtgaatt   191160
tggatataac attcgtcttt gtgaggtgta agtttcttct tttaaaaaaa aatgcatctt   191220
tatttagtcc tgacatttca aaccaacaga atcagcatca gtatagtgaa aggttaaagt   191280
ccagctattg tcagtttcta catatgtcat attggccaat ttacttaact ttattatact   191340
tcatttcctc atttttaaaa tgagaaatgg agtgttatct ctttcactgg gtcattacag   191400
ggatgaaatg aaataacatg tggaaacatg ttataagctc taaagtggtg gaaagaagat   191460
aaaaataaag tagtaatgtc acatctgtga tcttacggtc tcctttccta tcccatattg   191520
tagaggataa gccacactga atgtccattc agtttacatc agacttgttt gggaaagtta   191580
cagtttgcgt gggtatatcc agatcattat gtttttacaa gcttcacagt ctgacctagc   191640
atgaaaatta agtacatgaa aagtatttca gagtcttgta gttaatggac aaacttagat   191700
atccctaata ggtgcttcta agcacttatc aaacttttc  ttacctctta ctcatctggt   191760
tccttcacta cactgtaaac acttacgaag gcaaggttat attttcatca tccctatatt   191820
```

```
cacagcatca gtctttaaaa tgttttgaaa tttatttgtt taattgataa gcaaaaatgt    191880
atgtatttat aatgcatatg atgttttgaa atatgtatac taaagaatat ttgaataaat    191940
atggtcttat tcaattttac tttggccata atcattttca ataaaaagta taaaattttt    192000
taaaagttga cgatgtatta cttaattgta atacataatg tatgtttaaa actaatccat    192060
tactaaaaat aattgactat tataagtaaa ataaccttaa gccgttgaaa gtttatttac    192120
tattgatcta ttaatttaca taattcttcc atgtctagca gagcccactg attataaagt    192180
aatttacaga tatcaacttt ctaggctgtg aaggcttctg aaattataag gaagagacag    192240
ttgtgccgaa attgtgtggt ataaagctgt caaaatttga aatatagtta tagatttcag    192300
aatataaatg gttgtcatca gaacaagatt acaagtttca tgggctctga aaaacttagc    192360
ttatttaaca ctgaatcaat gacttcacaa ccaaactgag ttaaaacact tcagattctg    192420
aaagaatgtg ctcattcaac ttacaaagca gaatttcaaa atatccagcg tgtttggcag    192480
gaggtgacac aacaggccat tttgaggaac attttgctta gcccagtttt tctcagattt    192540 aatattttc atattttgc cattttcaca cactgtctcc actaatattt tcctttaaat     192600
acattctttt taacatattt accataattg taaaattata ttactgttat atataaaaga    192660
taagcatcac ttattacaaa taaataggac aaaaactgca aaacaaaat aatggtatca     192720 ttgtctgttt ggattcagtt gaaagctctg agccttagtc ctacactgca actgtttttt    192780
tttcttttta aagagaaatt taccaagtgt ttataaatgt gttaaagcct tattagcacc    192840
aaacttagac tcctcttggt ataatcagat ggttgaagag atgtgaaaag agaataactt    192900
tctcaccacg tgattcagtg ctatgtgata ccatgctgtg tcatgtccta tctccaatta    192960
tttcacgtag cacttgaagc aaaactggag ttgcatatta agtgtttgga attttataag    193020
ttcaagtaca tgtgcactta caatatttac ttgttatgtg gaatgtatag gatttaaact    193080
gaaaagacaa acatgcagat tttttacacc taaagacaaa gcaggttga taactagtat     193140 ggatgacttt agaagaagaa agtcatatca gagcagaaag aatcttagag gccatctgtt    193200
ctaaaggtgg gcaaactgag acacaaaagt gttttctttt ttttgagata cagtttcgct    193260
ctgtcgccca ggctggagtg cagtggcaca atctcggctc actgcaacct ccgcctcctg    193320
ggttcaagtg attctcctgc ctcagcctcc caagtagctg ggactatagg catgtgccac    193380
cacgcctttg ttgtattttt agtagagatg gggtttcact gggttagcca ggttggtctt    193440
gatctcctga cctcatgatc cacctgcctc agcctcccaa agtgctggga ttacaggcat    193500
gagccaacgt acccggtccc caaaatgttt ttttattgat ggtcatagaa ctaagaagtg    193560
ccccaagcag aaatggaacc caattgttct tgatggtcca gttcacttca ccaagatgat    193620
cctgttccat ctgttcatgg tggaagcagt taatttcata tgattttata ctcttattat    193680
ttatatgaga gtaggaggtt ttttaaaaga taagtcctac tgaggaaaga aaatttcaaa    193740
tgaaccattg ataatggttt ggctgtgtgc ccacccagat ctcatcttga attgtagttc    193800
ccataatccc tatgtttcat aggagggacc aaatgggagg taattgaatc atggggtgg    193860 ttcccctcat gtggttctca tgatagtgag tgagttctca caagatctga tggttttatg    193920
agggcttttt cccccttac tcagctcttc tccttccagc tgccctgtgg agaaggtgcc     193980
tctcttcccc tttaccttcc tccatgattt taagtttcct gaggccttcc tagccatgag    194040
gaactgcaag tcaattaaac ctcttttctt tgtaaattac ccagtcttgg gtatttttc     194100 aaagcagcat gagaatggaa taatacacct gtgaacttta aacacatttt attgtaactt    194160
attgtaacag atcttagtaa ttgtttaaga agacaatgct agttgattac cctagacaag    194220
```

```
agaaagatat aggtccctca ttattgtctt taaggattct cctgtgcttc ctgaaaactt   194280
ggacacaagt aagtaataac ttttggcca tctttggaag gatttctttt tgttttgttt   194340
tgttttgctt tttagagat ggtgtctcac tctgttgcct agcctggagt accgtgttgc   194400
gatcgcagct cactgcagcc ttgacctccc aggctcaagt gatccaccca cctcagcctc   194460
ctgggtggct tgggactaca ggtgcacacc atcatgccca gctaattttt aaaaaaaaaa   194520
tttgtagaaa cacggtctcc ctatgttgct caggctggtc ttgaactcct gacctcaagg   194580
gatccttttg cctcagcctc ccaaagtgat aggattacag gcatgagcca ctgtgcccag   194640
ccagaaggat atcttttaa aagcattgtg tatcatctga cttttgtac aaatatattc   194700 tccagccttt tttttggtga gagggatgtt gctacttgat tctatttttt cattaggtac   194760
atacctttga tgggatattt gttctcattt gaattgcttt attctgtaac tgtttggctt   194820
ccatgctttt attttttaaa aaagcagtct cacttttgt ttttcttatt ccttctcctc   194880
ttattcttct ttgtcttctt catcaccacc accagagatc attgccttaa tgacgtttac   194940
tagggctttt catttccttc ccagtctcta aggtattttt ttggcaatgg gtgaaaagtc   195000
ctgacattct gattgctatt cgtattagtc cgttctcaca ctgctataaa gatattaccc   195060
aagcctgggt aatttataaa cgaaagaggt ttaattaact cacagttcca catggctggg   195120
gaggcctcag taaacttaca atcatggcag aacgcaaagg ggaagcaagc ttggaccttc   195180
tcacgtggct gctgcaggag agagaagaat gaggagcgaa ggggttctta ccttataaaa   195240
caatcagatc tcctgagagc tcactatcac aagaacagca cggggaaac cacccccatg   195300 atccaatcgc ctcccaccag gtcgctccct agacacttgg ggattatggg gattacagtt   195360
caagatgaga tttaggtggg gacacagcca aaccatttca ggacttaaca gttctatgtt   195420
attgacacct gcccagcact gtgaccactc atgcctcatg cactgaggag agaactgagg   195480
actttcaagg tctcttatag acaaatagag ttgtaactgc ttgtaaagca ctttgctaat   195540
acagagtgtg aagaaatgat aaatacgaat gattattatt gacagtggtg attggccatc   195600
atcatctctt catttctggc tatttctcat gcaaacgcta ttttagctta aatttttcaa   195660
ccttgaatcc aatgaatcta atcagaatga aggaaacaga cctatttcta gcaatgttaa   195720
acaaatgatg acttttgtgt tcaattagtt ggtttataga gactcatcca ttttaataa   195780 attgattttg tttattttt ctattttatt ttacatttga atgaagtggg tttactatat   195840
gactacaaat gcatttgtgt tctctcctac tcaagctagc ctcaatccta gaaagtatag   195900
tcctagttct gctgcaaact atgatgtata aaagagtat aaatattaa atattatact   195960 ttttagccaa gttaccaatt ctatcattct tatagcagca tagtttatac acaataataa   196020
atttttaaaa aaggatata aggcattgaa ctgtcttcat gccagatgag agataatggt   196080
ttaagtatga aaaaacagt tgaatcactt tcactatgtt gctatgtgat ttgagagaat   196140
ttctcagcaa ctcttttcc tctgtttctt catttctaaa atgcagagaa tacttaagcc   196200 aactttttg tatgtatgtg gaatacatgt aaaaaatact tgtacatgca aatataagct   196260
aatattccta ttactgttat tgttgggtgt gaaaatcacc actatacaat gccctgaatt   196320
acatgttgta tattccatca aatgcttacc gcaatccagg gctaagaaaa tgcacaatta   196380
tctatacaga gtgactagag tttaagactc caataagccc ttatcatgtt caaacaaaag   196440
tactgattta acattccagg ctttgatgtc agaagtaaat tacagagtag aatcatgctt   196500
ttttggtata agtaatggta tatttcagtc acaaaaatag tatttactct ttcacattga   196560
```

-continued

```
atgaggaata tgatatcaca gaggatcaat aaaaatactt tttatacttt ataagaagat  196620
aaaaattcta acataaatga ccacctcaag gcttagagga atttaggctg gatctaaaac  196680
caaactaaac tcttagcgta taaaaattcc agtaaaatcc atgattatgt tttataagat  196740
taatactaaa tttcacactt taaaaagtca tagtcaaaag aaatattatt caattattta  196800
ctaagtgcta gttaaatttc tgctatacac ttttatttgg aacttacgta agtcatatgt  196860
atgacatttt atttatttaa caaatactca ttatttacca cattttagtt ctcagatgct  196920
atatatgagt aaaacatgct tatatttacc gctacccata tcataccacc tcttaggcca  196980
agaattatct gaacatcttg ctggtcttgt tttttgcttg tttatactgc agatttctat  197040
ttagactgaa taatataaga ataagaagtg tttatgtatg aactggaaaa tgataagaaa  197100
acaaacagat aaagttattt gcaaatatat ttttccttt aagttttat aaacctttct  197160
aagtaataag gaccagaagc ttccacagca tcagttcatt attagcactg atatgaaatg  197220
gttttataac cttcagcaga atttaagggt ttctggtaag aatttcttct tactgcagaa  197280
caaattgcat ctcttatggt tactgtacat ttgcaattga tgagccatca gaaaaaatct  197340
tggaaaagtg atgcaaccgg taacttgtat tatttttttt ttaaatggag tgtttgaatt  197400
atttattgaa tctaggtcat gtgagtcact tccacttcac aaataagttg aaaaccctac  197460
agtgaagaaa taggtactta attagtgggt gaaggatttt tgaaataaga tgagacatcg  197520
agtttgtttc ttactcttaa tttgagccaa ttgtattaga gaaagactaa tgaaatcaaa  197580
aatgacaaag cccaatgtca aaaaaaaagt aagaaagcc ttaatagcca attaatacta  197640
gttcaggcat accacacaga acagagacca agggcttggg tgtgaggata agaatttcag  197700
agattcattc agtcctctag acatatattt tatgttttcca tcaatagcca ggtactatgc  197760
aagacactta gaatgtaatg gtgcaactga aagacatacg cctcgttctt acagagttta  197820
caaactggtt gaagaggcag atgataaaga gataaaccaa tcaataaata tttaacttaa  197880
ttaaaagag tactatgaag ggaggctctt tttttttttt tttttgagat ggagtctcgc  197940
tctgtcaccc aggctggagt ccagtggcgc gatctcggct cactgcaagc tccgcctccc  198000
gggttcacgc cattctcctg cctcagcctc ccgagtagct gggattacag gcgcccgcca  198060
ccacgcccctg ctaattttt gtattttttg tagagacggg gtttcgccgt gttagccagg  198120
atggtctcga tttcctgacc tcgtgatcca cccgcctcgg cctcccagag tgctgggatt  198180
acaggcgtga gccaccgcgc ccagccggga gacatgttta cgctgtgcta gagattaaga  198240
taaaaacat acttgaaggt taaaagaaaa agaaggatac cttcagaaag taatgtctaa  198300
tctgagtctt aaatgataaa aaggagatag catgcaaagg ccagcagaaa gcattccaga  198360
tgaaaattaa aaagcgcatg gtctctggga agagcttggt gtgtttgagg aattgaagtt  198420
taggcaacat atgctgacct ttggcagcaa cgaggggagt ggttttcaat acatttgaat  198480
gtataggatc caaatgataa aggaattta ggctacagta aggaatttcg aattgtttac  198540
agagaaatgt ggaataatta gggctacaga aggatagatt aataactctg gatgttttgc  198600
taaggactca atacagttgg gtgaagtgga agtagaacga ccagcaaata ggctattgcc  198660
atttgtccag gcagaaaggg atctatttt ccatctggtt ttaattattc cccttccctg  198720
tctccctcc tgcttctcct atctccccta aagatgcttt tcctgtttta aagacataac  198780
cccagctctc caataactta actgacttct aggtgtttca atctacccctt cgaggtgagt  198840
aggactgacc ccatactatg ttatcagact gttcagggtc aggataccttt tcttagcagt  198900
cacagtgagt aggaaatgct ccttgtaaac acaggaaaca gagccactga ggcagtcagc  198960
```

```
taacatctgc tagaaaatga gatttgagtt acaagataaa gttcaaacac caattttacc    199020
taacagcgat gttggtacta aaatcttata aagcttacaa tctgaaatgc acctgtccca    199080
ctgatactct ttgtgatgtt cattaaaaaa actaggtgga atattgaagt taatatcttt    199140
aagtgaatgt gtataaacat tgtgatagaa aaaataaaa atttataaat aacttctaaa    199200 tttttgtgtct aagcatcccc tgtgccacct gtatacataa ctccctgttt tcctgttgac   199260
cattgtttaa taacctgctc tctggatagt tttaggtttt tacagtttca catatggtcc    199320
catctgctgg caattcaact cctattcaac caagaagcaa tcgaactaag acctgaaagg    199380
aagaatacag ctggaggcct tgaatgcagc tccactggga ctgaatttat atagggtaca    199440
gagggctact actgagtttg tgcagagaag tgccatttaa gatactgtta aaggaaggca    199500
aacagaggga agatttgttt attaaatgcc tactctatac caggaactct acataaatag    199560
tctcatttat tcttattagt tctggtatta tcctcctttt atgaaaaaag gtaactgaat    199620
ctcagcttgc ttgtctaagt tgacataata aatggctgtg cttatttagt tctatggcag    199680
tcataaatag aatcaagatt aatataaaag gattgattgt cttgccttta aaagtccgtc    199740
gtctgcccct aatgaatact ttacctactt tagtttactg aacctgccaa accgggaagt    199800
tataaaatac aagcaagcct tgtcatacag tttttgagtc agaaaatata ttcatgtcac    199860
ctagtatcat tatagctttc tatcacttat gatggcaaaa ataagtatat ctgattctaa    199920
taagaatatg aagaatcaaa aaatggaaa aatattgaag ggaaaagac gtaattctac     199980 cagaaaaatc acgacaaaac atctaacaaa ataacatatt taataataa agaaccccctt    200040 ttttaaaaag cagattgatg atgattatat ctataattat gtcaggggag gcataaaata    200100
ggcatatttg tagagctgtg attagtataa acagggctgg gtatgagctg agtcatctcc    200160
ttgccactgt attaaaacta caaaataata attccaagtt taatacttta aaatgattta    200220
ttaactaggt ttcataatca ccaaaggtaa cttatttcca tgttaaacta ctctttattc    200280
agaaagttgt ctttaatatt taaactaagt tgtaactatt gtagttcaag cccaatccac    200340
tcagctccaa gtgtctagtg ggaatcacag ttcccttctc tcatttgtag tatctctttc    200400
ctaggtgtaa atagttactc tgcttctctg ttatctttcc ttctgtctga gcatgcctgg    200460
ttcccttaat gtttccttat agatctcatt ttccagggct tttatcattt ttgttgctct    200520
cttctgaact gatttaaact tatctatgat tcttttttcaa ctgaggaaca aacactaaac    200580
acagttatcc aattgaggcc taaagtgtgc ttgtagaaca aaataattac ctctcatttt    200640
atccacgttc tccctattaa tataccccaa agcagtgtct gggattttat atgacaccat    200700
tgtattgttg acttattgtc aatttatctt tcattatagc ttatatctcc atccccgtgg    200760
aacaattgtt tgtgcggttt atatttgttt ttattgaatc ctattttatt gatttcagcc    200820
ccacattcta tttatcaaga tggttgtttg taatactaac ctctaatttg cctccaacag    200880
tacatgatcc ccaagttctt aactgtgtaa atgattagca tactttctgt tttatctcac    200940
caaatctctg agtacacagc tgaatgtggg gtttgttttt gttcgttttt gtttttttga    201000
ctaacaaaaa aagttgtgat agaatttaaa atatttcccc ttactgctta tagtgctaac    201060
ctcaaaagct atgatttttgg gtgcccatga tattgctgag actgtttgcc atcatattaa    201120
tcctttaaca atattcctga ggtctgatta acccaatctt acagagaaaa agactctaag    201180
ggccatagat gtccagtaac tttctcagca cgtaactagg aaggagagga gctggaactt    201240
gaacttggtc tgtttggtct taccaccaag tactttccag tacacctgta aataattcaa    201300
```

```
ttcaattcac aactaacagc ttgttatatt aataagtttc tcacccattc tgctattact   201360
ggacaggatt ttatgaaaac catgacagtg ttttcactcc agggagtctt cttttagaaa   201420
gatgttgtgg gtgctatgaa tgatgaggcc attgttcctg ggcacagaga tgattccagt   201480
gacaaaatta ctgtttacta tgtgaaagcc atggtatctg aaagcctaac aaatagagtt   201540
gatcataggt tgttcccgct ccttttgcta tattaaaaaa ccattccaac taaggcaata   201600
tgataattaa cttgacttct atttgtttct ttgtatcaaa gtgattgaat ccaaacacta   201660
tccatccaaa tcactggcct aagtcaatgg ttgctaaatg aggtgctaag actctgctga   201720
gtattttaaa agttcctaaa ggatgctgta gattttagta tactagaatg taaaaagtac   201780
aatgcatgtt taattaagac tttatgagct gactgtgtga cttgcccaca tcagcaactt   201840
agccctgatc tcttgaaatc caagtgcat atatactcac ttagctggtg attgctgaat   201900
tcagctgctt catggattgc atacagcagg tctgttttgc aaaatgggct tgttcataag   201960
gttaatattt gcattagtcc attttcacgc tgctgataaa gacatacctg agactgggaa   202020
atttataaag aaaaagaggt ttaatggact cacagttcca cttggctggg gaggcctcac   202080
aatcatggca gaaggtgaaa ggcacatctt acatagtggc aggcaagaga gaatgacagc   202140
caagcaaaac aggaaatccc ttttcaagcc atcagatctg gtgagactta ttgtctacca   202200
ggagaacagt atgggggaaa ccaccccat gattcaatta tctcccatgg ggtccctccc   202260
acaacacgtg ggaattatgg gagctacata caattcaaga tgagatttgg gtggagaaac   202320
agccaaacca tatcaatatt aatatgccta tttcttaatg taaaacaaat tgtaaggac   202380
aagaacaaat aatggatgat gctaataaca tcttattaaa attggagagt ttaggtaatt   202440
taaaataatt atcaagaata catgggtttg ctgttctagg atagttgcct agtaatgagt   202500
ttcccttagt atctgcaagt attttatcct ttccttaaat gcattaaaat gtgtcaaaca   202560
gtttggtttt caatagacag aggagaaaat tatctactaa atttaactac tttctggcag   202620
atcaattaag aagatattaa gttctgagtt cagattttgt taaagtgtg cattagttga   202680
tggtgaaata taaagacact gagttcaaga tcactaacaa ggagcttgag aagtagaaga   202740
aggctgaaga gtataatcat atatcatgca gatgttggct agcttagggg tactgtccag   202800
gaagaggaat tctctgctgg tactggagcc tcatcccttg attgcctagg tgcaaggttt   202860
gggcatatac atccttcgtg tctgagaaga tgttactcct caaagacttg ggagtagttt   202920
acacataaat gagaggatta aaaaggcac aatagagggg aaataatttt cctcttattt   202980
atttttctgaa tacctcccta cctatttcct tcttgttata tgaggtttat tctcttcagt   203040
aataaacaat ttaaaaaaaa acactcaaag cagatattgt aaattcacag tattaatgtt   203100
tttaatttat attaaaacat acaaaatag gtttctaata ggtagactaa tattcttcct   203160
ggcttaaaaa ttgttcctca tttaataatg tttgatcaca ctgagattat actttatttt   203220
tctgtttgca tcatctcttt cttagttta tctttccttc atacctttct cttacatcag   203280
atttttcatc ttagtctttc aggaatttgt ttgtttattt gcagtttgta caagagaaca   203340
cattagaaaa cgtagggctc agaacccact acccgaaagt atgatacttt ggcatgctga   203400
gtattttaaa ctgaaggaga ctggaagacc tcagaagtga ggtctttctg atcttctcca   203460
atcatgtctc ctacctctct ctctccctgg aagtgaaaca tagaaatcag tatttctttt   203520
ctccaaggct ggttacagaa gctagaactc atcttcccca aagcatggca taaaacctag   203580
aaaggtaact ctctcccttt tcccttgaag accctcattg caggtggtca gtgcctcata   203640
cccagaagga agaagtgcta cagagaggcc agaaagaatc tgatcagacg ggcctagctg   203700
```

```
ggttcaccct cttagtttat taccattaga tatacccttt tatctaatca catttctaca  203760
tagctgtcca ttcttcatag aatctaagca taaatgtgga cagttttccc tggaatttgg  203820
gtcttcattt ctaaaggctc tagtgagaca taaaattttg attaataaat ttgttgtgct  203880 ttttgttgt taaactgtgt ttggtttatg agagtgttgg atgaggaaca ttcacccact  203940
tacgatgggt gagaaaaagt atcacacgtt tctgccctg caggaccaaa gttgttacaa  204000 atatatttt aaatcttaaa aacggaatag attaatccag gaaatatcta ttgctaatgc  204060
caaaaatggt tcctttggca ccgtgcatgt aattgtgtgc cagaacctga tgaaagagaa  204120
gtgattgtta agagaaggaa gaaggactaa tcagaattga gttaaatact gggaaagata  204180
gaagtcaaga gatgctcgtc taataaaatg agcaaagcag ttgcatccag gtagccccag  204240
ttagagttat attttcatga gaagttagaa gagtcagact aaggatacag ttagacttgc  204300
ccacatttaa ggtctgtttg gttaatgagt tagatttgtt gactcctccc ttttcaattg  204360
ttttcaaaag aaagtggtta aaatatata gtctgcaaaa atgaagtatt tgttccaact  204420 gaaaaaact aaagcaaata attcagcttt ttgttctatg tatccacatg cacacaaaca  204480
cacacatatt aaacacacaa aaagtgagaa atttagtttt cagaattgca gaaatgccta  204540
ataggaataa cattctaagg accaggaagg cgcaggatct attaagttaa aaacactaac  204600
aataaaaaaa tatataaaaa ggaaacaaaa actaaaacac ctcagctact tcattttgag  204660
tcttatggag gaaacaaca aacaaaatta atatttaaag ttaaattaa aatttccaaa  204720 atacattctt tgggatgttt tcagcaaaca atgtaaaaaa ataagcttat ttccaaatac  204780
aaacttattt atcatctaat tctattcaat ggcaaattgg tgttactgtt ttattcggtt  204840
tcactgagat tttcaagcgt gtttagaatt gaaagtgtt ttctgtctct taagtgtgat  204900
gacaaaacat taactgatca ttttttattct gttgacaaga caatctactt catggattta  204960
taaattgctc caaggcaaag ataatcatgt aattttctta tcacagccaa tgttaataat  205020
ttattattaa cattatttt aatttgaata caagtggaag gcatcccaaa gaagggaata  205080
ttgtataata ttcagaaaaa aatcttaact tcataaaaag tgaaaagtca ctattctgtc  205140
tttggatttt tttttttttt ttttgagct aaagaaagat tcaacagagc atttgctagc  205200
tcatattcag ttcctttgct ttccatttca attaaagatt tattttctat ttgtcaagtt  205260
ttaagaaaaa ttaactggca gtatgttgat gaaatgtgtt tcactaatca tctactctca  205320
gaaacagtgg aaaattttct ttaataggtg atttattttg gtgataccaa ctttattcta  205380
attttgaagc taactggaca ctccacttat gtattgacat gtttaactaa ttacatcaaa  205440
tcacgctatg caagaaaatt aatacacatt ccattagtag gaatgaatac ttacttaaag  205500
atcaggcctg gccaccttac aactccaaaa gtttgggaag tacacaagat aaaattgata  205560 tcttttttt aagaaagga atgtcaacag ataaaaacag atcaagtagg taccagaata  205620
tcatcaaaat gtcacttagc aaaaatctag tttcattggg aatattcaat attgtacaaa  205680
tcttcaaata aaagataatt gctaatcata cagtgactta tgaaaacatt tgttacagga  205740
ttcaatctaa acagatttta ttatatctat atctgacaga tatagtaatg ttaataagag  205800
ccaactgttg gaaattgtac tggatattac aatattgtta cacagaaatg gttattgaac  205860
aatattcgtt aaaatgggag tttatactag ttgcaattaa ctcccaccat tggaaatgca  205920
tatttatttt aaaatatccc aaaaatacac acacaaaaac cttaatgcat acataaataa  205980
atcttacttc ttagatattt gaatcatttt aattagcctt acttttgaga atatttcatt  206040
```

```
ttgaggccag agaattgaag tttgtcctta acattaatct aactgctact taagtgattc   206100
tcatttagac tgtagctctt tcaatacaaa ggcctaactc cttttaaagt tctttcctag   206160
atctccttcc ctgaataaca taaataatgt tgagtatttg ttgaattgta tctaacaaat   206220
atctggaatc acaccatctt ccatttataa tgagaagtta ggtctgtcag ataaaaaaca   206280
taatttatg ctaaaacagc aacaaaataa tgtattttga catttatttc agcatatacc   206340
agctgtgttt ttttgagaca catacaaatg tcctccaaaa tcgccattta taaatccagg   206400
tttttaaacg aaaatatttt ttcttatgaa aggcatttgt aaatctcaag gaaagataaa   206460
atgtactcta gtctttgaca acttggtttg ttgttattgg tagcctatgg ttagtttgta   206520
cttactagag tcccttaacg ttggatatca ggaacggata ctcttattca ggaggaattg   206580
tctggtacaa atggccaact gtgtatcttt agctgtcaac acaaacact ggcaaagcat    206640
gtgatatagc aaagcatgaa tatcccagta gatatggtta tttatgtttc tagaaataac   206700
caaaaccaga caatgagcgc ctgcatttgt agacctaaat gggaatttgc ttccttatca   206760
ggcgtagtga taaaaagtc ctgttgtttt gtgggtgtct tgaatactgc ctgagactgg    206820
aatttgatag tgggcacatt acacctctat aatcatttcc gacatccagc tatgcctctc   206880
tgtgaaataa accacaaaaa ttgggcactt ttctgaagac aataatagta gctgagtttt   206940
ctacaaaatc agaacatatt tagttttttc agtaaaaagc ataacagata taaggcttgc   207000
tttgaaaata aagcgttcca ccagtagaag aaatagatag ctatcttgtg cacccaaaat   207060
agaattctgt acaccttcct tggaacatag atgagactac tttaaagatg atggcccagt   207120
ggaacttagc agttgatagg ctaggaccaa ctgctgagtt ggtttaactg gcacaaacat   207180
tggcatagaa agagcacact actatgtatt aaatcaataa agcaaggtag caaagaaatc   207240
aggtccatcc ataaatgttc actctttgta gaatagtgtc atataagttc ctcggtggac   207300
ttgaggtgtt tgaggtctgg gaagcatccc taatccttct cctgcaatct ccaccctcca   207360
tgcagcacca aatcacaggt gaccctggag tctggcaact tctctccata tgacctgcca   207420
atatcttagt cgaagatact gtcatctctt gcctacgata gtcttctttt tggtctcctt   207480
ttgtctactg ggctcaatct aattcatctt gtccactaaa tcagaagata ttttaaatca   207540
caaacgaaat gattactcct tcatcctacc accaccacac ccttaaatca ttcaatggct   207600
ttccattagt cttatgataa agactaaaat cttttggagga gccttggtgg tactttatag   207660
tctgactctg cctctctctt cattcttatc ttaacccaca taccctctgg ctctcaggat   207720
ggcaggaatg ccaggcatct ttctgtgaca gaaatgtccc acattgtcca tgctgtttcc   207780
cctgcttaga atgcttcctg cccacctcct ttccctagcg aagtcctgtt cattagcatt   207840
tgatcattca tttccttagg gaaatctttc ccaacctcca tattatgtac cgtgctatga   207900
attcttacag tactacattg ccctcttttt gaaagcatgt aactccattt gaaataatga   207960
attcattagt gtgattattt aattaatgtc tgctttcctc ttggactaca cttttcatga   208020
tagaaggaat gtggctattt ttgcccagta ctctgtcctt gggacaaggc agaaagtctg   208080
tcacctagca ctagctccag aaatacagtt gttggatgaa tggaagaatt aacgaatgag   208140
actctgggtc tctttcacag aagtgaggat gaacagtgag caaactatac acagattttt   208200
gcctatcttt ttagcctgta tcagtgtttt aagtagtttg ctggggttac ctatttaatt   208260
tgaatacatt aatatttatg aggtaaaatat aataagtatc tctattaatc taaactgagt   208320
ataccgaact cttgattttt ttcctctcac tattaccttt tagaaggtca gctggtctaa   208380
ccaactaagc tcatttacta tagccgatat ctactatctt gagaaagatg tggatatttc   208440
```

```
taatgcacat ccaatcactt gctggtggta taatgatttt tgtgtttata tatctctcct 208500
aattccaaaa tgcctgtata tttattgtgt cattatctga aaatatccag tgtggtagat 208560
gtgtatgggt attatcccca ttttactgct ggagaaaagg taaaacattt tggagggcag 208620
cttgtcatat gatacactgt tgttttttgt ggggttttttg tttgtttctc cctaccatgc 208680
aatccaacaa tgaactcaca aaggttgctg tacaacagaa catttgccta ggatatcatc 208740
acctagcttt ataggaatgt gaagaagttg aagaattaag gtaataggaa gcagaactat 208800
ctgcgctttt tggtagctta ggaaagtaac caaggagctg acttactgtt aaatgaaaga 208860
aagccaagct gtagcaatgt gagtcaaagt tctgagctag gggatcccag gaaatagagg 208920
ccagtattgg gaaaatatag taagggcaca tcaattgttg attctaagtg tttaaaattc 208980
attctgccat attactaagc tctttttttct ttcaaggaag agtcttatca gtagaaatat 209040
tagccatgcc ttcatagtcc ttatatctta ctaatgtgca tctatttgct atctactgtt 209100
gacaaaaaat gccaaacctg gtaaaacatt taaacaagtt tattctgagc ctcatatttg 209160
agtgaccatg gctcatgaca cagcctaggg aggtcctgag aacatgtgcc caggtggttg 209220
ggttacagct tggttttaca catttttagag agacacaagt tacaggcaaa gacataagtc 209280
aatatgtata tgtatatatt ggttcagccc agaatggcag aatacctaga agctgggggt 209340
ggtgggaagg agcttccagg tcataggtgg cttcaaagat ttcctgattg gcaattggta 209400
gaaagagtta tgctttgcag gaagagttga agtcatcata aagaaatgct tgagttaaaa 209460
tacgggtgat tgtgaaagcc aaggttcttg ttatatagaa gaagcctcta attaacaggc 209520
tttacagata atagatggta aatgtctctt acctgacctt aaaagatgtc agactctctg 209580
gaaaagacct accaaggaaa ggaaagttta ctatgtgtca ggatgtccta gttagtttat 209640
tttattgaat tctcattaac aacaacaaaa tgaagaagaa agcagaagtg aagcttttga 209700
agcttaagct gccaggtcct tgcttgtact gcctccttca caaccccaaa cccccacatt 209760
tccccaagag atggctttgc agggccattt caaaatctgt caaagaaaat atattttaag 209820
gtaaaatact ttgatttcct tcagggcctg cttttccgtca tgtgatgcta taccagagtc 209880
aggttagagc tgagtatctt atcactacaa agaatctgtt ttgtctctta tgatctctat 209940
tttaatgtta aatctggtca gttgtgccca aactccaaaa ggaggagaat agagtgaggc 210000
aggtccattg ccccccttca catcatggcc tgaaccagtt tttcatgttt ctttgggatc 210060
cccttggcca agatgggttc tttcagttga ctgggggta ttagaatctt atatttggtt 210120
cacactgcca tgcaatgtaa tggttaaaat cataatttct agggttacat gatcagggtc 210180 cagaacatttt cttcatctgt tcctagttct tgttaacttg aattcaatgt ttcagttttct 210240 tcatctgtaa aacagggatt ctaagtatag tttcaggaat gaattcatgt tttatagagt 210300
ctgaagatta gattgcataa tagggaaggg tgtctctttta ttaaaaaata aaataaata 210360 aaaaaataag catacataca gccaggcgtg gtggctcacg cctgtaatcc cagcactttg 210420
ggaggccgag gtgggtggat cacgaggtca ggagatcgag gccatcctgg ctaacacagt 210480
gaaaccccgt ctctactaaa aatacaaaaa attagccggg cgtggtggtg ggtgcctgta 210540
gtcccagcta ctcgggaggc tgaggcagaa gaacggcgtg aacccgggag gcagagcttg 210600
cagtgagctg aggtcgcgcc actgcactcc agcctgggca acagagagag actccgtcta 210660
aaaaaaaaaa aaaaaaaaag catacataca aagtgcccac aggcgcacag ctcagaaacc 210720
tctctttctg gggtttggaa ggaggctgtc caagcaagga cctggcagct taagcttcaa 210780
```

```
aagcttcact tttgctttct tcttcatttt gttgttgtta atgagaattc aataaaataa    210840
actatgcagc acatcctgac acacagtaaa cacttctaag tacgagtctt catcctcatt    210900
attactttta ctataacata caaatgctta aagagtaaat aatttctatt tttgattcat    210960
aaaatttttaa ttttattctt ttgaggctac ctgctggaga gaactaaagt tattagtgaa    211020
agagtggtgc atgttaagga atgagcttct ttgttctttt gtttacagaa caaagtatat    211080
caagcagcta ctatgctcca ggcaaggaat agggagggga gggacataca aatgaaaaat    211140
tcaaaacaaa tttaaagatg cataataaca aatgtgtgtg agtgccatgg agctaataag    211200
aggatgctag tatagagaat aatggggaga gacactaatt ggcccagatg cagagagaca    211260
ctaattggct cagatagtaa agggagacct ggctggagga gataatcatt aagtgggaat    211320
ttgaatatta taacagatcc tgtaatcacc tgaccactgc acagacaaaa tcagttcact    211380
gagactgtgg tactgcagta aagaaagagt ttaattaatg cgaggcttgc catgtgagag    211440
aactggagtt atcactcaaa tcagtctccc caaaggctga gagcttaggg tttctcaaga    211500
gcagtgggct agagaatggg tgttgctgat tggttgggga tgaaatcata ggtgtgtgga    211560
aaacatccct catgcattga gtctgcctct ggatgagggg gcacaggacc agttgagtca    211620
tgagtcacaa gtcctgttgg catcagttgg ttgccagaaa gcctaaaaaa aaaaatctca    211680
aaaggctaat cttaggttcc ataataatga tattatctgt gggagcattt agggaagtca    211740
caaatcttgt gatctttggc cacatgactc caaagcagta aggtattatg cctacatctt    211800
agcagaattc aggcccctcc aattctccaa ttatcttaat ctcatggcct ttcattcgtt    211860
ttcagtccct gagcaaggag ggttttagtt ttagggagaa actattatta tccttgcttc    211920
catgttacac tatcaactaa attcctccca tagttagctt agcttatgcc taggaagaag    211980
caaagcccag ccagcctctg aggatggaag ccacatggag tctgctgtgt tcaattcctc    212040
tcactgctat tatctttgca aaagcagttt caatgccctg aagagacgct gggaatagca    212100
ttccagacca aaaaaaagtc atgtgtgaag gctctactag aaagaacatg acacattcta    212160
ggaatctagg caccataaat aggccacatg ttacaagaat gatatgagag ccagtgacta    212220
attgatcata aatgctttag tgagataaat tcctaaagga acaaataaca gattttgatg    212280
gagtcaaaca cctaaagctt ggatttgctg ctggaaaaac atcttcctct atattactat    212340
gagctcttag catagaattg ccttacttta cctcttctgc tggcttatgg aagcaagctt    212400
ggaaaagtcc agggcctagt gtgctaatct cttcttctgtct cagacagaca tattaaaatg    212460
aactagatta agtaatacct aatgagcacc cttaagtgta aaataatagt tgctttaaaa    212520
taatttttaa aaaataaact atattgtcaa cattaaatta agggcagaaa atgtattaa    212580
agttctaaaa ctacagaatg aataattgaa atattctaac ctagaagagt aaaaaattgg    212640
tgaatgtcat taaaggtttc taacagaaga tccacttagg aagagaagtg ggatacaaat    212700
tgctagtaag aaaagggaga gggggaatag aatatacgta tgtttaaaac ttccaacatc    212760
ctttttcctag cccctgatct atgcaaaatg aagtcttact aagtctcaaa acagtattct    212820
ttacatttca ttttctttct ttttcaatca ttgttttga gaaaatccta aaccaaagca    212880
aaaaagagag aatctgccag tgaagcagct gaagtttcag gaataacta aaccatccca    212940
tgctcacccc aaaaagtatt catttgactc ttttttttc tttttttttt ttttgtaaga    213000
caggtcttgc tctgtcacca aggctagagt ttggtggcaa gatcatactt cactgtaacc    213060
tggaacttct gggcccaggt gatactcctg cctcagcctc ctgagtacct aggactatag    213120
gctcatgcca ctgcaccagg aattttatt atttatttat ttttattttt ttagagatgt    213180
```

```
ggtcttccta tcttgctcac gctggtctca aactcctagc ctcaagcaat cctcccacct 213240
tggcctcagc ctcccaacat gttgggatta caggtgtgag ctataccact cctggcccct 213300
aggagctaat ttcatcttga tgtgaagagt aaagttgcta tgtatttttg tggaggcagc 213360
cagttaatgc ttgttaaaca acaacaaca acaacaacaa aaacaatat atacaaaggc 213420
acctacagaa aatctcattt cagacatccc tatcaatata aatagtatca ccatggcaag 213480
caagtgcatt gttcatgtgt gtcccagtgt tactttgatg atctattaaa tcatcaagta 213540
tatttttgtg ccatatgaaa aatacacatc tttcctgtta actcttgcat tcgatcaatt 213600
gtaagattta cccaaaaggg tctaactgtc cacaaaattg tccctgcctt ttatcatttt 213660
tgctttcttt cagggttcat tcttccaagt tgttaaaggg tgtcagttag attgcaacag 213720
aggttgcaac tctcattaat ccaggaatca cataaaagta ttctcaattt ctaccactgc 213780
ctccagttag aagcctttct gactattgat gcctgtaact atgtaaatgt gcgtgattta 213840
ggggaattgc taacctggcc atatctatca ggctgacttg agaaagggca ctggagctat 213900
ctcaataatg gcatggtctg gctttaagga ttaaggttac tattttttctg gggaagattt 213960
ctccctaatg atacaattca aagtgaaatt ctacttgttt cttcatttaa aatgagacta 214020
gagtctgtct tttcatctct catatagata tagatataga tatagatata tataaaacag 214080
ttcttcaata gatactgagt taaactacat acattcctat ctatcatcat tcctaggatg 214140
agaacaacag tgaaatggat acttatatct ctgcatgatc tgttttgacc atgaaaacat 214200
ggccacctac acaaaccatt tggttcttaa tgagccataa tatctgtact gggtaaatga 214260
acacaaaaat agtggtttag aaacaagcat ttcaaacagt tgtgtttgta ttgcctaaga 214320
gcctcacagg gcctgtagag tttattatga acatgtcata ggtcttacac tgggatgagg 214380
cttttgtgtt tttttttttt tttttttttt gttttttttt ttggtgcacg tttgaacaac 214440
aaatggcatc ttcacaagtc tcaaaagctt ttatgggcat ttcaggtcct aacattttca 214500
catacgttgg tttgactgct ggacagtaat gtcttatgct aaattagtaa gggacaaatt 214560
tcaatagata tttcatatta tttttctgaa aattgtaaat tcataaacat tattttctgg 214620
acttttcttt ttcctcccctg tggtcatcac ctaccattta tctgattatg actcaaaagg 214680
aaacatgtgt gttgatttag actgcttcaa cattccagtt ccaatctgaa gctatctatc 214740
ttcccaaatg gaatgttatg cagacctctt gtcctccctc ctgcttgttg tggcagagat 214800
ttatacttgt aatttcccag aacatttgaa ttagagatgt gagccccgat gccaactgtc 214860
tacaggttga agttataaag gtaaaaactt ggtccagcaa atcttcctct cctttcactc 214920
caggattcac ttttcttagt gcccaagtaa tatttatgag gctcttgtta tttagctgtt 214980
gtattatatt tatgttaaat acatttctaa caaattctac tgcatttaca tttattattc 215040
aacaagacat cacaatatga tagcagataa tgatgaatct ccagataatt cttaccgcta 215100
agtcttcagt tgtctaaagt cacacacaca cacatacaca catacacata cacacatatg 215160
cacacacaca gagtcagagt ttggattacc aaatgagaaa taattcctta gtgtgtgcag 215220
tacttttgc tctcaaatgt ttcttttctt cacacatact tatttgaccc attcagctaa 215280
aagcaacatg catcttacta attctataaa tgtgtatact agagttctta ccttttgaa 215340
agattaatta atacagtcat ggctaattat ctgtaactgg ttatatgagc aaggccatta 215400
tacacagtga acattataaa gataatcatt tttctttagc ctctcagcac aggtcaggat 215460
aaaaccgtaa tatccttcat aaataggaac actggccatc actggagagt aaaatgacca 215520
```

```
ctggtccagt ctggtaaata ttcgttcatg gttatgctct taaaaagtgt ttaggaaata   215580
agagagaaaa aaataggaaa aaaattacaa aaaaaaaaaa acccaaacac atatagactt   215640
gaagagttgc tctcagatca aaatatcctg caataatctg aagtagaaaa gtatcattat   215700
gacctaagaa ggttcatgaa aatgtttctc atcatagtag ctcagaagga ctgatttaga   215760
atgttgccca tggatttctg tttgcttgcc tgtgtaaata aatacatgta tagatggggg   215820
agaaatttga ttttaacaca tagccttagt gttcaacttt aagttacata agatgggtct   215880
ggggacatta tctaaatttt ggatttctga aaaatatgta ggtctggctc tgaaatctga   215940
gttttaatcc atattctaaa aatttgcaaa ctaaagcttc ctctttttc ttcacagagg   216000 cttaggcaca tcatgttgaa gggagcaatt tgggaaggta ggcaaagcta taatcaatca   216060
accaaggctg ctgaaagtcg gggtgaataa atactcaacg atcagtctat ctaatgtaca   216120
tcaaccctaa cttattataa aagatcgtta aacctttgaa aggtcaatgt atatactgct   216180
atctatcaca ggcgggcacc attcattatg tcctgtcagt ggctctccac tggccaaccc   216240
ttcaaggtgt caagccgaga cgctcagagg ccatgtggtc atgagggccc aagcttcctc   216300
cccaaatata gttttatttt tccatctcat tctattgcct tgccttttt ctactttggt   216360 ttctcttcct gcttccctca atttggaagt ctctcatttc cccatgaacc acagacattc   216420
ttcattaacc aagttaaggg ccatgccttt tgggggtta ttctttagct attcatgcct   216480
ctgctttgtg aattccattt caaccaattt ttgttttcat ttttataaat ggtattgttg   216540
ttgttgtttt gtttcctctc cgctacgtcc tttcagccat gaaagatgca tcttctactt   216600
ttatattccc ctcaatatca tatatagcaa atgctttata aaaattataa taaagcatat   216660
tttaggtttt tttgtttgag gttgcttttt ttttttttt ttgacagagt ctcactgtgt   216720
tgcccaggct ggagtacaat gctgccatct cggttcactg caacctccat ctcccaggtt   216780
caagcaattc tcatgcccca gcctctggag tagatgggat tacaggcaca caccaccaag   216840
ttcagctaat tttttgtat tttagtaga gatagggttt caccatgttg ggcaggctgg   216900
tctcgaactc ctgacctcaa atgccttggc ctcctaaagt gccaggatta caggcctgag   216960
ccaccacacc tgaccataaa gcaggtttct taaacagcaa tctgtagacc agccttatag   217020
gaattatctg aagtgtgtgt gcagtatgca catttctggg ccacacccta gacttgctga   217080
acaagaaact atatttttaa gctagaaggg agacacatat atgccctgaa gtttgaaatc   217140
aattgaccta gaaacatagt ttccctaagc agtccaagca taagaatcat ttgaggcagc   217200
tgtaaaaact acacattcca gatctccgtc agatcttcag aaggaaaatc cctagagcag   217260
taacatggga atgagccttt ttcaccccac tctggctcac tagatcattc taaccatgag   217320
gcaaggtgat gaaactttct ctaaactatt agtagtgctt ttccaaatgg ataaaagcac   217380
attttgcaga ataatgtaat ataattattt tctcaacatt ttgccttaat tataatcagt   217440
ttcataattt aaagcattca tagtttgaga aatgtaagcc aaagaataat gcatttgttt   217500
tctaaattat tatcccctga ttgagttagt agccttgtag ataaactgca atagcataaa   217560
aataacaaaa tttgcagctg ccaaaattta tcctacctt gacatttatg gactggtggg   217620
tgtgagaaag ttatcaaatc cctaggaaat tcagtttcct cttaaaaaa aatgggggac   217680 catgatacct aacttgcaag aaaatagatg tagcacacta caatgtgagc cacaatgctt   217740
tatttattca aaactctaaa attccagcaa actgagggaa agtgtgaaag gttcatgggg   217800
ctggccgtaa gagccttcgt gtacctcttg gttcctctgt gccagcaaac agaagacttc   217860
tcttcacaag accacttggt agcctatgtg gattgactct gcattacaga tctctgactt   217920
```

```
ccatactggt tgtggctgc aatagaggac tcttcacgtc tttctaaccc tcctcaattg 217980
tagaaacatg gaacagcaac attcttaaat gctcatgtac ctttattaaa gtattatatt 218040
tgcagtgatc atttaataag tagataggct gaatatttta taatcttttc tgagccaatt 218100
gtttgtgtgt gttttgctga aaatgacctt tttaaaaaat agccataatg tttatagagc 218160
ataaaataat aaaagggaaa tgaaaaccac ccaatgaaaa tcactattgc tgctttcaaa 218220
tacatgtttc attttttttcc tagaaatatg tattttttgtc ttttttttaaa tggaaagata 218280
ttacatagtg atcttttccct aatgttatat catgtgcatt tctacattca ttcaaatagt 218340
ctttgaaaaa tgatggctaa taaatactta acatttctta ctgtaacagt tgcgtgattt 218400
gtttaagtgc tcttctatta ttggacattt tgttttcttc tgttttacta ttataaggag 218460
ttttaaaatg ctctcccaac agaaaacctt gattgcatct ttaattaccct tcttagaagt 218520
catttctaga agtgatatca ctaggtcaaa aggaggaatg tttcttaaag ctcatgatat 218580
atatctcgca attacttctc agaaatgttg ctaatttaaa ctctatcatt ttccctccta 218640
cccaagaagg aatttcatta tatccaatat caaagcatta ataaattttt aggttattgt 218700
ttaataaccc ctaaagaaaa tttcatgctt taatttgtat gttttttcatt aatattaagt 218760
ttgctctttt gtcatttact ttgtttctgt gttttctcct tgtcccctttt ttataataaa 218820
aagccagtgt tttctcagtg atttgtaatc acactgttta tttggagagt aaatccctag 218880
ctatattagt tgaacatgtt tttcctaggc tgaaatttgc cttttaaattt atttagttaa 218940
aatattaata tttattttga tagacatatt ttttcttctt ctgaacatct tttaaacatt 219000
ttattataaa cattttttaaa cattcataaa agttgcaaga attgtacagt gaacacctga 219060
tatttaggac ttctattctt taaaaaatat tttttatcattt tctttataat atagctaatc 219120
atctactgga aattttttata cttgcttata gtcaattatt tttccttaat cccacttctc 219180
tgaatttaat caaaagaaat atttgctaaa gtataagttt cattccaagt aagttcttca 219240
tctgccttgc cttccgatgt accccactat ctggaacagg acctatcgca ttgtaacact 219300
cactaaataa ttgttgattg aatgactttt ctcaatgagg ggaaatttttt cctgctctag 219360
gagaataaag atgactcttt aatatgttga ggcctcaaga ctttaaaatc tactcggtac 219420
aaagaagcat agcatactct agaaccagta agagataact ggcttttttta attagtatgc 219480
taagttttttc aaaatgtatg ccttaaaata tgagagacat caagtatctt ttatctacaa 219540
ataagcaaag aacttgtgga caaactgtca tagtttctgg gtaatggttt gcatctttta 219600
atggcaatat cccatatctg ggagagaatt agaattcaaa acatttttcaa ttccttcccg 219660
aaaatgatga gctaatgttg aaatgcctat gaagacagaa gaacaaaaga aaatgttgca 219720
ggctaaggta tctgacaaga atggagaaaa gtgtgtcaca gattgtaaaa tttagctcat 219780
tgagaaggga acagaaaaat gatgcatgat acttcaaaag ggggaaaaaa gtctgtcatg 219840
aagcttctga gtccagattg tctggatgag cagaaatatt agaaacaagc taatcactgt 219900
ctgtctttta ctctcccagt taaaaacaaa agggaaaaag aagccactcg gtatttccta 219960
cgtgtactaa tgaaaaaaac ttttattgtt cctttctcag gagttgtgga gcaaaggtaa 220020
ctttatcatg tggttgcagt cataaccact tgtgaaactt aaaataatga tgcctagaca 220080
ctattgcaga ccaatgaaat caaaatctct aagggctggg tacggtggga gggttggagg 220140
cattgatata aaatttctgc aagtcatcct agtgtacagt tatgaaagca aaacattgga 220200
agaaatagtg cagcaaggaa ggcatggact agtcaacctt gcagagtgtt cagttctgtt 220260
```

```
ccagaattttt gttcgtatac aaccatcatt caaatgggag caaagagaag aaaacgcttt    220320
ccaaatatttt ctgatttctg ctaattctca cccaaatgtc aggttcatgc atcattttt     220380
gtggaaaagg gtaagggagg tgttcatgat gagtcaggtt tttcctttgt atgttaaaca    220440
ctgcataggt taagctgata cgagtttaag gaatacttta tttacatgaa acaaaataaa    220500
gcaaaaacag gaataaagca cctagaccag gctctagagc gttttggtcc ctaacttttc    220560
tgctgttgat gttctgcaat ataaatgaaa tcaagtattt ggagctgtcc tgaaagaaca    220620
gattctagtt aagggggcaa tgagggagag cattcttcta taaattgact ttctaaatat    220680
atcatgtttt tcataagcac ttcataaatc ttgacacatt tctttgaaag tatattatca    220740
ccactttata ggcaaggaaa ttgttttgga aagcagagct gggatttgaa ctagcattgc    220800
ctgatcctag tgccttatgc tcttataatt actgttttcc acatttactt aacctttat    220860
caattttga catttagagc atttctcatt tccaacaatt ataaaattgt tggatggttt     220920
catgtctgta ttttcttccc catgtttgga gttacttctt tggaacagaa tctcagaagt    220980
tattcgagac tgtgacaagg tttatgtttt ttttttttta catattgcca aattgcttgc    221040
aaaggagttg tacaaaatta caatgcatcc agaaaggtat gatagctagg tctcaagaat    221100
atttaattat tttcaattta ataggcaaaa atatatatat tttatctcat ttcttaattt    221160
tcatttggtt tatcggtgaa tcagggcatt tccgtgtggt aagttggttt gctttgtcca    221220
tttatctatt ggaatcttca tttatgatct ttgatatgac ttgatttgta gaattcttga    221280
cagttgtaat gtatgttttt tgtggcatta tgttcaatgc ctgtctctcc agatacacag    221340
taaggcacct gagaacagat cttgtacctg tttggtttat ttttgctttc tggtacctca    221400
tactgtgcct ggcacataat atgtgctaaa gctatacatg atcagaaaga catatttctt    221460
tccccatata tgggagaaca atacactgga ttttttttata gtgttgattt tatggttgtt    221520
ttgagtggtt tagggcagta ccaaggctag tcagtaacct tcacaaagcc attcattcgt    221580
aaatgaaatt gtcactgagg agtcataaaa tttaaaaggc aatttgaatg aaatgggaat    221640
aatgtagaaa atcttcaggg aagaggtgag atctctttac tgataagacc ttttcaaatg    221700
aagaaaatag ttttgtggta tcttccctgt tgggggttct gctgataacc ttttatagga    221760
ccaagtggaa caacccatat taagtaggct gtagtggact cctaattagt ccaattaatg    221820
tgatggcttt aatttgtaag agatctaatg gtgtagaatc tgatttcttt gaaatcactc    221880
ctctctagaa tgtaaaacaa caatgaaagg cagctaaagc agtcctggag tggctaagta    221940
ctgcatttag ttattgtatt tccccacccct tccctcctta aagagaaaat aaaaggtatt    222000
tcttcctcca tattattccc cctggcatgc tgcctttgtt aggacaacag cagccaagag    222060
cagatttgaa atgactcctc ggcatttcct taagatgagt ccagtggagg ctcttcaatt    222120
agtagtggtc atgtgtgccg gggtcaatat tccagaatac ttaagttttt gctctttcct    222180
gcagaaataa acattattat tgttgttgtt attaaaatcc aaaaggaaac tataatgtct    222240
gaggcaaact gttcttgtca cagcctgcta ttcccatgag ccgagaagca tcacaataca    222300
ttgcctgctg tctcaaccca tggaaagtct gattagctct ctagcaatct gatctccaga    222360
aatcgccctt tccttactat ctcaacaccc tttcatggaa aacagtatgc gtgcttctct    222420
gttcagactc cactgtaaaa ttttaagcc aattcccatg ggattctgat ggttttatg     222480
taagtaaagg aaccaaagat tttcaatgag aactattgag cccgacaaag gcttactgat    222540
ttatgtagtt accacctgaa gtaagaaagc cactttgata tttaaaaacc attctaggcc    222600
gggtgcagtg gttcacgcct gtaatcccag tattttgaga ggccgaggtg gcggatcac     222660
```

```
gaggtcaaga gattgagact atcctggcca acatggtgaa accccgtctc tactaaaaat  222720
acaaaagtta gctggtcatg gtggcacgcg tctgtagtcc tagctacttg ggaggctgag  222780
gcaggagaat cgcatgaacc tgggaggcag aggctgcagt gagcccagat tgtgccactg  222840
cactccagcc tggcaacaag agcgagtctc tgtcacaaaa aaataaacaa ataaaaataa  222900
aagtaaacaa aaactattct aaattaagtg gctggccttc cttccttctt tcttttcttc  222960
cttccactgt ctttagcata tgttttggac aacttcatgt aaataaaatg gaagcacaat  223020
tgggagccac cataataacg tcagtaatct ggcaggaaat tttctacatt agtgattaat  223080
aaacaatgta tttttaatgc ccaaagttgc atttggcaca agtgtttgtt cagtgtttct  223140
aaaacaatta ttaaaactaa ttttaatcat ttagaacttt gctggttaat atagtagcta  223200
ctagtcacat gtggctatgt agcatttgtg actagcccaa actaagttgt gctgtcagta  223260
taaaatacac actggctctt gatgacttgt tattaaaaac atgtaaaata tctcattagt  223320
attcatgttt attgcatgtt gaaaggataa tagtttatat acataattaa aacatcttat  223380
gaaattcatt tcacccattt tgctgcttct ttaaaaatgt gacttctaga aaatttaaaa  223440
ttacatatgt gaaattgtat tatgtttata ttggatagca caagatagat atatttaggc  223500
tctagccctg ctggagttcc ccactaacag gatgatcaca attctctatc cagcagcaca  223560
atgtgagtgg aattatgcag gtaaacgtgt gctagtcagt tacagagcta gacctcaagg  223620
ggagcagatc atagcctaag gaagtagacc tctcaattcc cactgcctgc atgtcccaga  223680
cttagaacgt tatcatccct accatcgcaa acatggttgg gatgatctgg tcccagttga  223740
tctggtcata gtctgagcct caacccttca atctttaatc tgcactctgt gaccaataaa  223800
aattttagaa ttctcaagca agaacttgaa tactattttt ggcatttta aaacaaaaat  223860 ctgtaatggt tattaattga tgtaggcatg gttgaataga cagttttctt tgaaaacctt  223920
tgccattgag caaataaata cttaaaccaa atttcatcaa agtgcagtcc tgctgtagca  223980
gaatcaaatg caatagttgt ttaaaatgca gatttcagag ccccaccacc aataatgata  224040
atttagtagg tctagaccag ggaacagaat ctgagtttaa acagcatcat tctagttatt  224100
ctcatgcagt ctaaaatgtg ggaaccatca cttgaagcta tagttgtttt cctttaattg  224160
ttctatttta aataagtaca ttatatagca aatatactgt catatcatta tcctataaat  224220
ttagaggtta ggggtatcta cccaggaata tttggtttct ctattacttc attgtgagaa  224280
cctgaacaca atttactgtc acagtttccc aacaaatcta aaaatttact ggtgatatta  224340
tttatacttc taaagttatt taataaaaaa tatttaatta acatcttatt ctattatttg  224400
attatattcc taaaatgtaa acttctatga tagttcatac agttacaaat atccagcttg  224460
taaagaacat attagaaaga ctcatttttg ttgatgggga gggaatccca agaatttgcc  224520
attccctgga aatatattca ccaggaattt cctagaattt atgaaattat accacataaa  224580
tttccaccca tgtctaccca ctggtaaact gaggagagag aaaaatcagt gattatttgt  224640
ggattaaaaa tgagatacat cagacagcaa catgtcctag gtatcaaaac aaatcagaga  224700
gtattaacct ggagtcgtgt catgtaacac agaggaaaaa acagtgcatc atgtttcaaa  224760
gcctggattc ttgtttggag tcatccacta acagtgatgt gggcatctgt ttcctcatct  224820
gaaatttaag actgtgagac aagatgatac agagacatcc tctcagttct gacagtctgt  224880
gtttttcatc cacacttgca gtgatataga cctatcagga gggacgactg gaatcctgac  224940
tagattgagt tagatttaga gcatctcaga gataagcctg cgtgtggtct ccttacagga  225000
```

```
tagcaaaaaa tattgcaggg cacgcacata ggcaggagtg tgaggtttct agaatgtcat 225060
ggctgctgca ggataaggtt gaattgtggg tcctggaaag aggtgaccag ggagctcagc 225120
tgtgactgag gatgaggtga ttaggggaca gtttctgagt caggctgcct gaggcagggg 225180
agagggcctg agggcagggt cacttcctgg agcattacca gtcctgagca tcaccactta 225240
aacatcagag agaaaggaag aaaggcgata ggtaagtgac acttcccgat atcgccttgg 225300
gagaatggct tttgctttat ttttcttttc ttttattatt ttcaaaagaa aacatcagga 225360
aagctagtca agccagctgc cttttgagta aacaaagaac cagagttcag ggagcaaggg 225420
tggcagtaaa gatggataag tcagagggta ggtgtttttc tctcaacatg aattgtgaga 225480
agtttctcaa aacttacatt ataaataaat gatagtacta acattttttt cttttttctt 225540
tcttttctat tgactgacca tgacacttct gtctcacaat tcctcaccat tttgccatga 225600
ggttttctcc ttccccttgc ctaggttcag aataaaagat gcctatatat taggtcccgc 225660
cagaaaaaaa ggcaagaact cacgtgttag taaaacattt aataaacctc agcacacact 225720
tggccaaatt cctggaagat cagagctgca tccctgaaat ttcttttat cttgatccag 225780 ttaactgcct gttagagta aatgatgtgc tcccacgttc tttatactgt cctccccata 225840
taagcatata cacgagagga ttatacctgc tctccggaag cttataattc agacgttatt 225900
accccttttg gaagtattct ctgggaagct cttttcacta atgttcaatt tcaacaatag 225960
tattactata atagctaagt ttcatttagt gcttagtgtg ttctaagcac tctcaaaagt 226020
gcttcatata tatttaatca ttaactctta ccataactct atgccctagg taatattatt 226080
gtccccattt tacaaataag aaaacaagca ccaagagatg ttaggtgaac ttgcctagag 226140
ttacacaaag aataagtgac tgagccactc attgaaatgc tgctcttgca agaaaacata 226200
aaattgtatg atggtgccac ataacacata cttgacacgg gctttgaagg cagagaagcc 226260
tgggttcaaa taaaattcag ccacatacta gctgcatgat tctaggacaa gttacagaac 226320
ctgaggccat cagttatcat ctgtcaaaat ggagtgaata cttataaagg ttacatgagg 226380
gtcaaaaata atgtataaaa ggagcctggt acatagttgt cattcaaaga gagctgctga 226440
tgttattaac attagttgac tatgtaatat tacttaaaac tcttacttcc tatttttctt 226500
cctactgcaa taaagtttct gccatttctt ctctctgtgt gaagtttttc ttcttcctcg 226560
gtctgtagct ggaatgtgcc tttctgtgcc aagcccactg actcatggtg atatagccca 226620
cagagcaggg tgcaagcaat agaagggcca taccaggcca caacatatgt ctcagattcc 226680
caggacaagc tttgttcacg gcatggaaga atggctggtt aacttaatcc cagggttgca 226740
ttctccgtaa tgatacatct caggccatcg atccatggct ttatttttcaa gcttgtttaa 226800 gcaggagcta taaaaaacag agcatcatgc acgtgcaata tggaattaag cctcacactc 226860
ttaccactct aattctctta gatacctatt tgtttgtctt gattttagaa agcagaattc 226920
agtaaagaaa caaattgggg aatatttttt agggttataa tcttccacgt aatgatataa 226980
acgattctgt gtagaattgc tatcttgctg gtgagttgtt ttctgaaata atgtgcccaa 227040
aacagaaatc agcattgttt ttttgaggca attcactgtg gcattgtggc tgctgtgaat 227100
gttctagaaa ttgtaaaata cgcttttgca aacgtagaga tggttttagt tttcttatat 227160
caataagcag taggattaaa tgtaacaggc ttacagaaaa tgagggaaat attcaatgca 227220
ttttgcgata aagagcaaag gaagctcaaa gctccttcag ccataacgac atccttgttt 227280
cttcttcctt ttcctttccc agtgtgtgta tgaaaaccag gaaacaaggg agaatcaagt 227340
gctgggttgg gtgaggttaa gagaatcggg ttctcttcac atttaccttg gacttttcag 227400
```

-continued

```
gaactttcct ataattcatt taagctcaat aagttctatt atcttctttg gtagagcttg    227460
ttgggggggac tatagtaatc ctgccaagaa aatgttatct tgttcctcaa ataacaaaaa    227520
agtgatttgt ataaaagcaa ggttcataat gtaaaatcta agtatatttg aaagaaaaaa    227580
tttctaaaat atttgagtct cgagtaaatt ccttgagctt cacaccatac aacttagttc    227640
ttggtaaatt aaaagtaggg cttctagtga tttgcataaa aactctcaag aggaggacct    227700
cagatacatg gcttatcaaa ctggcacttc atagagtctg ggccatatca gatccttgaa    227760
tgcttgcttc ttaatagtaa ctcctatata gtttctaagg ggtttcggct gtctatatta    227820
tgaggagtgc atgtttttaa gagctttaca ggggtcagga gaattggctt ctctctcttc    227880
atttgcattt aacgttctaa aagttcttaa gctggaaatg atctgagaac tctctctggg    227940
aatctatttc ttagtttcta aataatcaaa cctatcatca gtcaatgcac tgttttatct    228000
tccttcaggc aagtttaaaa tatgtacata tatatgttat agaagctgtt ttttttttcaa    228060
acctcattt atgagccaat atgtttgttt cccaaagaaa aaaatgttt gttttcatga    228120
ttttggcaga aacaaatgtt ttctttgggg ctgttcaaat agtcatattt tcaagttttc    228180
ttgcttcttt ctattgggggg gagcacccccc tggtggaata ccatgaaaat gtttgccacg    228240
tgttttgact ctaatattca acagacagat gtgttttgca aatattactt ttacacaaag    228300
cacactcaga accattttgc caatgttaat gtcttggaaa attccatgcc ttcttttctaa    228360
ttatcaccac agtattcaga atgggctccc ttgttttagg tgttacacag ttgtggtcag    228420
agatgctgca gcagtctctg tgggtcagaa atgagtcggg aagggcactc tggcattatg    228480
ttcctacttg tgggaaaaaa gggaccctt tctcctttcc ctcagttctt ccttctttcc    228540
ttccatttct tcctgctact acaaacaaaa tggcattgt tggagggtct gactgggtga    228600
gaaaacagtc ggccatgaca gtgcccagtt ataggtaaag cctaaggtac atctctttcc    228660
agagtaacgt ccctgtcact gcaagctggg ggagattaac agaaagggaa tttgctggga    228720
gatattctta atcccccata tccccccaaa tataaattta aattagtact aaaaacatat    228780
cagattaatc aataagcctg taatttctgt atcttataga gaaaaaagta tcatcccaa    228840
ggtaactgga aaggatgggg cactattgtt tatcattgct gttgtgtgct gaattgtgtc    228900
tcccctcctc ataattcata tgttgcagct ctaactttca gcaactcaga atgtgccttt    228960
atttggaaac agggttttgc agacgtaatt agttaagatg agggtatgct ggggtagggt    229020
gaccaatgtg actggtgtcc ttataaaaaa gggaaatttg gacacagaca aacacacaga    229080
gaacagtatg tgaacatgaa ggcagagatt gcagtaatac atctacaaac cacatttcta    229140
agaagagacc aatcctacca agaccttgat tttgaacttg tagcctccag agttttcaga    229200
cgatacatta ctgttatgta agccactcag tttgtggtac ttggttacaa caatcctagc    229260
aaatgaacct tcctctgaac tcaagtggtg gtcccttccc acacataacc tttctgagta    229320
gagaccagtt tttgtagctg ctgttgtttt aaagtaagga ctgaaacagt ttactgcctc    229380
catcaactat tgcatcatgt tatgcagcct gtattttctt aagaatgaaa ataacgtttt    229440
ctttataaaa gcaagccaaa atggactata aattatatag atgtttcttg gctcacagag    229500
aactataatt catctggaac caagtaggaa tggatctcca tatttttaaa ttttttatatt    229560
tttaaatttt gtgggtacat agtaggtgta tatatatata tgtgggggtac atgagatatg    229620
ttgatacagg catacaatgt ataataatca catcagcata aatggagtct ctatcatgtt    229680
aagcatttat cctttctttg tgttacaaac aatccaatta tacatttagt tattgttcaa    229740
```

```
tgtacaataa attattattg actgtagtta ccccgttgtg ctatcaaata ctagatccta   229800
gtcatcctat ttaactatat tcttgtatac attaaccatc tctacttccc catcacctca   229860
ctacccttcc cagcctctag taaccatcct tctactctcc atctccagga gtttaattgt   229920
tttaacgttt agctcccaca gataaatgag aaaatacaaa gtttgtcttt ctgtgccttg   229980
ctcatttcac ttaacataat gacctccagt tccatccatg ttgctgcaaa tgacaggatc   230040
tcattctttt ttatggctga atagtactcc actgtgtata tgtaccacat ttttaaaaat   230100
ccattcatct gttgatgggc acttagattg cttcaaatta ttggttgttc tgcatagtgc   230160
tgtaataaac atgggattac agacagctct ttgattcact gattttcttt cttttggata   230220
tatacctagc catgggattg ctggacccta tggtagttct attgtaagtt ttctgaggaa   230280
actccaaact gttctccata gtggttgtac taatttacat tcccaccaac agtgtacaaa   230340
ggttcccttt tctccacatc attgccagca tttgttattg ctcatctttt gaataaaaca   230400
agttttaact tgttttattc aaaagaggta agatcatgtc tcattgtggt attgatttgc   230460
atttctctga tgatgaatga tatcgagcac cttttcatat acctgtttgg catttgtatg   230520
tcttcttttg agaaagtcta ttcagatctt ttgtctattt tttaattgga ttttagatt    230580 ttttcctagg gagttgcttg agccccttat tctagttatt aatcccttgt cagatgcata   230640
gtttgtaaat attttctccc attctgtgga ttgtctcttc actctgttga ttgtttcctt   230700
tgctatgcag aagcctttta acttcacgtg atcccatttg tctatttta ttttggttgc     230760 ctgtgcttat ggagtattac tcgagaaatt tttgcctggc ccaatatcct ggagagtttt   230820 cctaatatt tcttttttgta gtttcatact ctgaggtctt agattttaat tccttaatct   230880
acattgtctt ggttttgta tatggtgaga gatagggttc tggttttac ttttctgcat    230940 agggatatcc agttttctca gcaccatttt attgaagaga atgtcctttc cccaatgtat   231000
gttcttgcca cacttgtcaa aaatgagttc actctagatg tatgaatttg tttttgggtt   231060
ctctattctg ttctgttggt ctatgtgtcc gttttttacaa cagtatcatg ctgttttggt   231120
tactatagct gagtagagac caatttgaat gatctctgtt actacagctg aatagaggca   231180
aatctgaatt gtctctactg agccacagta acttcccatg gtccccaggc catcccatgg   231240
tctcctggcc aactactttc aaaagcactt aagacaaaga tggaaggtag atagcaggtt   231300
ggatgctggg caatatatgg ccagtctccc aagtcccaag tgattcttcc ccaatacaaa   231360
gtcctaacaa taactttcac tgccactgcg cagaacctaa atgtaatggc aaaactgcta   231420
aagagctcag agtctctctc catgttctgt gttcccgata acctgagtgt ggttattcta   231480
gcaggcaaac aaaatagaaa cagagatatg tgtcacctga aatacctgtg ttggttggag   231540
ttttcttcaa aactcttcta cctgtctttg atacagcagt tcattacagc gagtctcatc   231600
ctctactata caaggtcatg attctcttgc ccaagggact gtcctccatg ctgttcccca   231660
aatacagcaa aaccttttcc ccatttgatc tgctcattgt acagtctgca tctcccaaag   231720
gcattctctg ttggacattt atggaaatcc acttcatctt tcagatccag cttgagtcca   231780
gccttttaca tgaagccttt cccagtcata caaaaccaca tctatgtctg aattcctgtg   231840
agacttgttg actatgcttt agcctctgtg aaattctctc ccactttaaa tagcaaagtc   231900
caataaaagc aatggtaact cattctattt caaaggtaca acttacagta tatttcaggc   231960
tgctggggat acagtgggta agcaatacag gcttacttgc taaaataaaa tgaataatac   232020
taattatttt gatggatatc tgtctccaag ttatatacat atatgtgaat aatgattttt   232080 aatttttttat taatgagttt taatttgcac tatgtcatat aatccttaca gcaaccctga   232140
```

```
gagatagcta ttcttacaat agcattgatg gtttagaatt agctaaaagg tagtctaaaa 232200
cagcttcaga gtattaggat ttcaggcata tgatcctcac aaattggtat tttgtagaaa 232260
aactactcaa gaaaagaagg aaaactctac tcagagagga actttcagcc ttcagagttg 232320
tttttcccct cttcatcttt cttctccttt catttaaatt cctggttaat gaaaccccca 232380
cctcactatc atccttcaaa caactatgca gattgcactt tcatcacacg gtctgtctta 232440
aacagctctc caaaagaaat aaaaagaatt ctgtgctatt tactttttt ttaaacgatg 232500
aaacaaataa caaggagaaa gagccatcta acaaaccttc accctagcaa aatgctgagc 232560
tgcttgcagc taccagccag tttgattaag gtgtcatccc tcctcttcat ttatatttat 232620
tatttttgga agactttttt tcccttagt gtttgtttat cttttccaat tttttaaaag 232680
tcatgaatca tagtttgatt tacaaccttg ctcaggggag atcggcaact ctaatgaagg 232740
agccgtctgc aagtgtaatt aatacctgcc agacatttta ccacattagc gtgccagtat 232800
cctgggctgg ggaagaatga agccgggaga cacatgcacc gagctatgca gccactcaca 232860
cagtgcatca gcagagatta gtgatatgaa gtgggagggt gcagaggatc accaccccac 232920
tggtcaagct cagaagactg gaagaacagg caggtgagag gagcagagag tctgagagcc 232980
tggtgaggaa gatgagcaag gtgcatggag ggggatgtg gagacagaga cactgcatgt 233040
ggctgatgga tcactcccat ttagaacaca aaaataaggc agcttgccag agcagtttgg 233100
gccagtttca ttaaaactct tcattcatca tactgaaatg aggcagtatt tgttattgca 233160
cgggtgccgt tctagcacga aagctattcc aatactaagc agtaattcaa gaaaggcaga 233220
gtagcaggtg ggaaggaga ctgaagaaag gaagaccagc atgcattggt gtttgcccca 233280
ttctctccct cagccctgca cccagcagta cataggcatg tggaaaaggc ccagaacctc 233340
catcatggtg aagagccagg aacccacatt ccactctaaa gccactccca tgggacaaaa 233400
taatcagaat gatcatcatc tggcttctca gtagggaagt tacggaggag cagctgcatt 233460
ttcatatgtt gccttaatgt gctcatggaa gaataagttt tcataaatgt acaaaaataa 233520
ttataagtgt gtgtgtgtgt gtgtgtgtgt gtgtgtgtgt gcgcgtgcag aaaggtgttc 233580
ctgcccatcc ttaaggtgaa atacaactat gaaaatggtt aaaatgatag caccctaaaa 233640
tttccccagt tattttgtc ttcttcatca taaaactctt ttgtttgctt ttaaatacct 233700
taatggggaa gagaaaagac agaattagat tacaatgtaa aaggtctgca ctaataattg 233760
ggtctaacac tggtaccgat acttccttat acccgattac acagacgaag agaaaagaaa 233820
aaaatagcta cacaagaaag gcctgaccat tgtttctcat gcatcagttg ctgcgtccct 233880
ggccatgcta cgccagtctt ttcttggtac aatactcacc ctgagatatt tctgacagtc 233940
agattatgaa agcttatgta gtaatgttgt aggtgttata aaatgaacaa actcgcccac 234000
agctgtaaag acatgactgg cagtgatgtt ccaagatgag gagtgaactg catatatcaa 234060
acttgtctcc agccttttga tcgattcttt gtttgctgcc tgatgatgcc aagactgcat 234120
ctggagccaa agcttcggta gtagctaacg gatagcatgc attgttaaat tacacacaga 234180
actgctgtgg aggattgcga ctatagtagt ttattttcca ggattgaggt tggcatctga 234240
ataacacaga atccatttt cagcttggaa tactgaccag aaatatggca tctcatatgt 234300
gatatgaaga attatttaaa ttgtgttcta attttgttcc ttaacattaa ttcatctctc 234360
atttatttac ttattcagca gcaagagtgt ttctaatgac tgtagggcaa gttgtaggca 234420
agggagatgc agagatgaat aagatacaat ttccctgcca aaggtgtgca tttgagttat 234480
```

```
gtttacaaat aagatatcca taataagtga cattagaatg ataaaaggat tctatgaagg   234540
agactaagtg ctgacaaaat atattctcac agacacacaa atatacacag tctgtcagct   234600
tatgggtgtt gcaactatga atttggcttt aaatactaac atcaagaata caatagtctg   234660
acctcatcca tgggggatac tttgtaagac cccccagtgg atgcttaaaa ccattgatag   234720
cagcaaccct tacatccact acgttttctc ctacgcatac ctatctatga taaagtttaa   234780
tttataaatc aggcacagta agaaattaac aacgataact aataataaag tagaacaatt   234840
ataacaacat gctgcaataa aagttatgtg aatgtagcct ttctctccaa aatatcttat   234900
tgtactgtat tgcaggtaac tgaaaccata gaaagcaaaa ctgtggaaaa ggggactcta   234960
ctgtactgca tattattttc aacattaaat taaaaaaaac ctccactgaa aacacaatct   235020
cactttagcc ctgcatttga cttttttgct gtttgacctt tcaaaccct gaagtccaac    235080
tatcttacat gagactcacc taagcttcct acctcctttc tgttctctag gataaagctg   235140
ttgatgaatg gccaaaaaag gacaagttaa ggggaaaaat tggaaccaaa gagcccaggt   235200
aattattaga ctgaataatt gccttctgca aaatgagtg ttgattgtac atataaatta    235260
ctagttaaca aaaatatta atatgtaggt ccagaatgaa aattataaca ttcaaaatag    235320
gtaatttggt gagatggaaa tatgccctat aagtcaaatg ttaaaaagca aggttatcat   235380
tcatttgatg tcaactgatt aattataaac tcactgtagc ctagaatagc tcactaatag   235440
gaaagcagtg gctccatcat tttccttatc actgtcaaaa aataactaaa ttaccataaa   235500
agagtggcgc ctccatgtga ggtcttcctg gcccattatc aagctgccca acaaaatata   235560
tctacttgtc ctgctagaca taacctcaac catttttttat ttattgtggt tggggagggt   235620
agagatggta taaataaatc tatagaaaaa aacccaagcc ttacattagc taatggttta   235680
accttcttag aatttccact gctgtcttta gagatgtgga ttttctatat atctgaaaaa   235740
gtaaaccaaa gaaaaatata ttaagcttcc tttcttgtca tgcataagta gcttccaagg   235800
aaatagctaa tgctcaatga aatggacaag agacacagta agcaaggtag gatagggctt   235860
agagaaacat gctgagttag cacatttcaa attattaaat tagattgcct tttggaggaa   235920
tctatctgct accttacatg aattaaagat tgactagtta taggacgtag aagataaaag   235980
agaactaaca tagtatgctt tcagcctctg tgatatgcca ggaactatgg acatgctacc   236040
tcattgattc ttttatgaca tatttaaaa ggtaggtata ttccatttaa taggcaagaa    236100
aattgaggct tagaaagttt tagtaattta atcaaatttt tgcagctaat aaatgatgaa   236160
gttaaaatga aacctctgtc ttacctactc cactccacag ttttcctccc tagaacacat   236220
tatttaaca ttttaactgt ttgcctatat tggaagcagc agggaacact gaagacacct    236280
gtacagccct gaagaacaac tcagtttata cactgggtgc acacacacac acacacacac   236340
acacacacac aaattcacat aaacatgctc catcaaaatg caagctgcat agtcaaaaac   236400
acaatggatt gatttactat caatagagat gtgtcagact tgctttagaa aatccttgtt   236460
aaggggggatt tttcatctca tttttgggcca cttttatttt gactggcaat cttatctcag   236520
cactttggag ttatttctca attcagtacg ctttacatca ttctgcagcg aacaatgaag   236580
acccatcttt taaataagat gaacagcagt atttcatgtt accataggtt caaatctcag   236640
tgctgctacc ttttatctca gtgaccttga aaaagttact gaaactctat gtcccaattt   236700
cctcattcat aaaataagaa taatattaac atgcttacca tgaatggtta atacacgtaa   236760
aatacttaaa agggtgcctg gtgcccattt actgtgatat aatattttgc ctttattata   236820
ctgataacat agataaagca tatagcccgg ggcctagaac tgaacagggg cttaacagtt   236880
```

```
cctatttcc tttcctcata tgaaaacaca tagtcacttt ccttcagaaa aaaactgtag   236940
ctgaattaag ttcattcact gttcaatgtc cttttatttc ttccactcct ctaactctcc   237000
agtatcccta ccttagattt ttactactct tgggaaacac gtatagtgtt atttacatat   237060
gccctcacat atcccgagag tctaattact gccattcatg ggctaaccct ggaactctga   237120
tgggttcatt ttatgataaa aataagaaaa tatatcagta taaaccccctg cttaaatttc   237180
actgagtctg aattacagta aaaataaaa agaagaagaa aaggtaaaa tgacaatcgc   237240
tgagctggga attatcttaa atcttatcct ctccctttgg catctgatgt ttaataatta   237300
tgtgatggaa cagaacagac taggctctgt ttaaatattt acattctaag aattttttaa   237360
atgatgaaca tcatttaaat atatttcttt attttgagct gaaatgtcc tctcttccat   237420
tcattggccc tggatttgcc ttccatggaa atagcaccca cggttgtttc tggtatttgt   237480
agtagatgct gtggtgattc tctagaccct cacctgtagg agaagaacat tcactccccc   237540
actactgagt ctctcactga gatatcaatt gagtcttcct tcaaagtcac aacctttctg   237600
ggacagcctt tgcctaatga caggtctgtg cggggccata aagtcctggc ccctagcccc   237660
atgagtcctc tgttataagt aaattgtgga tcagcaactc tctctgccca atcatgccgc   237720
cttcactctc ccacaggtgt taaactcaat atcactttga atgaactttg gtctttgtct   237780
cagagtacgc ttcctatgga acttaatgag taatagtgta tctaccactt taagtttaaa   237840
ttgcactatt tccaagacct aatacgttac tcatttggtt tttcacttat ttatctgttc   237900
attcattcat ccatttagtc attcatttct tcattcaaca aaaggatttt gaataaggtt   237960
agcatatatg tatatggtaa catgctgagt accacaggga cagagaatgt cctttcccaa   238020
cccttatcct gatacagctt actgtctacc aggtaggatt gggtaagtat aacagtacac   238080
caaccataat actagggaga aaatagtgcc aagacagaga gagagagaga gagacagaga   238140
aagagagaaa gaaagagaga agcaagcaaa ttaaattcaa taaataaata aaaccaaaac   238200
aaattaccat cgaacatcat cacaggtgat atggtttagc tgtgtcccta cccaaatctc   238260
atcctgagtt gtagctccca taatccctac gtgttgtggg agggacatgg cagaagataa   238320
ctgaatcatg gaggcgggtt tttcccatgc tgttcttgtg atagtgagta agtctcatga   238380
gatctgatta ttttataaag ggcagatccc ctgcacacac tttcttgcct gccaccatgt   238440
aagatgtgcc tttgctcctc tttcgccttc tgctatgact gcgaggcctg cccagccatg   238500
tggaagtgcg agtccattaa accttttttt ctatataaat gacccagtct caggtatttc   238560
tttgtagcag tatgaaaatg gaccgataca agaaggatgt atgtactcac atgagtgtga   238620
taacttctta aagatataac tttctattga atcttttcta ctaaatccta ttatttagag   238680
tagtgttttt tcctgcaccc atgccattac tttcctcccc acctgcagct ctttatggat   238740
acctttctg tatacaacct tagacccctta tctaccttcc taggccctta cgattttcaa   238800
gtgtttcaaa tttgatttta tgcctgaagg atattgacac ctttctttcc cttaagcttc   238860
ctactaatcc actttctccc tttggtactt ctttctatat catctgaagt ttgaagagaa   238920
atgatatctc taatgaaaat cccatgaggg agaaggtgat aacaagtcaa gccttaaatc   238980
tctgctcata tctgccagaa agttgtagta aaatattgta gtctttcatt gacagaagag   239040
tttaagatta aaatccaatg ctcataaaat ataccaattt tagtaaaacc aactaacatg   239100
acactaagtt atatctgttg aaaaaaattc attaatgcaa tgagttagaa gtataaattt   239160
taaaatgaat aaatgaataa aactaattca atagtccact ctaaacagat tttaaagtat   239220
```

```
gattagcagc attacagtta aaatataatg catttatgtt tgggctataa agtattacgt   239280
gtaaatcata gatgtcgatc aggcaaatgt catctatgtc cactgagcac aagatcccag   239340
gttttttcct tgatagcaag agaatctaaa aagaaaagt gtctagaaaa tgtccactgg    239400
caataatttt acaaatcccc ccccccaaa aaataaactt gcaaattcca ctgaactggt    239460
cacataagaa atataaacat ctgcataaac cttttaaaag tataggttat atgttttcc    239520 ttttgttaga tttttcttgg taaataaaaa taaaaagttt ctaacatttg actgagacgc   239580
agtcatcttt gttctagtca atgatgaatc acaggtatct agaactgtgc caggtaccaa   239640
gtaggcactt gaattttgtg gaatgaatga ataaattcca tcttgacatc tgtaggcata   239700
tcctctgtca ctttaaatat attactcaac agagtagtat atttgaagta tatccttagt   239760
catttattca atatttaaca aatatctact gagtcatgac ttaatgaaag gtggtatctt   239820
ggatgttaaa ttcaggtttc actcaagggg agaaaggtat tcctagttaa gtataatatc   239880
cattaacaca atttgaaact ggaaggtaac acttaaatc tactactcaa agttcaaaat    239940
cattaaactt ttctcctgat tattcctaca caagccattt tattttttcc tcatattctc   240000
tgtggcaatg ctgcttccct gggattttcc ttatgctttc taattaggcg tccaattggg   240060
tgtctgaaaa caatctgaag taggtaacat gcattttaaa ttacttttat ctcaaaggag   240120
acaatatttt aacattccat tattacatta tcatcttgat tattgaagtg ctgttgtaa    240180 tagagttgtt ttatatttta tttgaccaaa tccaaattaa agaaacacaa agacataaaa   240240
tgatgagata tccttaaggg ataggggaga aagatgaag tagagaataa aatataataa    240300
agtacatatt cttaaattaa ttaaataatt tgatacctat tattattctt gccacacgaa   240360
ataatggaat taactggata atagtgaaga ttccactgca aaaaaaaatt ctacttaaaa   240420
ttttgggttc ataagactag aggtaggttt tctttctaac aataattctt attctgaaat   240480
atcaacaaca tatgcaatgt aaaccagtat aaattttaat tttttttatgg aaaaaaaatt  240540 tattttttgaa tgtggcctct gatttcatat ctgcactgtt ttcttcttgc taccttccag  240600
tttcaaattg tgttaatgga tattacactt aattaggaat accttctcc ccttgagtga    240660 aatctgaatt taacatccaa gatatcacct ttcattaagt catgactcag tagatatttg   240720
ttaaatattg aataaatgac taaggatcaa gtgcattgaa ttataacatt aaatatgggt   240780
gggttactac aaaaggaata aaagatattt tagttgatgt aatcaaaatt atagtactaa   240840 aataagaac atgcatttgt aacagtttgt atgtctctca tatttcatac catagtttaa    240900
tagttacact ctagtagtaa atactaagct attttttactc ctacttacat atagctgtgt   240960
cttctatgtg tttgcacatg cagtttgcct ggaatgtcct tcccatctca ccccgggcat   241020
ctggctgcaa tttctggtcc tccttcagat ctcaagttag aagtcacacc ttgaaaagac   241080
ttagtagaca cacccaccct tttaggaggt tttccgataa ggcatcatac taccctactc   241140
atatccctac aaaaagactt gaacgacata aggaaataaa ctttaattat atgtctttct   241200 ctttcccta agattgtgag ttccttgaaa gaagaatctg tgtcttgtgc accattgttc    241260
ttccttacct gtaacagaaa ccctggcacc aggtaggcaa gtctttgata aatatttctg   241320
gattgattaa gttgtatta ttcattaaat gtatgccaat ttcctttgtt tttgctacta    241380
tcctagcatt gcatgttact tccatgaagc tgatctatga aagcaaaata ttaacatctt   241440
atggcaggta atttttgcct tgatagcctg tgatgagtta ctgactgctt gttagaaatg   241500
tcactgcctt gttcctgtta ggcttacagc tgacatgttg aaaaatttat tcaatgtata   241560
aaaaagctct acaaagatat tcattgtatc actgtttata attgggaatt gtttggatag   241620
```

```
tcgaatgagc tgtgttacat ccaaactatg aaacattatg caacaattac gaagaagaag 241680
gtagatctat gtcttataaa ataaattgat attctactta aaaaaaagca aatggctaaa 241740
agatactttc agtacaatac catatttaaa aactgcagtg tactttctgt ggttaccata 241800
gaggtatagt tataacagag gcatatggac atatggaaaa taaccataga actcatatta 241860
aactcactta tgtgatcagt ggctacatct agaaaggtag agaggggacc aagaataagg 241920
cttggaggtc aaaagcgact tctttgaaat gtttttttt ttatggataa tgttttagtt 241980
ttttaataaa gagttcttag ttataaaatt aatcttaaac atgttgatac ttgatacatt 242040
tgaaagataa aaatatataa cctatgaaca attatgtaaa aatataccgt ccatgtatca 242100
atttatataa aggtagaatg ctaaaaatga aaatttggcc tatagtaaac atctctaaat 242160
caaaacattt tctttcataa taaataaaag agaaggaatt agctatattc tattagctca 242220
taattgtgtg gatagtagga tgaaataaaa atgactacat aagtcagaaa cataaaaaca 242280
gccattgatt tagaatctgt tgacatgaag gccaccccgg ctccaccaca tcttgaacta 242340
gatgagtcat aaactccaga gtatccatta tgctaaccta taaagtcaag gtggaaacta 242400
gagtagtgat tctcaaacct acaagtcatg attctcttgg gggaacacac acaaaaatat 242460
tatattgaag aatatgctgt tatatgctgc ttcataataa attactgtgc agataaatgg 242520
taatatgcag cacatttgtt tgtttcattt tgtgttttaa agctttctct tccagcagac 242580
tgatgtgaat ggaggcagag aacttgtttt agtcaatgta gtatcccttg cacttttcat 242640
actatgtagc acattataga tactcaataa cttgttttta atgaataaat ggcaaaatat 242700
cataggagaa aatttttaag atgattctgt ttattaaact atctcccagt acatgtagat 242760
aatcccacca ttattttatt atagaaaatc tacagtcgtt ccaacttcta aaatgcaatt 242820
aagaactcca gttatgataa tctttaagga tcattcttct ctaagataat atgtctctac 242880
agcttttact gcctttgaaa atcctctctg tcacatctcc tgaagaaaac agtttcttgt 242940
ccagatgaat tacagtgaaa aaggaaaagc atttatctga acattaaaat ccctttccat 243000
tacaaccctg aattctttag aataattctt gttcatttgg gtaatttccg attaccttaa 243060
accagtatac ttgttattct cataaagcgg atgtacaatt ctacctggtg taacatgaac 243120
tccggaacca ggttgcttgg gtttgaatcc taagtctacc aggtataagc tctataacct 243180
tgaacaagcc acttaatatt tccatgtctc aggttcctga tctccaaata agtaaaataa 243240
aaataattat atcaaaccct taatttaaag tttaactcag ttagtacatg tgaaatgcta 243300
agaacatggt ttggccggta gtagctgaga aaatggacct gtagtaactg ctatgcaaat 243360 attcttgaa ataaaaacaa aacgaaataa atatgctaat cttttttacca gattgcatga 243420 ctattcagtc ttaacaaagt tggctaagat taggccaaca tcatccagaa aaatgtcctc 243480
agttataaac agtagggaaa tcttagaaag aatgattgaa gcacacaaag taaacaacac 243540
aggaaaatta gcgatatatg tgtctgcaga aaaatgagaa ccaagggttc ctgaggtaga 243600
tggttaggca tttcatgtgt gtaaaagatt ccaattataa atctggaaga caaggcactg 243660
gtagagtacc tgaccctaat aaataaatac tcattaaaat tttgcttaat ttagtataaa 243720
taaatttaat taattattca gttaactggt aaatgaaata gttgtttgac tataagccaa 243780
gtcacttgac atgtctaggt tctgttttcct caactgttaa ataaggaaaa ttatctagat 243840 cagcattcc ttaattgtgt tcaactcaag actgggttct tagagttgtt aatcagctct 243900
tggaaacaaa tccatggttg aataattta ggaaaaccca tatgctatct ttctcttgca 243960
```

```
tttacaaaca aactggtata gtagacattt taagatcttt tattgtaagg aaattttatt    244020
tatctgacaa tttcccaaac ttaattgacc attgactctt ttcctctggt ttctagccta    244080
ttggtatttc acagaattac tgctattctg aacaaaaatt ggaataata ctactcaatg     244140
tttggtgtgt ggctcagtgt cagtctgcaa attatttacc agtctataac agaataagta    244200
caaaaactaa gagcaggcat ttaaaaactt ttatagcaat ttgacacagt aattttatgt    244260
ttattgaatc taataatgaa aatcagggat tgtattttgt aggttttccc ttcattgctt    244320
ttttccttat aaattaattt ttattagttg ttttttttt tttttttttt tttttttgag     244380
atggagtctt gctctttagc ccaggctgca gtgcggtggc atgatctggg ctcactgcaa    244440
gctccgcctc ccaggttcat gccattctcc tgcctcagcc tcagagtag ctgggactac     244500
aggcgcccac caccgtgcct ggctgatttt tttgtatttt tggtaaagac ggggtttcgc    244560
tgtgttagcc aggatggtct cgatctcctg acctcatgat cggcccacct cggcctccca    244620
aagtgctggg attacaggcg tgagccacag cgcctggcct tttattagat ttcacttagt    244680
ctcttgtaca ctgaaaattt tttctgaatg ttcacagcag ctttattcat aagagcaaaa    244740
aacaacaaaa aaattaaaat gggttcttta ccacagatag tttcagaaca ccaatgtcat    244800
ctccaaaaag attcacatta taaatccttc cactaattcc atgcagaagt ccatgaagat    244860
gaagtttcct gggttctact gcaaactttt atcagaatct ttagaatcat agggaatcta    244920
cattttcaca gcacccaagt aattctgact atattttgag cattacactg tggcaacctg    244980
atgggagaag ctgtattttt atttatcttt gttccatcag taacgaaccc acagtaaata    245040
aatatgtttg tagcatatgt aaatgagaaa aatcaagtaa cgatatggag tctctgaggt    245100
ctatgttcat ggatagttta gagttaaaca aaactggaaa caaattacta cccccaaaga    245160
atcaaatcct atacatcact tgtcaggaaa aaaaaaatgc cattctccag acacttccac    245220
ttacagccta cttcatgttt taattatctt gaagtgggtg ggatttttca gcatgatcct    245280
gcaaaactgt caatcatttc tcttcttatc caagcatagc accataacag aagttgatct    245340
actaaacagc tccttagtac tgcaatttaa tataaaaata cactctcagt ccatgtcata    245400
gccaacatta tattcactat gtggacacaa ataatttgaa cactttgtta aaatatactt    245460
ttactagtcc ttgcccagta aggcatcaat cagtttaatt ttactgtgga attttttgtac   245520
atgttttcat gttcatatct atagaaagct aaatgtttaa agtccagctt gacatgtttc    245580
tcatatttt actctgctaa taagtcaaaa tatgtgtgtg agacatgaat accttaggat    245640
attgtgtgtc tgtttgttga gatgacccta aactctgacc ctaaacagtg gtcctccact    245700
tggaccacac tttggaattg tctgaagtac tgagaaatac agtgcttact ttggcagcac    245760
atgtactaaa attggaacaa tacagagaag attagcgtgc cccctgagca agatgatat     245820
gcagactcat gaagcattcc atgttttga gaaaagaaa tgcttttaca ttgttggtgg      245880
ggatgaaaat tagttcaacg attgtggaag acagtgtgac aattcctcaa agatctgaaa    245940
gcaaaaaata ccatttgacc cagcaatccc attactaggt atatactcaa aggaatataa    246000
atcattctat tataaagata catgcatgtg tatgctcatt gcagcactat tcacaacagc    246060
caagacatgg aatcaaccca cgtgcccatc agtgacagac tggataaaaa aagtggtata    246120
tataaaccat ggaataccat gcagccatta aaagtaacaa gatcatgtcc tttgcaggga    246180
catggatgga gctggaaatt gttatcctca gcaaactaac acaggaacag aaaaccaaac    246240
accgcatgtt ctcacttaca agtgggaggc gaatgatgag aacacatgga acaacataca    246300
ctgtggcctc tatgggggtt gggggaaggg agagcatcag gaagaatagc taatggatgc    246360
```

```
tgggttagat acctaagtga tgggttaatc tgtgcagcaa accaccacag cacacatcta    246420
gagtttctga ttgaattcat tattggagtg gtctgaaagt cagaattttt aaggcttctt    246480
aaataattct aatatatatc ctgagttgag aaccataaat aaaatcaggt gcagttctta    246540
tcaaaaaaaa aaaactgcag taattatgag agatcccata tccaaggtaa atgggtggat    246600
ttgtatttga attgaattag agaagggtca gctgtgaacc caccatgaaa gggtttcttt    246660
tcacttactg agaattaaga agactgatga tgttcagtct taggagagaa acgtacatcc    246720
ttctctacac tcctcacccg tttcctctgc acaccttcag caatcattat ttgctcatca    246780
gactaaggtt gtttatgggg aaaaaaaaaa agttaagaga cagataataa gggaccgaaa    246840
aagatgagag agacagagta agacagagtg agagagaatg tcttcattaa attactaaaa    246900
caaaacaaaa catttatcac tctttcagct tcaggccctc atctctaata cgctcctgaa    246960
ctactggggt cctgaaggca taaaattctt ttctcaggct cagatccttt cacctctaga    247020
tacagccaga agtcctggag agaggaaggg aaaggagtaa ggaagaaaga aaggaaaagc    247080
attactttgg gggcaagaga gatttgcctc ttccctttcc ttcctgcatg tatggagggg    247140
caaggaaaga cttacttgac cttcagccag ataacggctt gtggctttct cttacacacc    247200
cagaggccac attccttgat tcaatctact ttcagctgca caagctctgt gccttcattt    247260
cattagaagg gtagtttcta ccacaaacaa gtcttcgttc ctggtactag ggttaggcct    247320
ggtaacgctt caaaatctta agaaaaaatt taaaaccccg atttatatg tagagaacca    247380
tctcttttga ttaagaatat tttacatcat aatgaaatgc agtcaaagct gagggcaat    247440
ttgtcctctg gggtatcact tctctgagtt caaaaaaata ttcctgtttg ttctaaatca    247500
cctctaaatt tactttgatt tgcaaattca atgtactttg tataaacaaa cactgacaat    247560
gaattaacaa tactatatga cccctttcac tgaatgaata tagattttca tgctcagatg    247620
atatttgtgt ccctgtcaca tattttactt cagatcttaa tgagtaacct tgagtcttaa    247680
taacttttcc tttaagccaa gctctcttat ttttctttga tattttcatc aactacacac    247740
catcccctgt aataaatgag aaaaggagag ggtgcccagt cacagtggta ttctgtccag    247800
ataggagcac gtttctatcc tgtctacttc ctactggcaa aagcaatgca tgataatttg    247860
ctgccagtat tactcaacct taccatatag acaaattatg ttatctacga aatccactct    247920
aagggaaatt attgttctgt ttcaatcgat ttcttcattc ctcactatca ccaaaccata    247980
ttctccttca gttgatttgt atttagtatt cactcaacaa accttaattg agaactacca    248040
tgtgccaggc atcattgtgt atttaggaaa tagtttagac tcttggtatc aactctcaaa    248100
gaactggaca gctcacttgg gtagaagaaa taagaaaacc aaagattaca aaaaggaaa    248160
tagacaggaa gacttatttta cttatttgac agacagccat agtctttcca taggcctgca    248220
gagaaaggtt agagcagcta atgcattttg gcttgggaga gaatagtaag aaatagtcta    248280
gaaagacttt agaaaccaga cagagaatag aacaggcgta aaaactgatc ccagagtaac    248340
tccacgttta aggaatacaa cagaataaca gtatgaactg tgattggtgt ggggatattt    248400
ttgaaacaat gtaaagagaa tttgagtata attataatca gaaagtaagg gaccaatgtc    248460
tttaaaaatg tatgtaaaaa taaggcaaga actgatgaac caaggtctca gaagaggtag    248520
aacatgggac tgtctcctac tctacagggt caccacaagg gcaggttcca ggcatggatt    248580
acatcataac acttatacca ctaatctctg tttagaagtg aaatcccata gctgatagca    248640
gccattaaaa ggcatgggtg acatatgatg acagtagaga atatagagac agtgtgtgca    248700
```

-continued

```
ggtgtgcagg aagactagat ttggacattg gctgtaaatg acttaatgga ttcaaccaaa   248760
atgtaatgag cacttgtaca gaggccacgg atgtgtgtca ttcagatgcc gtttctggag   248820
aacctgaccg tttggagaga agaagtgaca gagagccctg gttgctgccc ctttgggtca   248880
actgcacagt cttgtcaagg ccaccctcct gccaagcttt tctcagtcaa tgcctggtcc   248940
cagcagtgct accgattctg acccattcct attggatttc tgtaacaggt cacttttgct   249000
tttccatcag tctggctgag atctttctaa gaactgtgcc gcagtctatg actctcccta   249060
caaaatcctt tctcccttct ctcctttcag cattgcagtc tgaagccttt ccctgcctat   249120
acctcctttc cccccattta tccaacactg gcagttctta ccataaatct cttgtactta   249180
taattctgtc ttggcatctg tttctgagat agcccaaact aactcatggg attagtttaa   249240
gggctaagga ttttaaaaaa ctgacaaaaa agacaaagtt tctaccacca aaggtatgag   249300
aattcattgt tttaaaatat agaacattag tgggtatatc ttgcttctgt tttcagtttc   249360
tgtaaagaga gtgatccctt tcttttttttt cttttgtttt gctttaattc attgcttag    249420
tattggtata ctctaggata cctagggctg cttttcatat ctctcaattt gagtttatac   249480
tgtttccctt acatctctgc cagtatcaga gtatcatttt tccttacctt tatgagcaat   249540
ctcatcattt ataatttgtc tctcacagct gcccttggc actgtagcag aaagtgagtc    249600
atcctacatc tatgaaatct aagatgattc tgagataatt tagtaaagat taactatctc   249660
acatctttcc ccctcactct gttttttcatt ctggctccct gccctggct gacaacatgt    249720
gcacgtaact ttactcattc tgaactgcac aggctagaat gtctctacac tcacatgcct   249780
ttcatcaaaa tcctacattg atttaaaatg catgagtcac tttattcata tcttgggttt   249840
tgtttgggaa aatgctgatg ctagaaaatg ggagtctcat ttcttccccc tcctttattt   249900
tcaatgttcc tccatagcct atgtagcaat tctggttcac gcttggtatg gcccatggct   249960
tgcaatgctc cttagtcaca aaggcccaat gattcacagg tttggcagga ttgctacttg   250020
atctggtatg ctgacccttt ccctaaaggt cttaaggccc tccttctttg tggaaggaaa   250080
aattgttctt ctggtatatg tgtatggaaa ggagtggaaa gggaagagga tttagggtga   250140
gattgagagg acagaggcat ctcaccatgg aagtatgata actcactgcc tctcatggat   250200
gatatgatcc atctcatttt ctgctttttct gctttacctg gtataaagcc ttataaacca   250260
ttcaaaacaa tccattttgc aataaaatgc tgttgcattc cagtatgact gtctgtagct   250320
caagttaaac tcgaccccac atcaaaagtg agtgaaacga gtcagctgct aagtctcagt   250380
ggatgctcgt aggttgtctt cagggcttga aaaatgttga aggaaaccac attttaaaac   250440
aaagtacatt gtatatcagt ggacatgctt caatagatgg gagtgttgct gcaggactcc   250500
ttagaatgca agcactaaag ctctgtaggt tggtgcacag gagaatctag tcttcttata   250560
ttaataaatt tttaaattca agtagaaaca aaaatatgaa aagatgtgaa ggagttagga   250620
acaagcgtta gggataatga acctcagtgg atttaagggc ataatctgaa atcaggagca   250680
ctgggtaagc ttccttacct ccttggagcc cttatggcag tgatggcaaa acagtgagat   250740
aagatgctat ggggtaaaat gcctggctga acaatactgc tctcctactt tgggaggatg   250800
aattggctct gatctcactg tgtctctcac tgtcttctaa aattatattc aaagttcatt   250860
ttttgggaaa cattccagac taatcctatt agtcaggtat gtttgcatag gtgtattaaa   250920
ttaataaaca tgcacagaga tatagatgta agggtagaca tatagcttct tccatgtgtg   250980
ccagttaagc tactttcttc ctagtgcatg gataatagag gcttttttgt atgtttgttc   251040
tgccctctgc attaagtggc taactcttat agggcaagga tcatagctac acaatccgtt   251100
```

```
gtctctagac acccatctga gaaaggcaga ttattctttt gtacgaatgg tgaactttac  251160
ggtcagaaaa tcatggatct acttttatac aaatttagtc agataataat ctctaggtac  251220
ctcagactcc cctgctgtaa atcaggatca gaaataattt ctttgtgggg gtggtctgag  251280
aattctgata atggagggca agggaatgta caaggcaaag gtggtgtgga atttcacagt  251340 gctgttttt cactactcta gtcttccagt ttgcgaagag attccatttt aatccattgg  251400
ctgtttattg aggacacttt atttctccat aagagctaac tctgcccct tgtgctgagt  251460 aaaataattt ttctatttta ttcggtttaa ttttatttgc atttaagtgt ttatacctat  251520
ttgaaaaatc atatccagct actcttttca ataagtcaag ttatataagt gtattttctt  251580
taataggttc cctggagtaa tttttccttt ttttcatatt tttttccttt cttcaattca  251640
tctgcaacct tttatgttta aagtgcaatt cttcacaagg tctccctgat gctattcatt  251700
acaggctttt ctctgttgag tactgtcaca attagttta ctgtccaatc tttaccatgt  251760
cataaggaat aactaagact taagggtcaa aagaccgaaa tgagatagca agagctgagg  251820
gcagcgttga aacttttga agagtgtaac aaatggatcc atcaattcaa aaagtgtact  251880
tgggagtttc acaaggattg cctcttttc tgattgaaga cgtgttttca ttgttctgat  251940
caataagtga tataggtcct tttttaaaga gttcaggcat aaatgaataa aaacattcta  252000
ctagattcca tgggaaacaa ctcgtcctgc agagctaaaa gtctaattgc ttagttaaat  252060
aacaatacaa aaaaacagga tacaattaag aattaccaat ctaattgacc aaaaaaatga  252120
gtacttttga acttctgagg atatgtatat tcaagtggtc tgaaaaaagt aggtgatgaa  252180
acttaaagta ggccttgaag gataagatat ggtgatgtat taaaaataaa ttcagtagtt  252240
cacagaatta atgacagaac tggagaacaa ggctcaaggt tacgggaaaa gaaatgccc  252300 caaaccacct tagaattggt tctgagcagg aaaaaaaaaa agtctgcttc cagagagaga  252360
acttgtacca cttgcttctc aaagtgtctt aagcatagcc agtggccctg gggtattttc  252420
ttcccaaaat gtaggtctca aaatgtagct tatgccacag ctgaagggga agctgagaaa  252480 gtcagttcc tctccagtag tggaagtaat ctcttcactg agacatcaaa tgtggttaga  252540
aggggaatgg aaatctccaa acgtacacat ggatgggcag atatcaggcg ccactgtga  252600 atgacaaaca cttgctatca gcagcctctt ttcagtcagc atcagctcat gagacttcaa  252660
aagatttcac aggaagagtg tatccatgtt ctcaaactct caacatttca gagctagcag  252720
ggacattaaa actccttcag cccaatcttt ttaataagta aaccaagtct cagagacatg  252780
agaagctata tccagggtca cacagctgat tactggtgca gccatgatta atgctctggt  252840
cttctaatcc ctaccggtg tagtgcttgc gaatctgttc tatgggcaat tataagaaa  252900 atgcgcaatt ataagagaaa tgcttacttc ttggaagaat gaaagcagca tcatatcttc  252960
tctacacttg agaaaggctt cctttctgc ctgtcagatg caaagtttta gaaaagtcag  253020
gactgctctg caggccttga aacaaacccc tatgggatta ttctcttcca ccagcccag  253080 gtcatgctcc ttgtgcccca agactccacc actggtttac attgtgtttg actacgactg  253140
tcgcccaggc tggagtgcag tggtgcgatc tcggctcact gcaagctccg cctcccggat  253200
tcacgccatt ctcctgcctc agcctccaga gtagctggga ctacaggcgc ccgccaccgt  253260
gccacgctaa ttttttgtat ttttagtaga acagggtttt caccgtgtta gccaggatgg  253320
tctcgatctc ctgaccttgt gatcgcctgc ctcggcctcc caaagtgctg ggattacagg  253380
cgtgagccac ggcgcccagc catatttat tctctttttat aaatctgagc acttcctttg  253440
```

```
ggatagactc agtggcaatg aattactgta ttaaagaaaa gctctgtcct tcactgacat    253500
gtgaatttgt acatttcact tctcctttct gagacttact ttcctgatct gtaatatcaa    253560
ggtatatatc tgtcagtttt ttagttttgt tttgtttgtg tttgtttctt ttaggatcca    253620
aagagaccac caatgcacta aataggtaca taataaacgt tcactgaatg aatgaacagt    253680
gcatgtttca aaatatgtat ttatttgtag atataagaaa atcaagcttc tctctcacat    253740
cctcattctc agtcatacgc tctctctctc tctctctctg tctctttagc tcgcattctc    253800
ttttcttttc tcctttcctc actctgttct tttggcccgc tttctattct ctctctctct    253860
ttctccccca atgtctccat agtgcataca taaataatat acagacatct acaatagata    253920
tgtatgttga tcaaaaaagt aggtactact tctacccctt tatccataaa catgttatta    253980
aggaacataa actttgcaag tctctaccaa gaagccacag ctgtttatcc tctttatcat    254040
ccagtgtttg gcctctgctt ccagttttga tgtcaggata atgttaccat tctcaccatt    254100
tctttggttt agtagtctcc cacacaacaa agtcctaacc atgtttgtga attgggtacc    254160
cacctgtggc ctattgagca ctggtcttag cacacttaca caatatgcat tttgcctta     254220 ttctacagga gatattaatc ttcctttcat ttcttttacc acatacccctt ttaaaaaatt   254280 tatgttttcc acatacactg gcttgaattt taattttgtg ttttttgggtc tatgatccta   254340 aacactttat gtctatgatc ctttctgctt ttctcaagct ttaatgtgct tgaaacacct    254400
tctttcttag tgttctccaa ataaatatgc catcgatgtt atttatttag tttccagatt    254460
tctaatacag actttaatct ctgcccacca cttgtcactg aaataacttc ccaagtaagt    254520
atgtagatgg accagttctt agtagagaaa tttccatctg tgtgtaagta gtcacatatt    254580
ttatcctgat tgttttgcta tcagattgta attcctaata ttctaaaagt gttgacctat    254640
aaaagtttca attgtacata gttaaatcca ctgtatctac tgtgaaaaga gtacaagact    254700
tgaagtcagg agccatgagc taatttctgc cactgagtga ttgtaggcat ttacttttct    254760
ttacctctct aggcttcagt tcccacaact ttaggatgaa gctttaaatt aaatgatttc    254820
tcactttccc tctagccttt aaaaaatcca tatacacctg tcttgaagct tgtttaaacc    254880 tatcttaaa aaaactttta aaacattttt taaagtgttc agagacagaa catataaaat     254940
accttggaaa atagttctgg aagattttgc atcagaggct attttgtagaa atttggagat   255000 aaactctgtc tgccacagaa gttaagaaaa aaaattgttt tcacctcaag taacacctac    255060
ctatcagctc attgggaatg cctgcatgtt tatgatacccc aacgtgtagg ataggccaaa   255120
gtgaaccaat tgtctcttac agctttgcta tgagaacttt actacaacta acaactcatt    255180
actcagagtc ataggctctg agtcatcctt gacttctgct ctttgctttc tccattcaat    255240
cagctgccac atttctaccc actttcagtt cctcactaat tctgtactcc acacctatca    255300
cccaaattca ggccccatga accgttaact agattatttt aatcatccaa caactaccat    255360
tcctgcttcc aagatctacc cattttttag aatttatttt tttaatttta ttttttcactc   255420 aaagcaaaaa tggtcaatat ccatttttaa tttaacctac ataagtctat cagttaaaat    255480
tccttaacta taactctgat cacattaatc tcaaacacag ccattagctt actaatgtct    255540
aacaaagttt aaaatccttt ggtctattaa aaattattct gagatttaat cccaaccatc    255600
tcccttatct tgtattctgc tgggtcaaat taatgttatt caagctccaa agttaatctt    255660
ttcttaaaac accccttagc tgttacaata aatcttctga tccctcaaat taactccctc    255720
aaagaactca tgactttgta gcagaaatca taatttcttg tgtacccatt agatcacttt    255780
ttattgaagg aaaatagggt gtatatttttc tttcaatatt acagcctcca ttatcacttg   255840
```

```
gagagagatt attatatgag tatagcataa acagatgact ttcctctttc ctatggtaaa 255900
aaagaaattt actttctttt aggtaaaagt agggatgaaa ttattttgat accttatatt 255960
ttaaatacaa aattaaaatt aaaaggtata tcacatttat atatcttctt ttaaaacatc 256020
atacaagttt cataagccat ttctttagag agaaagatat tatctttatt tatttaataa 256080
agacatttca gtttcagaaa atgtgtttta cttatttatt taatacatgt gtttcagcat 256140
ttcgctaagt agtgatattc tccaagttca attccaatca tgactcattg gcttagccat 256200
caaagtttat ctttccttt gaactatgca caagataatg cctatcctat ccatcagtaa 256260
aagtcatgtg agtttctcta cttttcaagt aagtatactt tccaatccat caggttgaag 256320
agcaggatta aatacatatc aggaataaat aactccagta gtcaaaaaaa tagactcatc 256380
aatcagcttc ggaggtcaaa catttgacag gtgccaatga gcttgtttca atatcacctt 256440
tcagaaataa agacattaaa gaagttaatc aaggtatagt caaggagact accaacctaa 256500
ctgagacaaa agacactagt tggttccact caaggttcag gacaagctca gaaccagaat 256560
gtactttatg atattgttag ttgacccaaa taactaaaat tggtgaaata tttaacattt 256620
tcataaaaag tggtattaaa ggttgttcta agatatcaga gcagtatata tatttactat 256680
tattatcaat ctagtcagga tatccattgc ctctttaaaa acaactacaa caggcaaccc 256740
acaaaatggg agaaaatttt tgcaacctac tcatctgaca aagggctaat atccagaatc 256800
tacaatgaac tcaaacaaat ttacaagaaa aaaacaaac aaccccatca aaaagtgggc 256860
gaaggacatg aacagacact tctcaaaaga agacatttat gcagccaaaa aacacatgaa 256920
aaaatgctca ccatcactgg ccatcagaga aatgcaaatc aaaaccacaa tgagatatca 256980
tctcacacca gttagaatgg caatcattga aaagtcagga acaacaggt gccagagagg 257040 atgtggagaa ataggaacac ttttacactg ttggtgggac tgtaaactag ttcaaccatt 257100
gtagaaatca gtgtggtgat tcctcgggga tctagaacta gaaataccat ttgacccagc 257160
catcccatta ctgggtatat acccaaagga ctataaatca tgctgctata agacacatg 257220 cacacatatg ttcattgcgg cactattcac aatagcaaag acttgggacc aagccaaatg 257280
tccaacaatg atagactgga ttaagaaaat gtggcacata taccatgg aatactatgc 257340 agccataaaa aatgatgagt tcatgtcctt tgtagggaca tggatgaaac tggaaatcat 257400
cattctcagt aaactatcac aagaacaaaa aaccaaacac cgcatattct cactcatagg 257460
tgggaactga acaatgagaa cacatggaca caggaagggg aacatcacac tctgggact 257520 gttgtggggt ggggggagag gggagggata gcattgggag atatacctaa tgctagatga 257580
caagttagtg ggtgcagcgc acccgcatgg cacatgtata catatgtaac taacctgcac 257640
attgtgcaca tgtaccctaa aacttaaagt ataataataa aaaaaaaga agttgaaaa 257700 atcttagcac tcaaaaaaaa aaaactaca acatataagc agaaaattgg acttttttga 257760
tatatttgag gaacactttg agtcacattt attgaaaatg ctcatagaaa caaatagatt 257820
tttagctgac tatccttgac aacacctctt ttcatataac ccctggtatt atgaaaaaag 257880
aaaaaatatt ttatttgctt tatttgaaac acatgaaaat cacatagtca aaatgaggta 257940
ttatgtatct gaaacccag atacctctct ctctgccgtc tgcttgagac agtcctcact 258000
actcactgct cttgccaata aactggaagc caaggtcggg agtttgacat tcttattatg 258060
ttctgactac aggatagacc cttaattcag gcaacttaat ggcaaatacc tacaaaaga 258120 cttgatatgg tttgtatctg tgtccacatc caaatctcat gttgaattac aatccccaat 258180
```

```
gttggaggtg gggcctagtg gaaggtgatt ggatcatggg ggcagtttac aaaggattag   258240
caccaaccta ctagtgctga acttatgaca gagttctcac gagatctggc tgtttagaaa   258300
tgtgtagctc ctcccccttc tctcccttcc tcctggtctg gccatgtaaa tgtgcctgct   258360
tccgcttcac cttgtgctat gattgaaagt ttcctgacac acctccagaa gccatcatgc   258420
ttcctgtaca gcctgtggaa gagtgagcca attaaatttg ttttctttat aaattgccca   258480
gtcttcttta tagcagtgag agagtggact aatacaagac accaagaac cacagggtat    258540
cactgaaacc ttttcaaaca gtggaaaaa aaaacactt aaagtttatg cccaacacaa     258600
gtctttcaca aaacttccag gtgatgaaaa ttaatcttgt ttgtttcttg tatttatcat   258660
cttcttgagg accagattta atttccacag aatgaaatct ggggaaatta actccccaga   258720
tttttgcccc ctcattagac atacttagct gagtcagcac tccactcata tataaatagc   258780
aaaaacaaca catgacagat agcacatttc tttctctcag gctcttcttg ccttctacag   258840
aaaatctttc actgtccact acactatcag aaaataataa aggagggact atctcccac    258900
taggatcctc ctcccaacct ctacttcatc aggtaaggat cttatttttcc aactcaaggg  258960
agcatattcc actggccaca tttcaaacct gggtgctaat attaggaaac tgaacattta   259020
gagcactgct tgtgttactt ttatagggtc aacctatatt cttaataagc aatatattgt   259080
tgtctgtctc aaaggataga gcactgggaa taaagagcaa gcatcagtga atgaactcag   259140
cagccacaaa caaattacca gagatgtgta ccttcctgag aagcagagaa ttatagaggc   259200
aatgttgcat gatgggatat gtaaatacag ccttggaaga tcatgtgtgg atggaaacca   259260
attaagtaaa gcacttagga aaattgcttt ctactgtctg aataagaatt tatcatgaga   259320
cacagttttt taagtgaaaa acgtatatgt aaacctggac taagtgtttt gtccaaggtg   259380
acacaataag gcaggcaata gagataaaaa tagaatgctt gaaaccagcc tcctgatcta   259440
atcaccaaac actttgcaag tttatctctg aagaggacct aatgcaaagt agaacccttta 259500
gagtgagagg tcagcataag gattgcagca gccaactggg cagcaataga aatggaattg   259560
attgcttccc taaaaaatga tgaaatgtta tcaataacta cacagcaaaa gaaaaaaatg   259620
cagcgatatg catcatgaag gagaaagcat tttctccact aaaatagctt tgttaatca    259680
ttaccagtca ttaaagaaca caaggtttca gatcttcctt aatccaggca ttctgcttga   259740
agttataaac aaataatttc attatgtctt tgtctatttta aaaaaacata ttttggtatg  259800
atttctctca ctcattcaaa gttttacaga gcatctgcta aatatcaagt cctgtgaagg   259860
gtatataaaa atggagggg catatttcca cctttcaagg aactcaggtt ctgttgtaca    259920
tggatgctta gataatattt gtggacacaa agtggtaagt gctctaaaag aaataaggtt   259980
aaagtcctgt gggaatacaa cagggcaga agaaagcga gattaagaaa gaaagatata    260040
gaagttccgc aatggtggag ttaaatcaag ccacgggagt tgatgacttt gcaggtggat   260100
acaggggaat atcatagaag agaatagaat tctgggcaaa agaaataatt taagcaaaag   260160
ctctgctact ttatttagca gatttcccctt ttcagacatt tatttctcac ctcaacccaa  260220
gctttattcc ccattggctg ttttaagttt cttaatcttg atgattttca gtttcctgtc   260280
ttataggatg gtgatttcta atattgttgt cctgaggatt aaatgagata ttcctttcaa   260340
ggacttcaat agaaataaaa caaacattag atggattagg taatgattcc ctgagaagga   260400
tgcattcaat tagttagtca ttgcaaaaca agaaatgagt aaaccagctt taactagcaa   260460
gagctgcaaa gtgcagacc ccaaggagat gggaagcaag tagatatatt ttgatgtgaa    260520
gaaaaatcgg cagtgtcaca gtggagaata cttgaggggc aacagaatat cagatgagca   260580
```

-continued

```
aaatactcag aaaaaaatca cctacaacat agttctgact ggtggaacac cccaagagac  260640
tgtaattagg gtatcatcta ttggcttaga aggaatgctt caaaagtcca tcacataatc  260700
aatatggaca ggatggttag ggctacaggg atgatgataa acatgaact atttcttcct  260760 gggaatattc cccctcaccc ccactaccta aaggtaccca gagaaactta taaacaattt  260820
atgaataaga tggtggaagg gggaatacaa attaaaaatc acccgccagg tgcagtggct  260880
caagcctgta atcccagcac tttgggaggc tgaggcaggc ggatcatgag gtcaggagat  260940
agagaccatc ctggctaaca cggtgaaaca ccgtctctac taaaaataca aaaaattagc  261000
cgggcttggt ggcagcgcct gtagtcccag ctactcggga ggctgaggca ggagaatggc  261060
gtgaacccgg gaggcagagc ttgcagtgag ccgagatagc gccactacac tccggcctgg  261120
gcgaaagagc aagactccgt ctcaaaaaaa aaaaaaaaa aaaaatcac cacacactta  261180 ggtgttatta aaaattcatt ttactggaaa aggcattttg ttgttgttgt ttttaagaca  261240
gagtctcact ctgtcatcca cactggagtg cagtggcatg atctcggctc actgcaacct  261300
ctgcctcatg ggttcaagct actgtctttc ctcaacctct cgaatgactg ggattacagg  261360
cgcatgccac aatgcccagc taatttttg tatttttag tagagatggg tttcaccatg  261420
ttggctaggc tggtcttgaa ctactgacct caaattatcc atccacctca gcctcccaaa  261480
gtgctgggat tgcaggcgtg aacccggcct ggaaaaggca ttttacgttg tgagcaggta  261540
ctcttcctaa gaattactgt gagtgtaagt gtgtttgtgg tgaggagggg ttgcacagga  261600
tgcatataag aagtatctaa atgtaacctg tatttgttac ttcagactca atgatatagt  261660
atgaagaata attatgacgg aatcacccat tgaaaagtga cacagatgcc catgctgtct  261720
tgggaaggaa gagaaagtgg gaacaaaaat gatttcttac tacatgaatt gctttataaa  261780
gaggagcct                                                          261789
```

<210> SEQ ID NO 2
<211> LENGTH: 19
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is g or t

<400> SEQUENCE: 2
tgcgcgtgtn tggtgtgtg                                                19

<210> SEQ ID NO 3
<211> LENGTH: 23
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is g or a

<400> SEQUENCE: 3
aaataaatta acntttatca tca                                           23

<210> SEQ ID NO 4
<211> LENGTH: 17
<212> TYPE: DNA
<213> ORGANISM: Homo sapiens
<220> FEATURE:
<221> NAME/KEY: misc_feature
<222> LOCATION: (8)..(8)

<223> OTHER INFORMATION: n is g or a

<400> SEQUENCE: 4
atttctcntt aaaattt                                                                                    17

<210> SEQ ID NO 5
<211> LENGTH: 21
<212> TYPE: DNA
<213> ORGANISM: Homo sapiens
<220> FEATURE:
<221> NAME/KEY: misc_feature
<222> LOCATION: (12)..(12)
<223> OTHER INFORMATION: a is absent or present

<400> SEQUENCE: 5
atttcatatc taggaaaaaa c                                                                               21

<210> SEQ ID NO 6
<211> LENGTH: 23
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is t or c

<400> SEQUENCE: 6
ccacctagnt tttttaatga aca                                                                             23

<210> SEQ ID NO 7
<211> LENGTH: 23
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is c or a

<400> SEQUENCE: 7
atcttgattn tatttatgac tgc                                                                             23

<210> SEQ ID NO 8
<211> LENGTH: 21
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n is t or a

<400> SEQUENCE: 8
gcttagttgg ntagaccagc t                                                                               21

<210> SEQ ID NO 9
<211> LENGTH: 21
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is a or c

<400> SEQUENCE: 9
cctcactctn ttctcctcct t                                                                               21

<210> SEQ ID NO 10
<211> LENGTH: 18

```
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is t or a

<400> SEQUENCE: 10
ggtgcagngg catgagcc                                                    18

<210> SEQ ID NO 11
<211> LENGTH: 30
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n is a or g

<400> SEQUENCE: 11
aaccctcctc aattgtngaa acatggaaca                                        30

<210> SEQ ID NO 12
<211> LENGTH: 32
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a or g

<400> SEQUENCE: 12
ggaacagcaa cattcttana tgctcatgta cc                                     32

<210> SEQ ID NO 13
<211> LENGTH: 34
<212> TYPE: DNA
<213> ORGANISM: Homo sapiens
<220> FEATURE:
<221> NAME/KEY: misc_feature
<222> LOCATION: (20)..(20)
<223> OTHER INFORMATION: n is c or a

<400> SEQUENCE: 13
attcttaaat gctcatgtan ctttattaaa gtat                                   34

<210> SEQ ID NO 14
<211> LENGTH: 34
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n is t or a

<400> SEQUENCE: 14
atgtgcattt ctacantcat tcaaatagtc tttg                                   34

<210> SEQ ID NO 15
<211> LENGTH: 22
<212> TYPE: DNA
<213> ORGANISM: Homo sapiens
<220> FEATURE:
<221> NAME/KEY: misc_feature
<222> LOCATION: (12)..(12)
<223> OTHER INFORMATION: a is present or absent

<400> SEQUENCE: 15
```

```
aatgataaaa tattttttaa ag                                              22

<210> SEQ ID NO 16
<211> LENGTH: 19
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is t or g

<400> SEQUENCE: 16
tcccaccgna cccagccct                                                  19

<210> SEQ ID NO 17
<211> LENGTH: 19
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is t or g

<400> SEQUENCE: 17
ttatatcaan gcctccaac                                                  19

<210> SEQ ID NO 18
<211> LENGTH: 20
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n is a or g

<400> SEQUENCE: 18
acttgcagaa nttttatatc                                                 20

<210> SEQ ID NO 19
<211> LENGTH: 20
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n is t or a

<400> SEQUENCE: 19
ggttgactag nccatgcctt                                                 20

<210> SEQ ID NO 20
<211> LENGTH: 18
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n is a or g

<400> SEQUENCE: 20
aacagaactk ancactct                                                   18

<210> SEQ ID NO 21
<211> LENGTH: 21
<212> TYPE: DNA
<213> ORGANISM: Homo sapiens
<220> FEATURE:
<221> NAME/KEY: misc_feature
```

```
<222> LOCATION: (11)..(11)
<223> OTHER INFORMATION: n is t or c

<400> SEQUENCE: 21
gtccaaaaca natgctaaag a                                              21

<210> SEQ ID NO 22
<211> LENGTH: 18
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a or g

<400> SEQUENCE: 22
ttatttacnt gaagttgt                                                  18

<210> SEQ ID NO 23
<211> LENGTH: 15
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is a or g

<400> SEQUENCE: 23
acatcttntg aaatt                                                     15

<210> SEQ ID NO 24
<211> LENGTH: 23
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n is g or a

<400> SEQUENCE: 24
ttgttggggg nactatagta atc                                            23

<210> SEQ ID NO 25
<211> LENGTH: 22
<212> TYPE: DNA
<213> ORGANISM: Homo sapiens
<220> FEATURE:
<221> NAME/KEY: misc_feature
<222> LOCATION: (15)..(15)
<223> OTHER INFORMATION: n is t or g

<400> SEQUENCE: 25
gaccctccaa caaangccat tt                                             22

<210> SEQ ID NO 26
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is g or a

<400> SEQUENCE: 26
agtttggant ttcctca                                                   17

<210> SEQ ID NO 27
```

```
<211> LENGTH: 19
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n is c or a

<400> SEQUENCE: 27
tcagagaaat gnaaatcaa                                               19

<210> SEQ ID NO 28
<211> LENGTH: 100
<212> TYPE: DNA
<213> ORGANISM: Homo sapiens
<220> FEATURE:
<221> NAME/KEY: misc_feature
<222> LOCATION: (50)..(76)
<223> OTHER INFORMATION: 27 basepair sequence may be absent or present

<400> SEQUENCE: 28
ctggaggaga taatcattaa gtgggaattt gaatattata acagatcctg ggaatttgaa   60
tattataaca gatcctgtaa tcacctgacc actgcacaga                        100

<210> SEQ ID NO 29
<211> LENGTH: 33
<212> TYPE: DNA
<213> ORGANISM: Homo sapiens
<220> FEATURE:
<221> NAME/KEY: misc_feature
<222> LOCATION: (18)..(20)
<223> OTHER INFORMATION: caa may be absent or present

<400> SEQUENCE: 29
ataagcaagt ataaaaacaa tttccagtag atg                               33

<210> SEQ ID NO 30
<211> LENGTH: 22
<212> TYPE: DNA
<213> ORGANISM: Artificial
<220> FEATURE:
<223> OTHER INFORMATION: PCR primer

<400> SEQUENCE: 30
gggcctagtg tgctaatctc tt                                           22

<210> SEQ ID NO 31
<211> LENGTH: 24
<212> TYPE: DNA
<213> ORGANISM: Artificial
<220> FEATURE:
<223> OTHER INFORMATION: PCR primer

<400> SEQUENCE: 31
ttattttaca cttaagggtg ctca                                         24

<210> SEQ ID NO 32
<211> LENGTH: 22
<212> TYPE: DNA
<213> ORGANISM: Artificial
<220> FEATURE:
<223> OTHER INFORMATION: PCR primer

<400> SEQUENCE: 32
ccagtttttg tagctgctgt tg                                           22
```

<210> SEQ ID NO 33
<211> LENGTH: 24
<212> TYPE: DNA
<213> ORGANISM: Artificial
<220> FEATURE:
<223> OTHER INFORMATION: PCR primer

<400> SEQUENCE: 33
tttatagtcc attttggctt gctt                                              24

<210> SEQ ID NO 34
<211> LENGTH: 20
<212> TYPE: DNA
<213> ORGANISM: Artificial
<220> FEATURE:
<223> OTHER INFORMATION: PCR primer

<400> SEQUENCE: 34
cttgcacctg ggaggtagag                                                   20

<210> SEQ ID NO 35
<211> LENGTH: 20
<212> TYPE: DNA
<213> ORGANISM: Artificial
<220> FEATURE:
<223> OTHER INFORMATION: PCR primer

<400> SEQUENCE: 35
cacaactgtt gcttttccat                                                   20

<210> SEQ ID NO 36
<211> LENGTH: 22
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' FAM modification
<220> FEATURE:
<221> NAME/KEY: misc_feature
<222> LOCATION: (22)..(22)
<223> OTHER INFORMATION: 3' MGB modification

<400> SEQUENCE: 36
aggtattact taatctagtt ca                                                22

<210> SEQ ID NO 37
<211> LENGTH: 22
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' TET modification
<220> FEATURE:
<221> NAME/KEY: misc_feature
<222> LOCATION: (22)..(22)
<223> OTHER INFORMATION: 3' MGB modification

<400> SEQUENCE: 37
aggtattact caatctagtt ca                                                22

<210> SEQ ID NO 38
<211> LENGTH: 17
<212> TYPE: DNA

```
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' TET modification
<220> FEATURE:
<221> NAME/KEY: misc_feature
<222> LOCATION: (17)..(17)
<223> OTHER INFORMATION: 3' MGB modification

<400> SEQUENCE: 38
ccatcaacaa ttgcatc                                               17

<210> SEQ ID NO 39
<211> LENGTH: 18
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' FAM modification
<220> FEATURE:
<221> NAME/KEY: misc_feature
<222> LOCATION: (18)..(18)
<223> OTHER INFORMATION: 3' MGB modification

<400> SEQUENCE: 39
tccatcaact attgcatc                                              18
```